United States Patent
Celanire et al.

(10) Patent No.: US 12,421,222 B2
(45) Date of Patent: *Sep. 23, 2025

(54) SUBSTITUTED QUINAZOLINES AS HDAC6 INHIBITORS

(71) Applicant: AUGUSTINE THERAPEUTICS, Leuven (BE)

(72) Inventors: Sylvain Celanire, Leuven (BE); Joao Fernando Dos Santos Carvalho, Heverlee (BE); Frederik Jan Rita Rombouts, Leuven (BE); Peter Christian Sennhenn, Munich (DE); Michele Curcio, Bertem (BE); Joana Catarina Reis Pedro, Bertem (BE)

(73) Assignee: AUGUSTINE THERAPEUTICS, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 19/016,827

(22) Filed: Jan. 10, 2025

(65) Prior Publication Data
US 2025/0145604 A1    May 8, 2025

Related U.S. Application Data

(63) Continuation of application No. 18/723,237, filed as application No. PCT/EP2022/087613 on Dec. 22, 2022.

(30) Foreign Application Priority Data

Dec. 22, 2021 (EP) .................. 21217181
Dec. 22, 2021 (EP) .................. 21217182

(51) Int. Cl.
| | | |
|---|---|---|
| *A61K 31/517* | (2006.01) | |
| *A61K 31/519* | (2006.01) | |
| *A61K 31/5377* | (2006.01) | |
| *C07D 239/72* | (2006.01) | |
| *C07D 409/12* | (2006.01) | |
| *C07D 413/14* | (2006.01) | |
| *C07D 471/04* | (2006.01) | |
| *C07D 487/04* | (2006.01) | |

(52) U.S. Cl.
CPC .......... *C07D 413/14* (2013.01); *A61K 31/517* (2013.01); *A61K 31/519* (2013.01); *A61K 31/5377* (2013.01); *C07D 409/12* (2013.01); *C07D 471/04* (2013.01); *C07D 487/04* (2013.01)

(58) Field of Classification Search
CPC ........................... A61K 31/517; C07D 239/72
USPC ........................... 514/258.1; 544/253
See application file for complete search history.

(56) References Cited

U.S. PATENT DOCUMENTS

| | | |
|---|---|---|
| 2009/0023798 A1 | 1/2009 | Magda et al. |
| 2010/0009990 A1 | 1/2010 | Venkataramani |
| 2021/0261523 A1 | 8/2021 | Grindrod et al. |
| 2022/0040189 A1 | 2/2022 | Lengacher et al. |
| 2022/0348551 A9 | 11/2022 | Grindrod et al. |

FOREIGN PATENT DOCUMENTS

| | | |
|---|---|---|
| EP | 3 854 401 A1 | 7/2021 |
| EP | 4 111 863 A1 | 1/2023 |
| WO | WO 02/051831 A1 | 7/2002 |
| WO | WO 2005/014588 A1 | 2/2005 |
| WO | WO 2010/010380 A1 | 1/2010 |
| WO | WO 2011/106627 A1 | 9/2011 |
| WO | WO 2011/147813 A1 | 12/2011 |
| WO | WO 2012/045804 A1 | 4/2012 |
| WO | WO 2014/131855 A1 | 9/2014 |
| WO | WO 2017/053360 A1 | 3/2017 |
| WO | WO 2021/133957 A1 | 7/2021 |
| WO | WO-2023118507 A2 * | 6/2023 ........... A61K 31/437 |

(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*
"Compound Summary: N-[[5-[2-(1-methylpyrazolo[3,4-d]pyrimidin-4-yl)sulfanylacetyl]thiophen-2-yl]methyl]acetanide", Database accession No. 29743592, XP002808701, Publication date May 28, 2009, Total 8 pages.
"Compound Summary: N-[[5-[2-[2-(trifluoromethyl)quinazolin-4-yl]sulfanylacetyl]thiophen-2-yl]methyl]acetamide", Database accession No. 32278705 XP002808697, Publication date May 29, 2009, Total 9 pages.

(Continued)

*Primary Examiner* — Douglas M Willis
(74) *Attorney, Agent, or Firm* — Birch, Stewart, Kolasch & Birch, LLP

(57) ABSTRACT

The present invention relates to a compound of formula (I)

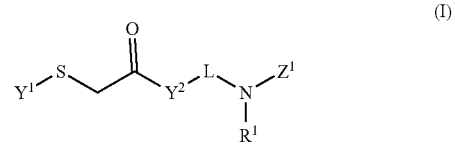

or a pharmaceutically acceptable salt and/or solvate thereof, wherein $Y^1$ is a 9- or 10-membered bicyclic heteroaryl, $Y^2$ is a 5-membered heteroaryl, $Z^1$ is selected from (C=O)—$R^9$, S(O)—$R^9$ and S(O$_2$)—$R^9$, L is an alkyl-, cycloalkyl- or heterocycloalkyl-based linker, and $R^1$ and $R^9$ may be various groups.
The present invention further relates to a compound of formula (I) as HDAC6 inhibitor, typically for use in the treatment and/or prevention of an HDAC6-associated disease, such as cancers, neurodegenerative diseases, neuropathies or cardiovascular diseases.

29 Claims, No Drawings

(56) References Cited

FOREIGN PATENT DOCUMENTS

WO     WO 2024/081587 A1     4/2024

OTHER PUBLICATIONS

"Compound Summary: N-[2-[5-[2-(2-cyclopropylquinazolin-4-yl)sulfanylacetyl]thiophen-2-yl]ethyl]acetamide", Database accession No. 24579390 XP002808699 Publication date Feb. 29, 2008 Total 8 pages.

"Compound Summary: N-[2-[5-[2-[(5-methyl-[1,3]oxazolo[4,5-b]pyridin-2-yl)sulfanyl]acetyl]thiophen-2-yl]ethyl]acetamide", Database accession No. 146132217, XP002808702. Publication date Jun. 5, 2020, Total 7 pages.

"Substance Record: Z166131206", Database accession No. 334588857, XP002808698, Publication date Apr. 25, 2017, Total 6 pages.

"Substance Record: Z227420638", Database accession No. 333973231, XP002808700, Publication date Apr. 25, 2017, Total 6 pages.

Abulwerdi, et al. "3-Substituted-N-(4-Hydroxynaphthalen-1-yl)arylsulfonamides as a Novel Class of Selective Mcl-1 Inhibitors: Structure-Based Design, Synthesis, SAR, and Biological Evaluation", Journal of Med. Chem. May 22, 2014; vol. 57, No. 10, pp. 4111-4133.

Bae et al., "CKD-506: A novel HDAC6-selective inhibitor that exerts therapeutic effects in a rodent model of multiple sclerosis", Nature Portfolio, Scientific Reports, 2021, vol. 11, No. 14466, pp. 1-16.

Bang et al., "A Linker for the Solid-Phase Synthesis of Hydroxamic Acids and Identification of HDAC6 Inhibitors," ACS Combinatorial Science, vol. 19, 2017, pp. 657-669.

Çakir et al., "Histone Deacetylase 6 Inhibition Restores Leptin Sensitivity and Reduces Obesity", Nat Metab, 2022, vol. 4, No. 1, pp. 44-59, pp. 1-51.

Colvin, "Chemotherapy-induced peripheral neuropathy (CIPN): where are we now?", Pain, PMC 2020, 160 (Suppl 1), S1-S10, pp. 1-22.

He et al., "Discovery of Highly Potent Microsomal Prostaglandin E2 Synthase 1 Inhibitors Using the Active Conformation Structural Model and Virtual Screen", Journal of Medicinal Chemistry, Apr. 25, 2013, vol. 56, No. 8, , pp. 3296-3309.

International Search Report (PCT/ISA/210) issued in PCT/EP2022/087613, dated Jun. 27, 2023.

Kishore et al., "Prevention of Atrial Fibrillation: Putting Proteostasis Derailment Back on Track", Journal of Clinical Medicine, 2023, vol. 12, No. 4352, pp. 1-15.

Li et al., "A novel HDAC6 inhibitor, CKD-504, is effective in treating preclinical models of huntington's disease", BMB Reports, 2023, vol. 56, No. 3, pp. 178-183.

Mead et al., "Amyotrophic lateral sclerosis: a neurodegenerative disorder poised for successful therapeutic translation", Nature Reviews Drug Discovery, Mar. 2023, vol. 22, pp. 185-212.

Paris, et al., "Histone Deacetylase Inhibitors: From Bench to Clinic", Journal of Medicinal Chemistry 2008, vol. 51, No. 6, pp. 1505-1529.

Rabal et al., "Design, synthesis, biological evaluation and in vivo testing of dual phosphodiesterase 5 (PDE5) and histone deacetylase 6 (HDAC6)-selective inhibitors for the treatment of Alzheimer's disease," European Journal of Medicinal Chemistry, vol. 150, 2018, pp. 506-524.

Ranjbarvaziri et al., "Targeting HDAC6 to treat heart failure with preserved ejection fraction in mice", Nature Communications, 2024, vol. 15, No. 1352, pp. 1-17.

Tarver Jr. et al., "Stimulation of cortical bone formation with thienopyrimidine based inhibitors of Notum Pectinacetylesterase", Bioorg Med Chem Lett., Mar. 15, 2016, vol. 26, No. 6, pp. 1525-1528.

Valente et al., "Small-molecule inhibitors of histone deacetylase for the treatment of cancer and non-cancer diseases: a patent review (2011-2013)", Expert Opinion Ther Pat., Apr. 2014, vol. 24, No. 4, pp. 401-415.

Written Opinion (PCT/ISA/237) issued in PCT/EP2022/087613, dated Jun. 27, 2023.

Yu et al., "Quinazolin-2,4-dione-Based Hydroxamic Acids as Selective Histone Deacetylase-6 Inhibitors for Treatment of Non-Small Cell Lung Cancer," Journal of Medicinal Chemistry, vol. 62, 2019, pp. 857-874.

Zhan et al., "Medicinal Chemistry Insights into Novel HDAC Inhibitors: An Updated Patent Review (2012-2016)", Recent Pat Anticancer Drug Discov. 2017; vol. 12, No. 1:16-34, pp. 1-19.

CAS Registry No. 941067-31-8, Database Registry [online], retrieved from STN, XP093231051, Jul. 4, 2007.

CAS Registry No. 949216-14-2, Database Registry [online], retrieved from STn, XP093231057, Oct. 5, 2007.

* cited by examiner

SUBSTITUTED QUINAZOLINES AS HDAC6 INHIBITORS

CROSS-REFERENCE TO RELATED APPLICATIONS

This application is a Continuation of copending application Ser. No. 18/723,237, filed on Jun. 21, 2024, which is a National Phase of PCT International Application No. PCT/EP2022/087613, filed on Dec. 22, 2022, which claims the benefit under 35 U.S.C. § 119(a) to Application No. 21217182.1, filed in Europe on Dec. 22, 2021, and Application No. 21217181.3, filed in Europe on Dec. 22, 2021, all of which are hereby expressly incorporated by reference into the present application.

FIELD OF INVENTION

The present invention relates to compounds useful as Histone Deacetylase subtype 6 (HDAC6) inhibitors. In particular, the present invention relates to compounds for use in the treatment and/or the prevention of proliferative diseases such as cancers, neurodegenerative diseases, neuropathies or cardiovascular diseases.

BACKGROUND OF INVENTION

Inhibition of the enzymes of the HDAC class, especially HDAC6 enzyme, plays a critical role in gene expression in humans. Thus, the development of potent HDAC inhibitors is of upmost clinical importance in severe medical conditions, including both major and rare diseases (Seidel C et al.: "Histone deacetylase 6 in health and disease." Epigenomics. 2015, Vol. 7, No. 1, pp. 103-18). HDAC6 inhibitors are expected to be useful for example in oncology, neurology, neuropsychiatry, neurodegeneration, inflammation (e.g., neuroinflammation), nephropathy, neuropathy and pain. Significant examples of HDAC6 inhibitors with potential medical applications in the treatment of proliferative diseases are drugs of the hydroxamate class (hydroxamic acid and salts thereof), which include vorinostat (or "SAHA", trade name Zolinza®), Trichostatin A (TSA), belinostat (trade name Beleodaq®), panobinostat (Farydak®) or romidepsin (Istodax®).

However, many HDAC6 inhibitors identified so far are not highly selective, so that they may cause significant side-effects. Poor pharmacokinetics and low bioavailability also limit the potency of some HDAC6 inhibitors. Thus, most of the HDAC6 inhibitors have a poor developability profile, even for life-threatening applications in oncology. For example, high doses of non-selective HDAC inhibitors are responsible of fatigue and nausea. Side-effects may be in particular be caused by the inhibition of class I HDACs. In addition, mutagenicity issues related to the hydroxamate function in approved HDAC inhibitors has been reported (Shen S. and Kozikowski A. P. ChemMedChem 2016, No. 11, pp. 15-21).

Therefore, there is an urgent need to develop highly selective HDAC6 inhibitors overcoming the limitations of some of the state-of-the-art HDCA6 inhibitors, such as hydroxamic acid-based HDCA6 inhibitors. Isoform-selective inhibitors over pan-HDAC are potentially advantageous both in terms of therapeutic efficacy and toxicity. In particular, selective inhibition of cytoplasmic HDAC6 may avoid toxicity resulting from inhibition of other HDACs.

The Applicant surprisingly found out that compounds of formula (I) as described herein were highly selective HDAC6 inhibitors. The use of these compounds may also represent significant improvements in terms of bioavailability, side-effects, pharmacokinetics and/or water-solubility over prior art drugs such as hydroxamates.

SUMMARY

This invention relates to a compound for use in the treatment and/or the prevention of an HDAC6-associated disease; wherein said compound is a compound of formula (I)

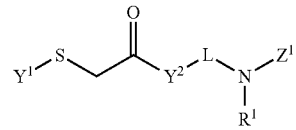

or a pharmaceutically acceptable salt and/or solvate thereof; wherein $Y^1$, $Y^2$, L, $R^1$ and $Z^1$ are as described in the claims or the detailed description.

This invention also relates to a pharmaceutical composition for use in the treatment and/or the prevention of an HDAC6-associated disease, wherein said pharmaceutical composition comprises a compound according to the invention and at least one pharmaceutically acceptable carrier.

According to one embodiment, the HDAC6-associated disease is selected from inflammatory diseases, autoimmune diseases, proliferative diseases such as cancers, neurodegenerative diseases, pains, neuropathies, psychiatric diseases, neurodevelopmental disorders, sleep disorders and cardiovascular diseases. In one embodiment, the HDAC6-associated disease is a cancer selected from malignant melanoma, multiple myeloma, leukemia, lymphoma, breast cancer and Hodgkin's disease. In one embodiment, the HDAC6-associated disease is a neurodegenerative disease selected from Alzheimer's disease, Parkinson's disease, Huntington's disease, frontotemporal dementia, Pick's disease, Niemann-Pick syndrome, Down's disease, Lewy body dementia, HIV dementia, amyotrophic lateral sclerosis (ALS) and multiple sclerosis. In one embodiment, the HDAC6-associated disease is a neuropathy selected from Guillain-Barre syndrome, chronic inflammatory demyelinating polyneuropathy (CIDP), multifocal motor neuropathy (MMN), Charcot-Marie-Tooth disease, hereditary sensory and autonomic neuropathy, familial amyloidotic polyneuropathy, chemotherapy-induced peripheral neuropathy (CIPN) using chemotherapeutic anticancer agents, diabetic peripheral neuropathy (DPN), neuralgia, pain and/or neuropathic pain. In one embodiment, the HDAC6-associated disease is a cardiovascular disease selected from heart failure, cardiomyopathy and/or myocarditis.

According to one embodiment, the compound is selected from the compounds listed in Table 2 herein, and pharmaceutically acceptable salts and/or solvates thereof.

This invention also relates to a compound of formula (I)

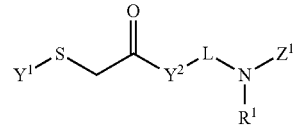

or a pharmaceutically acceptable salt and/or solvate thereof; wherein $Y^1$, $Y^2$, L, $R^1$ and $Z^1$ are as described in the claims or the detailed description.

According to one embodiment, the compound is selected from the compounds listed in Table 1 herein, and pharmaceutically acceptable salts and/or solvates thereof.

This invention also relates to a process for manufacturing a compound according to the invention, wherein the process comprises a step of reacting: (i) a linear or cyclic amine with an acyl chloride, a carboxylic acid or sulfonyl chloride; or (ii) a halo-ketone with a thiol.

This invention also relates to a pharmaceutical composition comprising a compound according to the invention and at least one pharmaceutically acceptable carrier.

This invention also relates to a compound according to the invention or a pharmaceutical composition according to the invention for use as a medicament. According to one embodiment, the compound or pharmaceutical composition is for use in the treatment and/or the prevention of an HDAC6-associated disease. In one embodiment, the HDAC6-associated disease is selected from inflammatory diseases, autoimmune diseases, proliferative diseases such as cancers, neurodegenerative diseases, pains, neuropathies, psychiatric diseases, neurodevelopmental disorders, sleep disorders and cardiovascular diseases.

Definitions

In the present invention, the following terms have the following meanings, unless indicated otherwise.

Chemical Definitions

When referring to combination of groups, such as, for example, "alkylene-heteroaryl", the point of attachment to the main structure is on the group cited on the left. Thus, the term "alkylene-cyclyl" and variants thereof (e.g., "alkylene-heteroaryl", "alkylene-heterocycle", "alkylene-cycloalkyl", "alkylene-aryl", "alkylene-heteroaryl", "alkylene-heterocycle" and "alkylene-cycloalkyl") refers to a cyclyl group that is attached via an alkyl moiety to the main structure. In other words, the point of attachment is the alkylene group, and not the cyclyl group.

"Alkene" or "alkenyl" refer to a linear or branched hydrocarbon chain comprising at least one double bond and typically from 2 to 12 carbon atoms, preferably 3 to 6 carbon atoms. Non-limiting examples of alkenyl groups include ethynyl, 2-propenyl, 2-butenyl, 3-butenyl, 2-pentenyl and its isomers, 2-hexenyl and its isomers and 2,4-pentadienyl.

"Alkyl" refers to a saturated linear or branched hydrocarbon chain, typically comprising from 1 to 12 carbon atoms, preferably from 1 to 6 carbon atoms, more preferably from 1 to 3 carbon atoms. In the present invention, alkyl groups may be monovalent or polyvalent (i.e., "alkylene" groups as defined herein are encompassed in "alkyl" definition) but alkyl groups are typically monovalent. Non-limiting examples of alkyl groups include methyl, ethyl, n-propyl, i-propyl, n-butyl, i-butyl, s-butyl and t-butyl, pentyl and its isomers (e.g., n-pentyl, iso-pentyl), and hexyl and its isomers (e.g., n-hexyl, iso-hexyl). Preferred alkyl groups include methyl, ethyl, n-propyl, i-propyl, n-butyl, s-butyl and t-butyl.

"Alkylene" refers to a divalent alkyl group. Non-limiting examples of alkylene groups include methylene, ethylene, n-propylene, i-propylene, divalent butyl, divalent pentyl and divalent hexyl. Preferred alkylene groups include methylene, ethylene, n-propylene, n-butylene and n-butylene.

"Alkyne" or "alkynyl" refer to a linear or branched hydrocarbon chain comprising at least one triple bond and typically from 2 to 12 carbon atoms, preferably 3 to 6 carbon atoms. Non-limiting examples of alkynyl groups include ethynyl, 2-propynyl, 2-butynyl, 3-butynyl, 2-pentynyl and its isomers, and 2-hexynyl and its isomers.

"Amine" refers to derivatives of ammonia ($NH_3$), wherein one or more hydrogen atoms have been replaced by a substituent such as, for example, alkyl or aryl.

"Amino" refers to the —$NH_2$ group.

"Aryl" refers to a cyclic, polyunsaturated, aromatic hydrocarbyl group comprising at least one aromatic ring. Aryl groups may have a single ring (i.e., phenyl) or multiple aromatic rings fused together (e.g., naphthyl) or linked covalently. Typically, aryl groups have from 5 to 12 carbon atoms, preferably from 6 to 10 carbon atoms. The aromatic ring may optionally include one to two additional rings (either cycloalkyl, heterocycloalkyl or heteroaryl) fused thereto. Aryl is also intended to include the partially hydrogenated derivatives of the carbocyclic systems enumerated herein, as long as at least one ring is aromatic. Non-limiting examples of aryl groups include phenyl, biphenyl, biphenylenyl, 5- or 6-tetralinyl, naphthalen-1- or -2-yl, 4-, 5-, 6 or 7-indenyl, 1-2-, 3-, 4- or 5-acenaphthylenyl, 3-, 4- or 5-acenaphthenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl. A preferred aryl group is phenyl.

"Bicyclic", when referring to a cyclic group, means that the cyclic group consists of exactly two fused rings. In monovalent bicyclic groups, the notation "[x, y]" wherein x and y are integers is used herein to indicated that one cycle is x-membered and the other cycle is y-membered and that the point of attachment to the main structure is located on the x-membered cycle. "Tricyclic" and the like should be construed accordingly.

"Cyano" refers to the —CN group.

"Cyclyl" collectively refers to "cycloalkyl", "heterocycloalkyl", "aryl" and "heteroaryl" groups as defined herein.

"Cycloalkyl" refers to a cyclic monovalent alkyl, typically comprising from 3 to 11 carbon atoms, preferably from 4 to 9 carbon atoms, more preferably from 5 to 7 carbon atoms. This definition encompasses polycyclic cycloalkyls (e.g., bicycles) and bridged cycloalkyl structures.

"$(C_x-C_y)$" preceding the name of a group means that the group comprises from x to y carbon atoms, in accordance with common terminology in the chemistry field.

"Difluoromethyl" refers to the —$CHF_2$ group.

"Halide", "halo" or "halogen" refers to a fluorine, chlorine, bromine or iodine atom, typically a chlorine or bromine atom.

"Heteroalkyl" refers to an alkyl group as defined hereinabove wherein one or more carbon atoms are replaced by a heteroatom selected from oxygen, nitrogen and sulfur. In heteroalkyl groups, the heteroatoms are bound along the alkyl chain only to carbon atoms, i.e., each heteroatom is separated from any other heteroatom by at least one carbon atom. The nitrogen and sulfur heteroatoms may optionally be oxidized and the nitrogen heteroatoms may optionally be quaternized. Heteroalkyl groups may further include one or more oxo (=O) groups. A heteroalkyl is bound to another group or molecule only through a carbon atom, i.e., the binding atom is not selected among the heteroatoms included in the heteroalkyl group. When substituted by one or more other group(s), an heteroalkyl may be substituted either through a carbon atom or through a heteroatom (e.g., nitrogen), unless otherwise specified. Non-limiting examples of heteroalkyl include alkoxy, ethers and polyethers, secondary amines, tertiary amines and thioethers.

"Heteroaryl" refers to aromatic rings or aromatic ring systems comprising from 5 to 12 carbon atoms, preferably from 6 to 10 carbon atoms, having one or two rings which are fused together or linked covalently, wherein at least one ring is aromatic, and wherein one or more carbon atoms in one or more of these rings is replaced by oxygen, nitrogen and/or sulfur atoms. "Heteroaryl" may also be viewed as an "aryl" group as defined herein, wherein at least one carbon atom in the aryl group is replaced with a heteroatom and wherein the resulting molecule is chemically stable. The nitrogen and sulfur heteroatoms may optionally be oxidized and the nitrogen heteroatoms may optionally be quaternized. Non-limiting examples of heteroaryl groups include furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1-(6H)-yl, 2-oxopyridin-1-(2H)-yl, 6-oxo-pyridazin-1-(6H)-yl, 2-oxopyridin-1-(2H)-yl, 1,3-benzodioxolyl, quinolinyl, isoquinolinyl, cinnolinyl, quinazolinyl, quinoxalinyl and phthalazinyl.

"Heterocycloalkyl" refers to a cyclic monovalent heteroalkyl, typically comprising from 2 to 7 carbon atoms, preferably from 3 to 6 carbon atoms, more preferably from 4 to 5 carbon atoms. This definition encompasses polycyclic heterocycloalkyls (e.g., bicycles) and bridged heterocycloalkyl structures, including cycles bound together through one atom ("spiro") or through two atoms. In one embodiment, the heterocycloalkyl is bound to another group or molecule through a carbon atom, i.e., the binding atom is not selected among the heteroatoms included therein. In one embodiment, the heterocycloalkyl is bound to another group or molecule through one of the heteroatoms included therein. When substituted by one or more other group(s), an heterocycloalkyl may be substituted either through a carbon atom or through a heteroatom (e.g., nitrogen), unless otherwise specified. Non-limiting examples of heterocycloalkyl include aziridine, pyrrolidine, piperidine, piperazine (also known as "hexahydropyrazine"), morpholine, thiomorpholine, azepane, azocane, octahydro-1H-isoindole, decahydroisoquinoline, tetrahydrofuran, tetrahydropyran, tetrahydroisoquinoline (e.g., 1,2,3,4-tetrahydroisoquiline), hexahydropyridazine, hexahydropyrimidine, decahydroquinoline, octahydropyrrolo[3,4-c]pyrrole, isoindoline, 1,2,3,4-tetrahydroquinoline and oxetane.

"Hydroxy" refers to the —OH group.

"Ketone" refers to a functional group with the connectivity C—(C=O)—C.

"Oxo" refers to the =O group, i.e., one oxygen atom which is double-bonded, typically to a carbon atom.

"Trifluoromethyl" refers to the —CF$_3$ group.

General Definitions

"About" is used herein to mean approximately, roughly, around, or in the region of. The term "about" preceding a figure means plus or less 10% of the value of the figure. When the term "about" is used in conjunction with a numerical range, it modifies that range by extending the boundaries above and below the numerical values set forth by 10%.

"Administration", or a variant thereof (e.g., "administering"), means providing a therapeutic agent (e.g., a compound of the invention) alone or as part of a pharmaceutically acceptable composition, to the patient in whom/which the condition, symptom, or disease is to be treated and/or prevented.

"Binding site" or "binding pocket" refers to a specific arrangement of amino acids located on a protein (e.g., on HDAC6) to which a compound (e.g., the compounds of the present invention) bind. Binding sites often consist of a chemically-active surface grouping of amino acids, and have specific 3-D structural characteristics as well as specific charge characteristics. Similarly to epitopes, binding sites can be linear or conformational, i.e., they can involve sequences of amino acids which are not necessarily contiguous in the primary structure of the protein.

"Comprise" or a variant thereof (e.g., "comprises", "comprising") is used herein according to common patent application drafting terminology. Hence, "comprise" preceded by an object and followed by a constituent means that the presence of a constituent in the object is required (typically as a component of a composition), but without excluding the presence of any further constituent(s) in the object. Moreover, any occurrence of "comprise" or a variant thereof herein also encompasses narrower expression "substantially consist of" or "consists essentially of", further narrower expression "consist of" and any variants thereof (e.g., "consists of", "consisting of").

"HDAC" or "Histone Deacetylase" refers to a class of enzymes that are able to remove acetyl groups (O=C—CH$_3$) from an ε-N-acetyl lysine amino acid on a histone, allowing the histones to wrap the DNA more tightly and condensate the chromatin. Gene expression is regulated by histone acetylation and de-acetylation, and thus by HDAC activity. In the invention, HDAC is typically "HDAC6" as defined herein.

"HDAC-associated disease" or "disease related to HDAC6 function" or a variant thereof (e.g., "HDAC6-associated disease") refers to a disease that it due to, caused by, or characterized by, the dysregulation and in particular the increase of activity of a least one HDAC enzyme in a subject, resulting in an abnormal acetylation profile of HDAC substrates (e.g., histones, tubulin, Hsp90, cortactin). In the present application, "HDAC-associated disease" and "disease related to HDAC6 function" are synonyms and may be used interchangeably. Typically, HDAC-associated diseases are associated with, inter alia, altered epigenetic regulation of gene expression and/or cell motility. This definition encompasses diseases wherein reducing (inhibiting) normal HDAC activity treat and/or prevent the diseases. Typically, an HDAC-associated disease may be prevented and/or treated by means of HDAC inhibition. Non-limitative examples of HDAC-associated diseases include neuropathies, neurodegenerative diseases, proliferative diseases (e.g., cancer), metabolic disorders, immune disorders and inflammatory diseases.

"HDAC6", "HDAC6 enzyme" or "Histone Deacetylase subtype 6" refers to a HDAC enzyme that is encoded by the HDAC6 gene in humans.

"HDAC6 gene" refers to the gene coding for HDAC6 in humans. HDAC6 gene is also interchangeably referred to as KIAA0901 or JM21.

"Human" refers to a male or female subject at any stage of development, including neonate, infant, juvenile, adolescent and adult.

"Patient" refers to an animal, typically a warm-blooded animal, preferably a mammal (e.g., mouse, rat, cat, guinea-pig, dog, monkey or human), more preferably a human, who/which is awaiting the receipt of, or is receiving medical care, or is/will be the object of a medical procedure. A patient may also be the subject of preventive care or procedure.

"Pharmaceutically acceptable" means that the ingredients of a composition are compatible with each other and not deleterious to the patient to which/whom it is administered.

"Pharmaceutically acceptable carrier" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, e.g., FDA Office or EMA.

"Prevent", "preventing" and "prevention" refer to delaying or precluding the onset of a condition and/or disease and/or any one of its attendant symptoms, barring a patient from acquiring a condition or disease, or reducing the risk for a patient of acquiring a condition and/or disease and/or any one of its attendant symptoms. The effect resulting from "preventing" a condition and/or disease is called "prophylactic".

"Prodrug" refers to a pharmacologically acceptable derivative of a therapeutic agent (e.g., a compound of the invention) whose in vivo biotransformation product is the therapeutic agent (active drug). Prodrugs are typically characterized by increased bioavailability and are readily metabolized in vivo into the active compounds. Non-limiting examples of prodrugs include amide prodrugs and carboxylic acid ester prodrugs, in particular alkyl esters, cycloalkyl esters and aryl esters.

"Selected from" is used herein according to common patent application drafting terminology, to introduce a list of elements among which an item is selected. Any occurrence of "selected from" in the specification may be replaced by "selected from the group comprising or consisting of" and reciprocally without changing the meaning thereof.

"Solvate" refers to molecular complex comprising a compound along with stoichiometric or sub-stoichiometric amounts of one or more molecules of one or more solvents, typically the solvent is a pharmaceutically acceptable solvent such as, for example, ethanol. The term "hydrate" refers to a solvate when the solvent is water ($H_2O$).

"Therapeutic agent", "active pharmaceutical ingredient" and "active ingredient" refer to a compound for therapeutic use and relating to health. Especially, a therapeutic agent (e.g., a compound of the invention) may be indicated for treating and/or preventing a disease, preferably an infectious disease. An active ingredient may also be indicated for improving the therapeutic activity of another therapeutic agent.

"Therapeutically effective amount" (in short "effective amount") refers to the amount of a therapeutic agent (e.g., a compound of the invention) that is sufficient to achieve the desired therapeutic or prophylactic effect in the patient to which/whom it is administered.

"Treat", "treating" and "treatment" refer to alleviating, attenuating or abrogating a condition and/or disease and/or any one of its attendant symptoms, e.g., an infectious disease.

DETAILED DESCRIPTION

Compounds

This invention relates to a compound of formula (I)

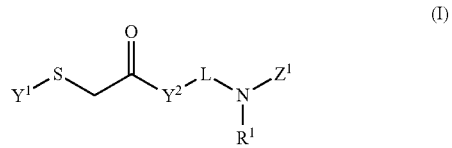

wherein Y, $Y^2$, L, $R^1$ and $Z^1$ are defined hereinafter in the detailed description.

In the compounds of formula (I) as described hereinafter in the detailed description, unless otherwise indicated, any alkyl group (which encompass alkylene group) may be "optionally substituted", i.e., each hydrogen atom bound to a carbon atom in the alkyl moiety can optionally be replaced by at least one low-molecular weight substituent such as, for example, a substituent selected from halogen, cyano, hydroxy, oxo, amino, —O—($C_1$-$C_6$) alkyl, —NH—($C_1$-$C_6$) alkyl and —N—(($C_1$-$C_6$) alkyl)$_2$. Only substitutions wherein the resulting molecule is chemically stable are encompassed by this definition. Typically, the ($C_1$-$C_6$) alkyl group(s) present in the substituents are not themselves further substituted. Preferred substituted alkyls include alkyls substituted by one or more fluorine atom(s) and/or hydroxy such as, for example, trifluoromethyl.

In the compounds of formula (I) as described hereinafter in the detailed description, unless otherwise indicated, any cyclyl group (i.e., cycloalkyl, heterocycloalkyl, aryl or heteroaryl group) may be "optionally substituted", i.e., each hydrogen atom bound to a carbon atom in the cyclyl moiety can optionally be replaced by at least one low-molecular weight substituent such as, for example, a group selected from halogen, cyano, hydroxy, oxo, amino, —($C_1$-$C_6$) alkyl, —$CH_2$—O—($C_1$-$C_6$) alkyl, —$CH_2$—NH—($C_1$-$C_6$) alkyl, —$CH_2$—N—(($C_1$-$C_6$) alkyl)$_2$, —O—($C_1$-$C_6$) alkyl, —NH—($C_1$-$C_6$) alkyl and —N—(($C_1$-$C_6$) alkyl)$_2$. Only substitutions wherein the resulting molecule is chemically stable are encompassed by this definition. Typically, the ($C_1$-$C_6$) alkyl group(s) present in the substituents are not themselves further substituted. Preferred substituted cyclyl groups include cyclyl substituted by substituted by one or more fluorine atom(s) and/or hydroxy such as, for example, difluorocyclopropyl.

In the formulae represented herein, the dotted line ---- represents the point of attachment of the depicted moiety to the main molecular structure.

$Y^1$ Definitions

In formula (I) above, $Y^1$ is a bicyclic heteroaryl. According to one embodiment, $Y^1$ is a 9- to 11-membered bicyclic heteroaryl. According to one embodiment, $Y^1$ is a 9- or 10-membered bicyclic heteroaryl. According to one embodiment, $Y^1$ comprises two fused rings selected from 5-membered heteroaryls and 6-membered heteroaryls.

According to one embodiment, $Y^1$ comprises two fused rings, said rings consisting of:

a first 5- or 6-membered heteroaryl ring selected from:
formula (Y$^1$-0-1-A-a)

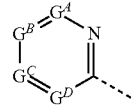
(Y$^1$-0-1-A-a)

wherein G$^A$ is selected from C—R$^2$ and N, G$^B$ is selected from C—R$^3$ and N, and G$^C$ and G$^D$ are independently selected from C—R$^2$, C—R$^3$ and N (wherein R$^2$ and R$^3$ are independently as defined hereinbelow), and
formula (Y$^1$-0-1-A-b)

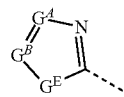
(Y$^1$-0-1-A-a)

wherein G$^A$ and G$^B$ are independently selected from C—R$^2$, C—R$^3$ and N, and G$^E$ is selected from O, S and N—R$^4$, in particular from O and N—R$^4$ (wherein R$^2$, R$^3$ and R$^4$ are independently as defined hereinbelow), and
a second ring selected from 5-membered heteroaryl, 6-membered heteroaryl and aryl, wherein the second ring is fused with G$^A$ and G$^B$, G$^B$ and G$^C$, G$^C$ and G$^D$, or G$^B$ and G$^E$ of the first ring, to form the 5-membered heteroaryl, 6-membered heteroaryl or aryl.

According to one embodiment, Y$^1$ is a 9- or 10-membered bicyclic heteroaryl selected from the following group of formulae (Y$^1$—I)

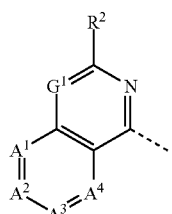
(Sc1)

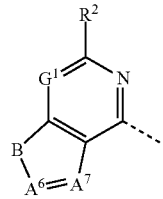
(Sc2)

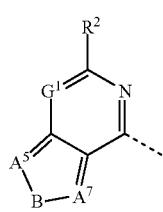
(Sc3)

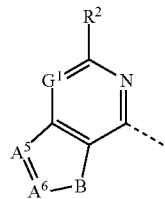
(Sc4)

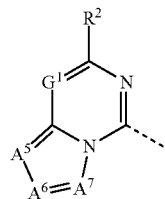
(Sc5)

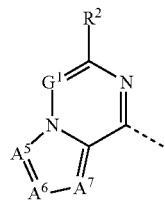
(Sc6)

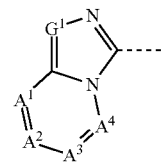
(Sc7)

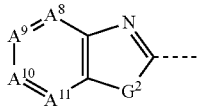
(Sc8)

wherein A$^1$, A$^2$, A$^3$, A$^4$, A$^5$, A$^6$ and A$^7$ are each independently selected from C—R$^7$ and N; A$^1$, A$^9$, A$^{10}$ and A$^{11}$ are each independently selected from C—R$^7$ and N; G$^1$ is selected from C—R$^3$ and N; G$^2$ is selected from O and N—R$^4$; and B is selected from O, S and N—R$^5$. "(ScX)" means "(Scaffold n° X)".

According to one embodiment, Y$^1$ is a 9- or 10-membered bicyclic heteroaryl selected from the following group of formulae (Y$^1$—I')

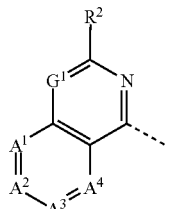
(Sc1)

(Sc2)
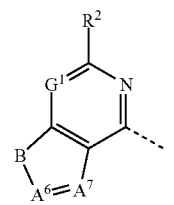

(Sc3)
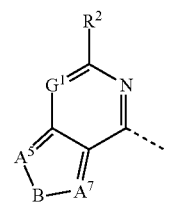

(Sc4)
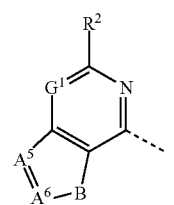

(Sc5)
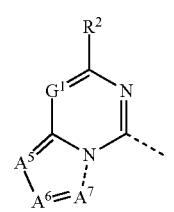

(Sc6)
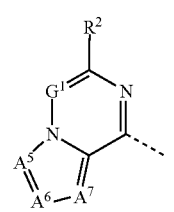

(Sc8)
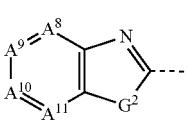

(Sc9)
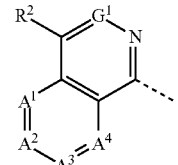

(Sc10)
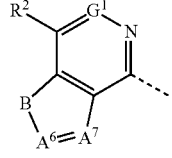

(Sc11)
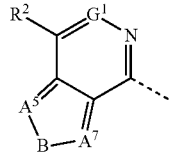

(Sc12)
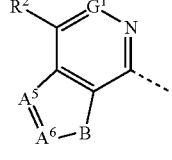

(Sc13)
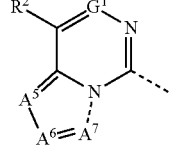

(Sc14)
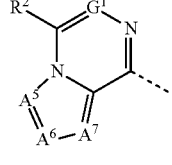

wherein $A^1$, $A^2$, $A^3$, $A^4$, $A^5$, $A^6$ and $A^7$ are each independently selected from C—$R^7$ and N; $A^1$, $A^1$, $A^{10}$ and $A^{11}$ are each independently selected from C—$R^7$ and N; $G^1$ is selected from C—$R^3$ and N; $G^2$ is selected from O and N—$R^4$; and B is selected from O, S and N—$R^5$. "(ScX)" means "(Scaffold n° X)".

According to one embodiment, $Y^1$ is a 9- or 10-membered bicyclic heteroaryl selected from the following group of formulae ($Y^1$-Ia)

wherein $A^1$, $A^2$, $A^3$, $A^4$, $A^5$, $A^6$ and $A^7$ are each independently selected from C—$R^7$ and N; $A^1$, $A^9$, $A^{10}$ and $A^{11}$ are each independently selected from C—$R^7$ and N; $G^1$ is selected from C—$R^3$ and N; and B is selected from O, S and N—$R^5$. "(ScX)" means "(Scaffold n° X)".

In one embodiment, when $A^1$, $A^9$, $A^{10}$ and $A^{11}$ are present, at least one of $A^1$, $A^9$, $A^{10}$ or $A^{11}$ is N. In one embodiment when $A^5$ and $A^6$ are present, when $A^5$ and $A^6$ are C—$R^7$, then B is not S. In one embodiment when $A^5$, $A^6$ and $A^7$ are present, when $A^5$, $A^6$ and $A^7$ are C—$R^7$, then B is not S. In one embodiment, $G^1$ is N.

According to one embodiment, $Y^1$ is a 9- or 10-membered bicyclic heteroaryl selected from the following group of formulae ($Y^1$—I-1)

(Sc1)

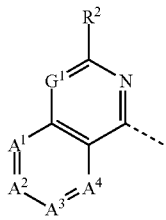

(Sc2)

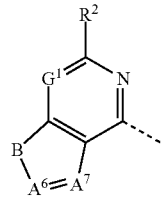

wherein $A^1$-$A^4$, $A^6$, $A^7$, $G^1$ and $R^2$ are independently as defined herein.

According to one embodiment, $Y^1$ is a 9-membered bicyclic heteroaryl selected from the following group of formulae ($Y^1$—I-2)

(Sc7)

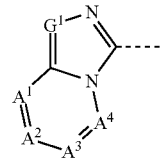

(Sc8)

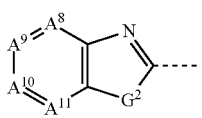

wherein $A^1$-$A^4$, $A^1$-$A^{11}$, $G^1$ and $G^2$ are independently as defined herein.

According to one embodiment, $Y^1$ is a 9-membered bicyclic heteroaryl of formula ($Y^1$-0-2)

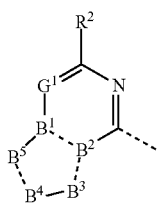

Wherein $G^1$ is selected from C—$R^3$ and N, $B^1$-$B^5$ are selected from O, S, and any one of $A^5$, $A^6$ or $A^7$ as defined herein; and $B^1$-$B^5$ form together a 5-membered heteroaryl, i.e., the bonds between $B^1$-$B^5$ are so arranged that the cycle is aromatic and at least one among $B^1$-$B^5$ is selected from O, S and N—$R^5$.

According to one embodiment, $Y^1$ is a 10-membered bicyclic heteroaryl of formulae ($Y^1$-Ia-1)

(Sc9)

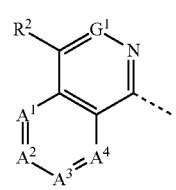

wherein $A^1$-$A^4$, $G^1$ and $R^2$ are independently as defined herein.

In $Y^1$ as defined herein, $R^2$ is selected from hydrogen, halogen, cyano, amino, hydroxy, —($C_1$-$C_6$) alkyl, —($C_3$-$C_7$) cycloalkyl, —($C_3$-$C_7$) heterocycloalkyl, aryl, heteroaryl, —($C_1$-$C_6$) alkylene-($C_3$-$C_7$) cycloalkyl, —($C_1$-$C_6$) alkylene-($C_3$-$C_7$) heterocycloalkyl, —$OR^{15}$, —($C_1$-$C_6$) alkylene-$OR^{15}$, —O—($C_2$-$C_6$) alkylene-$OR^{15}$, —$NR^{16}$($C_2$-$C_6$) alkylene-$OR^{15}$, —$NR^{17}R^{18}$, —($C_1$-$C_6$) alkylene-$NR^{17}R^{18}$, —O—($C_2$-$C_6$) alkylene-$NR^{17}R^{18}$, —$NR^{16}$—($C_2$-$C_6$) alkylene-$NR^{17}R^{18}$, —($C_1$-$C_6$) alkylene-$SO_2$—$NR^{17}R^{18}$, —$NR^{16}$—$SO_2$—$R^{15}$, —($C_1$-$C_6$) alkylene-$NR^{16}$—$SO_2$—$R^{15}$, —O—($C_2$-$C_6$) alkylene-$NR^{16}$—$SO_2$—$R^{15}$, —$NR^{16}$—($C_2$-$C_6$) alkylene-$NR^{17}$—$SO_2$—$R^{15}$, —C(O)—$NR^{17}R^{18}$, —($C_1$-$C_6$) alkylene-C(O)—$NR^{17}R^{18}$, —O—($C_1$-$C_6$) alkylene-C(O)—$NR^{17}R^{18}$, —$NR^{16}$—($C_1$-$C_6$) alkylene-C(O)—$NR^{17}R^{18}$, —$NR^{16}$C(O)—$R^{15}$, —($C_1$-$C_6$) alkylene-$NR^{16}$C(O)—$R^{15}$, —O—($C_2$-$C_6$) alkylene-$NR^{16}$C(O)—$R^{15}$, —$NR^{16}$—($C_2$-$C_6$) alkylene-$NR^{16}$C(O)—$R^{15}$, —C(O)—$R^{15}$, —C(O)$OR^{15}$, —($C_1$-$C_6$) alkylene-C(O)$OR^{15}$, —O—($C_1$-$C_6$) alkylene-C(O)$OR^{15}$, —$NR^{16}$—($C_1$-$C_6$) alkylene-C(O)$OR^{15}$.

In one embodiment, $R^2$ is a —($C_1$-$C_6$) alkyl such as, for example, methyl, iso-propyl, ethyl or alkyl, wherein the alkyl is optionally substituted by at least on fluorine atom. Preferred substituted —($C_1$-$C_6$) alkyls include difluoromethyl and trifluoromethyl.

In one embodiment, $R^2$ is hydrogen. In one embodiment, $R^2$ is a —($C_3$-$C_7$) cycloalkyl such as, for example, cyclopropyl optionally substituted by at least one methyl, hydroxy or fluorine atom. In one embodiment, $R^2$ is a —($C_3$-$C_7$) heterocycloalkyl such as, for example, tetrahydrothiophene or tetrahydrofuran, optionally substituted by at least one methyl. In one embodiment, $R^2$ is a heteroaryl such as, for example, thiophene or furan optionally substituted by at least one methyl or ethyl. In one embodiment, $R^2$ is a —($C_3$-$C_7$) heterocycloalkyl such as, for example, morpholine optionally substituted by at least one methyl, hydroxy or fluorine atom.

In Y as defined herein, $R^3$ is selected from halogen, cyano, amino, hydroxy, —($C_1$-$C_6$) alkyl, —($C_3$-$C_7$) cycloalkyl, —($C_3$-$C_7$) heterocycloalkyl, aryl, heteroaryl, —($C_1$-$C_6$) alkylene-($C_3$-$C_7$) cycloalkyl, —($C_1$-$C_6$) alkylene-($C_3$-$C_7$) heterocycloalkyl, —$OR^{15}$, —($C_1$-$C_6$) alkylene-$OR^{15}$, —O—($C_2$-$C_6$) alkylene-$OR^{15}$, —$NR^{16}$($C_2$-$C_6$) alkylene-$OR^{15}$, —$NR^{17}R^{18}$, —($C_1$-$C_6$) alkylene-$NR^{17}R^{18}$, —O—($C_2$-$C_6$) alkylene-$NR^{17}R^{18}$, —$NR^{16}$—($C_2$-$C_6$) alkylene-$NR^{17}R^{18}$, —($C_1$-$C_6$) alkylene-$SO_2$—$NR^{17}R^{18}$, —$NR^{16}$—$SO_2$—$R^{15}$, —($C_1$-$C_6$) alkylene-$NR^{16}$—$SO_2$—$R^{15}$, —O—($C_2$-$C_6$) alkylene-$NR^{16}$—$SO_2$—$R^{15}$, —$NR^{16}$—($C_2$-$C_6$) alkylene-$NR^{17}$—$SO_2$—$R^{15}$, —C(O)—$NR^{17}R^{18}$, —($C_1$-$C_6$) alkylene-C(O)—$NR^{17}R^{18}$, —O—($C_1$-$C_6$) alkylene-C(O)—$NR^{17}R^{18}$, —$NR^{16}$—($C_1$-$C_6$) alkylene-C(O)—$NR^{17}R^{18}$, —$NR^{16}$C(O)—$R^{15}$, —($C_1$-$C_6$) alkylene-$NR^{16}$C(O)—$R^{15}$, —O—($C_2$-$C_6$) alkylene-$NR^{16}$C(O)—$R^{15}$, —$NR^{16}$—($C_2$-$C_6$) alkylene-$NR^{16}$C(O)—$R^{15}$, —C(O)—$R^{15}$, —C(O)$OR^{15}$, —(C$_1$-C$_6$) alkylene-C(O)OR$^{15}$, —O—(C$_1$-C$_6$) alkylene-C(O)OR$^{15}$, —NR$^{16}$—(C$_1$-C$_6$) alkylene-C(O)OR$^{15}$.

In Y$^1$ as defined herein, R$^4$ is selected from hydrogen, —(C$_1$-C$_6$) alkyl, —(C$_3$-C$_7$) cycloalkyl, —(C$_1$-C$_6$) alkylene-(C$_3$-C$_7$) cycloalkyl, —(C$_1$-C$_6$) alkylene-(C$_3$-C$_7$) heterocycloalkyl, —(C$_1$-C$_6$) alkylene-aryl, —(C$_1$-C$_6$) alkylene-heteroaryl, —(C$_1$-C$_6$) alkylene-OR$^{15}$, —(C$_1$-C$_6$) alkylene-NR$^{17}$R$^{18}$, —(C$_1$-C$_6$) alkylene-C(O)—NR$^{17}$R$^{18}$, —(C$_1$-C$_6$) alkylene-NR$^{16}$C(O)—R$^{15}$, —(C$_1$-C$_6$) alkylene-C(O)OR$^{15}$, and —(C$_1$-C$_6$) alkylene-OC(O)—R$^{15}$.

In one embodiment, R$^4$ is hydrogen.

In Y$^1$ as defined herein, R$^5$ is selected from hydrogen, —(C$_1$-C$_6$) alkyl, —(C$_3$-C$_7$) cycloalkyl, —(C$_3$-C$_7$) heterocycloalkyl, aryl, heteroaryl, —(C$_1$-C$_6$) alkylene-(C$_3$-C$_7$) cycloalkyl, —(C$_1$-C$_6$) alkylene-(C$_3$-C$_7$) heterocycloalkyl, —(C$_1$-C$_6$) alkylene-aryl, —(C$_1$-C$_6$) alkylene-heteroaryl, —(C$_1$-C$_6$) alkylene-OR$^{15}$, —(C$_1$-C$_6$) alkylene-NR$^{17}$R$^{18}$, —(C$_1$-C$_6$) alkylene-C(O)—NR$^{17}$R$^{18}$, —(C$_1$-C$_6$) alkylene-NR$^{16}$C(O)—R$^{15}$, —(C$_1$-C$_6$) alkylene-C(O)OR$^{15}$, and —(C$_1$-C$_6$) alkylene-OC(O)—R$^{15}$.

In one embodiment, R$^5$ is a —(C$_1$-C$_6$) alkyl such as methyl. In one embodiment, R$^5$ is an aryl such as, for example, phenyl optionally substituted by at least one halo or methyl.

In Y$^1$ as defined herein, R$^7$ is independently selected from hydrogen, halogen, amino, hydroxy, —(C$_1$-C$_6$) alkyl, —(C$_3$-C$_7$) cycloalkyl, —(C$_1$-C$_6$) alkylene-(C$_3$-C$_7$) cycloalkyl, —(C$_1$-C$_6$) alkylene-(C$_3$-C$_7$) heterocycloalkyl, —(C$_3$-C$_7$) heterocycloalkyl, aryl, heteroaryl, —OR$^{15}$, —(C$_1$-C$_6$) alkylene-OR$^{15}$, —O—(C$_2$-C$_6$) alkylene-OR$^{15}$, —NR$^{16}$(C$_2$-C$_6$) alkylene-OR$^{15}$, —NR$^{17}$R$^{18}$, —(C$_1$-C$_6$) alkylene-NR$^{17}$R$^{18}$, —O—(C$_2$-C$_6$) alkylene-NR$^{17}$R$^{18}$, —NR$^{16}$—(C$_2$-C$_6$) alkylene-NR$^{17}$R$^{18}$, —SO—R$^{15}$, —SO$_2$—R$^{15}$, —SO$_2$NR$^{17}$R$^{18}$, —(C$_1$-C$_6$) alkylene-SO$_2$—NR$^{17}$R$^{18}$, —NR$^{16}$—SO$_2$—R$^{15}$, —(C$_1$-C$_6$) alkylene-NR$^{16}$—SO$_2$—R$^{15}$, —O—(C$_2$-C$_6$) alkylene-NR$^{16}$—SO$_2$—R$^{15}$, —NR$^{16}$—(C$_2$-C$_6$) alkylene-NR$^{17}$—SO$_2$—R$^{15}$, —C(O)—NR$^{17}$R$^{18}$, —(C$_1$-C$_6$) alkylene-C(O)—NR$^{17}$R$^{18}$, —O—(C$_1$-C$_6$) alkylene-C(O)—NR$^{17}$R$^{18}$, —NR$^{16}$—(C$_1$-C$_6$) alkylene-C(O)—NR$^{17}$R$^{18}$, —NR$^{16}$C(O)—R$^{15}$, —(C$_1$-C$_6$) alkylene-NR$^{16}$C(O)—R$^{15}$, —O—(C$_2$-C$_6$) alkylene-NR$^{16}$C(O)—R$^{15}$, —NR$^{16}$—(C$_2$-C$_6$) alkylene-NR$^{17}$C(O)—R$^{15}$, —C(O)—R$^{15}$, —C(O)OR$^{15}$, —(C$_1$-C$_6$) alkylene-C(O)OR$^{15}$, —O—(C$_1$-C$_6$) alkylene-C(O)OR$^{15}$, —NR$^{16}$—(C$_1$-C$_6$) alkylene-C(O)OR$^{15}$, —OC(O)—R$^{15}$, —(C$_1$-C$_6$) alkylene-OC(O)—R$^{15}$, —O—(C$_2$-C$_6$) alkylene-OC(O)—R$^{15}$, —NR$^{16}$—(C$_2$-C$_6$) alkylene-OC(O)—R$^{15}$ or —NR$^{16}$—C(O)OR$^{15}$.

In one embodiment, R$^7$ is hydrogen. In one embodiment, R$^7$ is a —(C$_1$-C$_6$) alkyl such as, for example, methyl.

In one embodiment, R$^7$ is (C$_3$-C$_7$) heterocycloalkyl such as, for example, optionally substituted morpholinyl, optionally substituted piperidinyl, optionally substituted 1,4-oxazepanyl, optionally substituted pyrrolidinyl, optionally substituted piperazinyl or optionally substituted 2-oxa-5-azabicyclo[2.2.2]octan-5-yl. In one embodiment, the (C$_3$-C$_7$) heterocycloalkyl is substituted by one or two —(C$_1$-C$_6$) alkyl such as, for example, one or two methyl.

In R$^2$, R$^3$, R$^4$ and R$^7$ as defined herein, R$^{15}$, R$^{16}$, R$^{17}$ and R$^{18}$ are each independently selected from hydrogen, —(C$_1$-C$_6$) haloalkyl, —(C$_1$-C$_6$) alkyl, —(C$_3$-C$_7$) cycloalkyl, —(C$_1$-C$_6$) alkylene-(C$_3$-C$_7$) cycloalkyl, —(C$_3$-C$_7$) heterocycloalkyl, aryl, heteroaryl, —(C$_1$-C$_6$) alkylene-(C$_3$-C$_7$) heterocycloalkyl, —(C$_1$-C$_6$) alkylene-heteroaryl, and —(C$_1$-C$_6$) alkylene-aryl; and/or two groups selected from R$^{15}$, R$^{16}$, R$^{17}$ and R$^{18}$ form together a cycle selected from —(C$_3$-C$_7$) cycloalkyl, —(C$_3$-C$_7$) heterocycloalkyl, aryl and heteroaryl.

In one embodiment, Y$^1$ is a 10-membered [6,6]bicyclic heteroaryl.

In one embodiment, Y$^1$ is selected from the following group of formulae (Y$^1$-1)

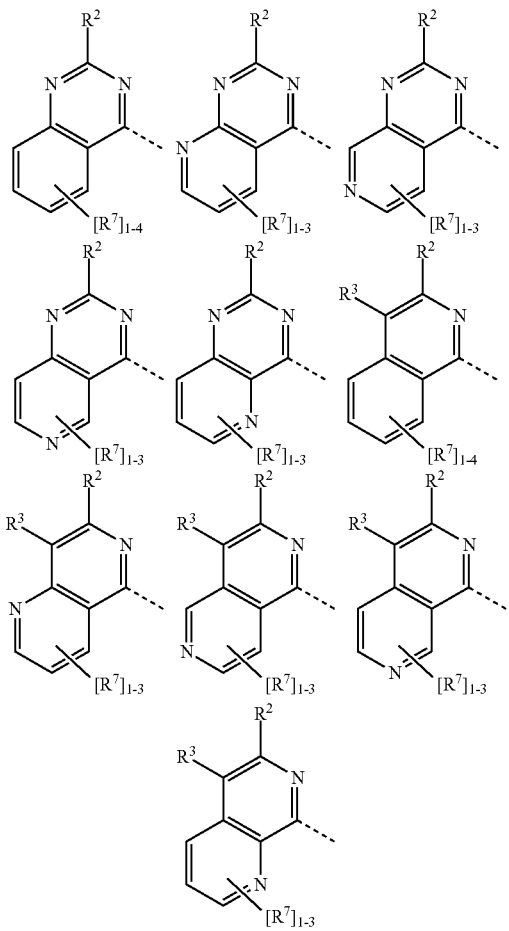

wherein R$^2$, R$^3$ and R$^7$ are independently as defined herein.

In one embodiment, Y$^1$ is a 9-membered bicyclic [6,5] heteroaryl.

In one embodiment, Y$^1$ is selected from the following group of formulae (Y$^1$-2)

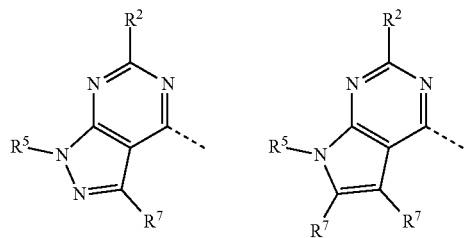

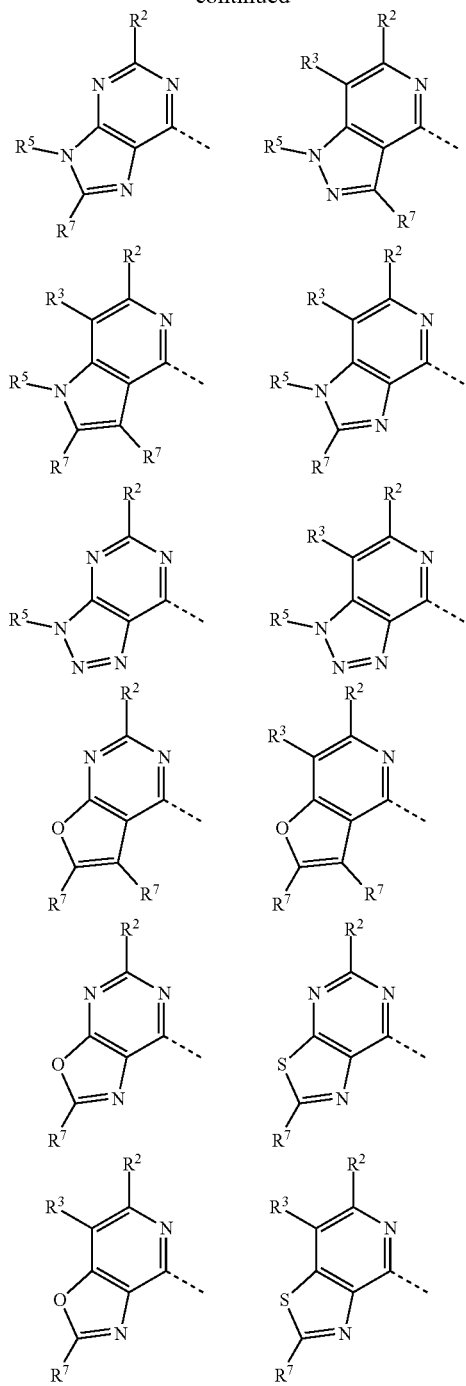

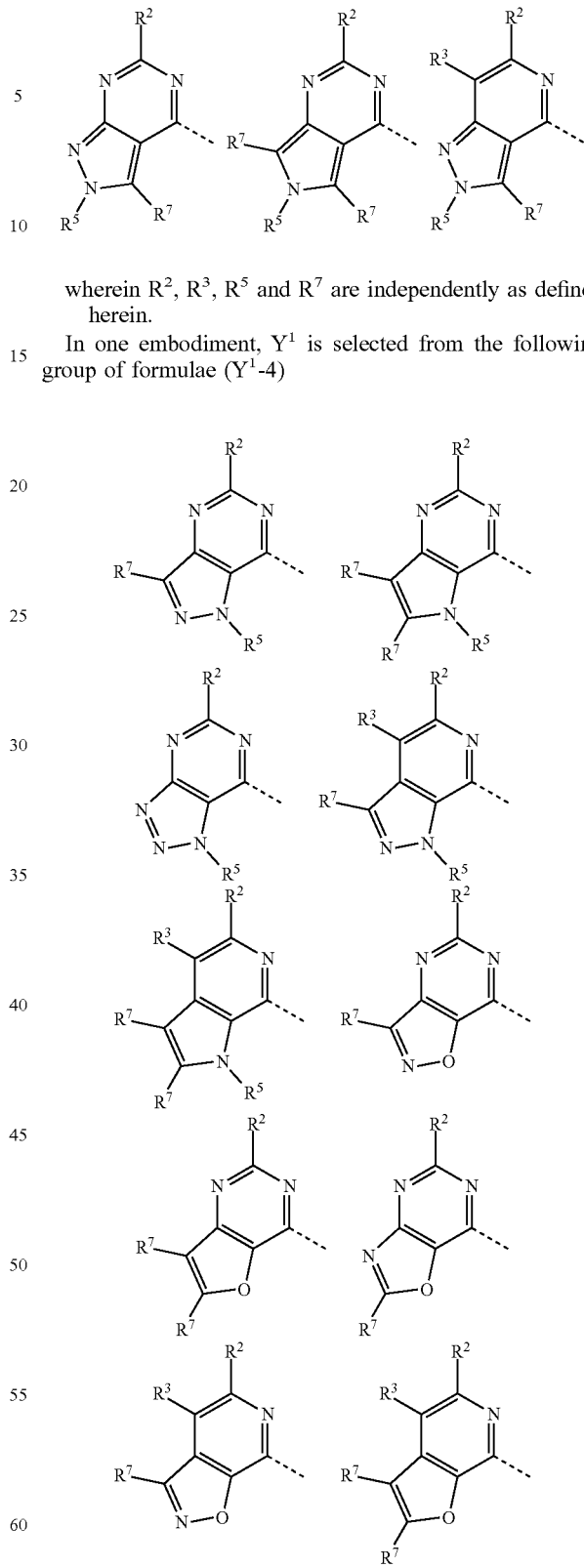

wherein R², R³, R⁵ and R⁷ are independently as defined herein.

In one embodiment, Y¹ is selected from the following group of formulae (Y¹-3)

wherein R², R³, R⁵ and R⁷ are independently as defined herein.

In one embodiment, Y¹ is selected from the following group of formulae (Y¹-4)

wherein R², R³, R⁵ and R⁷ are independently as defined herein.

In one embodiment, Y¹ is selected from the following group of formulae (Y¹-5)

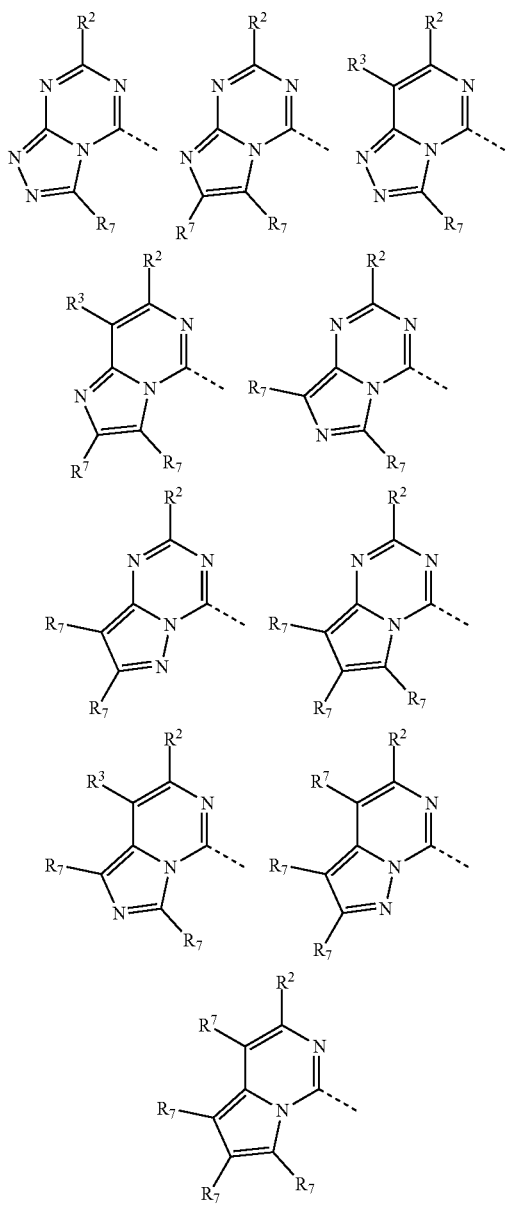

wherein $R^2$, $R^3$ and $R^7$ are independently as defined herein.

In one embodiment, $Y^1$ is selected from the following group of formulae ($Y^1$-6)

wherein $R^2$, $R^3$ and $R^7$ are independently as defined herein.

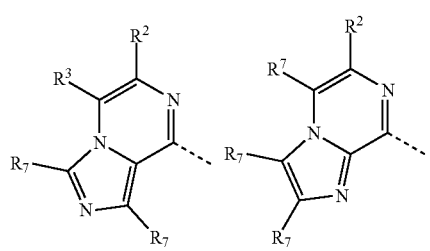

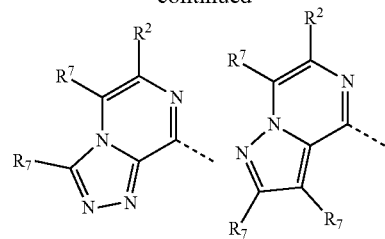

In one embodiment, $Y^1$ is a 9-membered bicyclic [5,6] heteroaryl.

In one embodiment, $Y^1$ is selected from the following group of formulae ($Y^1$-7)

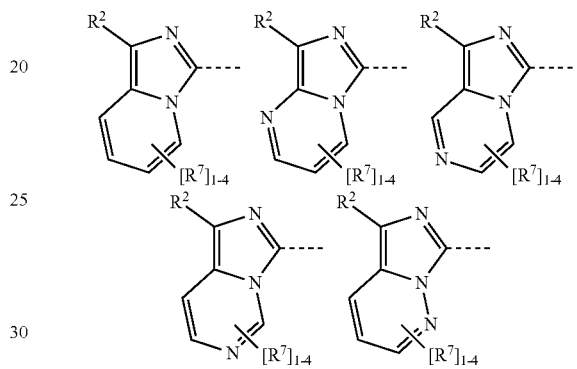

wherein $R^2$ and $R^7$ are independently as defined herein.

In one embodiment, $Y^1$ is selected from the following group of formulae ($Y^1$-8)

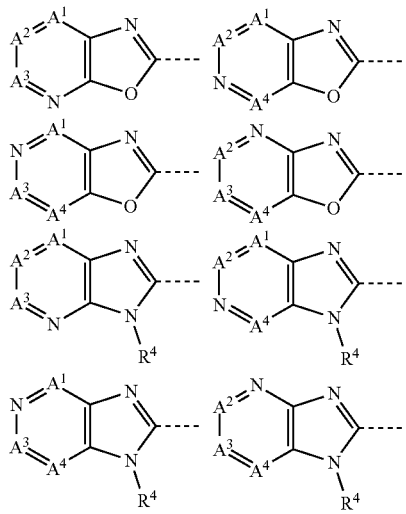

wherein $A^1$, $A^2$, $AA^4$ and $R^4$ are independently as defined herein.

In one embodiment, $Y^1$ is selected from optionally substituted naphthyridine (such as, for example, optionally substituted 1,7-naphthyridine, 1,6-naphthyridine or 2,7-naphthyridine), optionally substituted 1H-pyrazolo-pyrimidine, optionally substituted 2H-pyrazolo-pyrimidine, optionally substituted benzimidazole, optionally substituted benzoxazole, optionally substituted imidazo[1,2-a]pyrazine, optionally substituted imidazo[1,5-a]pyrazine, optionally substituted imidazo[4,5-b]pyridine, optionally substituted pyrazolo[1,5-a][1,3,5]triazine, optionally substituted pyrazolo[1,5-a]pyrazine, optionally substituted pyrido[2,3-d]pyrimidine, optionally substituted pyrido[3,2-d]pyrimidine, optionally substituted pyrido[3,4-d]pyrimidine, optionally substituted oxazolo[4,5-b]pyridine, optionally substituted oxazolo[4,5-c]pyridine, optionally substituted oxazolo[5,4-b]pyridine, substituted oxazolo[5,4-c]pyridine, optionally substituted quinazoline, optionally substituted quinoline, and optionally substituted phthalazine.

In one embodiment, $Y^1$ is optionally substituted 1H-pyrazolo-pyrimidine. In one embodiment, $Y^1$ is 1H-pyrazolo-pyrimidine. In one embodiment, $Y^1$ is optionally substituted 2H-pyrazolo-pyrimidine. In one embodiment, $Y^1$ is 2H-pyrazolo-pyrimidine. In one embodiment, $Y^1$ is selected from optionally substituted pyrido[2,3-d]pyrimidine, optionally substituted pyrido[3,2-d]pyrimidine and optionally substituted pyrido[3,4-d]pyrimidine. $Y^1$ is selected from pyrido[2,3-d]pyrimidine, pyrido[3,2-d]pyrimidine and pyrido[3,4-d]pyrimidine. In one embodiment, $Y^1$ is optionally substituted quinazoline. In one embodiment, $Y^1$ is quinazoline.

In one embodiment, $Y^1$ is selected from the following group of formulae ($Y^1$-1a)

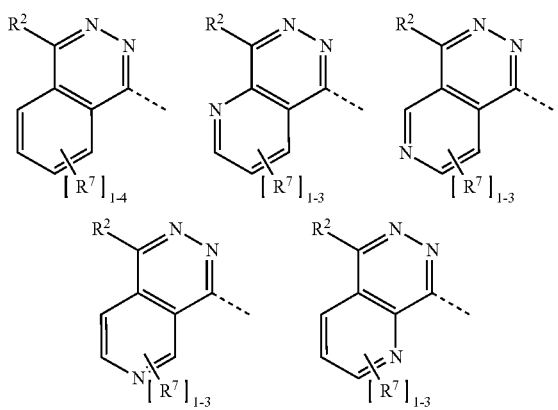

wherein $R^2$ and $R^7$ are independently as defined herein.

In one embodiment, $Y^1$ is selected from the following group of formulae ($Y^1$-2a)

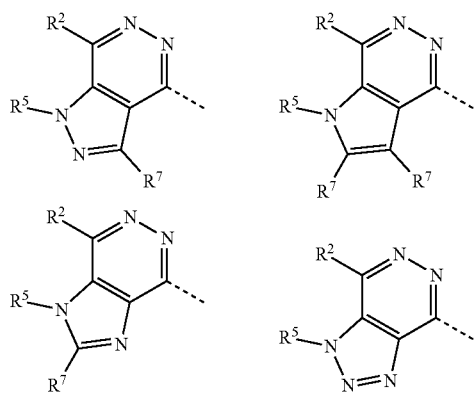

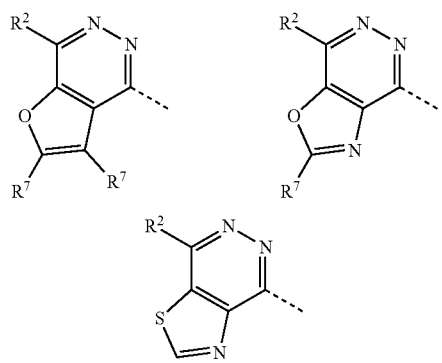

wherein $R^2$, $R^5$ and $R^7$ are independently as defined herein.

In one embodiment, $Y^1$ is selected from the following group of formulae ($Y^1$-3a)

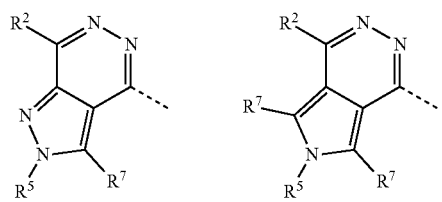

wherein $R^2$, $R^5$ and $R^7$ are independently as defined herein.

In one embodiment, $Y^1$ is selected from the following group of formulae ($Y^1$-4a)

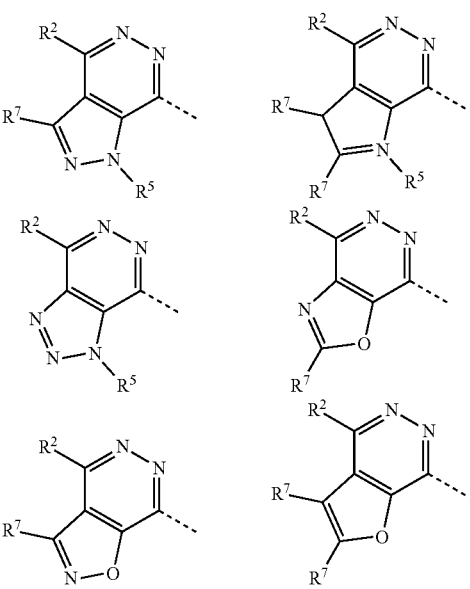

wherein $R^2$, $R^5$ and $R^7$ are independently as defined herein.

In one embodiment, V is selected from the following group of formulae ($Y^1$-5a)

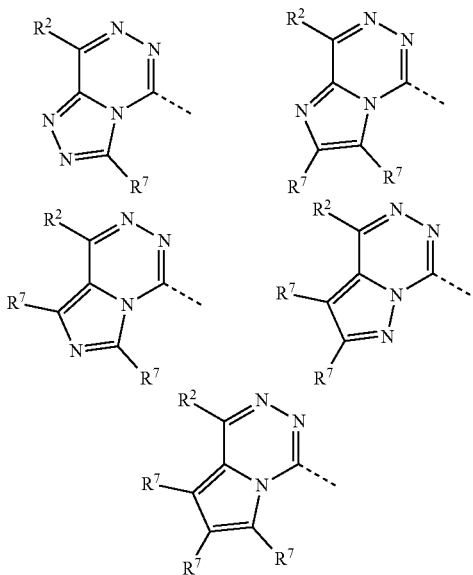

wherein $R^2$ and $R^7$ are independently as defined herein.

In one embodiment, $Y^1$ is optionally substituted phthalazine (such as, for example, phthalazin-1-yl).

In one embodiment, the bicyclic heteroaryl in $Y^1$ is substituted by one or two —($C_1$-$C_6$) alkyl such as, for example, one or two methyl.

$Y^2$ Definitions

In formula (I) above, $Y^2$ is a monocyclic heteroaryl or aryl. According to one embodiment, $Y^2$ is a 5- or 6-membered heteroaryl. According to one embodiment, $Y^2$ is a 5-membered heteroaryl.

According to one embodiment, $Y^2$ is selected from the following group of formulae ($Y^2$-0)

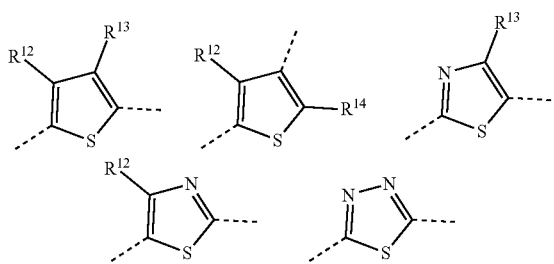

wherein $R^{12}$, $R^{13}$ and $R^{14}$ are each independently selected from hydrogen, halogen, cyano, hydroxy, amino, —($C_1$-$C_6$) alkyl, —$CH_2$—O—($C_1$-$C_6$) alkyl, —$CH_2$—NH—($C_1$—$C_6$) alkyl), —$CH_2$—N—(($C_1$-$C_6$) alkyl)$_2$, —O—($C_1$-$C_6$) alkyl, —NH—($C_1$-$C_6$) alkyl) and —N—(($C_1$-$C_6$) alkyl)$_2$.

According to one embodiment, $Y^2$ is selected from the following group of formulae ($Y^2$—I)

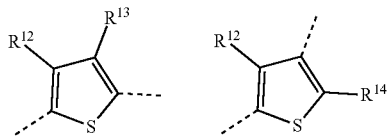

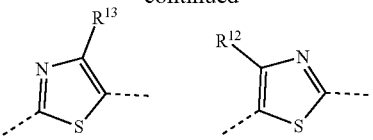

wherein $R^{12}$, $R^{13}$ and $R^{14}$ are each independently selected from hydrogen, halogen, cyano, hydroxy, amino, —($C_1$-$C_6$) alkyl, —$CH_2$—O—($C_1$-$C_6$) alkyl, —$CH_2$—NH—($C_1$—$C_6$) alkyl), —$CH_2$—N—(($C_1$-$C_6$) alkyl)$_2$, —O—($C_1$-$C_6$) alkyl, —NH—($C_1$-$C_6$) alkyl) and —N—(($C_1$-$C_6$) alkyl)$_2$.

In one embodiment, $Y^2$ is selected from the following group of formulae ($Y^2$-1)

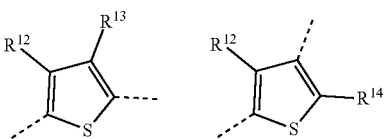

wherein $R^{12}$, $R^{13}$ and $R^{14}$ are independently as defined herein.

In one embodiment, $Y^2$ is selected from optionally substituted thiadiazole, optionally substituted thiazole and optionally substituted thiophene. In one embodiment, $Y^2$ is selected from thiophene, fluoro-thiophene, thiadiazole and thiazole.

In one embodiment, $R^{12}$ and $R^{13}$, or $R^{12}$ and $R^{14}$, are selected from hydrogen and ($C_1$-$C_3$) alkyl. In one embodiment, $R^{12}$ and $R^{13}$, or $R^{12}$ and $R^{14}$, are each hydrogen, i.e., $Y^2$ is a divalent unsubstituted thiophene.

L Definitions

In formula (I) above, L is selected from —($CR^{10}R^{11})_n$, —($C_3$-$C_7$) cycloalkyl and —($C_3$-$C_7$) heterocycloalkyl, wherein n is an integer ranging from 1 to 10; and $R^{10}$ and $R^{11}$ are independently selected from hydrogen, halogen, hydroxy, amino, —($C_1$-$C_6$) alkyl, —O—($C_1$-$C_6$) alkyl, —NH—($C_1$-$C_6$) alkyl and —N—(($C_1$-$C_6$) alkyl)$_2$.

According to one embodiment, n is an integer selected from 1, 2, 3 and 4.

According to one embodiment, $R^{10}$ and $R^{11}$ are independently selected from hydrogen, halogen, hydroxy, amino, —($C_1$-$C_3$) alkyl, —($C_1$-$C_2$) haloalkyl, —($C_1$-$C_2$) hydroxyalkyl, —($C_1$-$C_2$) aminoalkyl, —O—($C_1$-$C_4$) alkyl, —NH—($C_1$-$C_3$) alkyl and —N—(($C_1$-$C_3$) alkyl)$_2$.

In one embodiment, L is selected from —($C_4$-$C_7$) cycloalkyl and —($C_4$-$C_7$) heterocycloalkyl. In one particular embodiment, L is selected from —($C_5$-$C_6$) cycloalkyl and —($C_5$-$C_6$) heterocycloalkyl.

In one embodiment, n is an integer selected from 1, 2 and 3. In one embodiment, n is an integer selected from 1 and 2. In one embodiment, n is 1. In one embodiment, n is 2.

In one embodiment, $R^{10}$ and $R^{11}$ are each independently selected from hydrogen and ($C_1$-$C_3$) alkyl. In one embodiment, $R^{10}$ and $R^{11}$ are each hydrogen.

$Z^1$ Definitions

In formula (I) above, $Z^1$ is selected from (C=O)—$R^9$, S(O)—$R^9$ and S($O_2$)—$R^9$. According to one embodiment, $Z^1$ is selected from (C=O)—$R^9$ and S($O_2$)—$R^9$, In $Z^1$ as defined herein, $R^9$ is selected from amino, —($C_1$-$C_6$) alkyl, —($C_3$-$C_7$) cycloalkyl, —($C_3$-$C_7$) heterocycloalkyl, aryl, heteroaryl, —($C_1$-$C_6$) alkylene-($C_3$-$C_7$) cycloalkyl, —($C_1$-$C_6$) alkylene-($C_3$-$C_7$) heterocycloalkyl, —($C_1$-$C_6$) alkylene-aryl, —($C_1$-$C_6$) alkylene-heteroaryl, —($C_1$-$C_6$) alkylene-$OR^{21}$, —($C_1$-$C_6$) alkylene-$NR^{23}R^{24}$, —($C_1$-$C_6$) alkylene-C(O)—$NR^{23}R^{24}$, —($C_1$-$C_6$) alkylene-C(O)—$NR^{23}R^{24}$, —($C_1$-$C_6$) alkylene-$NR^{22}$—C(O)—$R^{21}$, —($C_1$-$C_6$) alkylene-C(O)$OR^{21}$, —$OR^{21}$, —$NR^{23}R^{24}$, —$NR^{22}$—($C_2$-$C_6$) alkylene-$OR^{21}$, —$NR^{22}$—($C_2$-$C_6$) alkylene-$NR^{23}R^{24}$, —$NR^{22}$—($C_1$-$C_6$) alkylene-C(O)$OR^{21}$.

In $R^9$ as defined herein, $R^{21}$, $R^{22}$, $R^{23}$ and $R^{24}$ are each independently selected from hydrogen, —($C_1$-$C_6$) alkyl, —($C_3$-$C_7$) cycloalkyl, —($C_1$-$C_6$) alkylene-($C_3$-$C_7$) cycloalkyl, —($C_1$-$C_6$) alkylene-($C_3$-$C_7$) halocycloalkyl, —($C_3$-$C_7$) heterocycloalkyl, aryl, heteroaryl, —($C_1$-$C_6$) alkylene-($C_3$-$C_7$) heterocycloalkyl, —($C_1$-$C_6$) alkylene-heteroaryl, and —($C_1$-$C_6$) alkylene-aryl; and/or two groups selected from $R^{21}$, $R^{22}$, $R^{23}$ and $R^{24}$ form together a cycle selected from —($C_3$-$C_7$) cycloalkyl, —($C_3$-$C_7$) heterocycloalkyl, aryl and heteroaryl.

In one embodiment, $R^9$ is selected from methyl, tert-butyl, cyclopropyl, O-tert-butyl, hydroxymethyl, (S)-3,3,3-trifluoro-2-hydroxypropyl, 2-hydroxypropan-2-yl, 1-hydroxycyclopropyl, methoxymethyl, pyridin-2-ylmethyl, pyridin-3-ylmethyl, pyridin-4-ylmethyl, phenylmethyl, phenyl 2,2-difluorocyclopropyl 2,2,3,3,3-pentafluoro-propyl, $H_2N$-methyl, N-methyl-NH-methyl, methylazetidinyl, 1-hydroxyethyl (e.g., (S)-1-hydroxyethyl or (R)-1-hydroxyethyl) and pyrrolidinyl. In one embodiment, $R^9$ is selected from cyclopropyl, hydroxymethyl, (S)-3,3,3-trifluoro-2-hydroxypropyl, 2-hydroxypropan-2-yl, 1-hydroxycyclopropyl, 2,2-difluorocyclopropyl and 2,2,3,3,3-pentafluoro-propyl.

$R^1$ Definitions

In formula (I) above, $R^1$ is either a singular non-cyclic moiety, or $R^1$ is merged with another moiety in formula (I) to form an heterocycloalkyl comprising at least one nitrogen atom.

According to a first embodiment of the invention, $R^1$ is selected from hydrogen, —($C_1$-$C_6$) alkyl, —($C_3$-$C_7$) cycloalkyl, —($C_3$-$C_7$) heterocycloalkyl, —($C_1$-$C_6$) alkylene-($C_3$-$C_7$) cycloalkyl, —($C_1$-$C_6$) alkylene-($C_3$-$C_7$) heterocycloalkyl, —($C_1$-$C_6$) alkylene-$OR^{19}$ and —($C_1$-$C_6$) alkylene-$NR^{19}R^{20}$, wherein $R^{19}$ and $R^{20}$ are each independently selected from hydrogen, —($C_1$-$C_6$) alkyl and —($C_3$-$C_7$) cycloalkyl; or $R^{19}$ and $R^{20}$ form together a cycle selected from —($C_3$-$C_7$) cycloalkyl and —($C_3$-$C_7$) heterocycloalkyl.

According to a second embodiment of the invention, $R^1$ and one of $R^{10}$ or $R^{11}$ from together a ($C_3$-$C_7$) heterocycloalkyl comprising at least one nitrogen atom;

According to a third embodiment of the invention, $R^1$ and $R^9$ (as defined herein in the definition of $R^9$) form together a ($C_3$-$C_7$) heterocycloalkyl comprising at least one nitrogen atom.

In one embodiment, $R^1$ is selected from hydrogen and ($C_1$-$C_3$) alkyl, preferably $R^1$ is hydrogen or methyl. In one embodiment, $R^1$ is hydrogen. In one embodiment, $R^1$ and one of $R^{10}$ or $R^{11}$ form together a 5- or 6-membered heterocycloalkyl comprising one nitrogen atom. In one embodiment, $R^1$ and one of $R^{10}$ or $R^{11}$ form together a pyrrolidine. In one embodiment, $R^1$ and $R^9$ from together a 5- or 6-membered heterocycloalkyl comprising one nitrogen atom. In one embodiment, $R^1$ and $R^9$ form together a pyrrolidinone or a morpholin-3-one.

Specific Compounds

According to one embodiment, the compound of formula (I) is selected from the compounds of Table 1 below.

TABLE 1

| Cpd # | Structure | Name |
| --- | --- | --- |
| 1 | 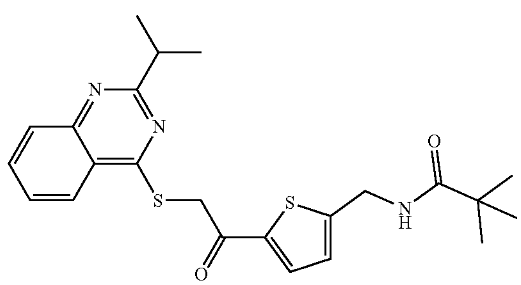 [SMILES: CC(C)c1nc(SCC(=O)c2ccc(CNC(=O)C(C)(C)C)s2)c2ccccc2n1] | N-((5-(2-((2-isopropylquinazolin-4-yl)thio)acetyl)thiophen-2-yl)methyl)pivalamide |
| 2 | 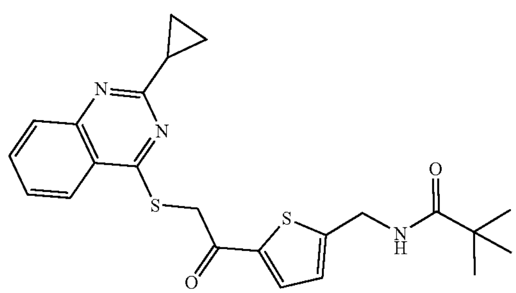 [SMILES: CC(C)(C)C(=O)NCc1ccc(C(=O)CSc2nc(C3CC3)nc3ccccc23)s1] | N-((5-(2-((2-cyclopropylquinazolin-4-yl)thio)acetyl)thiophen-2-yl)methyl)pivalamide |

TABLE 1-continued

| Cpd # | Structure | Name |
|---|---|---|
| 3 | 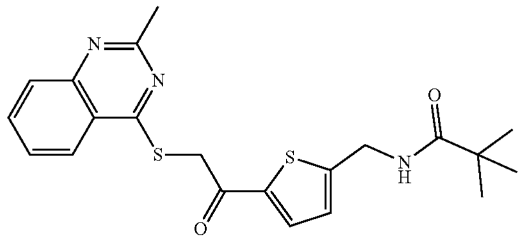 [SMILES: Cc1nc(SCC(=O)c2ccc(CNC(=O)C(C)(C)C)s2)c2ccccc2n1] | N-((5-(2-((2-methylquinazolin-4-yl)thio)acetyl)thiophen-2-yl)methyl)pivalamide |
| 4 | 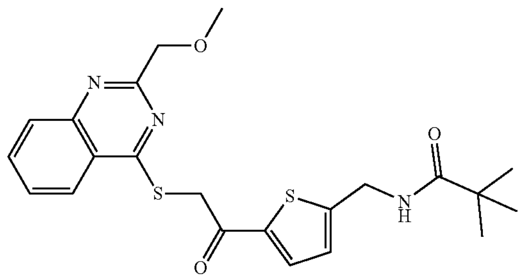 [SMILES: COCc1nc(SCC(=O)c2ccc(CNC(=O)C(C)(C)C)s2)c2ccccc2n1] | N-((5-(2-((2-(methoxymethyl)quinazolin-4-yl)thio)acetyl)thiophen-2-yl)methyl)pivalamide |
| 5 | 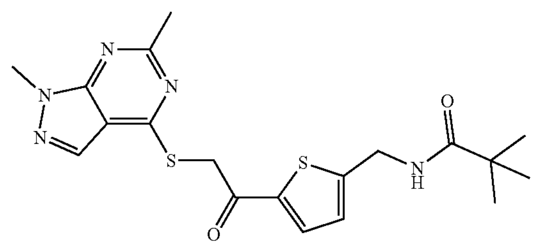 [SMILES: Cc1nc(SCC(=O)c2ccc(CNC(=O)C(C)(C)C)s2)c2cnn(C)c2n1] | N-((5-(2-((1,6-dimethyl-1H-pyrazolo[3,4-d]pyrimidin-4-yl)thio)acetyl)thiophen-2-yl)methyl)pivalamide |
| 6 | 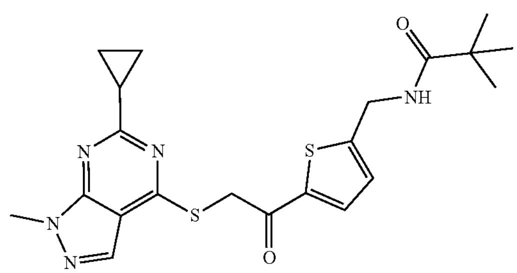 [SMILES: Cn1ncc2c(SCC(=O)c3ccc(CNC(=O)C(C)(C)C)s3)nc(C3CC3)nc21] | N-((5-(2-((6-cyclopropyl-1-methyl-1H-pyrazolo[3,4-d]pyrimidin-4-yl)thio)acetyl)thiophen-2-yl)methyl)pivalamide |
| 7 | 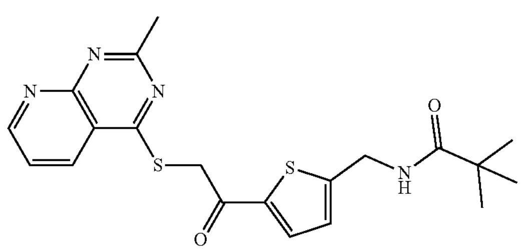 [SMILES: Cc1nc(SCC(=O)c2ccc(CNC(=O)C(C)(C)C)s2)c2cccnc2n1] | N-((5-(2-((2-methylpyrido[2,3-d]pyrimidin-4-yl)thio)acetyl)thiophen-2-yl)methyl)pivalamide |
| 8 | 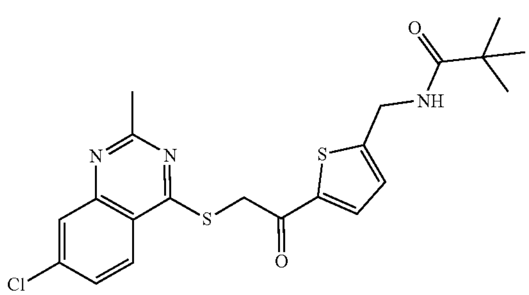 [SMILES: Cc1nc(SCC(=O)c2ccc(CNC(=O)C(C)(C)C)s2)c2ccc(Cl)cc2n1] | N-((5-(2-((7-chloro-2-methylquinazolin-4-yl)thio)acetyl)thiophen-2-yl)methyl)pivalamide |

TABLE 1-continued

| Cpd # | Structure | Name |
|---|---|---|
| 9 | 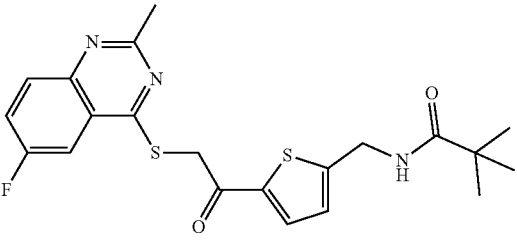 [SMILES: Cc1nc(SCC(=O)c2ccc(CNC(=O)C(C)(C)C)s2)c2cc(F)ccc2n1] | N-((5-(2-((6-fluoro-2-methylquinazolin-4-yl)thio)acetyl)thiophen-2-yl)methyl)pivalamide |
| 10 | 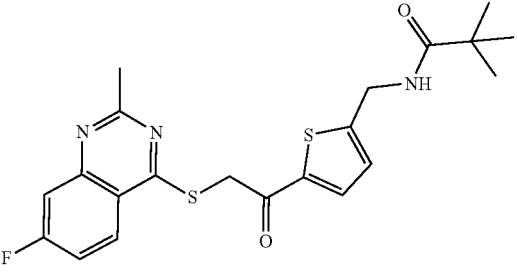 [SMILES: Cc1nc(SCC(=O)c2ccc(CNC(=O)C(C)(C)C)s2)c2ccc(F)cc2n1] | N-((5-(2-((7-fluoro-2-methylquinazolin-4-yl)thio)acetyl)thiophen-2-yl)methyl)pivalamide |
| 11 | 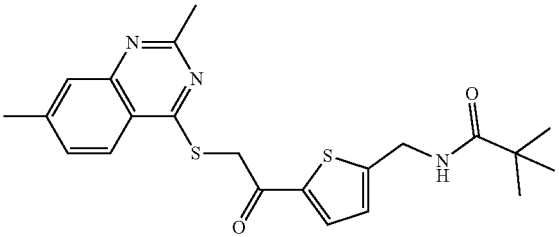 [SMILES: Cc1ccc2c(SCC(=O)c3ccc(CNC(=O)C(C)(C)C)s3)nc(C)nc2c1] | N-((5-(2-((2,7-dimethylquinazolin-4-yl)thio)acetyl)thiophen-2-yl)methyl)pivalamide |
| 12 | 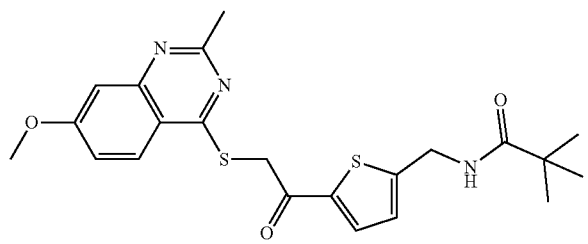 [SMILES: COc1ccc2c(SCC(=O)c3ccc(CNC(=O)C(C)(C)C)s3)nc(C)nc2c1] | N-((5-(2-((7-methoxy-2-methylquinazolin-4-yl)thio)acetyl)thiophen-2-yl)methyl)pivalamide |
| 13 | 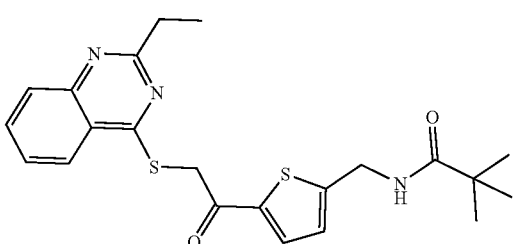 | N-((5-(2-((2-ethylquinazolin-4-yl)thio)acetyl)thiophen-2-yl)methyl)pivalamide |
| 14 | 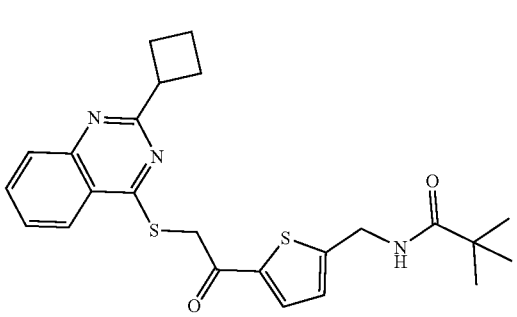 [SMILES: CC(C)(C)C(=O)NCc1ccc(C(=O)CSc2nc(C3CCC3)nc3ccccc23)s1] | N-((5-(2-((2-cyclobutylquinazolin-4-yl)thio)acetyl)thiophen-2-yl)methyl)pivalamide |

TABLE 1-continued

| Cpd # | Structure | Name |
|---|---|---|
| 15 | 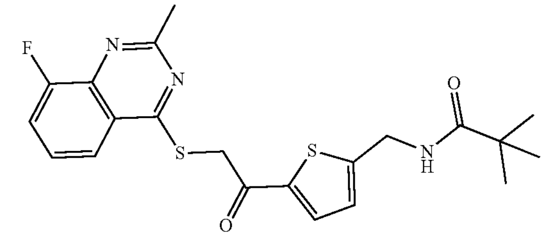 [SMILES: Cc1nc(SCC(=O)c2ccc(CNC(=O)C(C)(C)C)s2)c2cccc(F)c2n1] | N-((5-(2-((8-fluoro-2-methylquinazolin-4-yl)thio)acetyl)thiophen-2-yl)methyl)pivalamide |
| 16 | 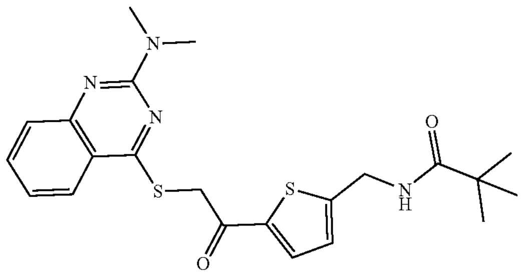 [SMILES: CN(C)c1nc(SCC(=O)c2ccc(CNC(=O)C(C)(C)C)s2)c2ccccc2n1] | N-((5-(2-((2-(dimethylamino)quinazolin-4-yl)thio)acetyl)thiophen-2-yl)methyl)pivalamide |
| 17 | 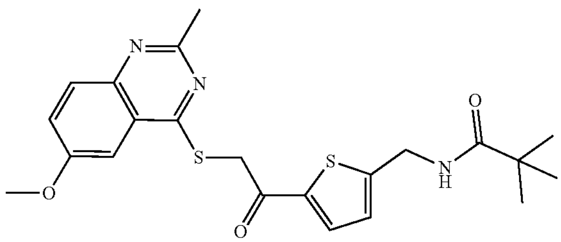 [SMILES: COc1ccc2nc(C)nc(SCC(=O)c3ccc(CNC(=O)C(C)(C)C)s3)c2c1] | N-((5-(2-((6-methoxy-2-methylquinazolin-4-yl)thio)acetyl)thiophen-2-yl)methyl)pivalamide |
| 18 | 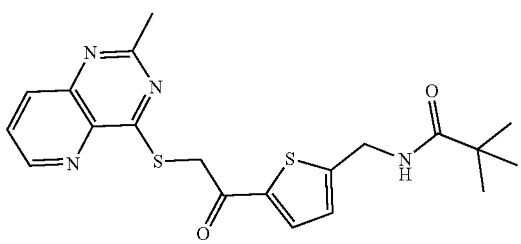 [SMILES: Cc1nc(SCC(=O)c2ccc(CNC(=O)C(C)(C)C)s2)c2ncccc2n1] | N-((5-(2-((2-methylpyrido[3,2-d]pyrimidin-4-yl)thio)acetyl)thiophen-2-yl)methyl)pivalamide |
| 19 | 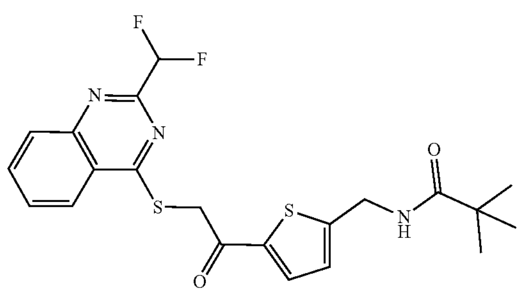 [SMILES: CC(C)(C)C(=O)NCc1ccc(C(=O)CSc2nc(C(F)F)nc3ccccc23)s1] | N-((5-(2-((2-(difluoromethyl)quinazolin-4-yl)thio)acetyl)thiophen-2-yl)methyl)pivalamide |
| 20 | 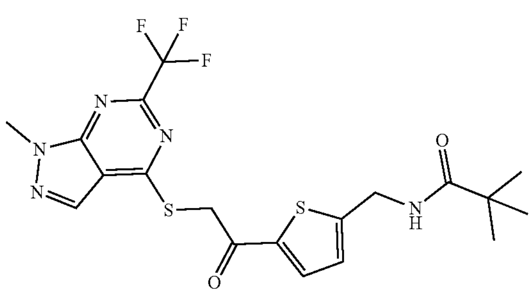 [SMILES: Cn1ncc2c(SCC(=O)c3ccc(CNC(=O)C(C)(C)C)s3)nc(C(F)(F)F)nc21] | N-((5-(2-((1-methyl-6-(trifluoromethyl)-1H-pyrazolo[3,4-d]pyrimidin-4-yl)thio)acetyl)thiophen-2-yl)methyl)pivalamide |

TABLE 1-continued

| Cpd # | Structure | Name |
|---|---|---|
| 21 | 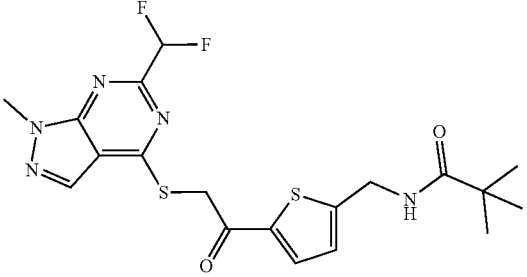 [SMILES: Cn1ncc2c(SCC(=O)c3ccc(CNC(=O)C(C)(C)C)s3)nc(C(F)F)nc21] | N-((5-(2-((6-(difluoromethyl)-1-methyl-1H-pyrazolo[3,4-d]pyrimidin-4-yl)thio)acetyl)thiophen-2-yl)methyl)pivalamide |
| 22 | 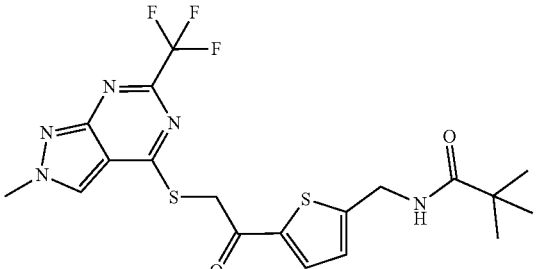 | N-((5-(2-((2-methyl-6-(trifluoromethyl)-2H-pyrazolo[3,4-d]pyrimidin-4-yl)thio)acetyl)thiophen-2-yl)methyl)pivalamide |
| 23 | 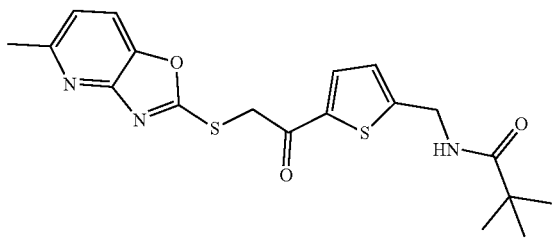 [SMILES: Cc1ccc2oc(SCC(=O)c3ccc(CNC(=O)C(C)(C)C)s3)nc2n1] | N-((5-(2-((5-methyloxazolo[4,5-b]pyridin-2-yl)thio)acetyl)thiophen-2-yl)methyl)pivalamide |
| 24 | 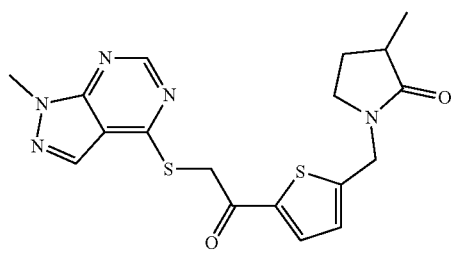 [SMILES: CC1CCN(Cc2ccc(C(=O)CSc3ncnc4c3cnn4C)s2)C1=O] | 3-methyl-1-((5-(2-((1-methyl-1H-pyrazolo[3,4-d]pyrimidin-4-yl)thio)acetyl)thiophen-2-yl)methyl)pyrrolidin-2-one |
| 25 | 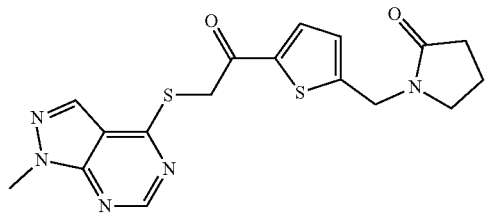 [SMILES: Cn1ncc2c(SCC(=O)c3ccc(CN4CCCC4=O)s3)ncnc21] | 1-((5-(2-((1-methyl-1H-pyrazolo[3,4-d]pyrimidin-4-yl)thio)acetyl)thiophen-2-yl)methyl)pyrrolidin-2-one |
| 26 | 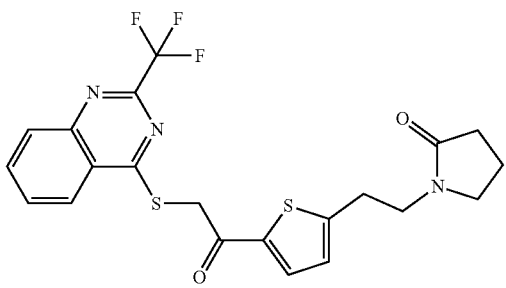 [SMILES: O=C(CSc1nc(C(F)(F)F)nc2ccccc12)c1ccc(CCN2CCCC2=O)s1] | 1-(2-(5-(2-((2-(trifluoromethyl)quinazolin-4-yl)thio)acetyl)thiophen-2-yl)ethyl)pyrrolidin-2-one |

TABLE 1-continued

| Cpd # | Structure | Name |
|---|---|---|
| 27 | 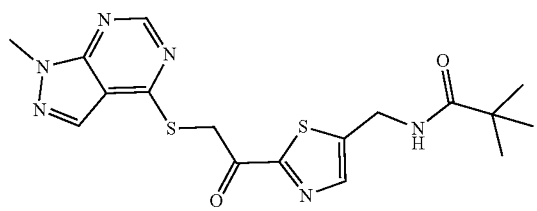 [SMILES: Cn1ncc2c(SCC(=O)c3ncc(CNC(=O)C(C)(C)C)s3)ncnc21] | N-((2-(2-((1-methyl-1H-pyrazolo[3,4-d]pyrimidin-4-yl)thio)acetyl)thiazol-5-yl)methyl)pivalamide |
| 28 | 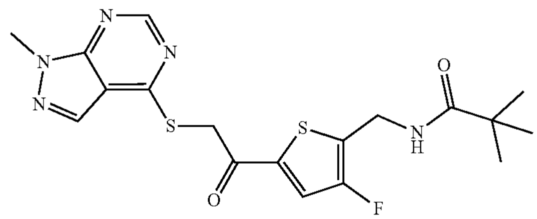 [SMILES: Cn1ncc2c(SCC(=O)c3cc(F)c(CNC(=O)C(C)(C)C)s3)ncnc21] | N-((3-fluoro-5-(2-((1-methyl-1H-pyrazolo[3,4-d]pyrimidin-4-yl)thio)acetyl)thiophen-2-yl)methyl)pivalamide |
| 29 | 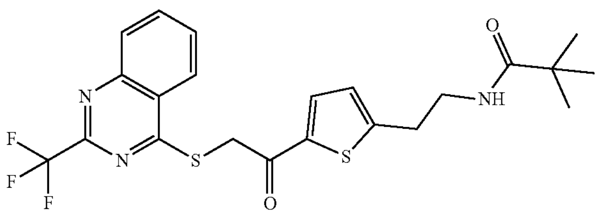 [SMILES: CC(C)(C)C(=O)NCCc1ccc(C(=O)CSc2nc(C(F)(F)F)nc3ccccc23)s1] | N-(2-(5-(2-((2-(trifluoromethyl)quinazolin-4-yl)thio)acetyl)thiophen-2-yl)ethyl)pivalamide |
| 30 | 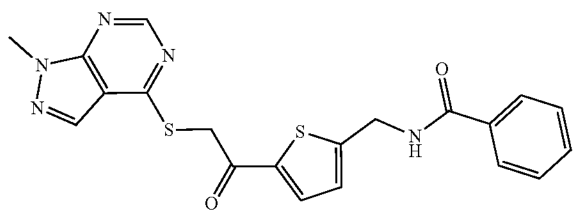 [SMILES: Cn1ncc2c(SCC(=O)c3ccc(CNC(=O)c4ccccc4)s3)ncnc21] | N-((5-(2-((1-methyl-1H-pyrazolo[3,4-d]pyrimidin-4-yl)thio)acetyl)thiophen-2-yl)methyl)benzamide |
| 31 | 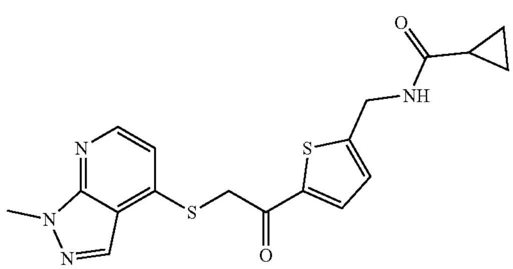 [SMILES: Cn1ncc2c(SCC(=O)c3ccc(CNC(=O)C4CC4)s3)ccnc21] | N-((5-(2-((1-methyl-1H-pyrazolo[3,4-d]pyrimidin-4-yl)thio)acetyl)thiophen-2-yl)methyl)cyclopropanecarboxamide |
| 32 | 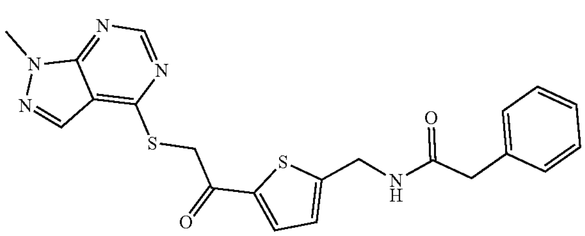 [SMILES: Cn1ncc2c(SCC(=O)c3ccc(CNC(=O)Cc4ccccc4)s3)ncnc21] | N-((5-(2-((1-methyl-1H-pyrazolo[3,4-d]pyrimidin-4-yl)thio)acetyl)thiophen-2-yl)methyl)-2-phenylacetamide |
| 33 | 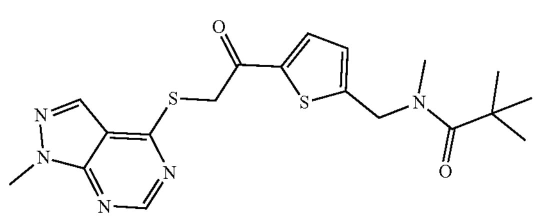 [SMILES: CN(Cc1ccc(C(=O)CSc2ncnc3c2cnn3C)s1)C(=O)C(C)(C)C] | N-methyl-N-((5-(2-((1-methyl-1H-pyrazolo[3,4-d]pyrimidin-4-yl)thio)acetyl)thiophen-2-yl)methyl)pivalamide |

TABLE 1-continued

| Cpd # | Structure | Name |
|---|---|---|
| 34 | 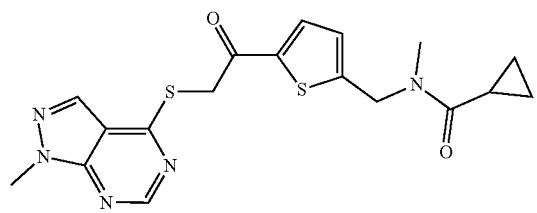 [SMILES: CN(Cc1ccc(C(=O)CSc2ncnc3c2cnn3C)s1)C(=O)C1CC1] | N-methyl-N-((5-(2-((1-methyl-1H-pyrazolo[3,4-d]pyrimidin-4-yl)thio)acetyl)thiophen-2-yl)methyl)cyclopropanecarboxamide |
| 35 | 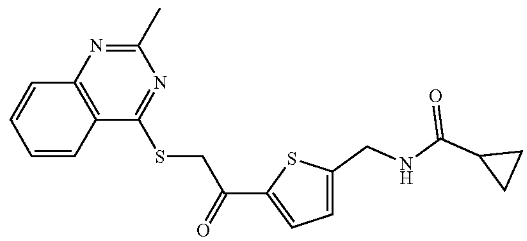 [SMILES: Cc1nc(SCC(=O)c2ccc(CNC(=O)C3CC3)s2)c2ccccc2n1] | N-((5-(2-((2-methylquinazolin-4-yl)thio)acetyl)thiophen-2-yl)methyl)cyclopropanecarboxamide |
| 36 | 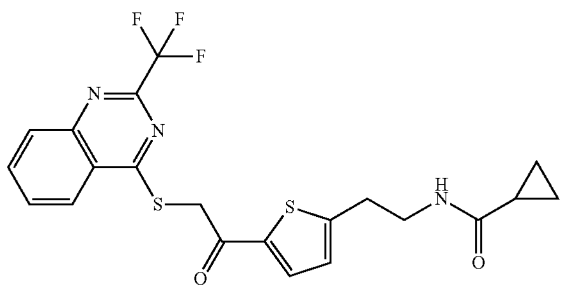 [SMILES: O=C(CSc1nc(C(F)(F)F)nc2ccccc12)c1ccc(CCNC(=O)C2CC2)s1] | N-(2-(5-(2-((2-(trifluoromethyl)quinazolin-4-yl)thio)acetyl)thiophen-2-yl)ethyl)cyclopropanecarboxamide |
| 37 | 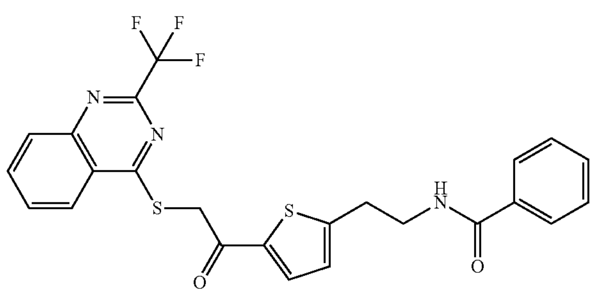 [SMILES: O=C(NCCc1ccc(C(=O)CSc2nc(C(F)(F)F)nc3ccccc23)s1)c1ccccc1] | N-(2-(5-(2-((2-(trifluoromethyl)quinazolin-4-yl)thio)acetyl)thiophen-2-yl)ethyl)benzamide |
| 38 | 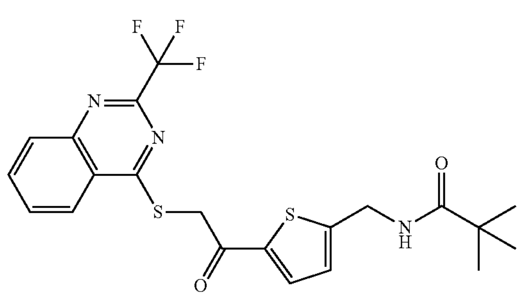 [SMILES: CC(C)(C)C(=O)NCc1ccc(C(=O)CSc2nc(C(F)(F)F)nc3ccccc23)s1] | N-((5-(2-((2-(trifluoromethyl)quinazolin-4-yl)thio)acetyl)thiophen-2-yl)methyl)pivalamide |
| 39 | 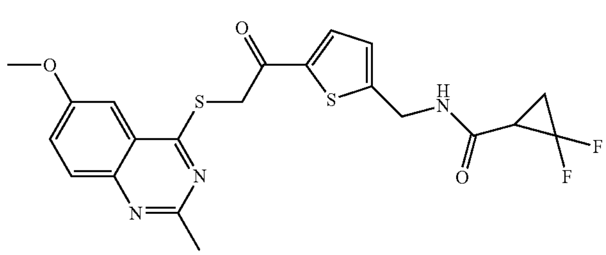 [SMILES: COc1ccc2nc(C)nc(SCC(=O)c3ccc(CNC(=O)C4CC4(F)F)s3)c2c1] | 2,2-difluoro-N-((5-(2-((6-methoxy-2-methylquinazolin-4-yl)thio)acetyl)thiophen-2-yl)methyl)cyclopropane-1-carboxamide |

TABLE 1-continued

| Cpd # | Structure | Name |
|---|---|---|
| 40 | 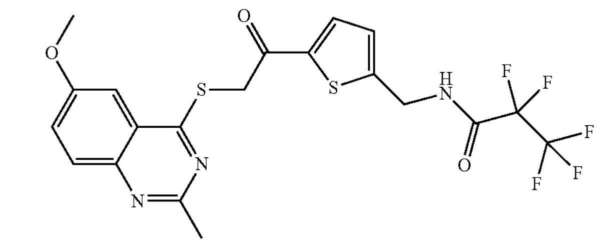 [SMILES: COc1ccc2nc(C)nc(SCC(=O)c3ccc(CNC(=O)C(F)(F)C(F)(F)F)s3)c2c1] | 2,2,3,3,3-pentafluoro-N-((5-(2-((6-methoxy-2-methylquinazolin-4-yl)thio)acetyl)thiophen-2-yl)methyl)propanamide |
| 41 | 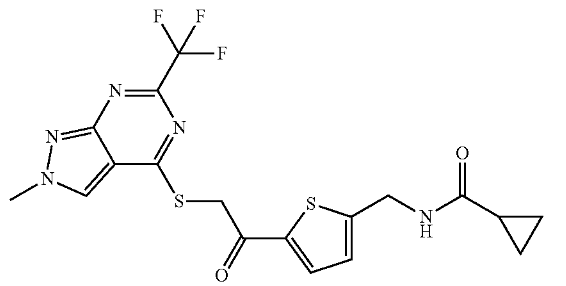 [SMILES: Cn1cc2c(SCC(=O)c3ccc(CNC(=O)C4CC4)s3)nc(C(F)(F)F)nc2n1] | N-((5-(2-((2-methyl-6-(trifluoromethyl)-2H-pyrazolo[3,4-d]pyrimidin-4-yl)thio)acetyl)thiophen-2-yl)methyl)cyclopropanecarboxamide |
| 42 | 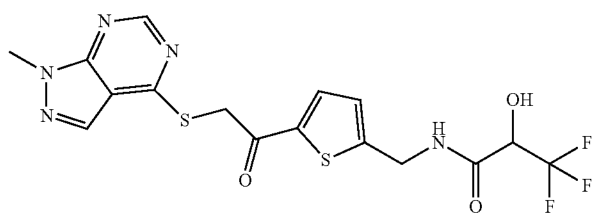 [SMILES: Cn1ncc2c(SCC(=O)c3ccc(CNC(=O)C(O)C(F)(F)F)s3)ncnc21] | 3,3,3-trifluoro-2-hydroxy-N-((5-(2-((1-methyl-1H-pyrazolo[3,4-d]pyrimidin-4-yl)thio)acetyl)thiophen-2-yl)methyl)propanamide |
| 43 | 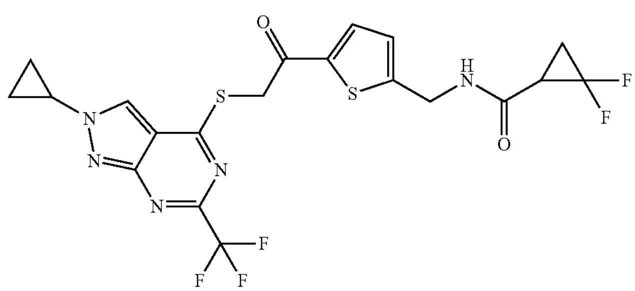 [SMILES: O=C(CSc1nc(C(F)(F)F)nc2nn(C3CC3)cc12)c1ccc(CNC(=O)C2CC2(F)F)s1] | N-((5-(2-((2-cyclopropyl-6-(trifluoromethyl)-2H-pyrazolo[3,4-d]pyrimidin-4-yl)thio)acetyl)thiophen-2-yl)methyl)-2,2-difluorocyclopropane-1-carboxamide |
| 44 | 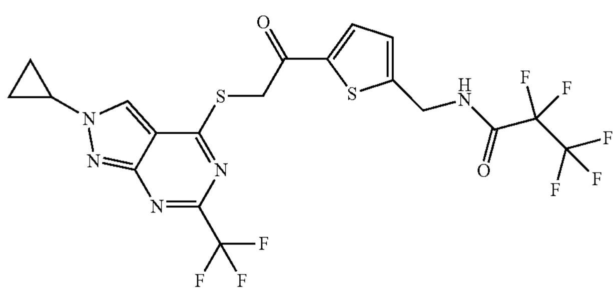 [SMILES: O=C(CSc1nc(C(F)(F)F)nc2nn(C3CC3)cc12)c1ccc(CNC(=O)C(F)(F)C(F)(F)F)s1] | N-((5-(2-((2-cyclopropyl-6-(trifluoromethyl)-2H-pyrazolo[3,4-d]pyrimidin-4-yl)thio)acetyl)thiophen-2-yl)methyl)-2,2,3,3,3-pentafluoropropanamide |
| 45 | 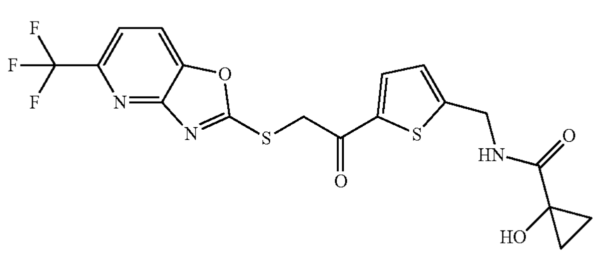 [SMILES: O=C(CSc1nc2nc(C(F)(F)F)ccc2o1)c1ccc(CNC(=O)C2(O)CC2)s1] | 1-hydroxy-N-((5-(2-((5-(trifluoromethyl)oxazolo[4,5-b]pyridin-2-yl)thio)acetyl)thiophen-2-yl)methyl)cyclopropane-1-carboxamide |

TABLE 1-continued

| Cpd # | Structure | Name |
|---|---|---|
| 46 | 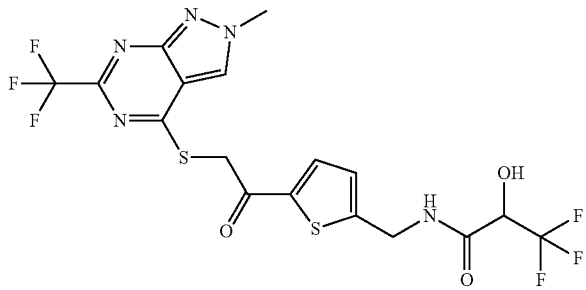 [SMILES: Cn1cc2c(SCC(=O)c3ccc(CNC(=O)C(O)C(F)(F)F)s3)nc(C(F)(F)F)nc2n1] | 3,3,3-trifluoro-2-hydroxy-N-((5-(2-((2-methyl-6-(trifluoromethyl)-2H-pyrazolo[3,4-d]pyrimidin-4-yl)thio)acetyl)thiophen-2-yl)methyl)propanamide |
| 47 | 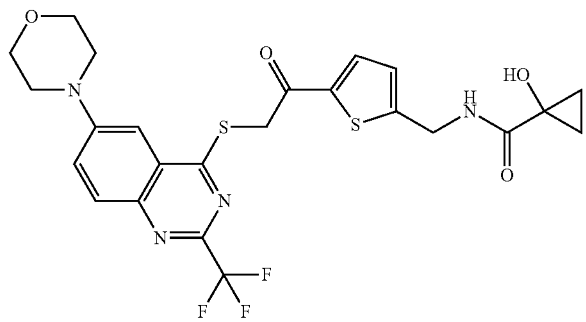 [SMILES: O=C(CSc1nc(C(F)(F)F)nc2ccc(N3CCOCC3)cc12)c1ccc(CNC(=O)C2(O)CC2)s1] | 1-hydroxy-N-((5-(2-((6-morpholino-2-(trifluoromethyl)quinazolin-4-yl)thio)acetyl)thiophen-2-yl)methyl)cyclopropane-1-carboxamide |
| 48 | 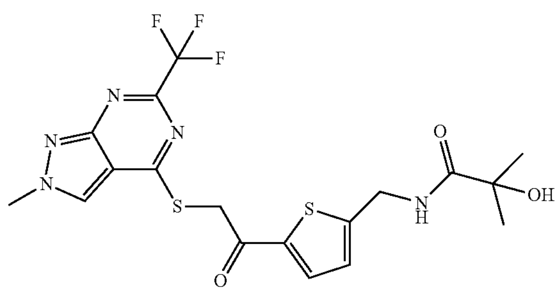 [SMILES: Cn1cc2c(SCC(=O)c3ccc(CNC(=O)C(C)(C)O)s3)nc(C(F)(F)F)nc2n1] | 2-hydroxy-2-methyl-N-((5-(2-((2-methyl-6-(trifluoromethyl)-2H-pyrazolo[3,4-d]pyrimidin-4-yl)thio)acetyl)thiophen-2-yl)methyl)propanamide |
| 49 | 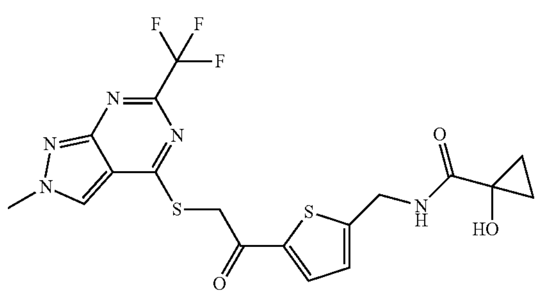 [SMILES: Cn1cc2c(SCC(=O)c3ccc(CNC(=O)C4(O)CC4)s3)nc(C(F)(F)F)nc2n1] | 1-hydroxy-N-((5-(2-((2-methyl-6-(trifluoromethyl)-2H-pyrazolo[3,4-d]pyrimidin-4-yl)thio)acetyl)thiophen-2-yl)methyl)cyclopropane-1-carboxamide |
| 50 | 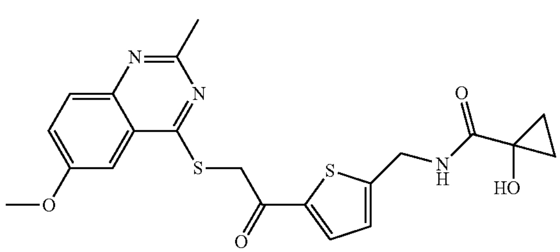 [SMILES: COc1ccc2nc(C)nc(SCC(=O)c3ccc(CNC(=O)C4(O)CC4)s3)c2c1] | 1-hydroxy-N-((5-(2-((6-methoxy-2-methylquinazolin-4-yl)thio)acetyl)thiophen-2-yl)methyl)cyclopropane-1-carboxamide |

TABLE 1-continued

| Cpd # | Structure | Name |
|---|---|---|
| 51 | 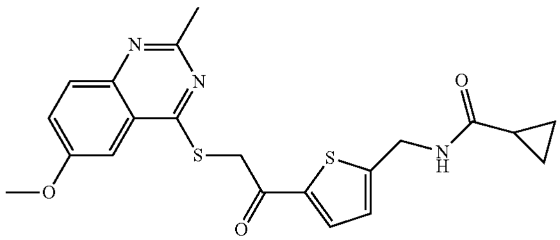 [SMILES: COc1ccc2nc(C)nc(SCC(=O)c3ccc(CNC(=O)C4CC4)s3)c2c1] | N-((5-(2-((6-methoxy-2-methylquinazolin-4-yl)thio)acetyl)thiophen-2-yl)methyl)cyclopropanecarboxamide |
| 52 | 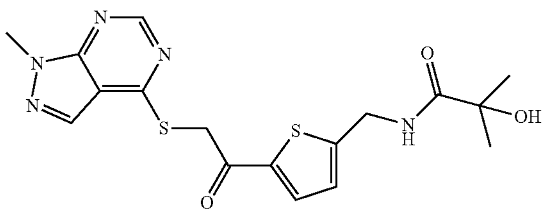 [SMILES: Cn1ncc2c(SCC(=O)c3ccc(CNC(=O)C(C)(C)O)s3)ncnc21] | 2-hydroxy-2-methyl-N-((5-(2-((1-methyl-1H-pyrazolo[3,4-d]pyrimidin-4-yl)thio)acetyl)thiophen-2-yl)methyl)propanamide |
| 55 | 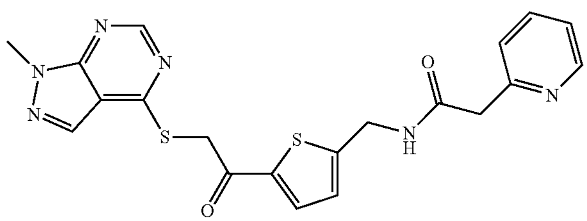 | N-((5-(2-((1-methyl-1H-pyrazolo[3,4-d]pyrimidin-4-yl)thio)acetyl)thiophen-2-yl)methyl)-2-(pyridin-2-yl)acetamide |
| 56 | 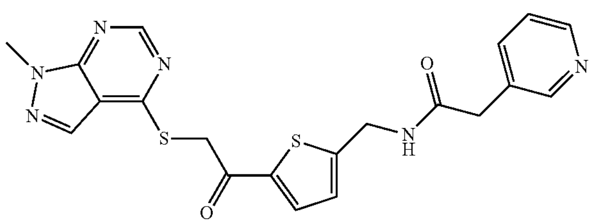 [SMILES: Cn1ncc2c(SCC(=O)c3ccc(CNC(=O)Cc4cccnc4)s3)ncnc21] | N-((5-(2-((1-methyl-1H-pyrazolo[3,4-d]pyrimidin-4-yl)thio)acetyl)thiophen-2-yl)methyl)-2-(pyridin-3-yl)acetamide |
| 57 | 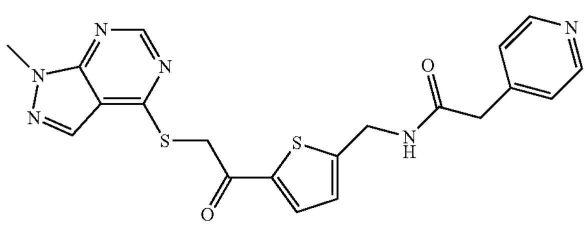 [SMILES: Cn1ncc2c(SCC(=O)c3ccc(CNC(=O)Cc4ccncc4)s3)ncnc21] | N-((5-(2-((1-methyl-1H-pyrazolo[3,4-d]pyrimidin-4-yl)thio)acetyl)thiophen-2-yl)methyl)-2-(pyridin-4-yl)acetamide |
| 58 | 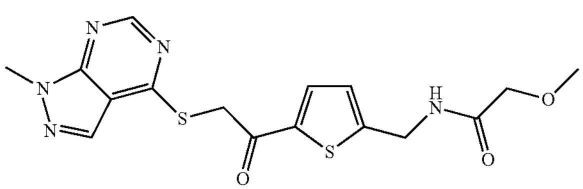 | 2-methoxy-N-((5-(2-((1-methyl-1H-pyrazolo[3,4-d]pyrimidin-4-yl)thio)acetyl)thiophen-2-yl)methyl)acetamide |

TABLE 1-continued

| Cpd # | Structure | Name |
|---|---|---|
| 59 | 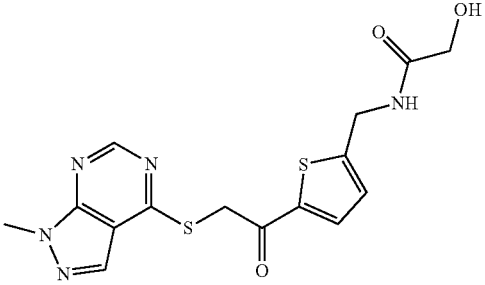 [SMILES: Cn1ncc2c(SCC(=O)c3ccc(CNC(=O)CO)s3)ncnc21] | 2-hydroxy-N-((5-(2-((1-methyl-1H-pyrazolo[3,4-d]pyrimidin-4-yl)thio)acetyl)thiophen-2-yl)methyl)acetamide |
| 60 | 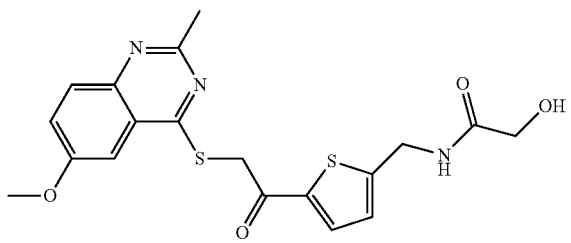 [SMILES: COc1ccc2nc(C)nc(SCC(=O)c3ccc(CNC(=O)CO)s3)c2c1] | 2-hydroxy-N-((5-(2-((6-methoxy-2-methylquinazolin-4-yl)thio)acetyl)thiophen-2-yl)methyl)acetamide |
| 61 | 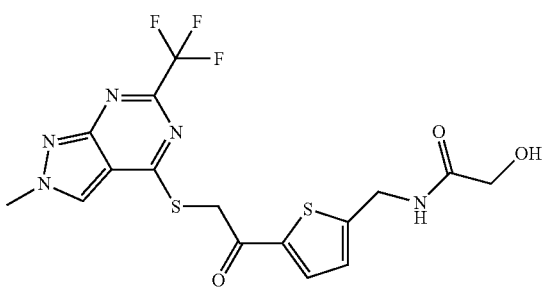 [SMILES: Cn1cc2c(SCC(=O)c3ccc(CNC(=O)CO)s3)nc(C(F)(F)F)nc2n1] | 2-hydroxy-N-((5-(2-((2-methyl-6-(trifluoromethyl)-2H-pyrazolo[3,4-d]pyrimidin-4-yl)thio)acetyl)thiophen-2-yl)methyl)acetamide |
| 62 | 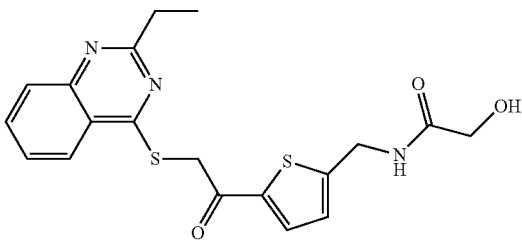 [SMILES: CCc1nc(SCC(=O)c2ccc(CNC(=O)CO)s2)c2ccccc2n1] | N-((5-(2-((2-ethylquinazolin-4-yl)thio)acetyl)thiophen-2-yl)methyl)-2-hydroxyacetamide |
| 63 | 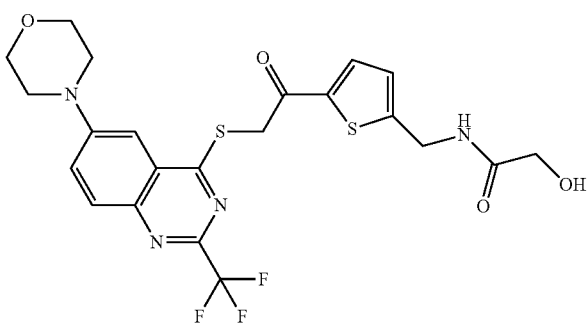 [SMILES: O=C(CO)NCc1ccc(C(=O)CSc2nc(C(F)(F)F)nc3ccc(N4CCOCC4)cc23)s1] | 2-hydroxy-N-((5-(2-((6-morpholino-2-(trifluoromethyl)quinazolin-4-yl)thio)acetyl)thiophen-2-yl)methyl)acetamide |

TABLE 1-continued

| Cpd # | Structure | Name |
|---|---|---|
| 64 | 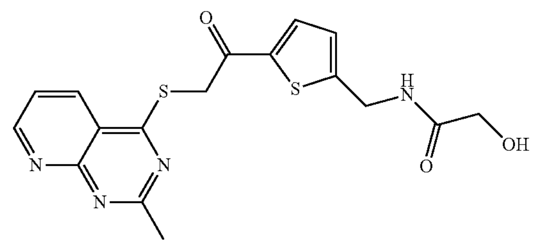 [SMILES: Cc1nc(SCC(=O)c2ccc(CNC(=O)CO)s2)c2cccnc2n1] | 2-hydroxy-N-((5-(2-((2-methylpyrido[2,3-d]pyrimidin-4-yl)thio)acetyl)thiophen-2-yl)methyl)acetamide |
| 65 | 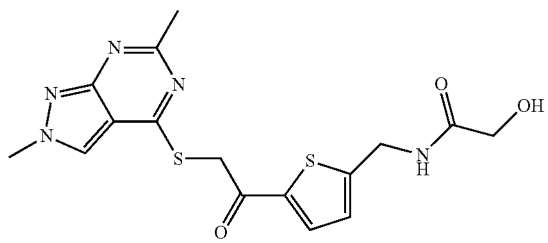 [SMILES: Cc1nc(SCC(=O)c2ccc(CNC(=O)CO)s2)c2cn(C)nc2n1] | N-((5-(2-((2,6-dimethyl-2H-pyrazolo[3,4-d]pyrimidin-4-yl)thio)acetyl)thiophen-2-yl)methyl)-2-hydroxyacetamide |
| 66 | 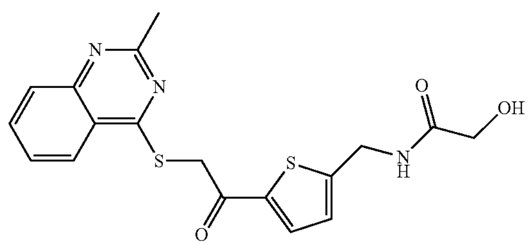 [SMILES: Cc1nc(SCC(=O)c2ccc(CNC(=O)CO)s2)c2ccccc2n1] | 2-hydroxy-N-((5-(2-((2-methylquinazolin-4-yl)thio)acetyl)thiophen-2-yl)methyl)acetamide |
| 67 | 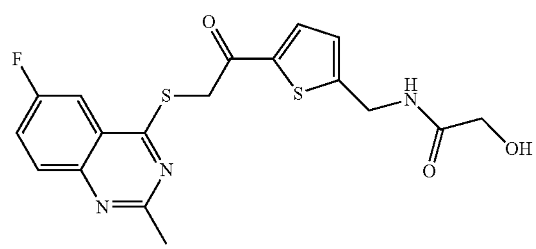 [SMILES: Cc1nc(SCC(=O)c2ccc(CNC(=O)CO)s2)c2cc(F)ccc2n1] | N-((5-(2-((6-fluoro-2-methylquinazolin-4-yl)thio)acetyl)thiophen-2-yl)methyl)-2-hydroxyacetamide |
| 68 | 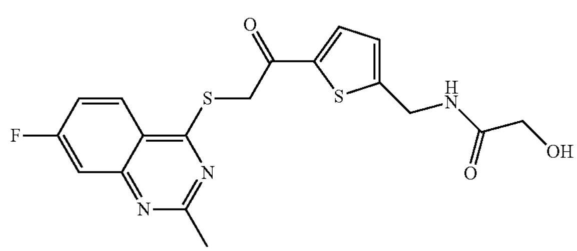 [SMILES: Cc1nc(SCC(=O)c2ccc(CNC(=O)CO)s2)c2ccc(F)cc2n1] | N-((5-(2-((7-fluoro-2-methylquinazolin-4-yl)thio)acetyl)thiophen-2-yl)methyl)-2-hydroxyacetamide |
| 69 | 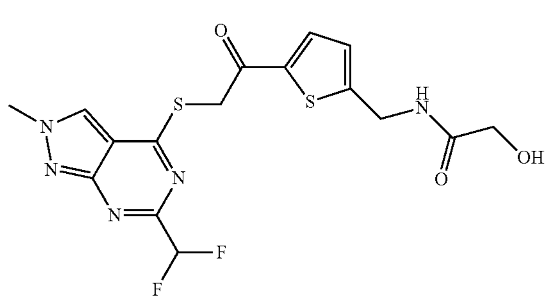 [SMILES: Cn1cc2c(SCC(=O)c3ccc(CNC(=O)CO)s3)nc(C(F)F)nc2n1] | N-((5-(2-((6-(difluoromethyl)-2-methyl-2H-pyrazolo[3,4-d]pyrimidin-4-yl)thio)acetyl)thiophen-2-yl)methyl)-2-hydroxyacetamide |

TABLE 1-continued

| Cpd # | Structure | Name |
|---|---|---|
| 70 | 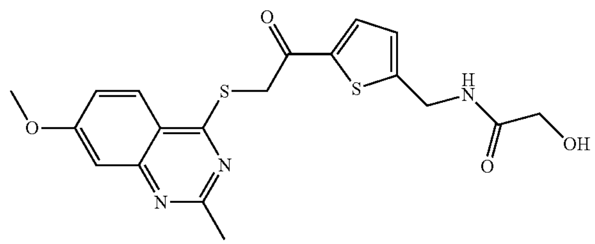 [SMILES: COc1ccc2c(SCC(=O)c3ccc(CNC(=O)CO)s3)nc(C)nc2c1] | 2-hydroxy-N-((5-(2-((7-methoxy-2-methylquinazolin-4-yl)thio)acetyl)thiophen-2-yl)methyl)acetamide |
| 71 | 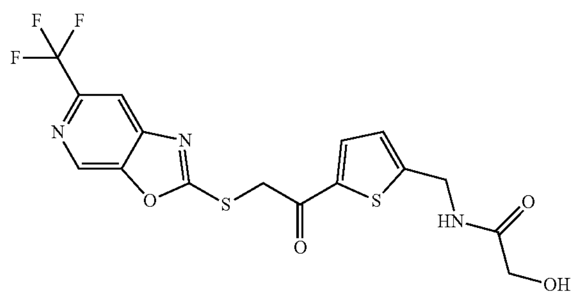 [SMILES: O=C(CO)NCc1ccc(C(=O)CSc2nc3cc(C(F)(F)F)ncc3o2)s1] | 2-hydroxy-N-((5-(2-((6-(trifluoromethyl)oxazolo[5,4-c]pyridin-2-yl)thio)acetyl)thiophen-2-yl)methyl)acetamide |
| 72 | 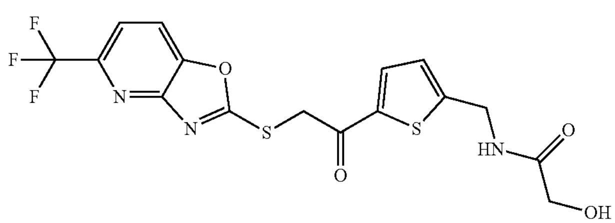 [SMILES: O=C(CO)NCc1ccc(C(=O)CSc2nc3nc(C(F)(F)F)ccc3o2)s1] | 2-hydroxy-N-((5-(2-((5-(trifluoromethyl)oxazolo[4,5-b]pyridin-2-yl)thio)acetyl)thiophen-2-yl)methyl)acetamide |
| 73 | 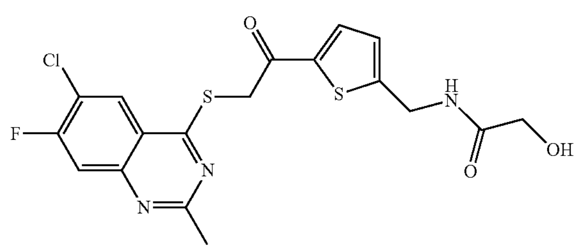 [SMILES: Cc1nc(SCC(=O)c2ccc(CNC(=O)CO)s2)c2cc(Cl)c(F)cc2n1] | N-((5-(2-((6-chloro-7-fluoro-2-methylquinazolin-4-yl)thio)acetyl)thiophen-2-yl)methyl)-2-hydroxyacetamide |
| 74 | 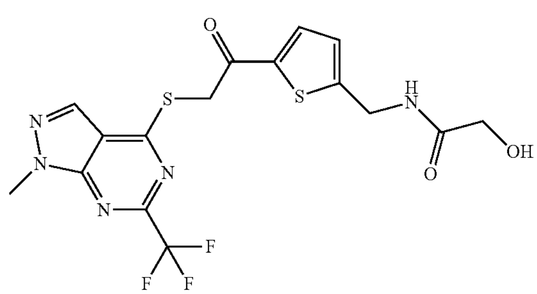 [SMILES: Cn1ncc2c(SCC(=O)c3ccc(CNC(=O)CO)s3)nc(C(F)(F)F)nc21] | 2-hydroxy-N-((5-(2-((1-methyl-6-(trifluoromethyl)-1H-pyrazolo[3,4-d]pyrimidin-4-yl)thio)acetyl)thiophen-2-yl)methyl)acetamide |
| 75 | 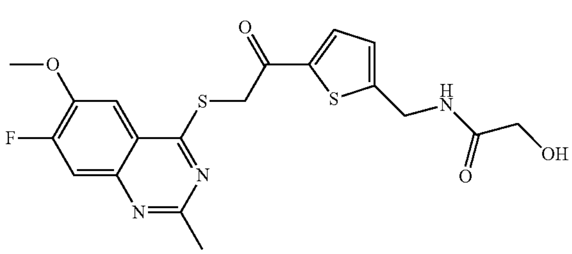 [SMILES: COc1cc2c(SCC(=O)c3ccc(CNC(=O)CO)s3)nc(C)nc2cc1F] | N-((5-(2-((7-fluoro-6-methoxy-2-methylquinazolin-4-yl)thio)acetyl)thiophen-2-yl)methyl)-2-hydroxyacetamide |

TABLE 1-continued

| Cpd # | Structure | Name |
|---|---|---|
| 76 | 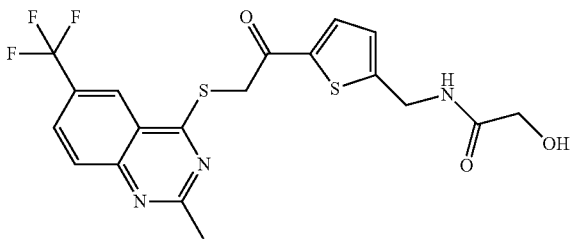 [SMILES: Cc1nc(SCC(=O)c2ccc(CNC(=O)CO)s2)c2cc(C(F)(F)F)ccc2n1] | 2-hydroxy-N-((5-(2-((2-methyl-6-(trifluoromethyl)quinazolin-4-yl)thio)acetyl)thiophen-2-yl)methyl)acetamide |
| 77 | 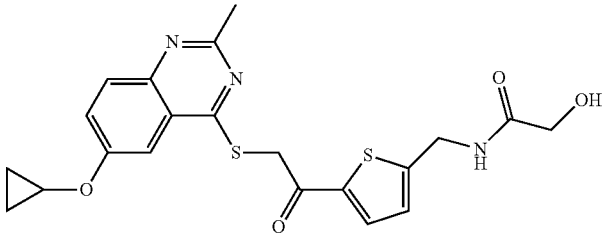 [SMILES: Cc1nc(SCC(=O)c2ccc(CNC(=O)CO)s2)c2cc(OC3CC3)ccc2n1] | N-((5-(2-((6-cyclopropoxy-2-methylquinazolin-4-yl)thio)acetyl)thiophen-2-yl)methyl)-2-hydroxyacetamide |
| 78 | 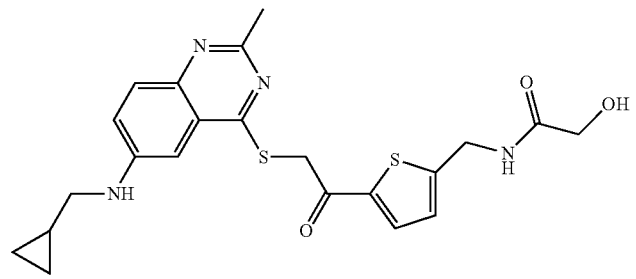 [SMILES: Cc1nc(SCC(=O)c2ccc(CNC(=O)CO)s2)c2cc(NCC3CC3)ccc2n1] | N-((5-(2-((6-((cyclopropylmethyl)amino)-2-methylquinazolin-4-yl)thio)acetyl)thiophen-2-yl)methyl)-2-hydroxyacetamide |
| 79 | 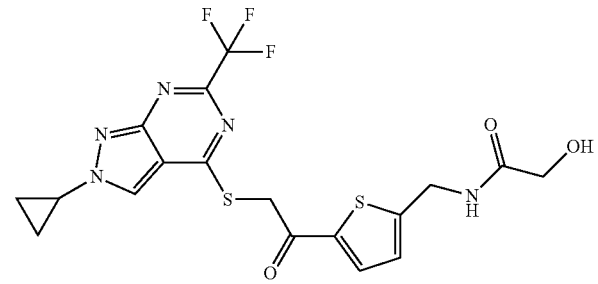 [SMILES: O=C(CO)NCc1ccc(C(=O)CSc2nc(C(F)(F)F)nc3nn(C4CC4)cc23)s1] | N-((5-(2-((2-cyclopropyl-6-(trifluoromethyl)-2H-pyrazolo[3,4-d]pyrimidin-4-yl)thio)acetyl)thiophen-2-yl)methyl)-2-hydroxyacetamide |
| 80 | 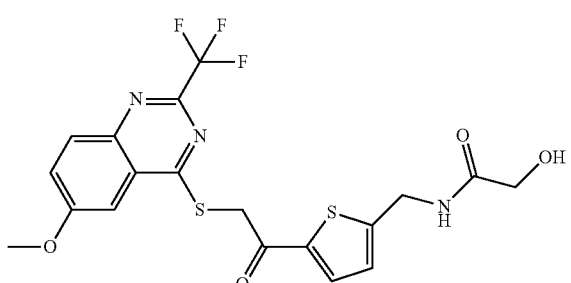 | 2-hydroxy-N-((5-(2-((6-methoxy-2-(trifluoromethyl)quinazolin-4-yl)thio)acetyl)thiophen-2-yl)methyl)acetamide |

TABLE 1-continued

| Cpd # | Structure | Name |
|---|---|---|
| 81 | 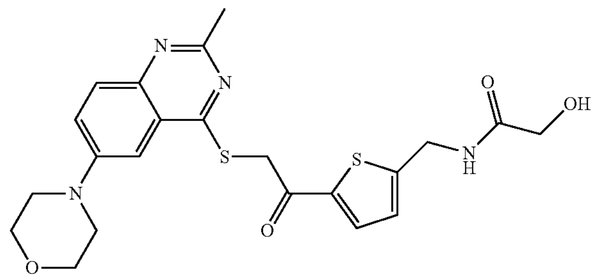 [SMILES: Cc1nc(SCC(=O)c2ccc(CNC(=O)CO)s2)c2cc(N3CCOCC3)ccc2n1] | 2-hydroxy-N-((5-(2-((2-methyl-6-morpholinoquinazolin-4-yl)thio)acetyl)thiophen-2-yl)methyl)acetamide |
| 82 | 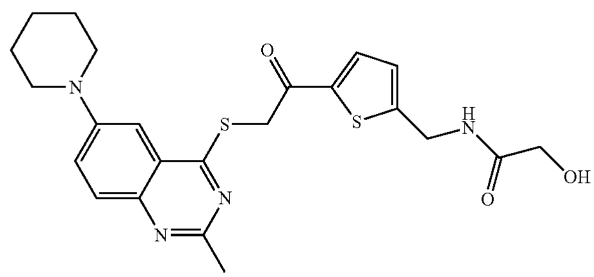 [SMILES: Cc1nc(SCC(=O)c2ccc(CNC(=O)CO)s2)c2cc(N3CCCCC3)ccc2n1] | 2-hydroxy-N-((5-(2-((2-methyl-6-(piperidin-1-yl)quinazolin-4-yl)thio)acetyl)thiophen-2-yl)methyl)acetamide |
| 83 | 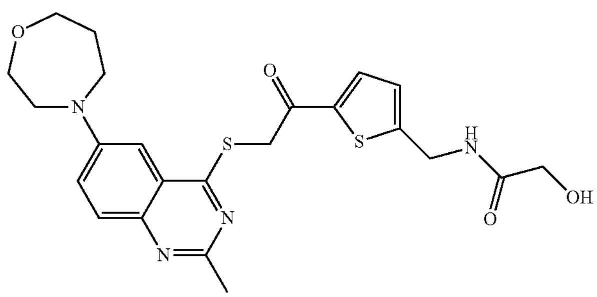 [SMILES: Cc1nc(SCC(=O)c2ccc(CNC(=O)CO)s2)c2cc(N3CCCOCC3)ccc2n1] | 2-hydroxy-N-((5-(2-((2-methyl-6-(1,4-oxazepan-4-yl)quinazolin-4-yl)thio)acetyl)thiophen-2-yl)methyl)acetamide |
| 84 | 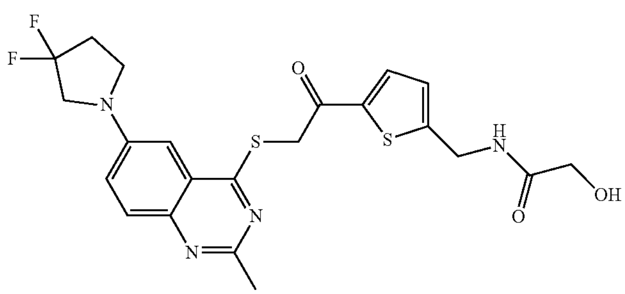 [SMILES: Cc1nc(SCC(=O)c2ccc(CNC(=O)CO)s2)c2cc(N3CCC(F)(F)C3)ccc2n1] | N-((5-(2-((6-(3,3-difluoropyrrolidin-1-yl)-2-methylquinazolin-4-yl)thio)acetyl)thiophen-2-yl)methyl)-2-hydroxyacetamide |
| 85 | 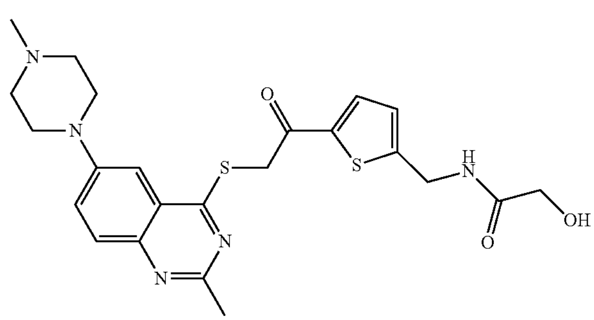 [SMILES: Cc1nc(SCC(=O)c2ccc(CNC(=O)CO)s2)c2cc(N3CCN(C)CC3)ccc2n1] | 2-hydroxy-N-((5-(2-((2-methyl-6-(4-methylpiperazin-1-yl)quinazolin-4-yl)thio)acetyl)thiophen-2-yl)methyl)acetamide |

TABLE 1-continued

| Cpd # | Structure | Name |
|---|---|---|
| 86 | 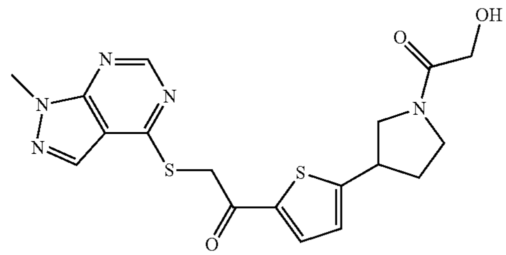 [SMILES: Cn1ncc2c(SCC(=O)c3ccc(C4CCN(C(=O)CO)C4)s3)ncnc21] | 2-hydroxy-1-(3-(5-(2-((1-methyl-1H-pyrazolo[3,4-d]pyrimidin-4-yl)thio)acetyl)thiophen-2-yl)pyrrolidin-1-yl)ethan-1-one |
| 87 | 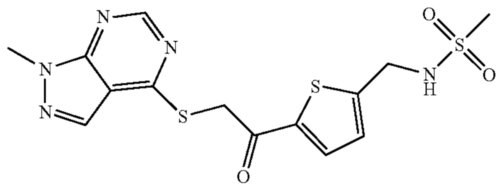 [SMILES: Cn1ncc2c(SCC(=O)c3ccc(CNS(C)(=O)=O)s3)ncnc21] | N-((5-(2-((1-methyl-1H-pyrazolo[3,4-d]pyrimidin-4-yl)thio)acetyl)thiophen-2-yl)methyl)methanesulfonamide |
| 88 | 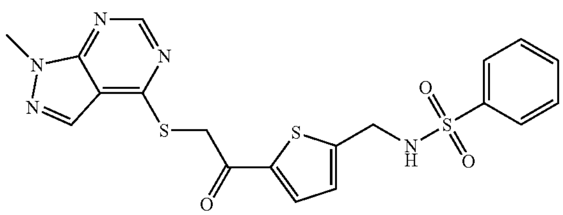 [SMILES: Cn1ncc2c(SCC(=O)c3ccc(CNS(=O)(=O)c4ccccc4)s3)ncnc21] | N-((5-(2-((1-methyl-1H-pyrazolo[3,4-d]pyrimidin-4-yl)thio)acetyl)thiophen-2-yl)methyl)benzenesulfonamide |
| 89 | 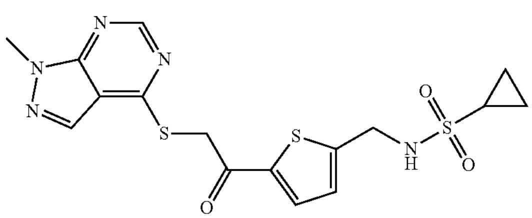 [SMILES: Cn1ncc2c(SCC(=O)c3ccc(CNS(=O)(=O)C4CC4)s3)ncnc21] | N-((5-(2-((1-methyl-1H-pyrazolo[3,4-d]pyrimidin-4-yl)thio)acetyl)thiophen-2-yl)methyl)cyclopropanesulfonamide |
| 90 | 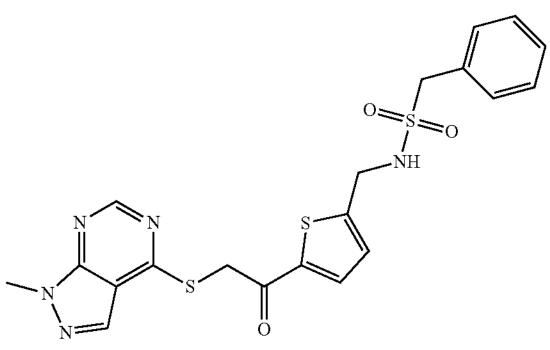 [SMILES: Cn1ncc2c(SCC(=O)c3ccc(CNS(=O)(=O)Cc4ccccc4)s3)ncnc21] | N-((5-(2-((1-methyl-1H-pyrazolo[3,4-d]pyrimidin-4-yl)thio)acetyl)thiophen-2-yl)methyl)-1-phenylmethanesulfonamide |
| 91 | 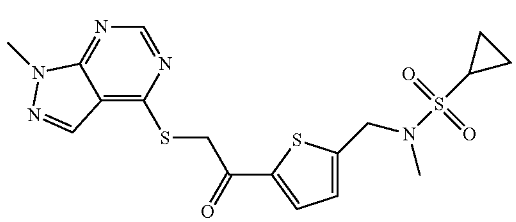 [SMILES: CN(Cc1ccc(C(=O)CSc2ncnc3c2cnn3C)s1)S(=O)(=O)C1CC1] | N-methyl-N-((5-(2-((1-methyl-1H-pyrazolo[3,4-d]pyrimidin-4-yl)thio)acetyl)thiophen-2-yl)methyl)cyclopropanesulfonamide |

TABLE 1-continued

| Cpd # | Structure | Name |
|---|---|---|
| 92 | 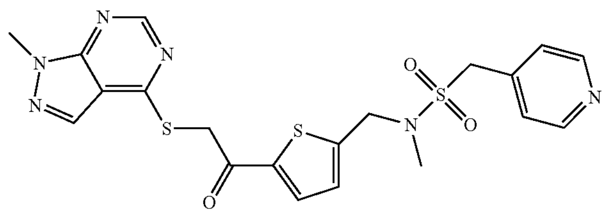 [SMILES: CN(Cc1ccc(C(=O)CSc2ncnc3c2cnn3C)s1)S(=O)(=O)Cc1ccncc1] | N-methyl-N-((5-(2-((1-methyl-1H-pyrazolo[3,4-d]pyrimidin-4-yl)thio)acetyl)thiophen-2-yl)methyl)-1-(pyridin-4-yl)methanesulfonamide |
| 93 | 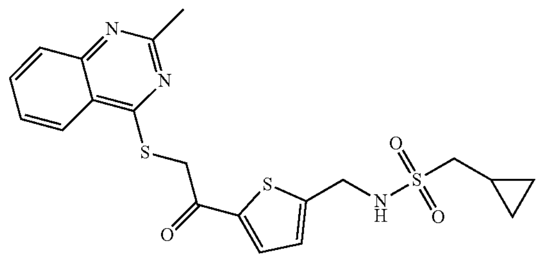 [SMILES: Cc1nc(SCC(=O)c2ccc(CNS(=O)(=O)CC3CC3)s2)c2ccccc2n1] | 1-cyclopropyl-N-((5-(2-((2-methylquinazolin-4-yl)thio)acetyl)thiophen-2-yl)methyl)methanesulfonamide |
| 94 | 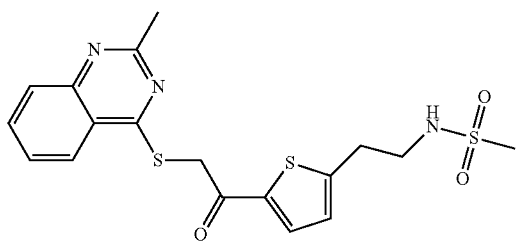 [SMILES: Cc1nc(SCC(=O)c2ccc(CCNS(C)(=O)=O)s2)c2ccccc2n1] | N-(2-(5-(2-((2-methylquinazolin-4-yl)thio)acetyl)thiophen-2-yl)ethyl)methanesulfonamide |
| 95 | 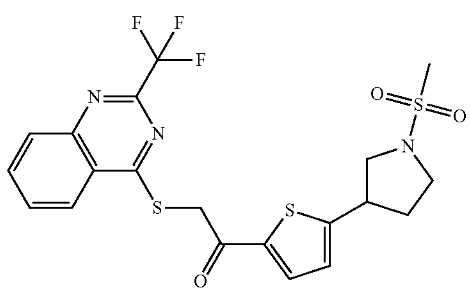 [SMILES: CS(=O)(=O)N1CCC(c2ccc(C(=O)CSc3nc(C(F)(F)F)nc4ccccc34)s2)C1] | 1-(5-(1-(methylsulfonyl)pyrrolidin-3-yl)thiophen-2-yl)-2-((2-(trifluoromethyl)quinazolin-4-yl)thio)ethan-1-one |
| 96 | 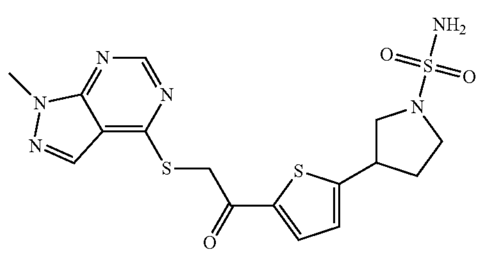 [SMILES: Cn1ncc2c(SCC(=O)c3ccc(C4CCN(S(N)(=O)=O)C4)s3)ncnc21] | 3-(5-(2-((1-methyl-1H-pyrazolo[3,4-d]pyrimidin-4-yl)thio)acetyl)thiophen-2-yl)pyrrolidine-1-sulfonamide |
| 97 | 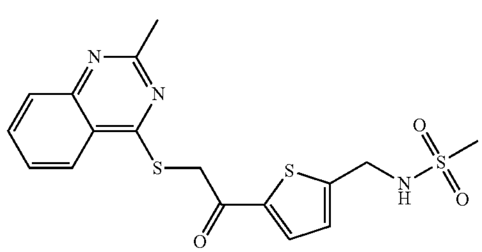 [SMILES: Cc1nc(SCC(=O)c2ccc(CNS(C)(=O)=O)s2)c2ccccc2n1] | N-((5-(2-((2-methylquinazolin-4-yl)thio)acetyl)thiophen-2-yl)methyl)methanesulfonamide |

TABLE 1-continued

| Cpd # | Structure | Name |
|---|---|---|
| 98 | 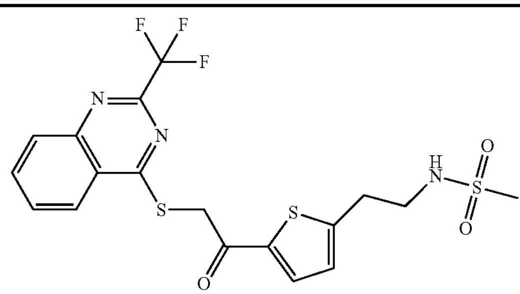 | N-(2-(5-(2-((2-(trifluoromethyl)quinazolin-4-yl)thio)acetyl)thiophen-2-yl)ethyl)methanesulfonamide |
| 105 | 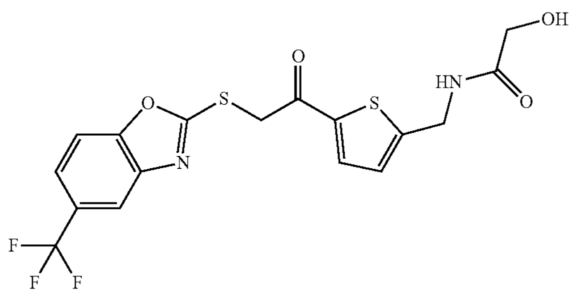 [SMILES: O=C(CO)NCc1ccc(C(=O)CSc2nc3cc(C(F)(F)F)ccc3o2)s1] | 2-hydroxy-N-((5-(2-((5-(trifluoromethyl)benzo[d]oxazol-2-yl)thio)acetyl)thiophen-2-yl)methyl)acetamide |
| 106 | 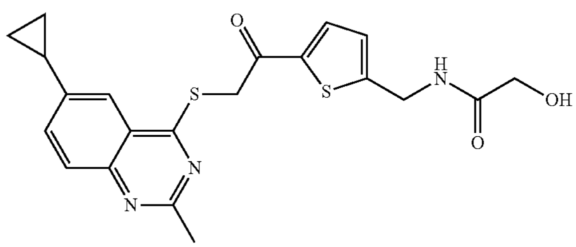 [SMILES: Cc1nc(SCC(=O)c2ccc(CNC(=O)CO)s2)c2cc(C3CC3)ccc2n1] | N-((5-(2-((6-cyclopropyl-2-methylquinazolin-4-yl)thio)acetyl)thiophen-2-yl)methyl)-2-hydroxyacetamide |
| 107 | 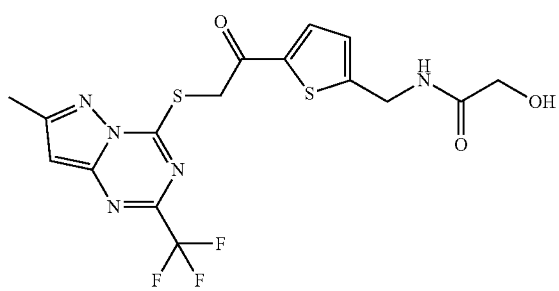 [SMILES: Cc1cc2nc(C(F)(F)F)nc(SCC(=O)c3ccc(CNC(=O)CO)s3)n2n1] | 2-hydroxy-N-((5-(2-((7-methyl-2-(trifluoromethyl)pyrazolo[1,5-a][1,3,5]triazin-4-yl)thio)acetyl)thiophen-2-yl)methyl)acetamide |
| 108 | 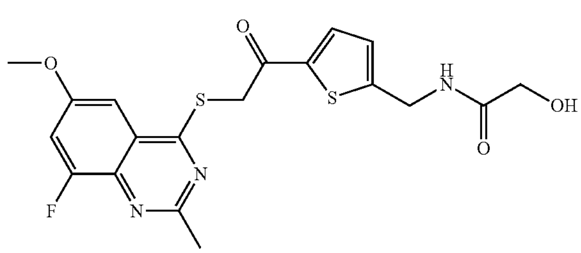 [SMILES: COc1cc(F)c2nc(C)nc(SCC(=O)c3ccc(CNC(=O)CO)s3)c2c1] | N-((5-(2-((8-fluoro-6-methoxy-2-methylquinazolin-4-yl)thio)acetyl)thiophen-2-yl)methyl)-2-hydroxyacetamide |
| 109 | 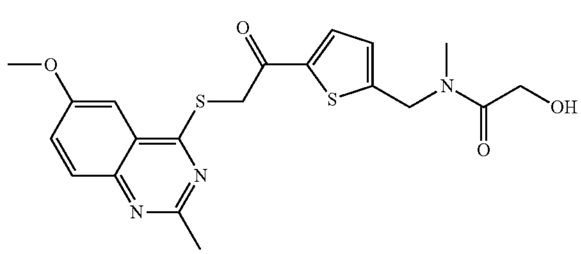 [SMILES: COc1ccc2nc(C)nc(SCC(=O)c3ccc(CN(C)C(=O)CO)s3)c2c1] | 2-hydroxy-N-((5-(2-((6-methoxy-2-methylquinazolin-4-yl)thio)acetyl)thiophen-2-yl)methyl)-N-methylacetamide |

TABLE 1-continued

| Cpd # | Structure | Name |
|---|---|---|
| 110 | 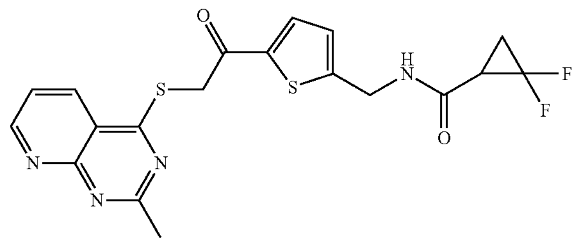 [SMILES: Cc1nc(SCC(=O)c2ccc(CNC(=O)C3CC3(F)F)s2)c2cccnc2n1] | 2,2-difluoro-N-((5-(2-((2-methylpyrido[2,3-d]pyrimidin-4-yl)thio)acetyl)thiophen-2-yl)methyl)cyclopropane-1-carboxamide |
| 111 | 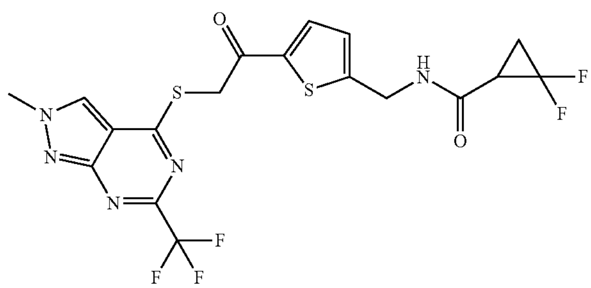 [SMILES: Cn1cc2c(SCC(=O)c3ccc(CNC(=O)C4CC4(F)F)s3)nc(C(F)(F)F)nc2n1] | 2,2-difluoro-N-((5-(2-((2-methyl-6-(trifluoromethyl)-2H-pyrazolo[3,4-d]pyrimidin-4-yl)thio)acetyl)thiophen-2-yl)methyl)cyclopropane-1-carboxamide |
| 112 | 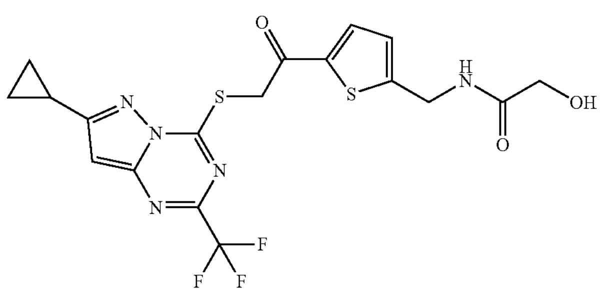 [SMILES: O=C(CO)NCc1ccc(C(=O)CSc2nc(C(F)(F)F)nc3cc(C4CC4)nn23)s1] | N-((5-(2-((7-cyclopropyl-2-(trifluoromethyl)pyrazolo[1,5-a][1,3,5]triazin-4-yl)thio)acetyl)thiophen-2-yl)methyl)-2-hydroxyacetamide |
| 113 | 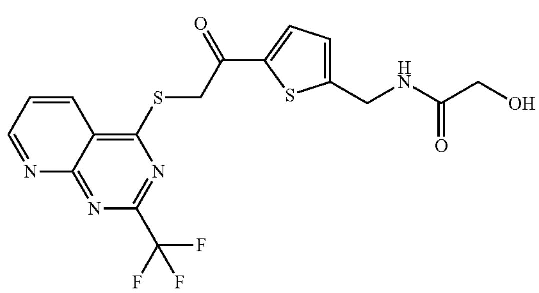 [SMILES: O=C(CO)NCc1ccc(C(=O)CSc2nc(C(F)(F)F)nc3ncccc23)s1] | 2-hydroxy-N-((5-(2-((2-(trifluoromethyl)pyrido[2,3-d]pyrimidin-4-yl)thio)acetyl)thiophen-2-yl)methyl)acetamide |
| 114 | 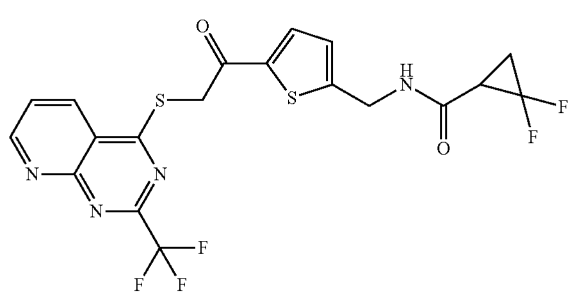 [SMILES: O=C(CSc1nc(C(F)(F)F)nc2ncccc12)c1ccc(CNC(=O)C2CC2(F)F)s1] | 2,2-difluoro-N-((5-(2-((2-(trifluoromethyl)pyrido[2,3-d]pyrimidin-4-yl)thio)acetyl)thiophen-2-yl)methyl)cyclopropane-1-carboxamide |

TABLE 1-continued

| Cpd # | Structure | Name |
|---|---|---|
| 115 | 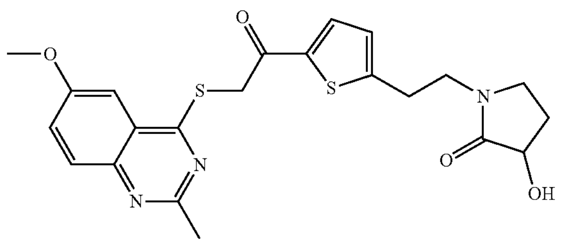 [SMILES: COc1ccc2nc(C)nc(SCC(=O)c3ccc(CCN4CCC(O)C4=O)s3)c2c1] | 3-hydroxy-1-(2-(5-(2-((6-methoxy-2-methylquinazolin-4-yl)thio)acetyl)thiophen-2-yl)ethyl)pyrrolidin-2-one |
| 116 | 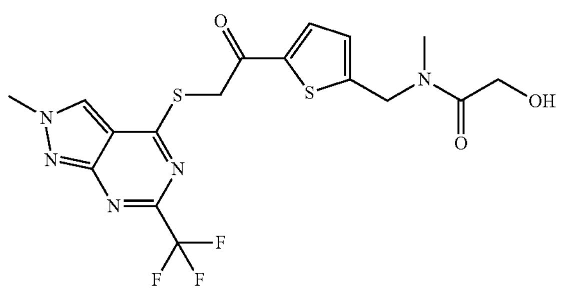 [SMILES: CN(Cc1ccc(C(=O)CSc2nc(C(F)(F)F)nc3nn(C)cc23)s1)C(=O)CO] | 2-hydroxy-N-methyl-N-((5-(2-((2-methyl-6-(trifluoromethyl)-2H-pyrazolo[3,4-d]pyrimidin-4-yl)thio)acetyl)thiophen-2-yl)methyl)acetamide |
| 117 | 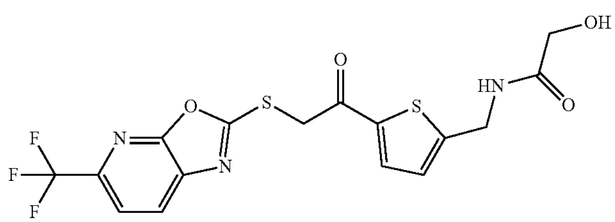 [SMILES: O=C(CO)NCc1ccc(C(=O)CSc2nc3ccc(C(F)(F)F)nc3o2)s1] | 2-hydroxy-N-((5-(2-((5-(trifluoromethyl)oxazolo[5,4-b]pyridin-2-yl)thio)acetyl)thiophen-2-yl)methyl)acetamide |
| 118 | 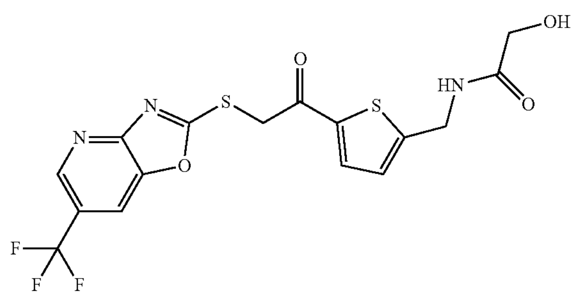 [SMILES: O=C(CO)NCc1ccc(C(=O)CSc2nc3ncc(C(F)(F)F)cc3o2)s1] | 2-hydroxy-N-((5-(2-((6-(trifluoromethyl)oxazolo[4,5-b]pyridin-2-yl)thio)acetyl)thiophen-2-yl)methyl)acetamide |
| 119 | 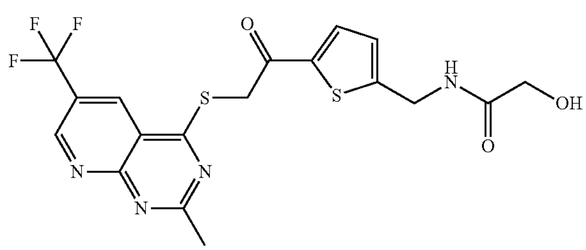 [SMILES: Cc1nc(SCC(=O)c2ccc(CNC(=O)CO)s2)c2cc(C(F)(F)F)cnc2n1] | 2-hydroxy-N-((5-(2-((2-methyl-6-(trifluoromethyl)pyrido[2,3-d]pyrimidin-4-yl)thio)acetyl)thiophen-2-yl)methyl)acetamide |
| 120 | 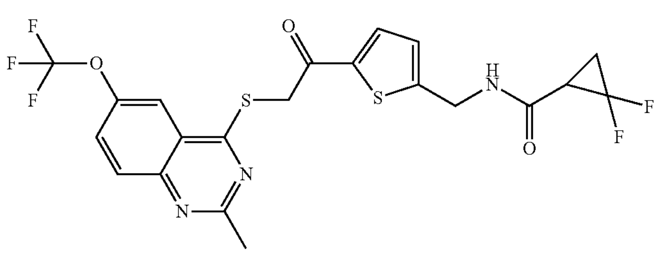 [SMILES: Cc1nc(SCC(=O)c2ccc(CNC(=O)C3CC3(F)F)s2)c2cc(OC(F)(F)F)ccc2n1] | 2,2-difluoro-N-((5-(2-((2-methyl-6-(trifluoromethoxy)quinazolin-4-yl)thio)acetyl)thiophen-2-yl)methyl)cyclopropane-1-carboxamide |

TABLE 1-continued

| Cpd # | Structure | Name |
|---|---|---|
| 121 | 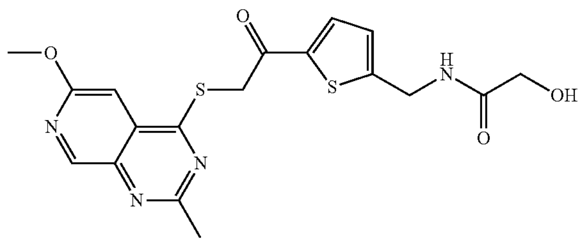 | 2-hydroxy-N-((5-(2-((6-methoxy-2-methylpyrido[3,4-d]pyrimidin-4-yl)thio)acetyl)thiophen-2-yl)methyl)acetamide |
| 122 | 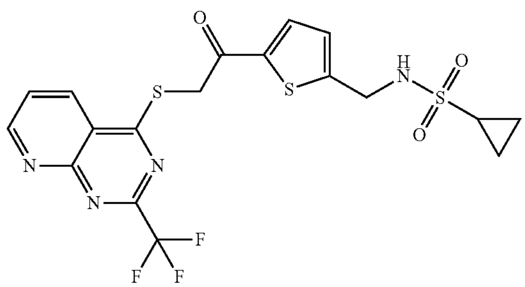 [SMILES: O=C(CSc1nc(C(F)(F)F)nc2ncccc12)c1ccc(CNS(=O)(=O)C2CC2)s1] | N-((5-(2-((2-(trifluoromethyl)pyrido[2,3-d]pyrimidin-4-yl)thio)acetyl)thiophen-2-yl)methyl)cyclopropanesulfonamide |
| 123 | 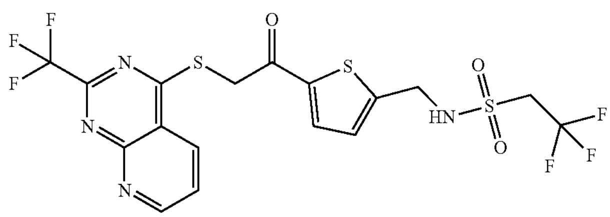 [SMILES: O=C(CSc1nc(C(F)(F)F)nc2ncccc12)c1ccc(CNS(=O)(=O)CC(F)(F)F)s1] | 2,2,2-trifluoro-N-((5-(2-((2-(trifluoromethyl)pyrido[2,3-d]pyrimidin-4-yl)thio)acetyl)thiophen-2-yl)methyl)ethane-1-sulfonamide |
| 124 | 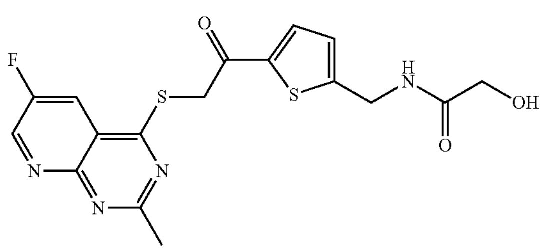 [SMILES: Cc1nc(SCC(=O)c2ccc(CNC(=O)CO)s2)c2cc(F)cnc2n1] | N-((5-(2-((6-fluoro-2-methylpyrido[2,3-d]pyrimidin-4-yl)thio)acetyl)thiophen-2-yl)methyl)-2-hydroxyacetamide |
| 125 | 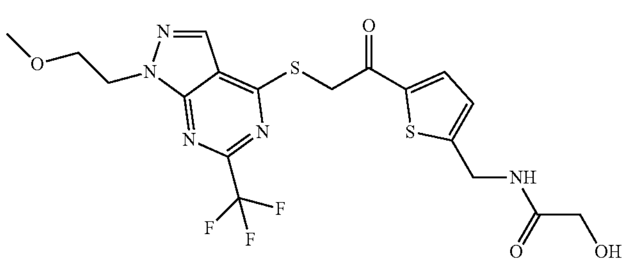 [SMILES: COCCn1ncc2c(SCC(=O)c3ccc(CNC(=O)CO)s3)nc(C(F)(F)F)nc21] | 2-hydroxy-N-((5-(2-((1-(2-methoxyethyl)-6-(trifluoromethyl)-1H-pyrazolo[3,4-d]pyrimidin-4-yl)thio)acetyl)thiophen-2-yl)methyl)acetamide |
| 126 | 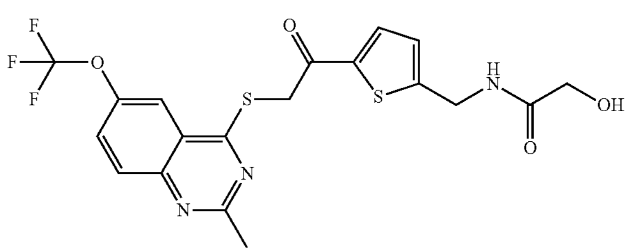 [SMILES: Cc1nc(SCC(=O)c2ccc(CNC(=O)CO)s2)c2cc(OC(F)(F)F)ccc2n1] | 2-hydroxy-N-((5-(2-((2-methyl-6-(trifluoromethoxy)quinazolin-4-yl)thio)acetyl)thiophen-2-yl)methyl)acetamide |

TABLE 1-continued

| Cpd # | Structure | Name |
|---|---|---|
| 127 | 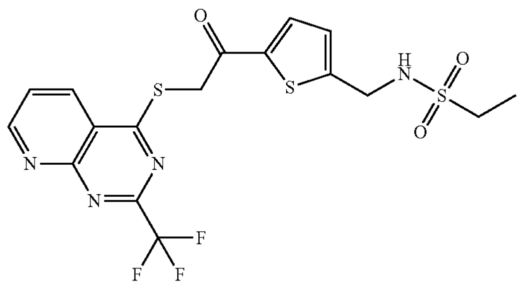 [SMILES: CCS(=O)(=O)NCc1ccc(C(=O)CSc2nc(C(F)(F)F)nc3ncccc23)s1] | N-((5-(2-((2-(trifluoromethyl)pyrido[2,3-d]pyrimidin-4-yl)thio)acetyl)thiophen-2-yl)methyl)ethanesulfonamide |
| 128 | 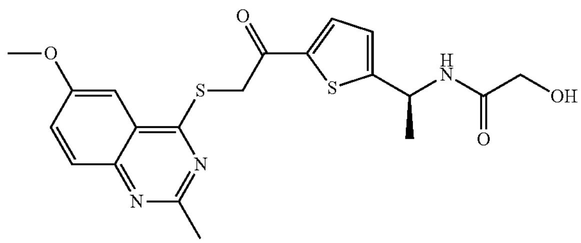 [SMILES: COc1ccc2nc(C)nc(SCC(=O)c3ccc([C@H](C)NC(=O)CO)s3)c2c1] | (S)-2-hydroxy-N-(1-(5-(2-((6-methoxy-2-methylquinazolin-4-yl)thio)acetyl)thiophen-2-yl)ethyl)acetamide |
| 129 | 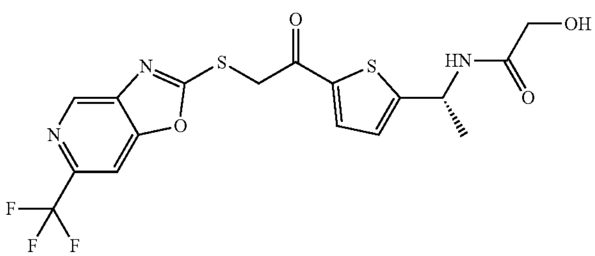 [SMILES: C[C@@H](NC(=O)CO)c1ccc(C(=O)CSc2nc3cnc(C(F)(F)F)cc3o2)s1] | (S)-2-hydroxy-N-(1-(5-(2-((6-(trifluoromethyl)oxazolo[4,5-c]pyridin-2-yl)thio)acetyl)thiophen-2-yl)ethyl)acetamide |
| 130 | 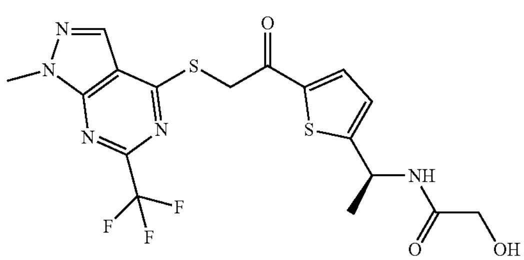 [SMILES: C[C@H](NC(=O)CO)c1ccc(C(=O)CSc2nc(C(F)(F)F)nc3c2cnn3C)s1] | (S)-2-hydroxy-N-(1-(5-(2-((1-methyl-6-(trifluoromethyl)-1H-pyrazolo[3,4-d]pyrimidin-4-yl)thio)acetyl)thiophen-2-yl)ethyl)acetamide |
| 131 | 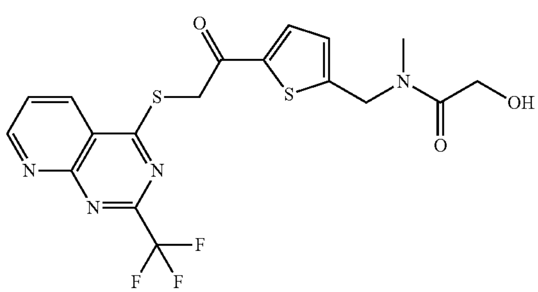 [SMILES: CN(Cc1ccc(C(=O)CSc2nc(C(F)(F)F)nc3ncccc23)s1)C(=O)CO] | 2-hydroxy-N-methyl-N-((5-(2-((2-(trifluoromethyl)pyrido[2,3-d]pyrimidin-4-yl)thio)acetyl)thiophen-2-yl)methyl)acetamide |

TABLE 1-continued

| Cpd # | Structure | Name |
|---|---|---|
| 132 | 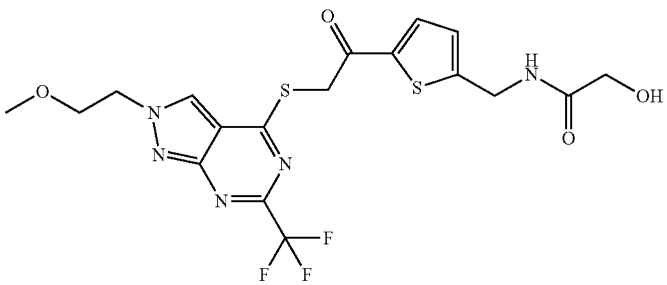 [SMILES: COCCn1cc2c(SCC(=O)c3ccc(CNC(=O)CO)s3)nc(C(F)(F)F)nc2n1] | 2-hydroxy-N-((5-(2-((2-(2-methoxyethyl)-6-(trifluoromethyl)-2H-pyrazolo[3,4-d]pyrimidin-4-yl)thio)acetyl)thiophen-2-yl)methyl)acetamide |
| 133 | 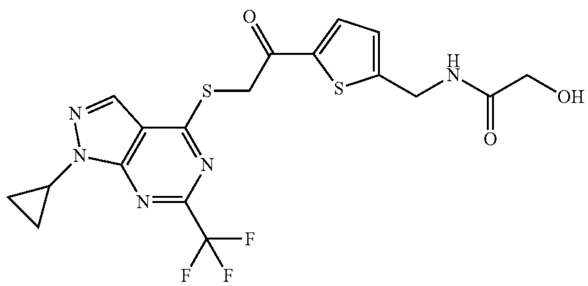 [SMILES: O=C(CO)NCc1ccc(C(=O)CSc2nc(C(F)(F)F)nc3c2cnn3C2CC2)s1] | N-((5-(2-((1-cyclopropyl-6-(trifluoromethyl)-1H-pyrazolo[3,4-d]pyrimidin-4-yl)thio)acetyl)thiophen-2-yl)methyl)-2-hydroxyacetamide |
| 134 | 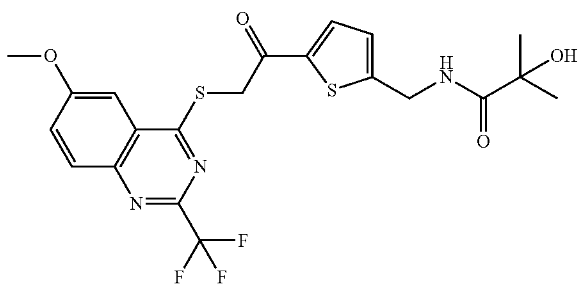 [SMILES: COc1ccc2nc(C(F)(F)F)nc(SCC(=O)c3ccc(CNC(=O)C(C)(C)O)s3)c2c1] | 2-hydroxy-N-((5-(2-((6-methoxy-2-(trifluoromethyl)quinazolin-4-yl)thio)acetyl)thiophen-2-yl)methyl)-2-methylpropanamide |
| 135 | 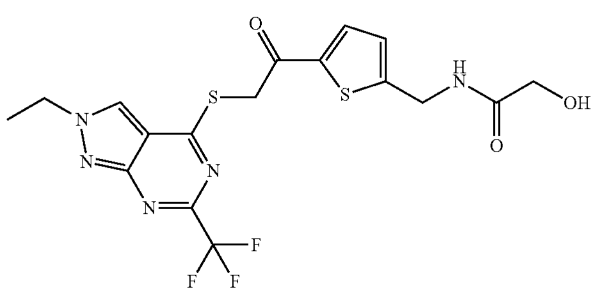 [SMILES: CCn1cc2c(SCC(=O)c3ccc(CNC(=O)CO)s3)nc(C(F)(F)F)nc2n1] | N-((5-(2-((2-ethyl-6-(trifluoromethyl)-2H-pyrazolo[3,4-d]pyrimidin-4-yl)thio)acetyl)thiophen-2-yl)methyl)-2-hydroxyacetamide |
| 136 | 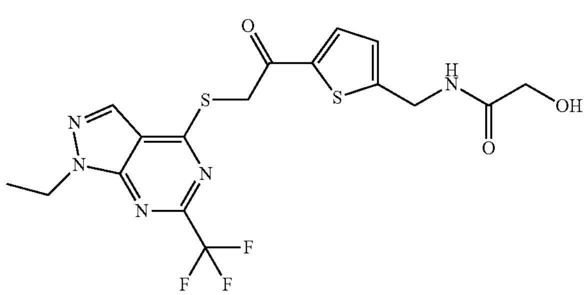 [SMILES: CCn1ncc2c(SCC(=O)c3ccc(CNC(=O)CO)s3)nc(C(F)(F)F)nc21] | N-((5-(2-((1-ethyl-6-(trifluoromethyl)-1H-pyrazolo[3,4-d]pyrimidin-4-yl)thio)acetyl)thiophen-2-yl)methyl)-2-hydroxyacetamide |

TABLE 1-continued

| Cpd # | Structure | Name |
|---|---|---|
| 137 | 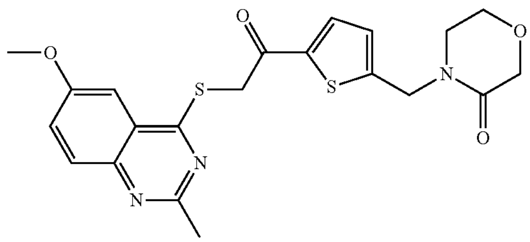 | 4-((5-(2-((6-methoxy-2-methylquinazolin-4-yl)thio)acetyl)thiophen-2-yl)methyl)morpholin-3-one |
| 138 | 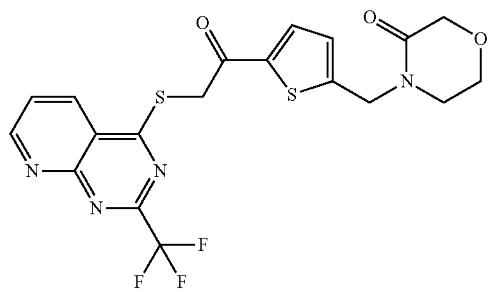 [SMILES: O=C(CSc1nc(C(F)(F)F)nc2ncccc12)c1ccc(CN2CCOCC2=O)s1] | 4-((5-(2-((2-(trifluoromethyl)pyrido[2,3-d]pyrimidin-4-yl)thio)acetyl)thiophen-2-yl)methyl)morpholin-3-one |
| 139 | 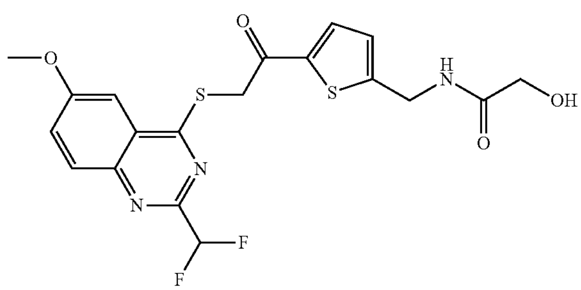 [SMILES: COc1ccc2nc(C(F)F)nc(SCC(=O)c3ccc(CNC(=O)CO)s3)c2c1] | N-((5-(2-((2-(difluoromethyl)-6-methoxyquinazolin-4-yl)thio)acetyl)thiophen-2-yl)methyl)-2-hydroxyacetamide |
| 140 | 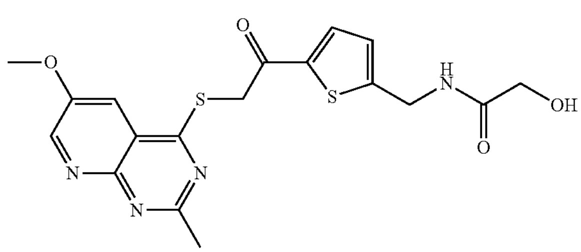 [SMILES: COc1cnc2nc(C)nc(SCC(=O)c3ccc(CNC(=O)CO)s3)c2c1] | 2-hydroxy-N-((5-(2-((6-methoxy-2-methylpyrido[2,3-d]pyrimidin-4-yl)thio)acetyl)thiophen-2-yl)methyl)acetamide |
| 141 | 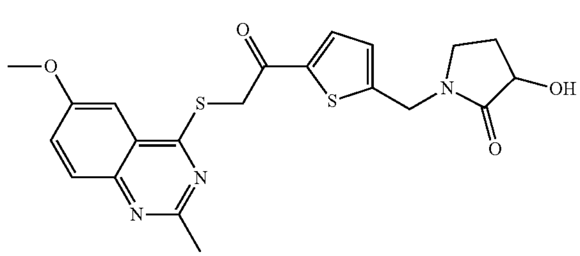 [SMILES: COc1ccc2nc(C)nc(SCC(=O)c3ccc(CN4CCC(O)C4=O)s3)c2c1] | 3-hydroxy-1-((5-(2-((6-methoxy-2-methylquinazolin-4-yl)thio)acetyl)thiophen-2-yl)methyl)pyrrolidin-2-one |
| 142 | 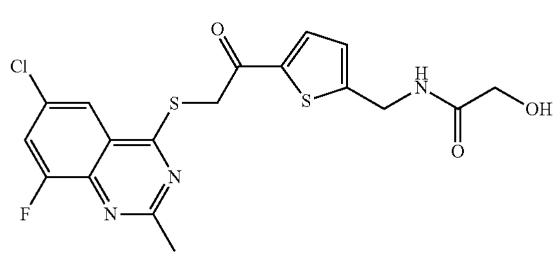 [SMILES: Cc1nc(SCC(=O)c2ccc(CNC(=O)CO)s2)c2cc(Cl)cc(F)c2n1] | N-((5-(2-((6-chloro-8-fluoro-2-methylquinazolin-4-yl)thio)acetyl)thiophen-2-yl)methyl)-2-hydroxyacetamide |

TABLE 1-continued

| Cpd # | Structure | Name |
|---|---|---|
| 143 | 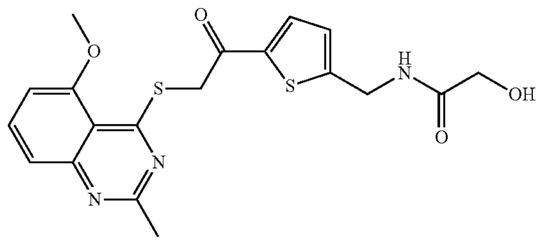 [SMILES: COc1cccc2nc(C)nc(SCC(=O)c3ccc(CNC(=O)CO)s3)c12] | 2-hydroxy-N-((5-(2-((5-methoxy-2-methylquinazolin-4-yl)thio)acetyl)thiophen-2-yl)methyl)acetamide |
| 144 | 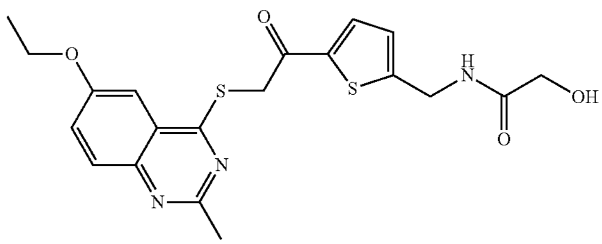 [SMILES: CCOc1ccc2nc(C)nc(SCC(=O)c3ccc(CNC(=O)CO)s3)c2c1] | N-((5-(2-((6-ethoxy-2-methylquinazolin-4-yl)thio)acetyl)thiophen-2-yl)methyl)-2-hydroxyacetamide |
| 145 | 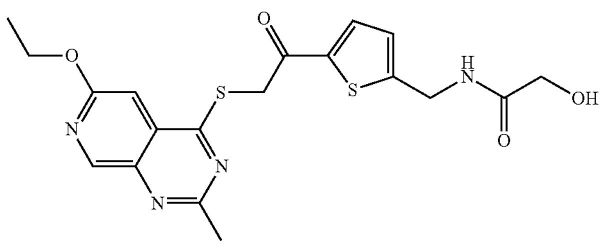 [SMILES: CCOc1cc2c(SCC(=O)c3ccc(CNC(=O)CO)s3)nc(C)nc2cn1] | N-((5-(2-((6-ethoxy-2-methylpyrido[3,4-d]pyrimidin-4-yl)thio)acetyl)thiophen-2-yl)methyl)-2-hydroxyacetamide |
| 146 | 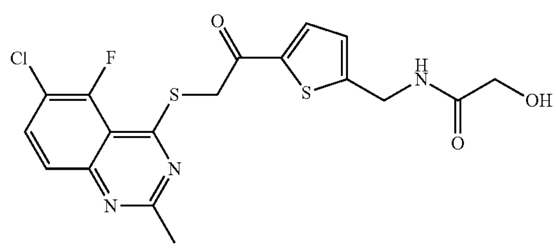 [SMILES: Cc1nc(SCC(=O)c2ccc(CNC(=O)CO)s2)c2c(F)c(Cl)ccc2n1] | N-((5-(2-((6-chloro-5-fluoro-2-methylquinazolin-4-yl)thio)acetyl)thiophen-2-yl)methyl)-2-hydroxyacetamide |
| 147 | 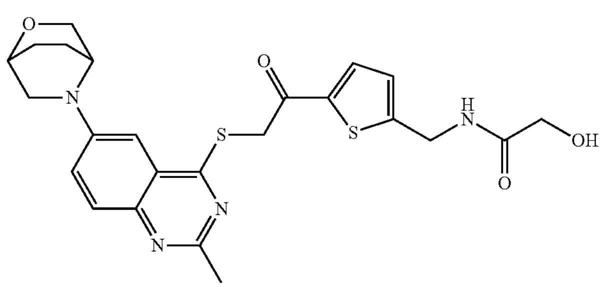 [SMILES: Cc1nc(SCC(=O)c2ccc(CNC(=O)CO)s2)c2cc(N3CC4CCC3CO4)ccc2n1] | N-((5-(2-((6-(2-oxa-5-azabicyclo[2.2.2]octan-5-yl)-2-methylquinazolin-4-yl)thio)acetyl)thiophen-2-yl)methyl)-2-hydroxyacetamide |
| 148 | 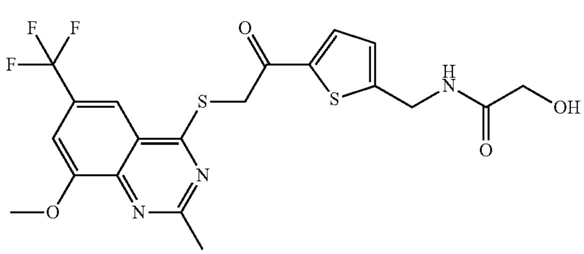 [SMILES: COc1cc(C(F)(F)F)cc2c(SCC(=O)c3ccc(CNC(=O)CO)s3)nc(C)nc12] | 2-hydroxy-N-((5-(2-((8-methoxy-2-methyl-6-(trifluoromethyl)quinazolin-4-yl)thio)acetyl)thiophen-2-yl)methyl)acetamide |

TABLE 1-continued

| Cpd # | Structure | Name |
|---|---|---|
| 149 | 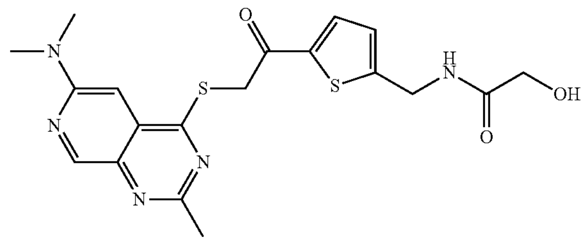 [SMILES: Cc1nc(SCC(=O)c2ccc(CNC(=O)CO)s2)c2cc(N(C)C)ncc2n1] | N-((5-(2-((6-(dimethylamino)-2-methylpyrido[3,4-d]pyrimidin-4-yl)thio)acetyl)thiophen-2-yl)methyl)-2-hydroxyacetamide |
| 150 | 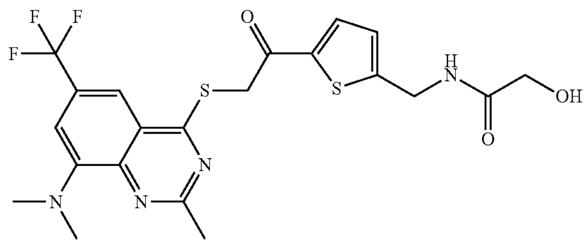 [SMILES: Cc1nc(SCC(=O)c2ccc(CNC(=O)CO)s2)c2cc(C(F)(F)F)cc(N(C)C)c2n1] | N-((5-(2-((8-(dimethylamino)-2-methyl-6-(trifluoromethyl)quinazolin-4-yl)thio)acetyl)thiophen-2-yl)methyl)-2-hydroxyacetamide |
| 151 | 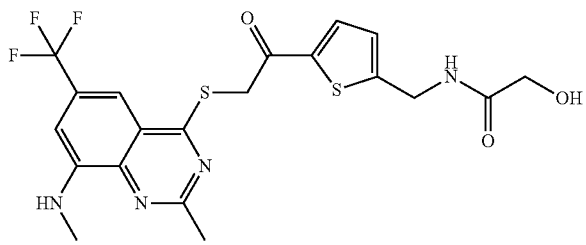 [SMILES: CNc1cc(C(F)(F)F)cc2c(SCC(=O)c3ccc(CNC(=O)CO)s3)nc(C)nc12] | 2-hydroxy-N-((5-(2-((2-methyl-8-(methylamino)-6-(trifluoromethyl)quinazolin-4-yl)thio)acetyl)thiophen-2-yl)methyl)acetamide |
| 152 | 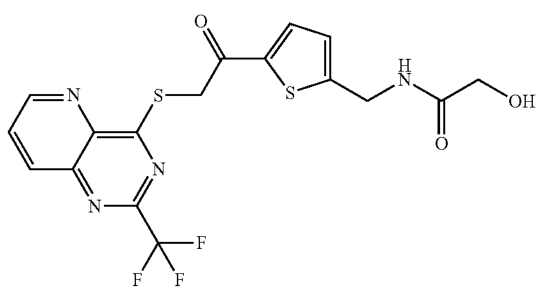 [SMILES: O=C(CO)NCc1ccc(C(=O)CSc2nc(C(F)(F)F)nc3cccnc23)s1] | 2-hydroxy-N-((5-(2-((2-(trifluoromethyl)pyrido[3,2-d]pyrimidin-4-yl)thio)acetyl)thiophen-2-yl)methyl)acetamide |
| 153 | 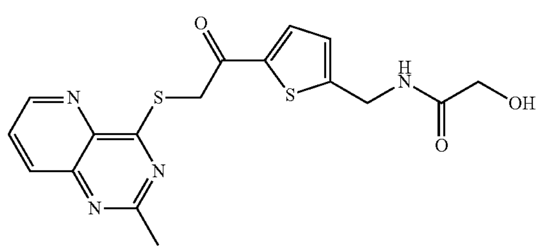 [SMILES: Cc1nc(SCC(=O)c2ccc(CNC(=O)CO)s2)c2ncccc2n1] | 2-hydroxy-N-((5-(2-((2-methylpyrido[3,2-d]pyrimidin-4-yl)thio)acetyl)thiophen-2-yl)methyl)acetamide |
| 154 | 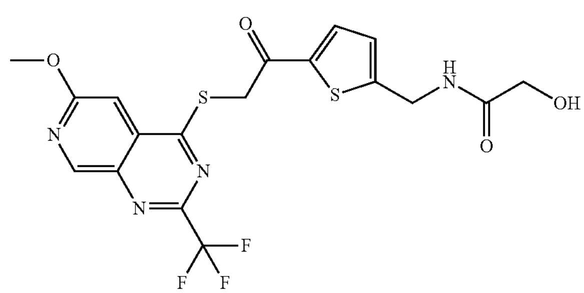 [SMILES: COc1cc2c(SCC(=O)c3ccc(CNC(=O)CO)s3)nc(C(F)(F)F)nc2cn1] | 2-hydroxy-N-((5-(2-((6-methoxy-2-(trifluoromethyl)pyrido[3,4-d]pyrimidin-4-yl)thio)acetyl)thiophen-2-yl)methyl)acetamide |

TABLE 1-continued

| Cpd # | Structure | Name |
|---|---|---|
| 155 | 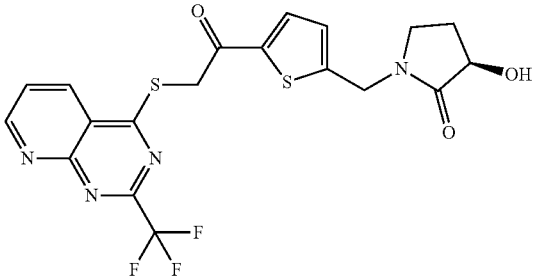 [SMILES: O=C(CSc1nc(C(F)(F)F)nc2ncccc12)c1ccc(CN2CC[C@@H](O)C2=O)s1] | (S)-3-hydroxy-1-((5-(2-((2-(trifluoromethyl)pyrido[2,3-d]pyrimidin-4-yl)thio)acetyl)thiophen-2-yl)methyl)pyrrolidin-2-one |
| 156 | 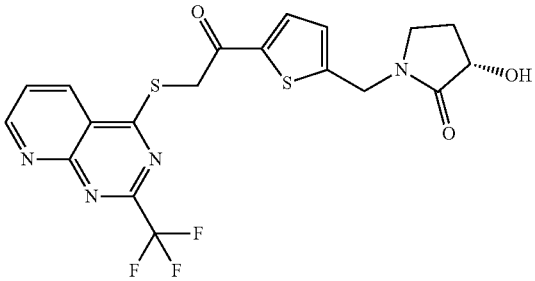 [SMILES: O=C(CSc1nc(C(F)(F)F)nc2ncccc12)c1ccc(CN2CC[C@H](O)C2=O)s1] | (R)-3-hydroxy-1-((5-(2-((2-(trifluoromethyl)pyrido[2,3-d]pyrimidin-4-yl)thio)acetyl)thiophen-2-yl)methyl)pyrrolidin-2-one |
| 157 | 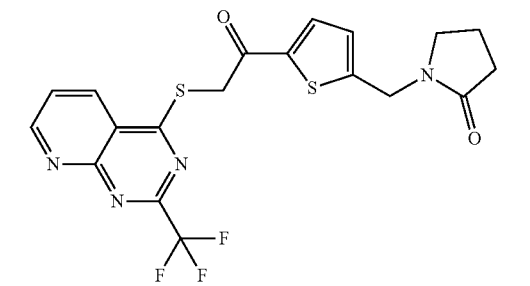 [SMILES: O=C(CSc1nc(C(F)(F)F)nc2ncccc12)c1ccc(CN2CCCC2=O)s1] | 1-((5-(2-((2-(trifluoromethyl)pyrido[2,3-d]pyrimidin-4-yl)thio)acetyl)thiophen-2-yl)methyl)pyrrolidin-2-one |
| 158 | 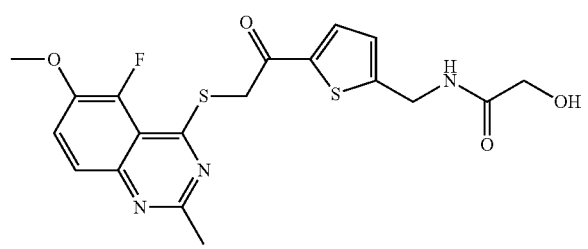 [SMILES: COc1ccc2nc(C)nc(SCC(=O)c3ccc(CNC(=O)CO)s3)c2c1F] | N-((5-(2-((5-fluoro-6-methoxy-2-methylquinazolin-4-yl)thio)acetyl)thiophen-2-yl)methyl)-2-hydroxyacetamide |
| 159 | 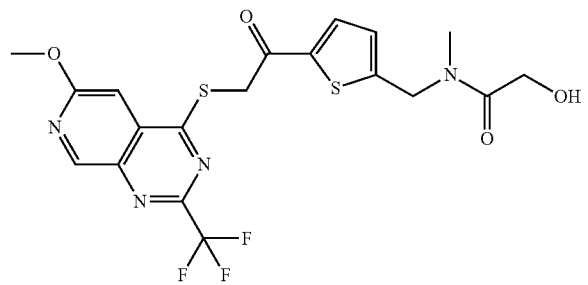 [SMILES: COc1cc2c(SCC(=O)c3ccc(CN(C)C(=O)CO)s3)nc(C(F)(F)F)nc2cn1] | 2-hydroxy-N-((5-(2-((6-methoxy-2-(trifluoromethyl)pyrido[3,4-d]pyrimidin-4-yl)thio)acetyl)thiophen-2-yl)methyl)-N-methylacetamide |

TABLE 1-continued

| Cpd # | Structure | Name |
|---|---|---|
| 160 | 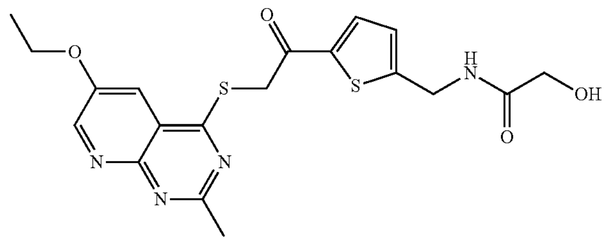 [SMILES: CCOc1cnc2nc(C)nc(SCC(=O)c3ccc(CNC(=O)CO)s3)c2c1] | N-((5-(2-((6-ethoxy-2-methylpyrido[2,3-d]pyrimidin-4-yl)thio)acetyl)thiophen-2-yl)methyl)-2-hydroxyacetamide |
| 161 | 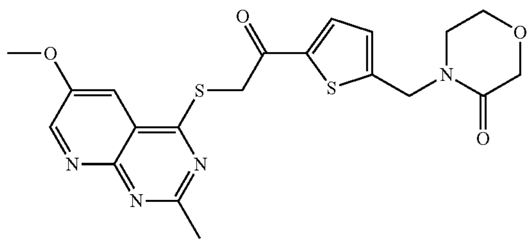 [SMILES: COc1cnc2nc(C)nc(SCC(=O)c3ccc(CN4CCOCC4=O)s3)c2c1] | 4-((5-(2-((6-methoxy-2-methylpyrido[2,3-d]pyrimidin-4-yl)thio)acetyl)thiophen-2-yl)methyl)morpholin-3-one |
| 162 | 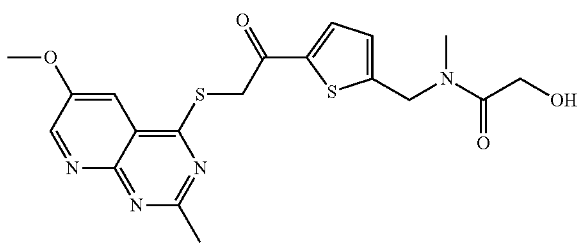 [SMILES: COc1cnc2nc(C)nc(SCC(=O)c3ccc(CN(C)C(=O)CO)s3)c2c1] | 2-hydroxy-N-((5-(2-((6-methoxy-2-methylpyrido[2,3-d]pyrimidin-4-yl)thio)acetyl)thiophen-2-yl)methyl)-N-methylacetamide |
| 163 | 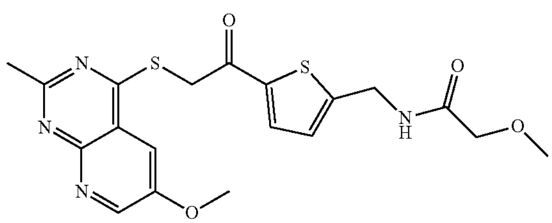 | 2-methoxy-N-((5-(2-((6-methoxy-2-methylpyrido[2,3-d]pyrimidin-4-yl)thio)acetyl)thiophen-2-yl)methyl)acetamide |
| 164 | 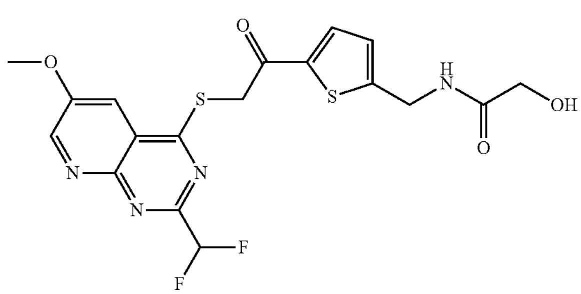 [SMILES: COc1cnc2nc(C(F)F)nc(SCC(=O)c3ccc(CNC(=O)CO)s3)c2c1] | N-((5-(2-((2-(difluoromethyl)-6-methoxypyrido[2,3-d]pyrimidin-4-yl)thio)acetyl)thiophen-2-yl)methyl)-2-hydroxyacetamide |
| 165 | 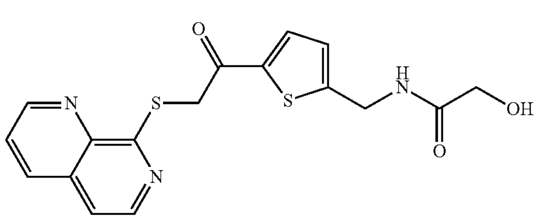 [SMILES: O=C(CO)NCc1ccc(C(=O)CSc2nccc3cccnc23)s1] | N-((5-(2-((1,7-naphthyridin-8-yl)thio)acetyl)thiophen-2-yl)methyl)-2-hydroxyacetamide |

TABLE 1-continued

| Cpd # | Structure | Name |
|---|---|---|
| 166 | 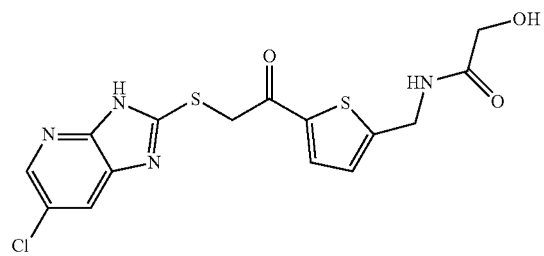 [SMILES: O=C(CO)NCc1ccc(C(=O)CSc2nc3cc(Cl)cnc3[nH]2)s1] | N-((5-(2-(((6-chloro-3H-imidazo[4,5-b]pyridin-2-yl)thio)acetyl)thiophen-2-yl)methyl)-2-hydroxyacetamide |
| 167 | 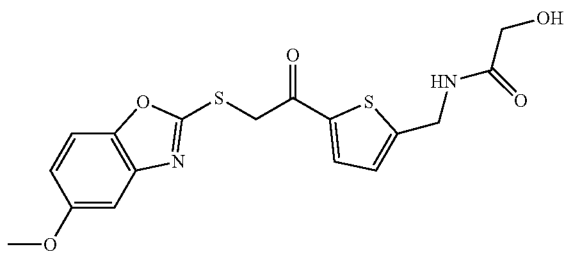 [SMILES: COc1ccc2oc(SCC(=O)c3ccc(CNC(=O)CO)s3)nc2c1] | 2-hydroxy-N-((5-(2-(((5-methoxybenzo[d]oxazol-2-yl)thio)acetyl)thiophen-2-yl)methyl)acetamide |
| 168 | 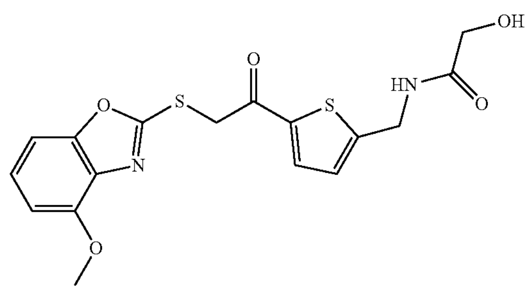 [SMILES: COc1cccc2oc(SCC(=O)c3ccc(CNC(=O)CO)s3)nc12] | 2-hydroxy-N-((5-(2-(((4-methoxybenzo[d]oxazol-2-yl)thio)acetyl)thiophen-2-yl)methyl)acetamide |
| 169 | 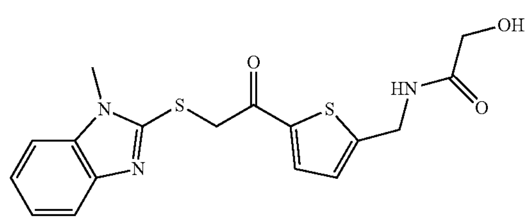 [SMILES: Cn1c(SCC(=O)c2ccc(CNC(=O)CO)s2)nc2ccccc21] | 2-hydroxy-N-((5-(2-(((1-methyl-1H-benzo[d]imidazol-2-yl)thio)acetyl)thiophen-2-yl)methyl)acetamide |
| 170 | 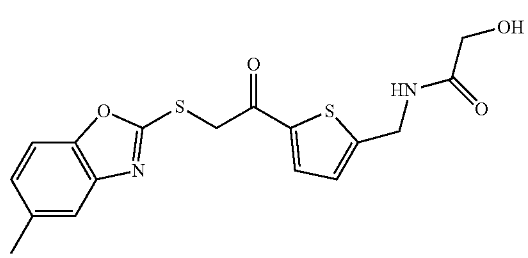 [SMILES: Cc1ccc2oc(SCC(=O)c3ccc(CNC(=O)CO)s3)nc2c1] | 2-hydroxy-N-((5-(2-(((5-methylbenzo[d]oxazol-2-yl)thio)acetyl)thiophen-2-yl)methyl)acetamide |
| 171 | 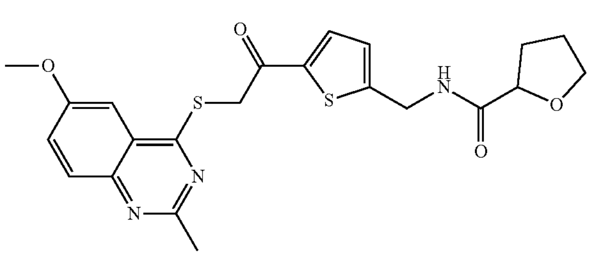 [SMILES: COc1ccc2nc(C)nc(SCC(=O)c3ccc(CNC(=O)C4CCCO4)s3)c2c1] | N-((5-(2-(((6-methoxy-2-methylquinazolin-4-yl)thio)acetyl)thiophen-2-yl)methyl)tetrahydrofuran-2-carboxamide |

TABLE 1-continued

| Cpd # | Structure | Name |
|---|---|---|
| 172 | 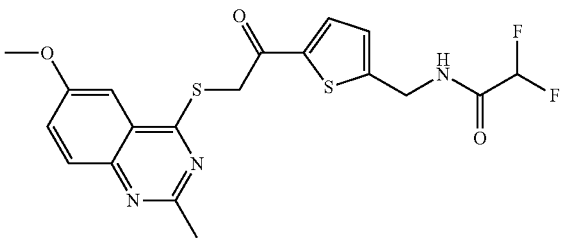 [SMILES: COc1ccc2nc(C)nc(SCC(=O)c3ccc(CNC(=O)C(F)F)s3)c2c1] | 2,2-difluoro-N-((5-(2-((6-methoxy-2-methylquinazolin-4-yl)thio)acetyl)thiophen-2-yl)methyl)acetamide |
| 173 | 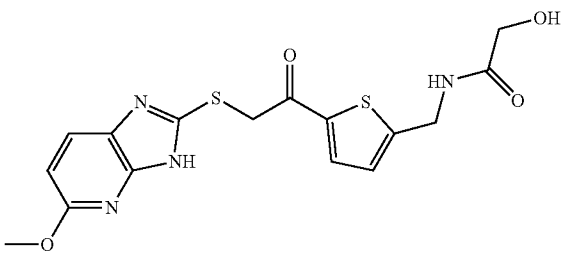 [SMILES: COc1ccc2nc(SCC(=O)c3ccc(CNC(=O)CO)s3)[nH]c2n1] | 2-hydroxy-N-((5-(2-((5-methoxy-3H-imidazo[4,5-b]pyridin-2-yl)thio)acetyl)thiophen-2-yl)methyl)acetamide |
| 174 | 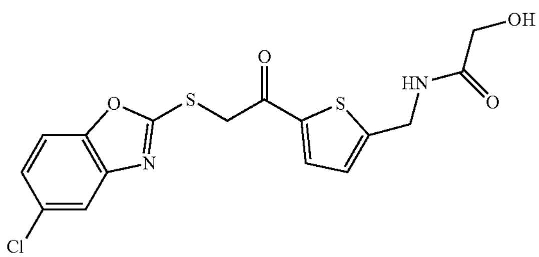 [SMILES: O=C(CO)NCc1ccc(C(=O)CSc2nc3cc(Cl)ccc3o2)s1] | N-((5-(2-((5-chlorobenzo[d]oxazol-2-yl)thio)acetyl)thiophen-2-yl)methyl)-2-hydroxyacetamide |
| 176 | 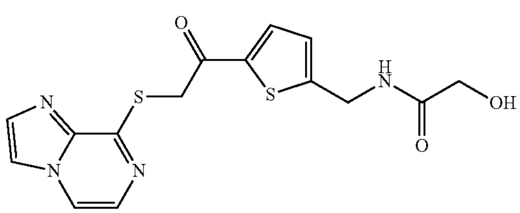 [SMILES: O=C(CO)NCc1ccc(C(=O)CSc2nccn3ccnc23)s1] | 2-hydroxy-N-((5-(2-(imidazo[1,2-a]pyrazin-8-ylthio)acetyl)thiophen-2-yl)methyl)acetamide |
| 177 | 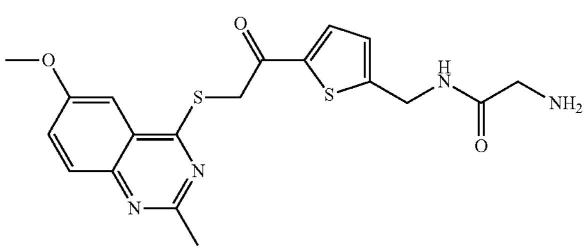 [SMILES: COc1ccc2nc(C)nc(SCC(=O)c3ccc(CNC(=O)CN)s3)c2c1] | 2-amino-N-((5-(2-((6-methoxy-2-methylquinazolin-4-yl)thio)acetyl)thiophen-2-yl)methyl)acetamide |
| 178 | 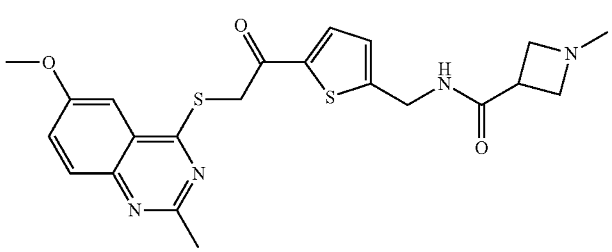 | N-((5-(2-((6-methoxy-2-methylquinazolin-4-yl)thio)acetyl)thiophen-2-yl)methyl)-1-methylazetidine-3-carboxamide |

TABLE 1-continued

| Cpd # | Structure | Name |
|---|---|---|
| 179 | 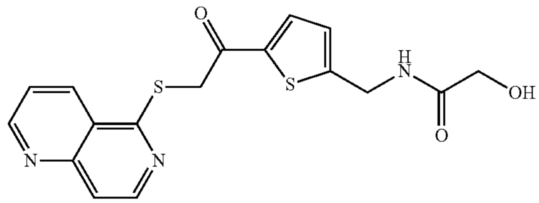 [SMILES: O=C(CO)NCc1ccc(C(=O)CSc2nccc3ncccc23)s1] | N-((5-(2-((1,6-naphthyridin-5-yl)thio)acetyl)thiophen-2-yl)methyl)-2-hydroxyacetamide |
| 180 | 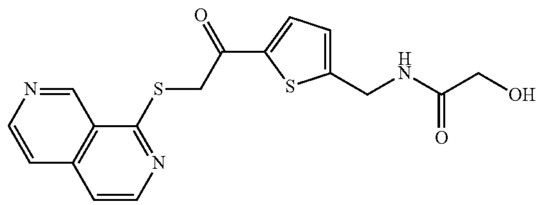 [SMILES: O=C(CO)NCc1ccc(C(=O)CSc2nccc3ccncc23)s1] | N-((5-(2-((2,7-naphthyridin-1-yl)thio)acetyl)thiophen-2-yl)methyl)-2-hydroxyacetamide |
| 181 | 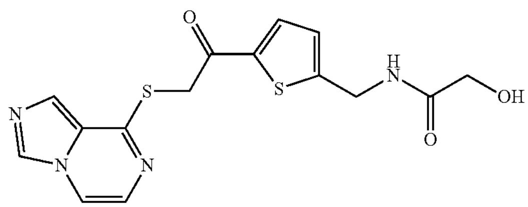 [SMILES: O=C(CO)NCc1ccc(C(=O)CSc2nccn3cncc23)s1] | 2-hydroxy-N-((5-(2-(imidazo[1,5-a]pyrazin-8-ylthio)acetyl)thiophen-2-yl)methyl)acetamide |
| 182 | 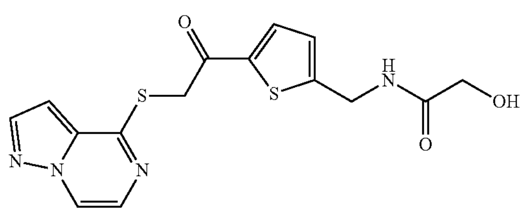 | 2-hydroxy-N-((5-(2-(pyrazolo[1,5-a]pyrazin-4-ylthio)acetyl)thiophen-2-yl)methyl)acetamide |
| 183 | 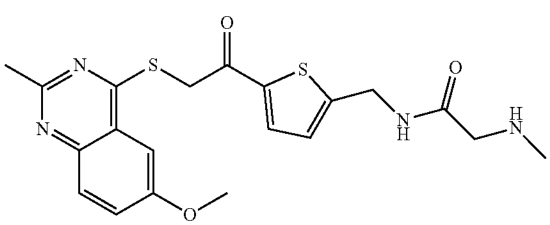 | N-((5-(2-((6-methoxy-2-methylquinazolin-4-yl)thio)acetyl)thiophen-2-yl)methyl)-2-(methylamino)acetamide |
| 184 | 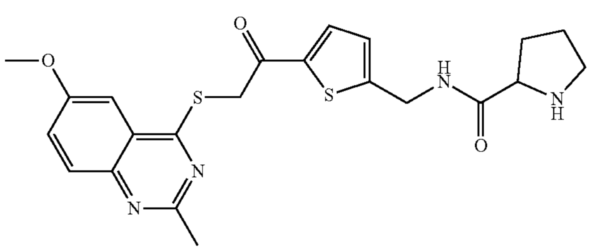 [SMILES: COc1ccc2nc(C)nc(SCC(=O)c3ccc(CNC(=O)C4CCCN4)s3)c2c1] | N-((5-(2-((6-methoxy-2-methylquinazolin-4-yl)thio)acetyl)thiophen-2-yl)methyl)pyrrolidine-2-carboxamide |
| 185 | 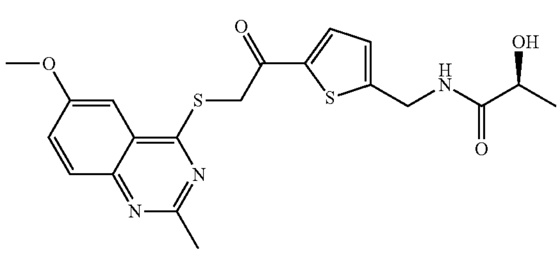 [SMILES: COc1ccc2nc(C)nc(SCC(=O)c3ccc(CNC(=O)[C@H](C)O)s3)c2c1] | (S)-2-hydroxy-N-((5-(2-((6-methoxy-2-methylquinazolin-4-yl)thio)acetyl)thiophen-2-yl)methyl)propanamide |

TABLE 1-continued

| Cpd # | Structure | Name |
|---|---|---|
| 186 | 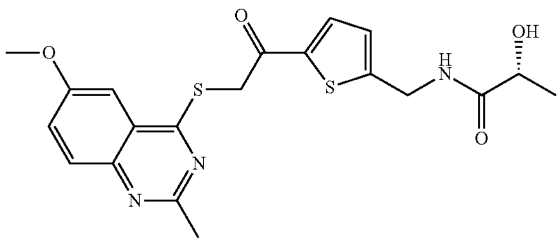 [SMILES: COc1ccc2nc(C)nc(SCC(=O)c3ccc(CNC(=O)[C@@H](C)O)s3)c2c1] | (R)-2-hydroxy-N-((5-(2-((6-methoxy-2-methylquinazolin-4-yl)thio)acetyl)thiophen-2-yl)methyl)propanamide |
| 189 | 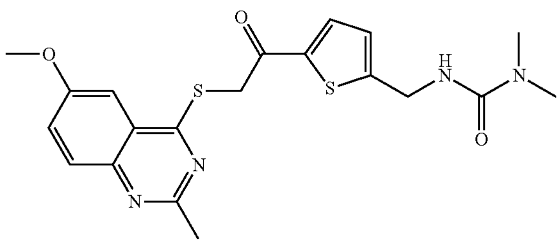 | 3-((5-(2-((6-methoxy-2-methylquinazolin-4-yl)thio)acetyl)thiophen-2-yl)methyl)-1,1-dimethylurea |
| 190 | 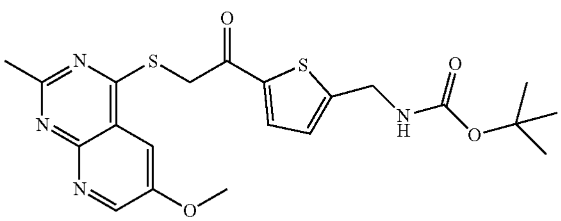 [SMILES: COc1cnc2nc(C)nc(SCC(=O)c3ccc(CNC(=O)OC(C)(C)C)s3)c2c1] | tert-butyl ((5-(2-((6-methoxy-2-methylpyrido[2,3-d]pyrimidin-4-yl)thio)acetyl)thiophen-2-yl)methyl)carbamate |
| 191 | 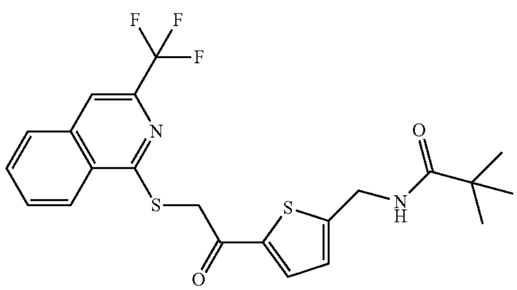 [SMILES: CC(C)(C)C(=O)NCc1ccc(C(=O)CSc2nc(C(F)(F)F)cc3ccccc23)s1] | N-((5-(2-((3-(trifluoromethyl)isoquinolin-1-yl)thio)acetyl)thiophen-2-yl)methyl)pivalamide |
| 192 | 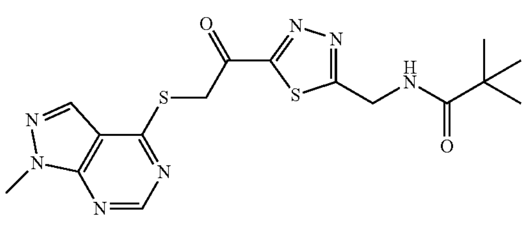 [SMILES: Cn1ncc2c(SCC(=O)c3nnc(CNC(=O)C(C)(C)C)s3)ncnc21] | N-((5-(2-(1-methyl-1H-pyrazolo[3,4-d]pyrimidin-4-ylthio)acetyl)-1,3,4-thiadiazol-2-yl)methyl)pivalamide |
| 193 | 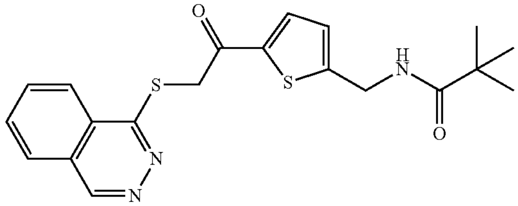 [SMILES: CC(C)(C)C(=O)NCc1ccc(C(=O)CSc2nncc3ccccc23)s1] | N-((5-(2-(phthalazin-1-ylthio)acetyl)thiophen-2-yl)methyl)pivalamide |

TABLE 1-continued

| Cpd # | Structure | Name |
|---|---|---|
| 194 | 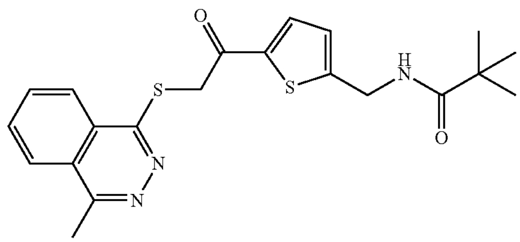 [SMILES: Cc1nnc(SCC(=O)c2ccc(CNC(=O)C(C)(C)C)s2)c2ccccc12] | N-((5-(2-((4-methylphthalazin-1-yl)thio)acetyl)thiophen-2-yl)methyl)pivalamide |
| 195 | 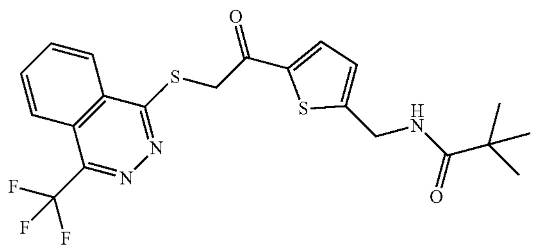 [SMILES: CC(C)(C)C(=O)NCc1ccc(C(=O)CSc2nnc(C(F)(F)F)c3ccccc23)s1] | N-((5-(2-((4-(trifluoromethyl)phthalazin-1-yl)thio)acetyl)thiophen-2-yl)methyl)pivalamide) |
| 196 | 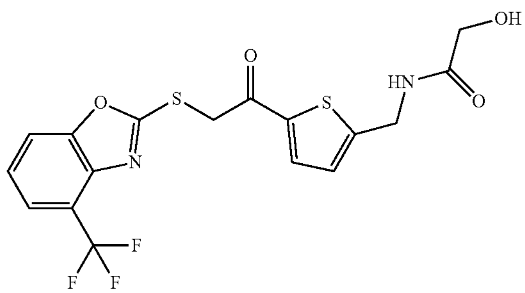 [SMILES: O=C(CO)NCc1ccc(C(=O)CSc2nc3c(C(F)(F)F)cccc3o2)s1] | 2-hydroxy-N-((5-(2-((4-(trifluoromethyl)benzo[d]oxazol-2-yl)thio)acetyl)thiophen-2-yl)methyl)acetamide |

According to one embodiment, the compound of formula (I) is selected from the

TABLE 2

| Cpd # | CAS# | Structure | Name |
|---|---|---|---|
| 99 | 1287068-38-5 | 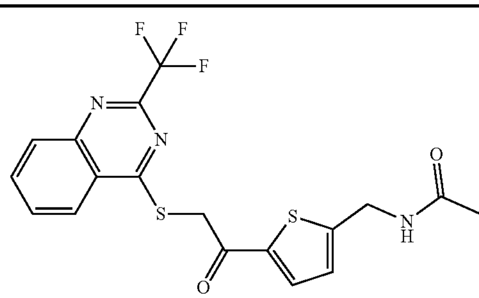 | N-((5-(2-((2-(trifluoromethyl)quinazolin-4-yl)thio)acetyl)thiophen-2-yl)methyl)acetamide |
| 100 | 1147354-39-9 | 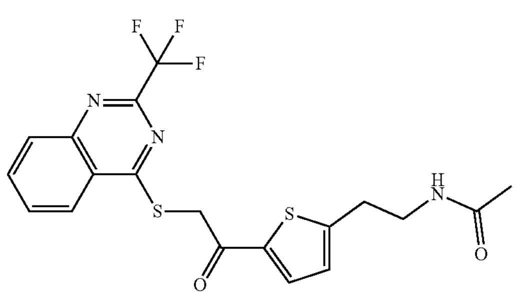 [SMILES: CC(=O)NCCc1ccc(C(=O)CSc2nc(C(F)(F)F)nc3ccccc23)s1] | N-(2-(5-(2-((2-(trifluoromethyl)quinazolin-4-yl)thio)acetyl)thiophen-2-yl)ethyl)acetamide |

TABLE 2-continued

| Cpd # | CAS# | Structure | Name |
|---|---|---|---|
| 101 | 1010596-81-2 | 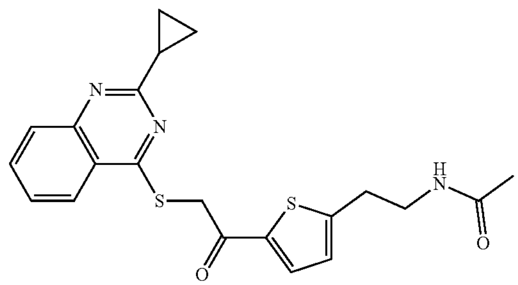 [SMILES: CC(=O)NCCc1ccc(C(=O)CSc2nc(C3CC3)nc3ccccc23)s1] | N-(2-(5-(2-((2-cyclopropylquinazolin-4-yl)thio)acetyl)thiophen-2-yl)ethyl)acetamide |
| 102 | 1210761-93-5 | 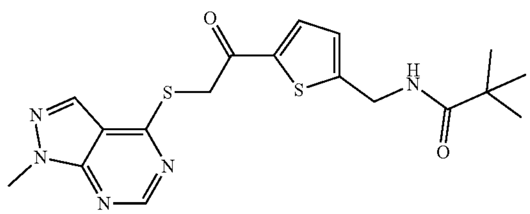 [SMILES: Cn1ncc2c(SCC(=O)c3ccc(CNC(=O)C(C)(C)C)s3)ncnc21] | N-((5-(2-((1-methyl-1H-pyrazolo[3,4-d]pyrimidin-4-yl)thio)acetyl)thiophen-2-yl)methyl)pivalamide |
| 103 | 1011002-97-3 | 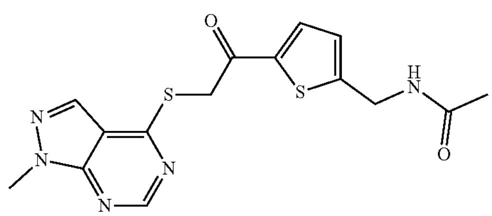 [SMILES: CC(=O)NCc1ccc(C(=O)CSc2ncnc3c2cnn3C)s1] | N-((5-(2-((1-methyl-1H-pyrazolo[3,4-d]pyrimidin-4-yl)thio)acetyl)thiophen-2-yl)methyl)acetamide |
| 104 | 2419446-18-5 | 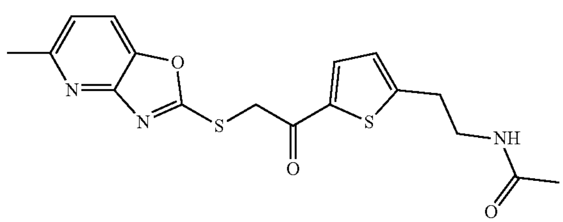 [SMILES: CC(=O)NCCc1ccc(C(=O)CSc2nc3nc(C)ccc3o2)s1] | N-(2-(5-(2-((5-methyloxazolo[4,5-b]pyridin-2-yl)thio)acetyl)thiophen-2-yl)ethyl)acetamide |

The compounds of Table 1 and Table 2 were named using ChemDraw® Professional 15.0 (PerkinElmer).

According to one embodiment, the compound of formula (I) is selected from the compounds of Table 1 or Table 2 herein.

Alternative Compounds

All references herein to a compound of the invention (e.g., a "compound of formula (I)") include references to salts—preferably pharmaceutically acceptable salts, solvates, multi component complexes and liquid crystals thereof. All references herein to a compound of the invention include references to polymorphs and crystal habits thereof. All references to a compound of the invention include references to pharmaceutically acceptable prodrugs thereof. All references to a compound of the invention include references to isotopically-labelled compounds, including deuterated compounds.

A compound of the invention (e.g., a "compound of formula (I)") and subformulae thereof may contain at least one asymmetric centre(s) and thus may exist as different stereoisomeric forms. Accordingly, all references to a compound of the invention include references to all possible stereoisomers and includes not only the racemic compounds but the individual enantiomers and their non-racemic mixtures as well. When a compound is desired as a single enantiomer, such single enantiomer may be obtained by stereospecific synthesis, by resolution of the final product or any convenient intermediate, or by chiral chromatographic methods as each are known in the art. Resolution of the final product, an intermediate, or a starting material may be carried out by any suitable method known in the art.

The compounds of the invention (e.g., a "compound of formula (I)") may be in the form of pharmaceutically acceptable salts. Pharmaceutically acceptable salts include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts. Suitable base salts are formed from bases which form non-toxic salts. Examples include the aluminium, arginine, benzathine, calcium, choline, diethylamine, 2-(diethylamino)ethanol, diolamine, ethanolamine, glycine, 4-(2-hydroxyethyl)-morpholine, lysine, magnesium, meglumine, morpholine, olamine, potassium, sodium, tromethamine and zinc salts. Hemisalts of acids and bases may also be formed, for example, hemisulphate and hemicalcium salts. When a compound contains an acidic group as well as a basic group the compound may also form internal salts, and such compounds are within the scope of the invention. When a compound contains a hydrogen-donating heteroatom (e.g., NH), the invention also covers salts and/or isomers formed by transfer of said hydrogen atom to a basic group or atom within the molecule. Pharmaceutically acceptable salts of compounds of the invention may be prepared by one or more of these methods: (i) by reacting the compound with the desired acid; (ii) by reacting the compound with the desired base; (iii) by removing an acid- or base-labile protecting group from a suitable precursor of the compound or by ring-opening a suitable cyclic precursor, e.g., a lactone or lactam, using the desired acid; and/or (iv) by converting one salt of the compound to another by reaction with an appropriate acid or by means of a suitable ion exchange column. All these reactions are typically carried out in solution. The salt may precipitate from solution and be collected by filtration or may be recovered by evaporation of the solvent. The degree of ionization in the salt may vary from completely ionized to almost non-ionized.

Further Compound Definitions

According to one embodiment, the compound of formula (I) is not CAS #1287068-38-5: N-((5-(2-((2-(trifluoromethyl)quinazolin-4-yl)thio)acetyl)thiophen-2-yl)methyl)acetamide) or a pharmaceutically acceptable salt or solvate thereof. According to one embodiment, the compound of formula (I) is not CAS #2182075-55-2: N-((5-(2-((2-methylquinazolin-4-yl)thio)acetyl)thiophen-2-yl)methyl)acetamide or a pharmaceutically acceptable salt or solvate thereof. According to one embodiment, the compound of formula (I) is not CAS #1147354-39-9: N-(2-(5-(2-((2-(trifluoromethyl)quinazolin-4-yl)thio)acetyl)thiophen-2-yl)ethyl)acetamide or a pharmaceutically acceptable salt or solvate thereof. According to one embodiment, the compound of formula (I) is not CAS #1010596-74-3: N-(2-(5-(2-((2-cyclopropylquinazolin-4-yl)thio)acetyl)thiophen-2-yl)ethyl)methanesulfonamide or a pharmaceutically acceptable salt or solvate thereof. According to one embodiment, the compound of formula (I) is not CAS #871674-28-1: N-((5-(2-((2-(thiophen-2-yl)quinazolin-4-yl)thio)acetyl)thiophen-2-yl)methyl)acetamide or a pharmaceutically acceptable salt or solvate thereof. According to one embodiment, the compound of formula (I) is not CAS #1147537-22-1: N-((5-(2-((2-(furan-2-yl)quinazolin-4-yl)thio)acetyl)thiophen-2-yl)methyl)acetamide or a pharmaceutically acceptable salt or solvate thereof. According to one embodiment, the compound of formula (I) is not CAS #1009199-55-6: N-(2-(5-(2-((2-(thiophen-2-yl)quinazolin-4-yl)thio)acetyl)thiophen-2-yl)ethyl)methanesulfonamide or a pharmaceutically acceptable salt or solvate thereof. According to one embodiment, the compound of formula (I) is not CAS #1010596-81-2: N-(2-(5-(2-((2-cyclopropylquinazolin-4-yl)thio)acetyl)thiophen-2-yl)ethyl)acetamide or a pharmaceutically acceptable salt or solvate thereof. According to one embodiment, the compound of formula (I) is not CAS #1089547-51-2: N-(2-(5-(2-((2-(furan-2-yl)quinazolin-4-yl)thio)acetyl)thiophen-2-yl)ethyl)acetamide or a pharmaceutically acceptable salt or solvate thereof. According to one embodiment, the compound of formula (I) is not CAS #1321173-73-2: N-((5-(2-((2-(morpholinomethyl)quinazolin-4-yl)thio)acetyl)thiophen-2-yl)methyl)acetamide or a pharmaceutically acceptable salt or solvate thereof. According to one embodiment, the compound of formula (I) is not CAS #1320446-60-3: N-(2-(5-(2-((2-(morpholinomethyl)quinazolin-4-yl)thio)acetyl)thiophen-2-yl)ethyl)acetamide or a pharmaceutically acceptable salt or solvate thereof.

In one embodiment, the compound of formula (I) is not selected from:
CAS #2182075-55-2: N-((5-(2-((2-methylquinazolin-4-yl)thio)acetyl)thiophen-2-yl)methyl)acetamide,
CAS #1010596-74-3: N-(2-(5-(2-((2-cyclopropylquinazolin-4-yl)thio)acetyl)thiophen-2-yl)ethyl)methanesulfonamide,
CAS #871674-28-1: N-((5-(2-((2-(thiophen-2-yl)quinazolin-4-yl)thio)acetyl)thiophen-2-yl)methyl)acetamide,
CAS #1147537-22-1: N-((5-(2-((2-(furan-2-yl)quinazolin-4-yl)thio)acetyl)thiophen-2-yl)methyl)acetamide,
CAS #1009199-55-6: N-(2-(5-(2-((2-(thiophen-2-yl)quinazolin-4-yl)thio)acetyl)thiophen-2-yl)ethyl)methanesulfonamide,
CAS #1089547-51-2: N-(2-(5-(2-((2-(furan-2-yl)quinazolin-4-yl)thio)acetyl)thiophen-2-yl)ethyl)acetamide,
CAS #1321173-73-2: N-((5-(2-((2-(morpholinomethyl)quinazolin-4-yl)thio)acetyl)thiophen-2-yl)methyl)acetamide,
CAS #1320446-60-3: N-(2-(5-(2-((2-(morpholinomethyl)quinazolin-4-yl)thio)acetyl)thiophen-2-yl)ethyl)acetamide, and
pharmaceutically acceptable salts and solvates thereof.

In one embodiment, the compound of formula (I) is not selected from:
CAS #1287068-38-5: N-((5-(2-((2-(trifluoromethyl)quinazolin-4-yl)thio)acetyl)thiophen-2-yl)methyl)acetamide
CAS #2182075-55-2: N-((5-(2-((2-methylquinazolin-4-yl)thio)acetyl)thiophen-2-yl)methyl)acetamide
CAS #1147354-39-9: N-(2-(5-(2-((2-(trifluoromethyl)quinazolin-4-yl)thio)acetyl)thiophen-2-yl)ethyl)acetamide
CAS #1010596-74-3: N-(2-(5-(2-((2-cyclopropylquinazolin-4-yl)thio)acetyl)thiophen-2-yl)ethyl)methanesulfonamide
CAS #871674-28-1: N-((5-(2-((2-(thiophen-2-yl)quinazolin-4-yl)thio)acetyl)thiophen-2-yl)methyl)acetamide
CAS #1147537-22-1: N-((5-(2-((2-(furan-2-yl)quinazolin-4-yl)thio)acetyl)thiophen-2-yl)methyl)acetamide
CAS #1009199-55-6: N-(2-(5-(2-((2-(thiophen-2-yl)quinazolin-4-yl)thio)acetyl)thiophen-2-yl)ethyl)methanesulfonamide
CAS #1010596-81-2: N-(2-(5-(2-((2-cyclopropylquinazolin-4-yl)thio)acetyl)thiophen-2-yl)ethyl)acetamide
CAS #1089547-51-2: N-(2-(5-(2-((2-(furan-2-yl)quinazolin-4-yl)thio)acetyl)thiophen-2-yl)ethyl)acetamide
CAS #1321173-73-2: N-((5-(2-((2-(morpholinomethyl)quinazolin-4-yl)thio)acetyl)thiophen-2-yl)methyl)acetamide
CAS #1320446-60-3: N-(2-(5-(2-((2-(morpholinomethyl)quinazolin-4-yl)thio)acetyl)thiophen-2-yl)ethyl)acetamide, and pharmaceutically acceptable salts and solvates thereof.

According to one embodiment, when $Y^1$ is optionally substituted quinazolinyl (e.g., quinazolin-4-yl), then $R^2$ is not an optionally substituted ($C_1$-$C_6$) alkyl, such as, for example, methyl or trifluoromethyl. In one embodiment, when $Y^1$ is optionally substituted quinazolinyl (e.g., quinazolin-4-yl), then $R^2$ is not an optionally substituted ($C_3$-$C_7$) cycloalkyl such as, for example, cyclopropyl. In one embodiment, when $Y^1$ is optionally substituted quinazolinyl (e.g., quinazolin-4-yl), then $R^2$ is not an optionally substituted heteroaryl such as, for example, furanyl or thiophenyl. In one embodiment, when $Y^1$ is optionally substituted quinazolinyl such as quinazolin-4-yl, then $R^2$ is not an optionally substituted —($C_1$-$C_6$) alkylene-($C_3$-$C_7$) heterocycloalkyl, such as, for example, —$CH_2$-morpholinyl.

In one embodiment, $Y^1$ is not optionally substituted quinazolin-4-yl. In one particular embodiment, $Y^1$ is not optionally substituted quinazolinyl.

According to one embodiment, when $Y^1$ is optionally substituted quinazolinyl (e.g., quinazolin-4-yl) and $R^1$ is hydrogen, then $Z^1$ is not an optionally substituted —C(O)—($C_1$-$C_6$) alkyl such as, for example, —C(O)-methyl.

According to one embodiment, when $Y^1$ is optionally substituted quinazolinyl (e.g., quinazolin-4-yl) and $R^1$ is hydrogen, then $Z^1$ is not an optionally substituted —S(O)$_2$—($C_1$-$C_6$) alkyl such as, for example, —S(O)$_2$-methyl.

According to one embodiment, the compound of formula (I) is not CAS #1210761-93-5: N-((5-(2-((1-methyl-1H-pyrazolo[3,4-d]pyrimidin-4-yl)thio)acetyl)thiophen-2-yl)methyl)pivalamide or a pharmaceutically acceptable salt or solvate thereof. According to one embodiment, the compound of formula (I) is not CAS #1011056-89-5: N-(2-(5-(2-((1-methyl-1H-pyrazolo[3,4-d]pyrimidin-4-yl)thio)acetyl)thiophen-2-yl)ethyl)acetamide or a pharmaceutically acceptable salt or solvate thereof. According to one embodiment, the compound of formula (I) is not CAS #1060780-01-9: N-(2-(5-(2-((1-phenyl-1H-pyrazolo[3,4-d]pyrimidin-4-yl)thio)acetyl)thiophen-2-yl)ethyl)acetamide or a pharmaceutically acceptable salt or solvate thereof. According to one embodiment, the compound of formula (I) is not N-(2-(5-(2-((1-phenyl-1H-pyrazolo[3,4-d]pyrimidin-4-yl)thio)acetyl)thiophen-2-yl)ethyl)methanesulfonamide [CAS #1326255-51-9] or a pharmaceutically acceptable salt or solvate thereof. According to one embodiment, the compound of formula (I) is not CAS #920953-29-3: N-(2-(5-(2-((1-(4-fluorophenyl)-1H-pyrazolo[3,4-d]pyrimidin-4-yl)thio)acetyl)thiophen-2-yl)ethyl)acetamide or a pharmaceutically acceptable salt or solvate thereof. According to one embodiment, the compound of formula (I) is not CAS #1324562-11-9: N-(2-(5-(2-((1-(4-fluorophenyl)-1H-pyrazolo[3,4-d]pyrimidin-4-yl)thio)acetyl)thiophen-2-yl)ethyl)methanesulfonamide or a pharmaceutically acceptable salt or solvate thereof. According to one embodiment, the compound of formula (I) is not CAS #1011002-97-3: N-((5-(2-((1-methyl-1H-pyrazolo[3,4-d]pyrimidin-4-yl)thio)acetyl)thiophen-2-yl)methyl)acetamide and or a pharmaceutically acceptable salt or solvate thereof. According to one embodiment, the compound of formula (I) is not CAS #1030737-65-5: N-((5-(2-((1-phenyl-1H-pyrazolo[3,4-d]pyrimidin-4-yl)thio)acetyl)thiophen-2-yl)methyl)acetamide or a pharmaceutically acceptable salt or solvate thereof.

In one embodiment, the compound of formula (I) is not selected from:
- CAS #1011056-89-5: N-(2-(5-(2-((1-methyl-1H-pyrazolo[3,4-d]pyrimidin-4-yl)thio)acetyl)thiophen-2-yl)ethyl)acetamide,
- CAS #1060780-01-9: N-(2-(5-(2-((1-phenyl-1H-pyrazolo[3,4-d]pyrimidin-4-yl)thio)acetyl)thiophen-2-yl)ethyl)acetamide,
- CAS #1326255-51-9: N-(2-(5-(2-((1-phenyl-1H-pyrazolo[3,4-d]pyrimidin-4-yl)thio)acetyl)thiophen-2-yl)ethyl)methanesulfonamide,
- CAS #920953-29-3: N-(2-(5-(2-((1-(4-fluorophenyl)-1H-pyrazolo[3,4-d]pyrimidin-4-yl)thio)acetyl)thiophen-2-yl)ethyl)acetamide,
- CAS #1324562-11-9; N-(2-(5-(2-((1-(4-fluorophenyl)-1H-pyrazolo[3,4-d]pyrimidin-4-yl)thio)acetyl)thiophen-2-yl)ethyl)methanesulfonamide,
- CAS #1030737-65-5: N-((5-(2-((1-phenyl-1H-pyrazolo[3,4-d]pyrimidin-4-yl)thio)acetyl)thiophen-2-yl)methyl)acetamide, and pharmaceutically acceptable salts and solvates thereof.

In one embodiment, the compound of formula (I) is not selected from:
- CAS #1210761-93-5: N-((5-(2-((1-methyl-1H-pyrazolo[3,4-d]pyrimidin-4-yl)thio)acetyl)thiophen-2-yl)methyl)pivalamide
- CAS #1011056-89-5: N-(2-(5-(2-((1-methyl-1H-pyrazolo[3,4-d]pyrimidin-4-yl)thio)acetyl)thiophen-2-yl)ethyl)acetamide
- CAS #1060780-01-9: N-(2-(5-(2-((1-phenyl-1H-pyrazolo[3,4-d]pyrimidin-4-yl)thio)acetyl)thiophen-2-yl)ethyl)acetamide
- CAS #1326255-51-9: N-(2-(5-(2-((1-phenyl-1H-pyrazolo[3,4-d]pyrimidin-4-yl)thio)acetyl)thiophen-2-yl)ethyl)methanesulfonamide
- CAS #920953-29-3: N-(2-(5-(2-((1-(4-fluorophenyl)-1H-pyrazolo[3,4-d]pyrimidin-4-yl)thio)acetyl)thiophen-2-yl)ethyl)acetamide
- CAS #1324562-11-9: N-(2-(5-(2-((1-(4-fluorophenyl)-1H-pyrazolo[3,4-d]pyrimidin-4-yl)thio)acetyl)thiophen-2-yl)ethyl)methanesulfonamide
- CAS #1011002-97-3: N-((5-(2-((1-methyl-1H-pyrazolo[3,4-d]pyrimidin-4-yl)thio)acetyl)thiophen-2-yl)methyl)acetamide
- CAS #1030737-65-5: N-((5-(2-((1-phenyl-1H-pyrazolo[3,4-d]pyrimidin-4-yl)thio)acetyl)thiophen-2-yl)methyl)acetamide, and pharmaceutically acceptable salts and solvates thereof.

According to one embodiment, when $Y^1$ is optionally substituted 1H-pyrazolo[3,4-d]pyrimidinyl (e.g., 1H-pyrazolo[3,4-d]pyrimidin-4-yl), then $R^5$ is not an optionally substituted ($C_1$-$C_6$) alkyl, such as, for example, methyl. In one embodiment, when $Y^1$ is optionally substituted 1H-pyrazolo[3,4-d]pyrimidinyl (e.g., 1H-pyrazolo[3,4-d]pyrimidin-4-yl), then $R^5$ is not an optionally substituted aryl, such as, for example, phenyl or fluorophenyl (e.g., 4-fluorophenyl).

In one embodiment, $Y^1$ not optionally substituted 1H-pyrazolo[3,4-d]pyrimidin-4-yl. In one particular embodiment, $Y^1$ not optionally substituted 1H-pyrazolo[3,4-d]pyrimidinyl.

According to one embodiment, when $Y^1$ is optionally substituted 1H-pyrazolo[3,4-d]pyrimidinyl (e.g., 1H-pyrazolo[3,4-d]pyrimidin-4-yl) and $R^1$ is hydrogen, then $Z^1$ is not an optionally substituted —C(O)—($C_1$-$C_6$) alkyl such as, for example, —C(O)-methyl and —C(O)-t-butyl.

According to one embodiment, when $Y^1$ is optionally substituted 1H-pyrazolo[3,4-d]pyrimidinyl (e.g., 1H-pyrazolo[3,4-d]pyrimidin-4-yl) and $R^1$ is hydrogen, then $Z^1$ is not an optionally substituted —S(O)$_2$—($C_1$-$C_6$) alkyl such as, for example, —SO$_2$-methyl.

According to one embodiment, the compound of formula (I) is not CAS #1325066-46-3: N-((5-(2-(imidazo[1,5-a]pyridin-3-ylthio)acetyl)thiophen-2-yl)methyl)acetamide or a pharmaceutically acceptable salt or solvate thereof. According to one embodiment, the compound of formula (I) is not CAS #1324658-47-0: N-(2-(5-(2-(imidazo[1,5-a]pyridin-3-ylthio)acetyl)thiophen-2-yl)ethyl)methanesulfonamide or a pharmaceutically acceptable salt or solvate thereof. According to one embodiment, the compound of formula (I) is not CAS #1325082-97-0: N-(2-(5-(2-(imidazo[1,5-a]pyridin-3-ylthio)acetyl)thiophen-2-yl)ethyl)acetamide or a pharmaceutically acceptable salt or solvate thereof. According to one embodiment, the compound of formula (I) is not CAS #949826-51-1: 2-(5-(2-((2,4-dimethyl-5-phenylimidazo[1,5-b]pyridazin-7-yl)thio)acetyl)thiophen-2-yl)acetamide or a pharmaceutically acceptable salt or solvate thereof. According to one embodiment, the compound of formula (I) is not CAS #1099735-84-8: N-((5-(2-((2,4-dimethyl-5-phenylimidazo[1,5-b]pyridazin-7-yl)thio)acetyl)thiophen-2-yl)methyl)acetamide or a pharmaceutically acceptable salt or solvate thereof. According to one embodiment, the compound of formula (I) is not CAS #1009471-75-3: N-(2-(5-(2-((2,4-dimethyl-5-phenylimidazo[1,5-b]pyridazin-7-yl)thio)acetyl)thiophen-2-yl)ethyl)acetamide or a pharmaceutically acceptable salt or solvate thereof. According to one embodiment, the compound of formula (I) is not CAS #1118826-22-4: N-(2-(5-(2-((6,8-dichloro-[1,2,4]triazolo[4,3-a]pyridin-3-yl)thio)acetyl)thiophen-2-yl)ethyl)methanesulfonamide or a pharmaceutically acceptable salt or solvate thereof. According to one embodiment, the compound of formula (I) is not CAS #1299961-73-1: N-((5-(2-((8-chloro-6-(trifluoromethyl)-[1,2,4]triazolo[4,3-a]pyridin-3-yl)thio)acetyl)thiophen-2-yl)methyl)acetamide or a pharmaceutically acceptable salt or solvate thereof. According to one embodiment, the compound of formula (I) is not CAS #1302276-01-2: N-(2-(5-(2-((8-chloro-6-(trifluoromethyl)-[1,2,4]triazolo[4,3-a]pyridin-3-yl)thio)acetyl)thiophen-2-yl)ethyl)methanesulfonamide or a pharmaceutically acceptable salt or solvate thereof. According to one embodiment, the compound of formula (I) is not CAS #1293687-72-5: N-((5-(2-((5,7-dimethyl-[1,2,4]triazolo[4,3-c]pyrimidin-3-yl)thio)acetyl)thiophen-2-yl)methyl)acetamide or a pharmaceutically acceptable salt or solvate thereof. According to one embodiment, the compound of formula (I) is not CAS #878598-17-5: N-((5-(2-((5,7-dimethyl-[1,2,4]triazolo[4,3-a]pyrimidin-3-yl)thio)acetyl)thiophen-2-yl)methyl)acetamide or a pharmaceutically acceptable salt or solvate thereof. According to one embodiment, the compound of formula (I) is not CAS #2184821-90-5: N-(2-(5-(2-((8-chloro-6-(trifluoromethyl)-[1,2,4]triazolo[4,3-a]pyridin-3-yl)thio)acetyl)thiophen-2-yl)ethyl)acetamide or a pharmaceutically acceptable salt or solvate thereof. According to one embodiment, the compound of formula (I) is not CAS #1297565-13-9: N-(2-(5-(2-((6-(trifluoromethyl)-[1,2,4]triazolo[4,3-a]pyridin-3-yl)thio)acetyl)thiophen-2-yl)ethyl)acetamide or a pharmaceutically acceptable salt or solvate thereof. According to one embodiment, the compound of formula (I) is not CAS #919869-52-6: N-(2-(5-(2-((5,7-dimethyl-[1,2,4]triazolo[4,3-a]pyrimidin-3-yl)thio)acetyl)thiophen-2-yl)ethyl)acetamide or a pharmaceutically acceptable salt or solvate thereof. According to one embodiment, the compound of formula (I) is not CAS #1001791-67-8: 2-([1,2,4]triazolo[4,3-a]pyridin-3-ylthio)-1-(5-(2-morpholino-2-oxoethyl)thiophen-2-yl)ethan-1-one or a pharmaceutically acceptable salt or solvate thereof. According to one embodiment, the compound of formula (I) is not CAS #874609-73-1: N-((5-(2-([1,2,4]triazolo[4,3-a]pyridin-3-ylthio)acetyl)thiophen-2-yl)methyl)pivalamide or a pharmaceutically acceptable salt or solvate thereof. According to one embodiment, the compound of formula (I) is not CAS #1010352-07-4: N-(2-(5-(2-((6-(N,N-diethylsulfamoyl)-[1,2,4]triazolo[4,3-a]pyridin-3-yl)thio)acetyl)thiophen-2-yl)ethyl)acetamide or a pharmaceutically acceptable salt or solvate thereof.

In one embodiment, the compound of formula (I) is not selected from:

CAS #1325066-46-3: N-((5-(2-(imidazo[1,5-a]pyridin-3-ylthio)acetyl)thiophen-2-yl)methyl)acetamide CAS #1324658-47-0: N-(2-(5-(2-(imidazo[1,5-a]pyridin-3-ylthio)acetyl)thiophen-2-yl)ethyl)methanesulfonamide CAS #1325082-97-0: N-(2-(5-(2-(imidazo[1,5-a]pyridin-3-ylthio)acetyl)thiophen-2-yl)ethyl)acetamide CAS #949826-51-1: 2-(5-(2-((2,4-dimethyl-5-phenylimidazo[1,5-b]pyridazin-7-yl)thio)acetyl)thiophen-2-yl)acetamide CAS #1099735-84-8: N-((5-(2-((2,4-dimethyl-5-phenylimidazo[1,5-b]pyridazin-7-yl)thio)acetyl)thiophen-2-yl)methyl)acetamide CAS #1009471-75-3: N-(2-(5-(2-((2,4-dimethyl-5-phenylimidazo[1,5-b]pyridazin-7-yl)thio)acetyl)thiophen-2-yl)ethyl)acetamide CAS #1118826-22-4: N-(2-(5-(2-((6,8-dichloro-[1,2,4]triazolo[4,3-a]pyridin-3-yl)thio)acetyl)thiophen-2-yl)ethyl)methanesulfonamide CAS #1299961-73-1: N-((5-(2-((8-chloro-6-(trifluoromethyl)-[1,2,4]triazolo[4,3-a]pyridin-3-yl)thio)acetyl)thiophen-2-yl)methyl)acetamide CAS #1302276-01-2: N-(2-(5-(2-((8-chloro-6-(trifluoromethyl)-[1,2,4]triazolo[4,3-a]pyridin-3-yl)thio)acetyl)thiophen-2-yl)ethyl)methanesulfonamide CAS #1293687-72-5: N-((5-(2-((5,7-dimethyl-[1,2,4]triazolo[4,3-c]pyrimidin-3-yl)thio)acetyl)thiophen-2-yl)methyl)acetamide CAS #878598-17-5: N-((5-(2-((5,7-dimethyl-[1,2,4]triazolo[4,3-a]pyrimidin-3-yl)thio)acetyl)thiophen-2-yl)methyl)acetamide CAS #2184821-90-5: N-(2-(5-(2-((8-chloro-6-(trifluoromethyl)-[1,2,4]triazolo[4,3-a]pyridin-3-yl)thio)acetyl)thiophen-2-yl)ethyl)acetamide CAS #1297565-13-9: N-(2-(5-(2-((6-(trifluoromethyl)-[1,2,4]triazolo[4,3-a]pyridin-3-yl)thio)acetyl)thiophen-2-yl)ethyl)acetamide CAS #919869-52-6: N-(2-(5-(2-((5,7-dimethyl-[1,2,4]triazolo[4,3-a]pyrimidin-3-yl)thio)acetyl)thiophen-2-yl)ethyl)acetamide CAS #1001791-67-8: 2-([1,2,4]triazolo[4,3-a]pyridin-3-ylthio)-1-(5-(2-morpholino-2-oxoethyl)thiophen-2-yl)ethan-1-one CAS #874609-73-1: N-((5-(2-([1,2,4]triazolo[4,3-a]pyridin-3-ylthio)acetyl)thiophen-2-yl)methyl)pivalamide CAS #1010352-07-4: N-(2-(5-(2-((6-(N,N-diethylsulfamoyl)-[1,2,4]triazolo[4,3-a]pyridin-3-yl)thio)acetyl)thiophen-2-yl)ethyl)acetamide, and pharmaceutically acceptable salts and solvates thereof.

In one embodiment, $Y^1$ is not an optionally substituted imidazo[1,5-a]pyridin-3-yl. In one particular embodiment, $Y^1$ is not an optionally substituted imidazo[1,5-a]pyridinyl. In one embodiment, $Y^1$ is not an optionally substituted imidazo[1,5-b]pyridazin-7-yl. In one particular embodiment, $Y^1$ is not an optionally substituted imidazo[1,5-b]pyridazinyl. In one embodiment, $Y^1$ is not an optionally substituted [1,2,4]triazolo[4,3-a]pyridin-3-yl. In one particular embodiment, $Y^1$ is not an optionally substituted

[1,2,4]triazolo[4,3-a]pyridinyl. In one embodiment, Y¹ is not an optionally substituted [1,2,4]triazolo[4,3-a]pyrimidin-3-yl. In one particular embodiment, Y¹ is not an optionally substituted [1,2,4]triazolo[4,3-a]pyrimidinyl. In one embodiment, Y¹ is not an optionally substituted [1,2,4]triazolo[4,3-a]pyridin-3-yl. In one particular embodiment, Y¹ is not an optionally substituted [1,2,4]triazolo[4,3-a]pyridinyl.

In one particular embodiment, Y¹ is not the group of formula (Sc7)

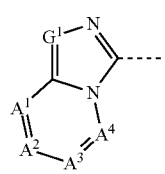

(Sc7)

wherein A¹-A⁴ and G¹ are independently as defined hereinabove.

According to one embodiment, the compound of formula (I) is not CAS #2419446-18-5: N-(2-(5-(2-((5-methyloxazolo[4,5-b]pyridin-2-yl)thio)acetyl)thiophen-2-yl)ethyl)acetamide [named using ChemDraw® Professional 15.0 (PerkinElmer)]

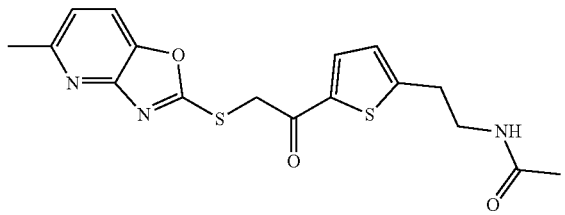 [SMILES: CC(=O)NCCc1ccc(C(=O)CSc2nc3nc(C)ccc3o2)s1]

nor a pharmaceutically acceptable salt and/or solvate thereof.

According to one embodiment, Y¹ is not an optionally substituted oxazolo[4,5-b]pyridin-2-yl such as, for example, 5-methyloxazolo[4,5-b]pyridin-2-yl. In one particular embodiment, Y¹ is not an optionally substituted oxazolo[4,5-b]pyridinyl such as, for example, 5-methyloxazolo[4,5-b]pyridinyl.

According to one embodiment, when Y¹ is an optionally substituted oxazolo[4,5-b]pyridin-2-yl (e.g., 5-methyloxazolo[4,5-b]pyridin-2-yl) and R¹ is hydrogen, then Z¹ is not an optionally substituted —C(O)—(C₁-C₆) alkyl such as, for example, —C(O)-methyl and —C(O)-t-butyl Manufacturing Process This invention also relates to process for manufacturing a compound of the invention as described herein. According to one embodiment, the process comprises a step of reacting: (i) a linear or cyclic amine with an acyl chloride, a carboxylic acid or sulfonyl chloride; or (ii) a halo-ketone with a thiol.

Pharmaceutical Compositions

This invention also relates to a pharmaceutical composition comprising a compound of the invention as described herein and at least one pharmaceutically acceptable carrier.

According to one embodiment, the pharmaceutical composition does not comprise any therapeutic agent other than the compound of the invention. According to another embodiment, the pharmaceutical composition further comprises at least another therapeutic agent. In one embodiment, the at least another therapeutic agent is selected from therapeutic agent known in the art for treating inflammatory diseases, autoimmune diseases, proliferative diseases (such as cancers), neurodegenerative diseases, pains, neuropathies, psychiatric diseases, neurodevelopmental disorders, sleep disorders, cardiovascular diseases, addiction-related disorders, gastrointestinal diseases, pulmonary diseases, metabolic or hormonal disorders, immune disorders, age-related diseases, and/or idiopathic diseases.

The compound of the invention may be formulated, alone or together, in suitable dosage unit formulations containing conventional non-toxic pharmaceutically acceptable carriers, adjuvants and vehicles appropriate for each route of administration.

Medical Uses and Methods of Treatment

This invention also relates to a compound of the invention as described herein, or a pharmaceutical composition of the invention as described herein, for use as a medicament.

According to one particular embodiment, the compound or pharmaceutical composition of the invention is for use in the treatment and/or prevention of an HDAC6-associated disease as defined herein.

This invention also relates to a method of inhibiting an HDAC6 enzyme. According to one embodiment, the inhibition of an HDAC6 enzyme treats and/or prevents an HDAC6-associated disease. According to one embodiment, the method comprises a step of administering to a subject in need thereof a therapeutically effective amount of a compound of the invention as described herein, or of a pharmaceutical composition of the invention as described herein.

This invention also relates to a method for treating and/or preventing a HDAC6-associated disease comprising a step of administering to a subject in need thereof a therapeutically effective amount of a compound of the invention as described herein, or of a pharmaceutical composition of the invention as described herein. This invention also relates to the use of a compound of the invention as described herein, or a pharmaceutical composition of the invention as described herein, in the manufacture of a medicament for the treatment and/or prevention of an HDAC6-associated disease. This invention also relates to the use of a compound of the invention as described herein, or a pharmaceutical composition of the invention as described herein, in the treatment and/or prevention of an HDAC6-associated disease.

Advantageously, the compound of the invention shows a superior inhibitory activity against an HDAC enzyme (e.g., class II HDAC enzyme, preferably HDAC6 enzyme) compared to state-of-the art compounds for treating and/or preventing an HDAC-associated disease. Advantageously, the compound of the invention shows a low toxicity (e.g., acute toxicity, chronic toxicity, genetic toxicity, hematotoxicity, reproductive toxicity, cardiotoxicity, carcinogenicity) against an HDAC enzyme (e.g., class II HDAC enzyme, preferably HDAC6 enzyme) compared to state-of-the art compounds for treating and/or preventing an HDAC-associated disease. In particular, the compound of the invention shows a low genetic toxicity.

According to one embodiment, the HDAC6-associated disease is selected from the group comprising or consisting of inflammatory diseases, autoimmune diseases, proliferative diseases (such as cancers), neurodegenerative diseases, pains, neuropathies, psychiatric diseases, neurodevelopmental disorders, sleep disorders, cardiovascular diseases, addiction-related disorders, gastrointestinal diseases, pulmonary diseases, metabolic or hormonal disorders, immune disorders, age-related diseases, and idiopathic diseases. According to one embodiment, the HDAC6-associated disease is selected from the group comprising or consisting of inflammatory diseases, autoimmune diseases, proliferative diseases (such as cancers), neurodegenerative diseases, pains, neuropathies, psychiatric diseases, neurodevelopmental disorders, sleep disorders and cardiovascular diseases. According to one embodiment, the HDAC6-associated disease is selected from the group comprising or consisting of proliferative diseases (such as cancers), neurodegenerative diseases, neuropathies and cardiovascular diseases.

A selection of references evidencing that inhibition of HDAC6 has the effect of treating and/or preventing a given class of diseases are listed on Table 3 below.

TABLE 3

| Diseases | References |
| --- | --- |
| Inflammatory diseases | Ran J and Zhou J.: "Targeted inhibition of histone deacetylase 6 in inflammatory diseases." Thorac. Cancer. 2019; 10(3): 405-412.<br>Lee J W et al.: "Histone Deacetylase 6 Inhibitor CKD-506 Inhibits NF-κB Signaling in Intestinal Epithelial Cells and Macrophages and Ameliorates Acute and Chronic Murine" Colitis. Inflamm. Bowel Dis. 2020; 26(6): 852-862.<br>Zhang Q et al. "Role of HDAC6 inhibition in sepsis-induced acute respiratory distress syndrome." Exp Ther Med. 2021; 21(5): 422. |
| Autoimmune diseases | Park J K et al.: "Therapeutic potential of CKD-506, a novel selective histone deacetylase 6 inhibitor, in a murine model of rheumatoid arthritis." Arthritis Res Ther. 2020; 22(1): 176.<br>Choi E W et al. "CKD-506, a novel HDAC6-selective inhibitor, improves renal outcomes and survival in a mouse model of systemic lupus erythematosus." Sci Rep. 2018 Nov. 23; 8(1): 17297. |
| Proliferative diseases | Yussuf K M et al. "Overcome the tumor immunotherapy resistance by combination of the HDAC6 inhibitors with antitumor immunomodulatory agents." Bioorg Chem. 2021; 109: 104754.<br>Yang J et al.: "Histone Deacetylase 6 as a Therapeutic Target in B cell-associated Hematological Malignancies." Front Pharmacol. 2020; 11: 971.<br>Batchu S N et al.: "The therapeutic hope for HDAC6 inhibitors in malignancy and chronic disease." Clin Sci (Lond). 2016; 130(12): 987-1003.<br>Giuliani N et al.: "Novel targets for the treatment of relapsing multiple myeloma." Expert Rev Hematol. 2019; 12(7): 481-496.<br>Li T et al.: "Histone deacetylase 6 in cancer." J Hematol Oncol. 2018; 11(1): 111. |
| Neurodegenerative diseases | Shen S and Kozikowski A P. "A patent review of histone deacetylase 6 inhibitors in neurodegenerative diseases (2014-2019)." Expert Opin Ther Pat. 2020; 30(2): 121-136.<br>Li Y et al.: "Inhibition of Histone Deacetylase 6 (HDAC6) as a therapeutic strategy for Alzheimer's disease: A review (2010-2020)." Eur J Med Chem. 2021; 226: 113874.<br>Zhang K et al.: "Targeting autophagy using small-molecule compounds to improve potential therapy of Parkinson's disease." Acta Pharm Sin B. 2021; 11(10): 3015-3034.<br>Lemos M and Stefanova N. "Histone Deacetylase 6 and the Disease Mechanisms of alpha-Synucleinopathies." Front Synaptic Neurosci. 2020; 12: 586453.<br>Bae D et al.: "CKD-506: A novel HDAC6-selective inhibitor that exerts therapeutic effects in a rodent model of multiple sclerosis." Sci Rep. 2021; 11(1): 14466.<br>Guo W and Van Den Bosch L.: "Therapeutic potential of HDAC6 in amyotrophic lateral sclerosis." Cell Stress. 2017 Dec. 19; 2(1): 14-16 |
| Pains | Sakloth F et al.: "HDAC6-selective inhibitors decrease nerve-injury and inflammation-associated mechanical hypersensitivity in mice." Psychopharmacology (Berl). 2020, 237(7): 2139-2149. |

TABLE 3-continued

| Diseases | References |
| --- | --- |
| Neuropathies | English K and Barton M C. "HDAC6: A Key Link Between Mitochondria and Development of Peripheral Neuropathy." Front Mol Neurosci. 2021; 14: 684714.<br>Rossaert E and Van Den Bosch L. "HDAC6 inhibitors: Translating genetic and molecular insights into a therapy for axonal CMT." Brain Res. 2020; 1733: 146692.<br>Prior R et al.: "HDAC6 as a potential therapeutic target for peripheral nerve disorders." Expert Opin Ther Targets. 2018; 22(12): 993-1007.<br>Van Helleputte L et al.: "Inhibition of histone deacetylase 6 (HDAC6) protects against vincristine-induced peripheral neuropathies and inhibits tumor growth." Neurobiol Dis. 2018; 111: 59-69. |
| Psychiatric diseases or Neurodevelopmental disorders | LoPresti P.: "HDAC6 in Diseases of Cognition and of Neurons." Cells. 2020; 10(1): 12.<br>Kozikowski A P and al.: "Brain Penetrable Histone Deacetylase 6 Inhibitor SW-100 Ameliorates Memory and Learning Impairments in a Mouse Model of Fragile X Syndrome." ACS Chem Neurosci. 2019; 10(3): 1679-1695. |
| Cardiovascular diseases | Patent application WO 2021/067859 A1 (2021 Apr. 8): Mandegar, M. A. et al. "5-Fluoronicotinamide Derivatives as HDAC6 Inhibitors for Treating Heart Diseases". |
| Immune disorders | Zhang L and al. "Diverse roles of HDAC6 in viral infection: Implications for antiviral therapy." Pharmacol Ther. 2016; 164: 120-5. |

According to one embodiment, the HDAC6-associated disease is an inflammatory disease such as, for example, acute pancreatitis, chronic pancreatitis, asthma, adult respiratory distress syndrome, chronic obstructive pulmonary disease (COPD), idiopathic pulmonary fibrosis, inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, diabetic nephropathy, uveitis, suppurative hidradenitis, cerebrospinal meningitis, inflammatory bowel disease, ulcerative colitis, Crohn's disease, and the like. In one embodiment, the inflammatory disease is selected from the group comprising or consisting of acute pancreatitis, chronic pancreatitis, asthma, adult respiratory distress syndrome, chronic obstructive pulmonary disease (COPD), idiopathic pulmonary fibrosis, inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, diabetic nephropathy, uveitis, suppurative hidradenitis, cerebrospinal meningitis, inflammatory bowel disease, ulcerative colitis and Crohn's disease.

According to one embodiment, the HDAC6-associated disease is an autoimmune disease, such as, for example, arthritis, rheumatoid arthritis, psoriasis, inflammatory bowel disease (e.g., Crohn's disease or ulcerative colitis), Sjogren's syndrome, multiple sclerosis, systemic lupus erythematosus, lupus nephritis, discoid lupus erythematosus, Castleman's disease, ankylopoietic spondylarthritis, polymyositis, dermatomyositis (DM), polyarteritis nodosa (PN), mixed connective tissue disease (MCTD), scleroderma, lupus erythematosus profundus, chronic thyroiditis, Graves' disease, autoimmune gastritis, type I diabetes, autoimmune hemolytic anemia, autoimmune neutropenia, thrombocytopenia, atopic dermatitis, pemphigus, chronic active hepatitis, myasthenia gravis, graft versus host disease, dermatitis, radiodermatitis, primary biliary cirrhosis, and the like. In one embodiment, the autoimmune disease is selected from the group comprising or consisting of arthritis, rheumatoid arthritis, psoriasis, inflammatory bowel disease (e.g., Crohn's disease or ulcerative colitis), Sjogren's syndrome, multiple sclerosis, systemic lupus erythematosus, lupus nephritis, discoid lupus erythematosus, Castleman's disease, ankylopoietic spondylarthritis, polymyositis, dermatomyositis (DM), polyarteritis nodosa (PN), mixed connective tissue disease (MCTD), scleroderma, lupus erythematosus profundus, chronic thyroiditis, Graves' disease, autoimmune gastritis, type I diabetes, autoimmune hemolytic anemia, autoimmune neutropenia, thrombocytopenia, atopic dermatitis, pemphigus, chronic active hepatitis, myasthenia gravis, graft versus host disease, dermatitis, radiodermatitis and primary biliary cirrhosis.

According to one embodiment, the HDAC6-associated disease is a proliferative disease, e.g., cancer, such as, for example, malignant tumor, angiogenesis glaucoma, infantile hemangioma, multiple myeloma, chronic sarcoma, metastasis melanoma, Kaposi's sarcoma, vascular proliferation, cachexia, metastasis of the breast cancer, colorectal cancer (e.g., familial colorectal cancer, hereditary nonpolyposis colorectal cancer or gastrointestinal stromal tumor), lung cancer (e.g., non-small cell lung cancer, small cell lung cancer or malignant mesothelioma), mesothelioma, pancreatic cancer (e.g., pancreatic duct cancer), gastric cancer (e.g., papillary adenocarcinoma, mucinous adenocarcinoma or adenosquamous carcinoma), breast cancer (e.g., invasive ductal carcinoma, ductal carcinoma in situ or inflammatory breast cancer), ovarian cancer (e.g., ovarian epithelial carcinoma, extragonadal germ cell tumor, ovarian germ cell tumor or ovarian low malignant potential tumor), prostate cancer (e.g., hormone-dependent prostate cancer or non-hormone dependent prostate cancer), liver cancer (e.g., primary liver cancer or extrahepatic bile duct cancer), thyroid cancer (e.g., medullary thyroid carcinoma), kidney cancer (e.g., renal cell carcinoma, transitional cell carcinoma in kidney or transitional cell carcinoma in urinary duct), uterine cancer, brain tumor (e.g., pineal astrocytoma, pilocytic astrocytoma, diffuse astrocytoma or anaplastic astrocytoma), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, chorionic disease, vaginal cancer, skin cancer, fungoid mycosis, basal cell tumor, soft tissue sarcoma, malignant lymphoma, Hodgkin's disease, myelodysplastic syndrome, adult T cell leukemia, chronic bone marrow proliferative disease, pancreatic endocrine, tumor fibrous histiocytoma, leiomyosarcoma, rhabdomyosarcoma, cancer of unknown primary, leukemia (such as acute leukemia (e.g., acute lymphatic leukemia or acute myelocytic leukemia), chronic leukemia (e.g., chronic lymphatic leukemia or chronic myelocytic leukemia)), myelodysplastic syndrome, uterine sarcoma (e.g., mixed mesodermal tumor, uterine leiomyosarcoma or endometrial stromal tumor) and myelofibrosis. In one particular embodiment, the proliferative disease is cancer. In one embodiment, the cancer is selected from the group comprising or consisting of malignant melanoma, multiple myeloma, leukemia, lymphoma, breast cancer and Hodgkin's disease.

According to one embodiment, the HDAC6-associated disease is a neurodegenerative disease, such as, for example, Alzheimer's disease, dementia of Alzheimer type, Alzheimer-type senile dementia, Parkinson's disease, muscular dystrophy, Parkinson's disease associated with dementia, senile dementia, age-related cognition memory disorders, Huntington's disease, multi-infarct dementia, frontotemporal lobar degeneration, frontotemporal dementia, Pick's disease, Parkinson's type dementia, Niemann-Pick syndrome, Down's disease, vascular dementia, postencephalitic parkinsonism, Lewy body dementia, Rubinstein-Taybi syndrome, HIV dementia, amyotrophic lateral sclerosis (ALS), motor neurogenesis disease (MND), Creutzfeldt, and the like. In one embodiment, the neurodegenerative disease is selected from the group comprising or consisting of Alzheimer's disease, dementia of Alzheimer type, Alzheimer-type senile dementia, Parkinson's disease, muscular dystrophy, Parkinson's disease associated with dementia, senile dementia, age-related cognition memory disorders, Huntington's disease, multi-infarct dementia, frontotemporal lobar degeneration, frontotemporal dementia, Pick's disease, Parkinson's type dementia, Niemann-Pick syndrome, Down's disease, vascular dementia, postencephalitic parkinsonism, Lewy body dementia, Rubinstein-Taybi syndrome, HIV dementia, amyotrophic lateral sclerosis (ALS), motor neurogenesis disease (MND) and Creutzfeldt. In one particular embodiment, the neurodegenerative disease is selected from the group comprising or consisting of Alzheimer's disease, Parkinson's disease, Huntington's disease, frontotemporal dementia, Pick's disease, Niemann-Pick syndrome, Down's disease, Lewy body dementia, HIV dementia, amyotrophic lateral sclerosis (ALS), and multiple sclerosis.

According to one embodiment, the HDAC6-associated disease is a pain (including central or peripheral pain), such as, for example, pain, cancer pain, acute pain caused by inflammation, pain associated with chronic inflammation, postoperative pain (e.g., incision pain, deep pain, visceral pain or chronic pain after operation), muscular pain (e.g., muscular pain associated with chronic pain disease or stiff shoulder), arthralgia, toothache, temporomandibular joint pain, headache (e.g., migraine, catatonic headache, headache associated with fever or headache associated with hypertension), visceral pain (e.g., cardiac pain, angina pain, abdominal pain, renal pain, urinary tract pain or bladder pain), obstetric and gynecologic pain (mittelschmerz, dysmenorrhea, labor pain), neuropathic pain (e.g., hernia of intervertebral disk, nerve root pain, neuralgia after herpes zoster, trigeminal neuralgia or lumbago), migraine, stress headache, catatonic headache, muscular spasm, irritable bowel syndrome, and the like. In one embodiment, the pain is selected from the group comprising or consisting of pain, cancer pain, acute pain caused by inflammation, pain associated with chronic inflammation, postoperative pain (e.g., incision pain, deep pain, visceral pain or chronic pain after operation), muscular pain (e.g., muscular pain associated with chronic pain disease or stiff shoulder), arthralgia, toothache, temporomandibular joint pain, headache (e.g., migraine, catatonic headache, headache associated with fever or headache associated with hypertension), visceral pain (e.g., cardiac pain, angina pain, abdominal pain, renal pain, urinary tract pain or bladder pain), obstetric and gynecologic pain (e.g., mittelschmerz, dysmenorrhea, or labor pain), neuropathic pain (e.g., hernia of intervertebral disk, nerve root pain, neuralgia after herpes zoster, trigeminal neuralgia or lumbago), migraine, stress headache, catatonic headache, muscular spasm and irritable bowel syndrome.

According to one embodiment, the HDAC6-associated disease is a neuropathy (including central or peripheral neuropathy), such as, for example, demyelinating diseases and neuropathy (e.g., multiple sclerosis, Guillain-Barre syndrome, Fisher syndrome, chronic inflammatory demyelinating polyneuropathy (CIDP), multifocal motor neuropathy (MMN), Charcot-Marie-Tooth disease, hereditary sensory and autonomic neuropathy or familial amyloidotic polyneuropathy), peripheral neuropathy (CIPN) derived from anticancer drugs and neurological symptoms associated therewith (e.g., chemotherapy-induced neuropathic pain (CINP)), diabetic neuropathy, autonomic ataxia, injury-related neuropathy (e.g., traumatic brain injury or cerebral apoplexy), and the like. Anticancer drugs susceptible to cause neuropathy include taxanes (e.g., paclitaxel (Taxol)), vinca alkaloids (e.g., vincristine), platinum-based agents (e.g., cisplatin, carboplatin or oxaliplatin), or other molecularly targeted drugs (e.g., bortezomib). In one embodiment, the neuropathy is selected from the group comprising or consisting of demyelinating diseases and neuropathy (e.g., multiple sclerosis, Guillain-Barre syndrome, Fisher syndrome, chronic inflammatory demyelinating polyneuropathy (CIDP), multifocal motor neuropathy (MMN), Charcot-Marie-Tooth disease, hereditary sensory and autonomic neuropathy or familial amyloidotic polyneuropathy), peripheral neuropathy (CIPN) derived from anticancer drugs and neurological symptoms associated therewith (e.g., chemotherapy-induced neuropathic pain (CINP)), diabetic neuropathy, autonomic ataxia and injury-related neuropathy (e.g., traumatic brain injury or cerebral apoplexy).

In one particular embodiment, the neuropathy is selected from the group comprising or consisting of Guillain-Barre syndrome, chronic inflammatory demyelinating polyneuropathy (CIDP), multifocal motor neuropathy (MMN), Charcot-Marie-Tooth disease, hereditary sensory and autonomic neuropathy, familial amyloidotic polyneuropathy, chemotherapy-induced peripheral neuropathy (CIPN) using chemotherapeutic anticancer agents, diabetic peripheral neuropathy (DPN), neuralgia, pain and neuropathic pain.

According to one embodiment, the HDAC6-associated disease is a psychiatric disease, such as, for example, depression, major depression, bipolar depression, psychotic major depression, refractory major depression, treatment-resistant depression, depression symptom, postpartum depression, bipolar disorder, schizophrenia (e.g., positive symptom, negative symptom or cognitive symptom), cognitive dysfunction associated with schizophrenia, stress disorder, mania, anxiety, generalized anxiety disorder, anxiety syndrome, panic disorder, social anxiety disorder, obsessive disorder, post-traumatic stress syndrome, post-traumatic stress disorder, dysthymic disorder, emotional disorder (e.g., seasonal affective disorder), phobia, social phobia, neurosis, chronic fatigue syndrome, epilepsy, cyclothymia, addiction, neurotic anorexia, eating disorder, anorexia nervosa, hyperorexia or other eating disorder, pharmacophilia, pharmacophobia, pharmacomania, and the like. In one embodiment, the psychiatric disease is selected from the group comprising or consisting of depression, major depression, bipolar depression, psychotic major depression, refractory major depression, treatment-resistant depression, depression symptom, postpartum depression, bipolar disorder, schizophrenia (e.g., positive symptom, negative symptom or cognitive symptom), cognitive dysfunction associated with schizophrenia, stress disorder, mania, anxiety, generalized anxiety disorder, anxiety syndrome, panic disorder, social anxiety disorder, obsessive disorder, post-traumatic stress syndrome, post-traumatic stress disorder, dysthymic disorder, emotional disorder (e.g., seasonal affective disorder), phobia, social phobia, neurosis, chronic fatigue syndrome, epilepsy, cyclothymia, addiction, neurotic anorexia, eating disorder, anorexia nervosa, hyperorexia or other eating disorder, pharmacophilia, pharmacophobia, and pharmacomania.

According to one embodiment, the HDAC6-associated disease is a neurodevelopmental disorder, such as, for example, Tourette syndrome, autism, autistic spectrum syndrome, fragile X syndrome, Rett syndrome, attention deficit hyperactivity disorder (ADHD), and the like. In one embodiment, the neurodevelopmental disorder is selected from the group comprising or consisting of Tourette syndrome, autism, autistic spectrum syndrome, fragile X syndrome, Rett syndrome, and attention deficit hyperactivity disorder (ADHD).

According to one embodiment, the HDAC6-associated disease is a sleep disorder, such as, for example, intrinsic sleep disorders (e.g., psychophysiological insomnia), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome or non-24-hour sleep-wake), parasomnia, sleep disorders associated with internal medical or psychiatric disorder (e.g., chronic obstructive pulmonary diseases, Alzheimer's disease, Parkinson's disease, cerebrovascular dementia, schizophrenia, depression or anxiety neurosis), stress, insomnia, insomnia, insomniac neurosis, sleep apnea syndrome, and the like. In one embodiment, the sleep disorder is selected from the group comprising or consisting of intrinsic sleep disorders (e.g., psychophysiological insomnia), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome or non-24-hour sleep-wake), parasomnia, sleep disorders associated with internal medical or psychiatric disorder (e.g., chronic obstructive pulmonary diseases, Alzheimer's disease, Parkinson's disease, cerebrovascular dementia, schizophrenia, depression or anxiety neurosis), stress, insomnia, insomnia, insomniac neurosis and sleep apnea syndrome.

According to one embodiment, the HDAC6-associated disease is a cardiovascular disease, such as, for example, chronic heart failure or acute heart failure, acute decompensated heart failure, ischemic heart disease, cardiomyopathy, myocarditis, valvular disease, hypertension, cardiac disease, tachycardia, congestive cardiac failure, and the like. In one embodiment, the cardiovascular disease is selected from the group comprising or consisting of chronic heart failure or acute heart failure, acute decompensated heart failure, ischemic heart disease, cardiomyopathy, myocarditis, valvular disease, hypertension, cardiac disease, tachycardia and congestive cardiac failure. In one particular embodiment, the heart-related disease is selected from the group comprising or consisting of heart failure, cardiomyopathy and myocarditis.

According to one embodiment, the HDAC6-associated disease is an addiction-related disorder, such as, for example, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, drug withdrawal, and the like. In one embodiment, the addiction related disorder is selected from the group comprising or consisting of alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity and drug withdrawal.

According to one embodiment, the HDAC6-associated disease is a gastrointestinal disease, such as, for example, peptic ulcer, stress gastrointestinal disorder, stress vomiting, peptic ulcer, diarrhea, constipation or postoperative ileus, and the like. In one embodiment, the gastrointestinal disease is selected from the group comprising or consisting of peptic ulcer, stress gastrointestinal disorder, stress vomiting, peptic ulcer, diarrhea, constipation ileus and postoperative ileus.

According to one embodiment, the HDAC6-associated disease is a pulmonary disease, such as, for example, hyperventilation, bronchial asthma, apnea, and the like. In one embodiment, the pulmonary disease is selected from the group comprising or consisting of hyperventilation, bronchial asthma and apnea.

According to one embodiment, the HDAC6-associated disease is a metabolic or hormonal disorder, such as, for example, obesity, diabetes, acromegaly, infertility, metabolic syndrome, and the like. In one embodiment, the metabolic or hormonal disorder is selected from the group comprising or consisting of obesity, diabetes, acromegaly, infertility and metabolic syndrome.

According to one embodiment, the HDAC6-associated disease is an immune disorder, such as, for example, allergic disease, immunodeficiency syndrome caused by HIV infection, immunodeficiency syndrome caused by stress, and the like. In one embodiment, the immune disorder is selected from the group comprising or consisting of immunodeficiency syndrome caused by HIV infection and immunodeficiency syndrome caused by stress.

According to one embodiment, the HDAC6-associated disease is an age-related disease, such as, for example, alopecia, glaucoma, impotence, climacteric disorder, incontinence, osteoporosis, and the like. In one embodiment, the age-related disease is selected from the group comprising or consisting of alopecia, glaucoma, impotence, climacteric disorder, incontinence and osteoporosis.

According to one embodiment, the HDAC6 associated disease is an idiopathic disease, such as, for example, Meniere's disease, sudden infant death syndrome, and the like. In one embodiment, the idiopathic disease is Meniere's disease or sudden infant death syndrome.

The compound or pharmaceutical composition of the invention may be administered by oral, parenteral (e.g., intramuscular, intraperitoneal, intravenous, intracerebroventricular (ICV), intracisternal injection or infusion, subcutaneous injection, or implant), by inhalation spray, nasal, vaginal, rectal, sublingual, or topical routes of administration. In the treatment and/or prevention of an infectious disease an appropriate dosage level may be from about 0.01 to 500 mg per kg patient body weight per day (mg/kg/day), which can be administered in single or multiple doses. Typically, the dosage level will be from about 0.1 to about 250 mg/kg/day, preferably from about 0.5 to about 100 mg/kg/day, more preferably from about 2.5 to about 20 mg/kg/day. The compounds may be administered on a regimen of 1 to 4 times per day, preferably once or twice per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular diseases and the host undergoing therapy.

Advantageously, the compound of the invention is selective over at least one HDAC other than HDAC6, preferably over at least one class II HDAC other than HDAC6, more preferably over any class II HDAC other than HDAC6, furthermore preferably over HDAC other than HDAC6. Particularly advantageously, the compound of the invention is selective over HDAC1. Particularly advantageously, the compound of the invention is selective over HDAC10. Selectivity is strongly associated with the avoidance of side-effects of HDAC inhibitors.

Kit

This invention also relates to a kit comprising a compound of the invention as described herein, or a pharmaceutical composition of the invention as described herein, and means to administer said compound or pharmaceutical composition.

EXAMPLES

The present invention is further illustrated by the following examples.

Example 1: Synthesis of the Compounds

The compounds of formula (I) (1)-(196) represented on Table 1 and/or Table 2 hereinabove were prepared as described hereinafter. Compounds 99 (CAS 1287068-38-5), Means for administering a compound or a pharmaceutical composition are well-known in the art and may be identified by a person skilled in the art depending of the desired administration route.

known in the art (A. R. Katrizky and C. W. Rees, 1984, *Comprehensive Heterocyclic Chemistry*, Pergamon Press).

The synthesis of the HDAC6 inhibitors disclosed in the present invention have been prepared using the following synthetic schemes. Specific conditions for carrying out these reactions are provided in the detailed examples. The synthetic schemes described below show exemplified approaches to compounds of the present invention, but these routes should not be taken as the only possible synthetic routes to compounds of the present invention.

Compounds of formula (I) may be obtained according to Scheme 1 below:

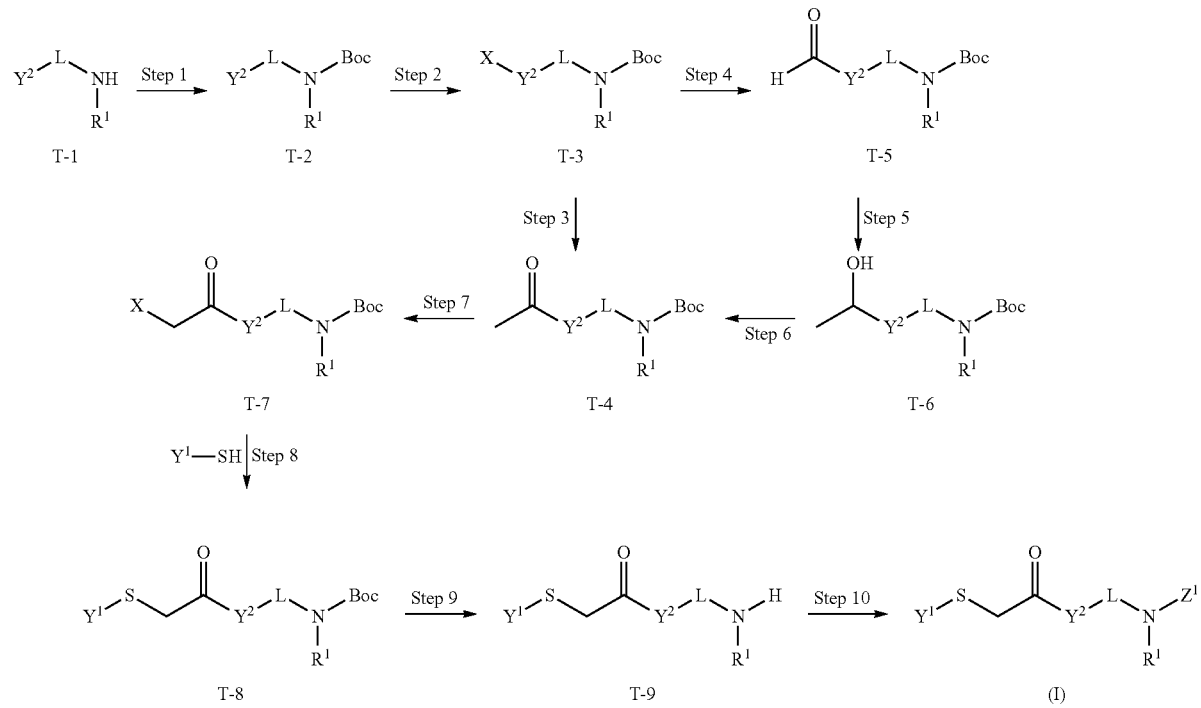

Scheme 1/Method 1

100 (CAS 1147354-39-9), 102 (CAS 1210761-93-5) and 104 (CAS 2419446-18-5) were commercially purchased. However, they may have been prepared by using similar methods.

General Synthetic Methods

The compounds according to the invention, in particular the compounds according to the formula (I), may be prepared by methods known to the person skilled in the art of organic synthesis or by using the following synthesis schemes. In all of the schemes described below it is understood that protecting groups for sensitive or reactive groups are employed where necessary in accordance with the general principles of organic chemistry. Protecting groups are manipulated according to standard methods (T. W. Green and P. G. M. Wuts, *Protecting Groups in Organic Synthesis*, 1991, John Wiley & Sons, Inc.). These groups are then removed at a convenient stage of the synthesis using methods that are readily apparent to those skilled in the art. Many of the heterocyclic compounds of formula (I) where $Y^1$ or $Y^2$ is a heteroaryl may be prepared using synthetic routes well Amines T-1 are commercially available or may be synthesized by a person skilled in the art of organic chemistry using multiple ways described in the literature. Intermediates T-2 may be prepared by protecting the amine group of T-1 (Step 1) by, for example using $Boc_2O$ in the presence of a base (e.g., $Et_3N$ or $NaHCO_3$) and in a solvent (e.g. DCM or THF) at the appropriate temperature. Protected amine intermediate T-2 can be engaged into a halogenation step to provide a T-3 in which X is a halo such as, for instance, bromo (Br) using, for example NBS or $Br_2$ in a solvent (e.g., DCM) at the appropriate temperature (Step 2). Halide T-3 can next be transformed into the corresponding ketone T-4 in a single or multiple step-sequence, for example: (Option 1) a 2-step sequence such as (i) metal-catalyzed cross coupling sequence using tributyl(1-ethoxyvinyl)tin, in the presence of a catalyst/ligand system (e.g., $Pd(PPh_3)_4$, a base (e.g., t-BuOK), in a solvent (e.g., dioxane)), at the appropriate temperature to provide the enol ether intermediate, which is turn transformed into the desired ketone T-4 using acidic media such as aqueous HCl or formic acid at the appropriate temperature (Step 3); or (Option 2) in a 3-step sequence such as (i) a metal-halide exchange, using for example n-BuLi, under inert atmosphere like nitrogen atmosphere, at controlled temperature like −78° C., in a non protic solvent like dry THF, followed by the introduction of dimethylformaldehyde, or equivalent reagent, to provide the corresponding aldehyde intermediate T-5 (Step 4). Intermediate T-5 can be treated with a methylating agent such as, for instance, MeMgBr, in a non-protic solvent (e.g., THF) at the appropriate temperature to provide the resulting alcohol T-6 (Step 5). Alcohol T-6 can be transformed into the corresponding ketone T-4 by the use of an oxidizing agent for example DMP or PCC in a solvent (e.g., DCM) at the appropriate temperature (Step 6). Ketone T-4 can be further engaged into a halogenation reaction, using for example NBS or phenyltrimethylammonium tribromide in a solvent (e.g., DCM or THF) at the appropriate temperature to provide halo-ketone T-7 (Step 7). Halo-ketone T-7 is then reacted with thiol hetero-aryl derivatives of Formula $Y^1$—SH in the presence of a base (e.g., MeONa or $K_2CO_3$) in a solvent (e.g., DMF or ACN) at the appropriate temperature to provide heteroaryl intermediate T-8 (Step 8). Heteroaryl $Y^1$—SH are commercially available or may be prepared by methods known to the person skilled in the art, for example from the corresponding heteroaryl $Y^1$—OH derivatives using Lawesson's reagent or $P_2S_5$ reagent in a solvent (e.g., toluene) at the appropriate temperature. Heteroaryl $Y^1$—OH are commercially available or may be prepared by methods known to the person skilled in the art. The protected amine T-8 can then be deprotected in acidic or basic media depending of the choice of the protecting group, for example in acidic media such as, for example, formic acid or aqueous HCl, to remove of a BoC-protecting group, or upon hydrogenolysis using $H_2$ in the presence a of catalyst (e.g., $Pd(OH)_2$) in a protic solvent (e.g., MeOH) to remove a benzyl-type protecting group such as, for example, Cbz, to finally provide the corresponding amine intermediate T-9 (Step 9).

Final compounds of formula (I) wherein $Z^1$ is CO—$R^9$ may be obtained by the reaction of amine T-9 with either an acyl chloride of Formula $R^9$—COCl in the presence of a base (e.g., $Et_3N$), a suitable solvent (e.g., DCM or THF) at the appropriate temperature (Step 10a). Alternatively, final compounds of formula (I) wherein $Z^1$ is CO—$R^9$ may be obtained by the reaction of amine T-9 or with a carboxylic acid of Formula $R^9$—$CO_2H$ acid in the presence of a coupling agent (e.g., HOBt or HATU), a base (e.g., $Et_3N$) in a solvent (e.g., DMF) at the appropriate temperature (Step 10b). Final compounds of formula (I) wherein $Z^1$ is CO—$R^9$ and $R^9$ is —$CH_2$—OH, may be obtained by the reaction of amine T-9 and with a carboxylic acid of Formula $HO_2C$—$CH_2$—$OSiR_3$, wherein $SiR_3$ is, for example, tert-butyldiphenylsilyl (TBDPS-) in the presence of a coupling agent (e.g., EDCI/HOBt or HATU), a base (e.g., $Et_3N$)) in a solvent (e.g., DMF) at the appropriate temperature, followed by the deprotection of the silyl ether function —$OSiR_3$ using a fluoride-based agent (e.g., TBAF) in a non-protic solvent (e.g., THF) at the appropriate temperature (Step 10c). Final compounds of formula (I) wherein $Z^1$ is $SO_2$—$R^9$ are obtained by the reaction of amine T-9 with either sulfonyl chloride of Formula $R^9$—$SO_2Cl$ in the presence of a base (e.g., $Et_3N$), a solvent (e.g., DCM or THF) at the appropriate temperature (Step 10b).

Compounds of formula (I) may be obtained also according to Scheme 2 (Method 2) below:

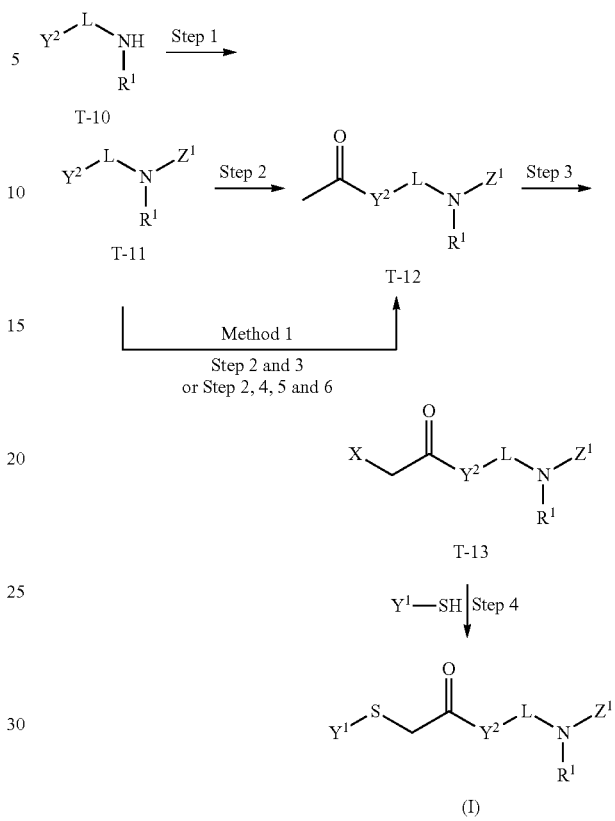

Scheme 2/Method 2

Amines T-10 are commercially available or may be synthesized by a person skilled in the art of organic chemistry using multiple ways described in the literature. Intermediate compounds T-11, wherein $Z^1$ is CO—$R^9$, may be prepared from the reaction of amines T-10 with either an acyl chloride of Formula $R^9$—COCl in the presence of a base (e.g., $Et_3N$), a solvent (e.g., DCM or THF) at the appropriate temperature; or with a carboxylic acid of Formula $R^9$—$CO_2H$ acid in the presence of a coupling agent (e.g., EDCI/HOBt or HATU), a base (e.g., $Et_3N$) in a solvent (e.g., DMF) at the appropriate temperature (Step 1a). Intermediate compounds T-11, wherein $Z^1$ is $SO_2$—$R^9$, can be obtained by the reaction of amine T-10 with either a sulfonyl chloride of Formula $R^9$—$SO_2Cl$ in the presence of a base (e.g., $Et_3N$), a solvent (e.g., DCM or THF) at the appropriate temperature (Step 1b). Heteroaryl intermediate T-11 are then reacted with an acylating agent for example acetyl chloride in the presence of a suitable catalyst such as, for example, $AlCl_3$, in a suitable solvent (e.g., DCM) at the appropriate temperature to provide intermediate ketone T-12, (Step 2). Alternative methods to prepare ketone T-12 can be used such as the method described in Scheme 1 (Method 1), either using from Scheme 1 the Step 2 and Step 3, or Step 2 to Step 6 synthesis sequence of reactions. Ketone T-12 can be engaged into a halogenation reaction, using for example NBS or phenyltrimethylammonium tribromide in a solvent (e.g., DCM or THF) at the appropriate temperature to provide halo-ketone T-13 (Step 3). Halo-ketone T-13 can be reacted with heteroaryl thiol derivatives of Formula $Y^1$—SH in the presence of a base (e.g., MeONa or $K_2CO_3$) in a solvent (e.g., DMF or ACN) at the appropriate temperature to provide the compound of Formula (I) (Step 4).

In some cases, $Z^1$ might carry a protective group such as, for example, tert-butyldiphenylsilyl (TBDPS). This protective group may be removed during one of the reactions steps such as, for instance, Step 3. Alternatively, this protective group may be removed in a separate deprotection step using an appropriate deprotection reagent such as, for instance, pyridinium fluoride (HF.Py) in a suitable solvent such as, for instance, ACN at a suitable temperature such as, for example, 30° C.

Compounds of formula (I) wherein L and $R^1$ are linked together to form a cyclic amine, may be obtained also according to Scheme 3 (Method 3) below:

media to remove of a BoC-protecting group using formic acid or aqueous HCl solution, to provide the corresponding amine intermediate T-20 (Step 6).

Final compounds of formula (I) wherein $Z^1$ is CO—$R^9$ can be obtained by the reaction of cyclic amine T-20 with either an acyl chloride of Formula $R^9$—COCl in the presence of a base (e.g., $Et_3N$), a solvent (e.g., DCM or THF) at the appropriate temperature; or with a carboxylic acid of Formula $R^9$—$CO_2H$ acid in the presence of a coupling agent (e.g., EDCI/HOBt or HATU), a base (e.g., $Et_3N$)) in a solvent (e.g., DMF) at the appropriate temperature (Step 7a).

Final compounds of formula (I) wherein $Z^1$ is $SO_2$—$R^9$ can

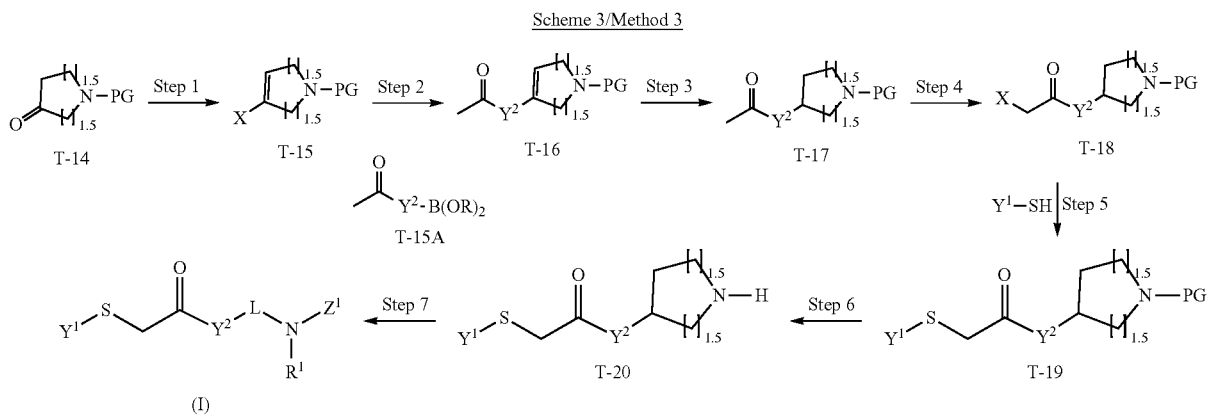

Scheme 3/Method 3

Protected cyclic amines T-14 are commercially available or may be synthesized by a person skilled in the art of organic chemistry using multiple ways described in the literature, for example using the Step 1 described in Scheme 1, Method 1 from the corresponding free cyclic amine. Compound T-14 can be reacted with phenyltriflimide, N-(5-chloropyridin-2-yl)-1,1,1-trifluoro-N-trifluoromethylsulfonyl)methanesulfonamide or trifluoromethanesulfonic anhydride in the presence of a suitable base (e.g., LiHMDS) and solvent (e.g., THF) at the appropriate temperature to provide the triflate enol ether T-15 in which X is an $OSO_2CF_3$ group (Step 1). A Suzuki cross coupling-type reaction of triflate T-15 with a boronic acid or boronic ester of Formula T-15A in the presence of a catalyst (e.g., $Pd(dppf)Cl_2$), a base (e.g., $Cs_2CO_3$), in a solvent (e.g., DMF) at the appropriate temperature may provide intermediate ketone T-16 (Step 2). Boronic acid or boronic ester of Formula T-15A may be commercially available or may be synthesized by a person skilled in the art of organic chemistry using multiple ways described in the literature. The double-bond of the cycle amine intermediate T-16 can then be reduced upon hydrogenation using $H_2$ in the presence a of catalyst (e.g., Pd/C or $Pd(OH)_2$) in a solvent (e.g., MeOH) to provide the corresponding saturated amine intermediate T-17 (Step 3). Ketone T-17 can be engaged into a halogenation reaction, using for example NBS or phenyltrimethylammonium tribromide in a solvent (e.g., DCM or THF) at the appropriate temperature to provide halo-ketone T-18 (Step 4). Halo-ketone T-18 can then be reacted with thiol hetero-aryl derivatives of Formula $Y^1$—SH in the presence of a base (e.g., MeONa or $K_2CO_3$) in a solvent (e.g., DMF or ACN) at the appropriate temperature to provide heteroaryl intermediate T-19 (Step 5). The protected amine T-19 can be deprotected in acidic, neutral or basic media depending of the choice of the protecting group, for example in acidic be obtained by the reaction of cyclic amine T-20 with either sulfonyl chloride of Formula $R^9$—$SO_2Cl$ in the presence of a base (e.g., $Et_3N$), a solvent (e.g., DCM or THF) at the appropriate temperature (Step 7b).

Compounds of Formula (I) wherein L and $R^9$ of the $Z^1$ group are linked together to form a cyclic heterocycle, for example cyclic amide, may also be obtained according to Scheme 4 (Method 4) below:

Scheme 4/Method 4

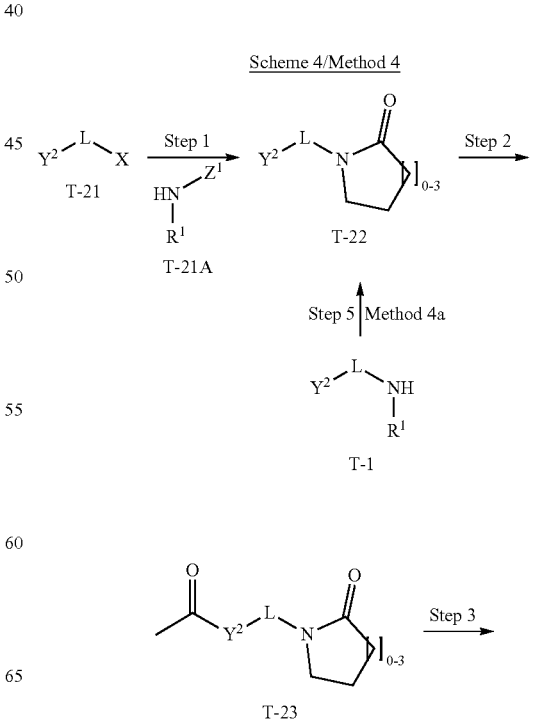

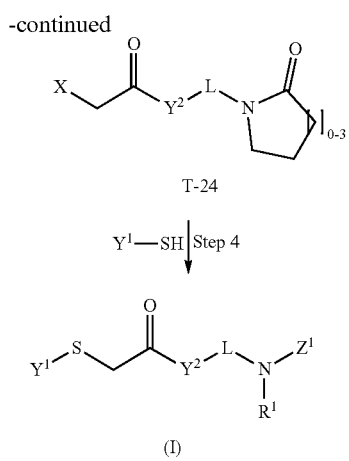

T-24

(I)

Intermediate T-21, wherein X is a halide, are commercially available or may be synthesized by a person skilled in the art of organic chemistry using multiple ways described in the literature, for example from the corresponding alcohol (X=OH) using a halogenating agent (e.g., $SOCl_2$) in a solvent (e.g., THF) at the appropriate temperature. Halide T-21 may be reacted with a heterocyclic amide Formula T-21A, in the presence of a base (e.g., NaH), in a solvent (e.g., THF) at the appropriate temperature to provide the corresponding intermediate T-22 (Step 1). Alternatively, compound T-22 can be prepared in 2-step sequence from intermediate T-1 aforementioned wherein $R^1$ is H (Step 5, Method 4a), that may react with chloro alkyl acyl chloride such as, for example, 3-chloropropionyl chloride, in the presence of a base (e.g., $Et_3N$), in a solvent (e.g., DCM) at the appropriate temperature (Step 1), followed by an intramolecular cyclization in the presence of a base (e.g., NaH), in a solvent (e.g., DMF) at the appropriate temperature (Step 2). Introduction of the ketone group on T-22 may be performed using the methods described previously in Scheme 1 (Step 2 and Step 3; or Step 2 to Step 6) or in Scheme 2 (Step 2) to provide ketone derivatives T-23 (Step 2). Ketone intermediate T-23 can be engaged into a halogenation reaction, using for example NBS or phenyltrimethylammonium tribromide in a solvent (e.g., ACN or DCM or THF) at the appropriate temperature to provide halo-ketone T-24 (Step 3).

Halo-ketone T-24 is then reacted with thiol hetero-aryl derivatives of Formula $Y^1$—SH in the presence of a base (e.g., MeONa or $K_2CO_3$) in a solvent (e.g., DMF or ACN) at the appropriate temperature to provide the final compounds of formula (I) (Step 4).

Synthesis of the Compounds—Experimental Results

Several methods for preparing the compounds of this invention are illustrated in the following Examples. Unless otherwise noted, all starting materials were obtained from commercial suppliers and used without further purification.

Specifically, the following abbreviations may be used in the examples and throughout the specification.

Materials and Analytical Methods

All reactions were monitored by TLC with 0.25 mm E. Merck precoated silica gel plates (60 F254) and Waters liquid chromatography-mass spectroscopy (LCMS).

LCMS (Method 1): LC-MS spectra were recorded on a Waters Acquity I class UPLC system using the following system. Formic acid and acetonitrile used as HPLC grade. For analytical RP-HPLC analysis the following gradient conditions were used:

| Column | ECLIPS XBD C18 (4.6 × 150 mm, 3.5 µm) |
|---|---|
| Column temperature | ambient temperature |
| Mobile phase A (MPA) | 0.01% FA in water |
| Mobile phase B (MPB) | MeCN |
| Flow rate | 0.8 mL/min |
| Injection volume | 10 µL |

| | | Time(min) | | |
|---|---|---|---|---|
| Gradient Ratio | | 0.01 | 2 | 20 | 30 |
| | A (%) | 90 | 90 | 10 | 10 |
| | B (%) | 10 | 10 | 90 | 90 |
| Detection | 225 nm and 254 nm | | | | |
| MS Mode | Positive | | | | |
| MS Range | 100-1000 | | | | |

LCMS (Method 2): LCMS were recorded on an Agilent 1200 & 6120B apparatus. The High-Performance Liquid Chromatography (HPLC) measurement was performed using a LC pump, a diode-array or a UV detector. Flow from the column was brought to the Mass Spectrometer (MS) which was configured with an atmospheric pressure ion source. It is within the knowledge of the skilled person to set the tune parameters in order to obtain ions allowing the identification of the compound's nominal monoisotopic molecular weight (MW) and/or exact mass monoisotopic molecular weight. Data acquisition was performed with appropriate software. An ES MS detector was used, acquiring in positive or negative ionization modes. Compounds can be described by their molecular ion corresponding to the [M+H$^+$](protonated molecule) or [M−H$^+$](deprotonated molecule). For molecules with multiple isotopic patterns (Br, Cl), the reported value is the one obtained for the lowest isotope mass. All results were obtained with experimental uncertainties that are commonly associated with the method used. The gradient conditions used are described below:

| Column: | Xbridge C18 2.1 * 50 mm, 5 μm |
|---|---|
| Column temperature: | 40° C. |
| Mobile phase A (MPA) | H₂O + 10 mM NH₄HCO₃ |
| Mobile phase B (MPB) | Acetonitrile |
| Flow rate: | 0.8 mL/min |

| | Time (min) | | | | | |
|---|---|---|---|---|---|---|
| Gradient Ratio: | 0.00 | 0.40 | 3.40 | 3.85 | 3.86 | 4.50 |
| A (%) | 95 | 95 | 5 | 5 | 95 | 95 |
| B (%) | 5 | 5 | 95 | 95 | 5 | 5 |

| Detection: | 220 nm |
|---|---|
| MS Mode: | Positive |
| MS Range: | 100-1000 |

LCMS (method 3): Liquid chromatography-mass spectroscopy (LCMS) spectra were recorded on a Waters Acquity I class UPLC system. The gradient conditions used are described below:

| Column | Method 3: Kinetex EVO C18 (2.1 × 50 mm, 1.7 μm) |
|---|---|
| Column temperature | 40° C. |
| Mobile phase A (MPA) | 0.01% FA in water |
| Mobile phase B (MPB) | 0.01% FA in ACN |
| Flow rate: | 0.8 mL/min |

| | Time (min) | | | |
|---|---|---|---|---|
| Gradient Ratio: | 0.01 | 0.2 | 1.5 | 3 |
| A (%) | 90 | 90 | 10 | 10 |
| B (%) | 10 | 10 | 90 | 90 |

| Detection: | 220 nm and 254 nm |
|---|---|
| MS Mode: | Positive and negative |
| MS Range: | 100-1000 |

LCMS (method 4): Liquid chromatography-mass spectroscopy (LCMS) spectra were recorded on a Waters Acquity I class UPLC system. The gradient conditions used are described below:

| Column | LUNA 5μ C18 (4.6 × 100 mm) |
|---|---|
| Column temperature | 40° C. |
| Mobile phase A (MPA) | 0.01% FA in water |
| Mobile phase B (MPB) | ACN |
| Flow rate: | 0.8 mL/min |

| | Time (min) | | | |
|---|---|---|---|---|
| Gradient Ratio: | 0.01 | 2 | 20 | 30 |
| A (%) | 90 | 90 | 10 | 10 |
| B (%) | 10 | 10 | 90 | 90 |

| Detection: | 220 nm and 254 nm |
|---|---|
| MS Mode: | Positive and negative |
| MS Range: | 100-1000 |

LCMS (Method 5): LCMS spectra were recorded on a Waters Acquity I class UPLC system using the following system. Formic acid and ammonia or TFA was used as HPLC grade. The following gradient conditions were used:

| Column | Interchim Acquity BEH C18 (2.1 × 100 mm, 1.7 μm) |
|---|---|
| Column temperature | ambient temperature |
| Mobile phase A (MPA) | 0.01% FA in water |
| Mobile phase B (MPB) | 0.01% FA in ACN |
| Flow rate | 0.4 mL/min |
| Injection volume | 10 μL |

| | Time(min) | | | |
|---|---|---|---|---|
| Gradient Ratio | 0.01 | 0.5 | 4 | 7 |
| A (%) | 90 | 90 | 10 | 10 |
| B (%) | 10 | 10 | 90 | 90 |

| Detection | 220 nm and 254 nm |
|---|---|
| MS Mode | Positive |
| MS Range | 100-1000 |

LCMS (Method 6): LCMS were recorded on an Agilent 1200 apparatus. The High-Performance Liquid Chromatography (HPLC) measurement was performed using a LC pump, a diode-array or a UV detector. The following gradient conditions were used:

| Column | Waters, Xbridge C18 50 * 2.1 mm, 5 um |
|---|---|
| Mobile Phase | A: water (4 L) + TFA (1.5 mL) |
| | B: acetonitrile (4 L) + TFA (0.75 mL) |

| TIME (min) | B % |
|---|---|
| 0 | 1 |
| 0.4 | 1 |
| 3.4 | 90 |
| 3.85 | 100 |
| 3.86 | 1 |

| Flow Rate | 0.8 mL/min |
|---|---|
| wavelength | UV 220 nm |
| Oven Temp | 40° C. |
| MS ionization | ESI |

LCMS (Method 7): LCMS were recorded on an Agilent 1200 apparatus. The High-Performance Liquid Chromatography (HPLC) measurement was performed using a LC pump, a diode-array or a UV detector. The following gradient conditions were used:

| Column | Waters, Xbridge C18 50 * 2.1 mm, 5 um |
|---|---|
| Mobile Phase | A: water (4 L) + TFA (1.5 mL) |
| | B: acetonitrile (4 L) + TFA (0.75 mL) |

| TIME (min) | B % |
|---|---|
| 0 | 10 |
| 0.4 | 10 |
| 3.4 | 100 |
| 3.85 | 100 |
| 3.86 | 10 |

| | |
|---|---|
| Flow Rate | 0.8 mL/min |
| wavelength | UV 220 nm |
| MS Mode: | Positive |
| MS Range: | 100-1350 |

LCMS (Method 8): LCMS were recorded on a Agilent 1200. The High-Performance Liquid Chromatography (HPLC) measurement was performed using a LC pump, a diode-array or a UV detector. The following gradient conditions were used:

| | |
|---|---|
| Column | Waters, Xbridge C18 50 * 2.1 mm, 5 um |
| Mobile Phase | A: water (4 L) + $NH_3/H_2O$ (1.5 mL)<br>B: Acetonitrile |

| TIME (min) | B % |
|---|---|
| 0 | 15 |
| 0.5 | 15 |
| 3.4 | 100 |
| 3.9 | 100 |
| 3.91 | 15 |
| 4 | 15 |

| | |
|---|---|
| Flow Rate | 0.8 mL/min |
| wavelength | UV 220 nm |
| MS Mode: | Positive |
| MS Range: | 100-1350 |

RP-HPLC: Reversed phase HPLC was performed on a Waters HPLC system using following system [solvent A: acetonitrile, solvent B: 0.1% $NH_3$ in water] or [solvent A: acetonitrile, solvent B: 0.1% TFA in water]. Ammonia was used as HPLC grade. All the separations were performed at ambient temperatures.

Flash column chromatography: Purification of reaction products was carried out by column chromatography using commercially available silica or flash chromatography using Combiflash Rf with Teledyne Isco RediSep Rf High Performance Gold or Silicycle SiliaSep High Performance columns (40, 80, or 120 g). The purity of all final compounds was over 95% and was analysed with a Waters LCMS system.

$^1$H NMR: $^1$H NMR spectra were recorded on Varian 400 MHz spectrometers and are reported in ppm with the solvent resonance employed as the internal standard [$CDCl_3$ at 7.26 ppm, DMSO-$d_6$ at 2.50 ppm]. Peaks are reported as (s=singlet, d=doublet, t=triplet, q=quartet, m=multiplet or unresolved, br s=broad signal, coupling constant(s) in Hz, integration).

DSC: Melting points were determined using differential scanning calorimetry. The following instrument, parameters and procedure was used:

| | |
|---|---|
| Instrument | Differential Scanning Calorimeter |
| Instrument Model | DSC 214 |
| Manufacturers | NETZSCH |
| Crucible Type | High-voltage gold-plated crucible |
| Gas | Nitrogen |
| Flow rate | 100 mL/min |

Temperature program:

| Starting Temp/° C. | Heating Rate/(K/min) | Final Temp/° C. |
|---|---|---|
| 30 | 10 | 400 |

Operation procedure:
Weigh 1-8 mg of sample into a high-pressure crucible; seal with the matching tool, place the prepared sample into the corresponding position of instrument, call the parameters in the software, and start the sequence run.

Abbreviations
Abbreviations are used as follows.

| Abbreviation | Name |
|---|---|
| aq. | aqueous |
| AMC | 7-amino-4-methylcoumarin |
| 1-BuOH | 1-butanol |
| ACN | acetonitrile |
| AIBN | azobisisobutyronitrile |
| BRET | Bioluminescence Resonance Energy Transfer |
| BSA | Bovine serum albumin |
| $(Boc)_2O$ | di-tert-butyl dicarbonate |
| cHex | cyclohexane |
| Cpd | compound |
| d | days |
| DBU | 1,8-diazabicyclo[5.4.0]undec-7-ene |
| DCM | dichloromethane |
| DEAD | diethyl azodicarboxylate |
| DIBAL-H | diisobutylaluminium hydride |
| DIPEA or DIEA | N,N-diethylisopropylamine |
| DMAP | 4-dimethylaminopyridine |
| DMF | N,N-dimethylformamide |
| DMSO | dimethyl sulfoxide |
| DPPA | diphenylphosphorylazide |
| DTT | dithiothreitol |
| EDCI | 1-ethyl-3-(3-dimethylamino-propyl)carbodiimide |
| EDTA | ethylenediaminetetra-acetic acid |
| $Et_2O$ | diethyl ether |
| EtOAc | ethyl atetate |
| eq. or equiv. | equivalents |
| FA | Formic Acid |
| g | gram |
| GST | Glutathione-S-transferase |
| h | hours |
| H | proton |
| HCl | hydrochloric acid |
| HATU | Hexafluorophosphate Azabenzotriazole Tetramethyl Uronium |
| HDAC | histone deacetylase |
| HOBt | 1-hydroxy-benzotriazol |
| Hz | Hertz |
| IPA | iso-propanol |
| J | scalar $^1$H-$^1$H coupling constant |
| $K_2CO_3$ | potassium carbonate |
| KOH | potassium hydroxide |
| LCMS | liquid chromatography - mass spectrometry |
| LiHMDS | lithium bis(trimethylsilyl)amide |
| M | molar |
| Me | methyl |
| MeOH | methanol |
| MeONa | sodium methoxide |
| mg | milligram |
| MHz | megahertz |
| μw | microwave |
| $N_2$ | nitrogen |
| NaH | sodium hydride |
| $Na_2CO_3$ | sodium carbonate |
| $NaHCO_3$ | sodium bicarbonate |
| NaOH | sodium hydroxide |
| $Na_2SO_4$ | sodium sulfate |
| NBS | N-bromosuccinimide |
| NMP | N-methylpyrrolidone |

| Abbreviation | Name |
|---|---|
| NMR | nuclear magnetic resonance |
| PBS | Phosphate-buffered saline |
| P$_2$S$_5$ | Phosphorus pentasulfide |
| PCC | Pyridinium chlorochromate |
| Pd/C | Palladium on charcoal |
| PdCl$_2$(dppf) | [1,1'-Bis(diphenylphosphino)-ferrocene]dichloropalladium (II) |
| Pd(PPh$_3$)$_4$ | Tetrakis(triphenylphosphine) palladium |
| Pd(OH)$_2$ | Palladium hydroxide |
| quant. | quantitative |
| R$_f$ or Rt | retention factor or retention time |
| RP | Reversed Phase |
| rt | room temperature |
| SAHA | suberoylanilide hydroxamic acid |
| Sat. | saturated |
| SFC | Supercritical fluid chromatography |
| SiO$_2$ | silica |
| SOCl$_2$ | thionyl chloride |
| TBAF | Tetrabutylammonium fluoride |
| TBATB | Tetrabutylammonium tribromide |
| TBDPS | tert-Butyldiphenylsilyl |
| TBS | tert-Butyldimethylsilyl |
| TEA | triethylamine |
| TFA | Trifluoroacetic acid |
| THF | Tetrahydrofuran |
| TLC | thin layer chromatography |
| TMSCF$_3$ | Trifluoromethyltrimethylsilane |
| TSA | Trichostatin A |

Preparation of Synthetic Intermediates

Synthesis of tert-butyl ((5-(2-bromoacetyl)thiophen-2-yl)methyl)carbamate (I-1), According to Method 1 (Scheme 1)

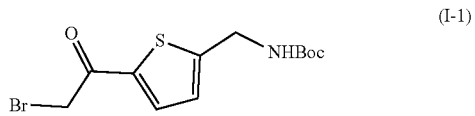 [SMILES: CC(C)(C)OC(=O)NCc1ccc(C(=O)CBr)s1]

(I-1)

Synthesis of tert-butyl (thiophen-2-ylmethyl)carbamate (I-1a) To a solution mixture of thiophen-2-ylmethanamine (50.0 g, 441.770 mmol) in THF (500 mL) was added NaHCO$_3$ (37.1 g, 485.947 mmol) and (Boc)$_2$O (111.5 mL, 441.770 mmol) slowly. The resulting mixture was stirred at rt for 4 h. The reaction mixture was diluted with 30% EtOAc in hexane and passed through silica get to afford compound (I-1a) (100 g, quantitative) as a white gummy solid. Synthesis of tert-butyl ((5-bromothiophen-2-yl)methyl)carbamate (I-1b) To a solution mixture of compound I-1a (50 g, 234.741 mmol) in DMF (500.0 mL) was added NBS (45.9 g, 258.215 mmol) at 0° C. The reaction mixture was stirred for 2 h at rt. Cold water was added to reaction mixture and it was extracted with EtOAc (2×500 mL). The combined organic layers were dried over Na$_2$SO$_4$ and concentrated in vacuo. The crude compound was purified by column chromatography over silica gel (100-200 mesh) and compound was eluted using 10% EtOAc in hexane to afford compound (I-1b) (60.5 g, Yield: 87%) as a brown gummy liquid. Synthesis of tert-butyl ((5-formylthiophen-2-yl)methyl)carbamate (I-1c) To a solution mixture of compound I-1b (30.0 g, 102.739 mmol) in Dry THF (600.0 mL) was added n-BuLi (1.6 M in hexane) (321 mL, 513.698 mmol) at −78° C. and stirring for 30 min at same temperature. DMF (39 mL, 513.698 mmol) was added dropwise at −78° C. and stirring was continued for 2 h. After completion of reaction, the reaction mixture was quenched with sat. NH$_4$Cl solution (200 mL) and extracted with EtOAc (2×500 mL). The combined organic layers were dried over Na$_2$SO$_4$ and concentrated in vacuo. The crude compound was purified by column chromatography over silica gel (100-200 mesh) and compound was eluted using 12% EtOAc in hexane to afford compound I-1c (12.0 g, Yield: 49%) as a brown gummy liquid. $^1$H NMR [400 MHz, CDCl$_3$]: 9.83 (s, 1H), 7.63 (d, J=3.6 Hz, 1H), 7.05 (d, J=3.6 Hz, 1H), 5.0 (s, 1H) 4.52 (d, J=6 Hz, 2H) 1.41 (s, 9H). Synthesis of tert-butyl ((5-(1-hydroxyethyl)thiophen-2-yl)methyl)carbamate (I-1d) To a solution of compound I-c (18.5 g, 76.7 mmol) in dry THF (400.0 mL) was added methyl magnesium bromide (1.0 M in THF) (767 mL, 767.0 mmol) at 0° C., after which it was stirred for 2 h at rt. The reaction mixture was quenched with sat. NH$_4$Cl solution (500 mL) and washed with EtOAc (2×500 mL). Combined organic layers were dried over Na$_2$SO$_4$ and concentrated in vacuo. The crude compound was purified by column chromatography over silica gel (100-200 mesh) and compound was eluted using 20% EtOAc in hexane to afford compound I-1d (13.0 g, Yield: 66%) as a brown gummy liquid. $^1$H NMR [400 MHz, DMSO-d$_6$]: 8.13 (s, 1H), 7.43 (s, 1H), 7.00 (s, 1H), 4.85 (d, J=5.6 Hz, 2H), 4.19 (d, J=2.0 Hz, 1H) 1.38-1.23 (m, 12H). Synthesis of tert-butyl ((5-acetylthiophen-2-yl)methyl)carbamate (I-1e) To a solution mixture of compound I-1d (6.5 g, 25.26 mmol) in DCM (65.0 mL) was added PCC (13.6 g, 63.15 mmol) at rt. The reaction mixture was stirred for 2 h at rt. After completion of reaction, mixture was filtered in vacuo and concentrated in vacuo. The crude compound was purified by column chromatography over silica gel (100-200 mesh) and the compound was eluted using 20% EtOAc in hexane to afford compound I-1e (4.9 g, Yield: 75%) as a brown gummy liquid. Synthesis of tert-butyl ((5-(2-bromoacetyl)thiophen-2-yl)methyl)carbamate (I-1) To a solution mixture of compound-6 (4.8 g, 18.8 mmol) in THF (50 mL) was added phenyltrimethylammonium tribromide (4.95 g, 13.1 mmol) at 0° C. The reaction mixture was stirred for 16 h at rt. After completion of reaction, mixture was filtered through a celite bed and concentrated in vacuo. The crude compound was purified using combi-flash C-18 purification to afford compound I-1 (1.5 g, Yield: 24%) as pale brown solid.

$^1$H NMR [400 MHz, DMSO-d$_6$]: 7.91 (d, J=4 Hz, 1H), 7.65 (t, J=6 Hz, 1H), 7.06 (d, J=3.6 Hz, 1H), 4.77 (s, 2H), 4.31 (d, J=6 Hz, 2H), 1.39 (s, 9H).

Synthesis of tert-butyl (2-(5-(2-bromoacetyl)thiophen-2-yl)ethyl)carbamate (1-2), according to Method 1 (Scheme 1):

(I-2)

Synthesis of tert-butyl (2-(thiophen-2-yl)ethyl)carbamate (I-2a) To a stirred solution of 2-(thiophen-2-yl)ethan-1-amine (20.0 g, 157.22 mmol) in dichloromethane (200 mL) cooled to 0° C. was added (Boc)$_2$O (41.1 g, 188.66 mmol) followed by Et$_3$N (24.6 g, 243.10 mmol). The resulting mixture was stirred for 16 h at rt, after which it was concentrated under reduced pressure. The crude residue was diluted with water (100 mL), extracted with DCM (2×100 mL), and the combined organic layers dried over Na₂SO₄, and concentrated in vacuo. The crude compound was purified by column chromatography over silica gel (100-200 mesh) eluting with 10% EtOAc in hexane, and the pure fractions were evaporated to afford compound I-2a (28 g, Yield: 74%) as a brown gummy liquid. Synthesis of tert-butyl (2-(5-bromothiophen-2-yl)ethyl)carbamate (I-2b) To a solution of compound I-2a (28 g, 123.172 mmol) in DMF (400 mL) cooled to 0° C. was added portion wise NBS (21.9 g, 123.172 mmol). The mixture was then stirred for 2 h at rt before it was poured to mixture of ice water (100 mL) and EtOAc (200 mL). The organic layer was separated, washed with brine solution (100 mL), dried over Na₂SO₄ and then concentrated under reduced pressure. The crude compound was purified by column chromatography over silica gel (100-200 mesh) compound was eluted using 10% EtOAc in hexane to afford compound I-2b (37.08 g, Yield: 98%) as an off-white solid. Synthesis of tert-butyl (2-(5-formylthiophen-2-yl)ethyl)carbamate (I-2c) To a solution of compound I-2b (20.0 g, 65.312 mmol) in dry THF (200 mL) cooled to −78° C. was added dropwise n-BuLi (1.6 M solution in hexanes) (204.0 mL, 326.563 mmol) and the resulting mixture was stirred for 15 min, after which dry DMF (35.9 g, 491.80 mmol) was added and stirring was continued for 30 min at same temperature. After completion of reaction, the reaction mixture was quenched with sat. aq. NH₄Cl solution (150 mL) and extracted with EtOAc (2×200 mL). The organic layer was separated, dried over Na₂SO₄, and concentrated under reduced pressure. The crude compound was purified by column chromatography over silica gel (100-200 mesh) compound was eluted using 15% EtOAc in hexane to afford compound I-2c (10.0 g, Yield: 57%) as gummy liquid. Synthesis of tert-butyl (2-(5-(1-hydroxyethyl)thiophen-2-yl)ethyl)carbamate (I-2d) To a solution of compound I-2c (18.0 g, 70.496 mmol) in dry THF (180 mL) cooled to 0° C. was added dropwise of methyl magnesium bromide (1.0 M solution in THF) (705.0 mL, 70.496 mmol), after which it was slowly warmed to rt and stirred for 2 h. The reaction mixture was diluted with ice water (100 mL) and extracted with EtOAc (2×300 mL). The organic layer was separated, dried over Na₂SO₄, and concentrated reduced pressure. The crude compound was purified by column chromatography over silica gel (100-200 mesh) compound was eluted using 20% EtOAc in hexane to afford compound I-2d (15.0 g, Yield: 78%) as gummy solid. Synthesis of tert-butyl (2-(5-acetylthiophen-2-yl)ethyl)carbamate (I-2e) To a solution of compound I-2d (10 g, 36.849 mmol) in dry DCM (100 mL) cooled to 0° C. was added Dess-Martin periodinane (46.8 g, 110.547 mmol) after which it was slowly warmed to rt and stirred for 16 h. The reaction mixture was filtered through a celite pad and washed with dichloromethane before the solvent was evaporated under reduced pressure. The crude compound was purified by column chromatography over silica gel (100-200 mesh) eluting with 15% EtOAc in hexane to afford compound I-2e (7.1 g, Yield: 72%) as gummy solid. Synthesis of tert-butyl (2-(5-(2-bromoacetyl)thiophen-2-yl)ethyl)carbamate (I-2) To a solution of compound I-2e (7.0 g, 25.987 mmol) in dry THF (70.0 mL) was added trimethylphenylammonium tribromide (7.8 g, 20.789 mmol), and mixture was then stirred at room temperature for 16 h. The solvent was then evaporated, and the crude was purified by Combi-flash reversed phase chromatography to afford I-2 (2.05 g, Yield: 23%) as an off-white solid.

Synthesis of tert-butyl ((5-(2-bromoacetyl)thiophen-2-yl)methyl)(methyl)carbamate (I-3), According to Method 1 (Scheme 1)

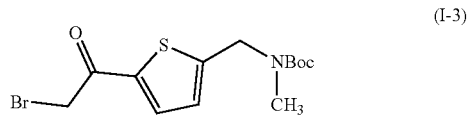

(I-3)

Synthesis of tert-butyl ((5-bromothiophen-2-yl)methyl)(methyl)carbamate (I-3a) To a solution mixture of tert-butyl ((5-bromothiophen-2-yl)methyl)carbamate (I-1b) (40 g, 136.986 mmol) in DMF (400.0 mL) was added NaH (6.56 g, 273.0 mmol) followed by methyl iodide (12.8 mL, 205.479 mmol) at 0° C. The reaction mixture was stirred for 3 h at rt. The reaction mixture was quenched with ice water (150 mL) and extracted with EtOAc (2×500 mL) and dried over Na₂SO₄, concentrated in vacuo gave crude 43 g of compound I-3a, which was taken to the next step without further purification. Synthesis of tert-butyl ((5-formylthiophen-2-yl)methyl)(methyl)carbamate (I-3b) To a solution mixture of compound (I-3a) (22.0 g, 71.89 mmol) in dry THF (400.0 mL) and added n-BuLi (1.6 M in hexane) (224 mL, 359.47 mmol) at −78° C. and stirring for 30 min at −78° C. After DMF (27.9 mL, 359.47 mmol) was added at −78° C. and stirring for 2 h, reaction mixture was quenched with Sat. NH₄Cl solution (200.0 mL) and extracted with EtOAc (2×500 mL) and the combined organic layers were dried over Na₂SO₄ and concentrated in vacuo. The crude compound was purified by column chromatography over silica gel (100-200 mesh) eluting with 12% EtOAc in hexane to afford compound I-3b (6.5 g, Yield: 35%) as gummy liquid, used without further purification. Synthesis of tert-butyl ((5-(1-hydroxyethyl)thiophen-2-yl)methyl)(methyl)carbamate (I-3c) To a solution mixture of compound I-3b (13.0 g, 50.9 mmol) in dry THF (250.0 mL) was added methyl magnesium bromide (1.0M in THF) (509 mL, 509.0 mmol) at 0° C. and stirred the reaction for 2 h at rt. The reaction mixture was quenched with sat. NH₄Cl solution (500 mL) and washed with EtOAc (2×500 mL). The combined organic layers were dried over Na₂SO₄ and concentrated in vacuo. The crude compound was purified by column chromatography over silica gel (100-200 mesh) eluting with 20% EtOAc in hexane to afford compound I-3c (10 g, Yield: 72%) as gummy liquid, used without further purification. Synthesis of tert-butyl ((5-acetylthiophen-2-yl)methyl)(methyl)carbamate (I-3d) To a solution mixture of compound I-3c (10.0 g, 36.9 mmol) in DCM (100.0 mL) was added PCC (19.8 g, 92.2 mmol) at rt. The reaction mixture was stirred for 2 h at rt. The reaction mixture after which it was filtered and concentrated in vacuo. The crude compound was purified by column chromatography over silica gel (100-200 mesh) compound was eluted using 20% EtOAc in hexane to afford compound I-3d (7.6 g, Yield: 77%) as gummy liquid, which was used without further purification. Synthesis of tert-butyl ((5-(2-bromoacetyl)thiophen-2-yl)methyl)(methyl)-carbamate (I-3) To a solution mixture of compound I-3d (4.3 g, 15.9 mmol) in THF (50 mL) and added phenyltrimethylammonium tribromide (4.20 g, 11.1 mmol) at 0° C. The reaction mixture was stirred for 16 h at rt. The reaction mixture was filtered through a celite bed and concentrated in vacuo. The crude compound was purified using combi-flash reverse phase purification (using an ACN and 0.001% TFA in Water) to afford compound I-3 (1.5 g, Yield: 27%) as pale brown solid.

Synthesis of N-((5-(2-bromoacetyl)thiophen-2-yl)methyl)pivalamide (I-4), according to Method 2 (Scheme 2):

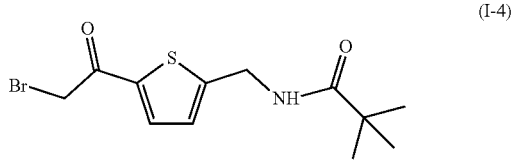 [SMILES: CC(C)(C)C(=O)NCc1ccc(C(=O)CBr)s1]

Synthesis of N-(thiophen-2-ylmethyl)pivalamide (I-4a) To a solution mixture of thiophen-2-ylmethanamine (30 g, 265.062 mmol) in DCM (300.0 mL) and added Et$_3$N (55.7 mL, 398.230 mmol) at 0° C. The resultant reaction mixture was stirred for 10 min at 0° C., after which pivaloyl chloride (39.14 mL, 318.584 mmol) was added. The reaction mixture was stirred for 2 h at rt. The reaction mixture was diluted with DCM (500.0 mL) and washed with water (2×100 mL) and organic layer was dried over Na$_2$SO$_4$ and concentrated in vacuo. The crude compound was purified by column chromatography over silica gel (100-200 mesh) eluting with 10% EtOAc in hexane to afford compound I-4a (40 g, Yield: 77%) as a gummy liquid, which was used without further purification. Synthesis of N-((5-acetylthiophen-2-yl)methyl)pivalamide (I-4b) To a solution mixture of AlCl$_3$ (14.05 g, 105.30 mmol) in DCM (166.0 mL) at 0° C., acetyl chloride (3.60 mL, 50.5 mmol) was added drop by drop. After 5 min, compound-I-4a (8.3 g, 42.1 mmol) was added at 0° C. The reaction mixture was stirred for 2 h at 0° C. The reaction mixture after which it was quenched with cold water (100 mL) and extracted with DCM (2×300 mL). The combined organic layers were dried over Na$_2$SO$_4$ and concentrated in vacuo. The crude compound was purified by column chromatography over silica gel (100-200 mesh) eluting with 20% EtOAc in hexane to afford compound I-4b (8.0 g, Yield: 80%) as a white solid. Synthesis of N-((5-(2-bromoacetyl)thiophen-2-yl)methyl)pivalamide (I-4) To a solution mixture of compound I-4b (25 g, 104.6 mmol) in THF (460 mL) and added phenyltrimethyl ammonium tribromide (27.53 g, 73.2 mmol) at 0° C. The reaction mixture was stirred for 16 h at rt. The reaction mixture was filtered through celite bed and concentrated in vacuo. The crude compound was purified using combi-flash reverse phase purification (using an ACN and 0.001% TFA in water) to afford I-4 (6.2 g, Yield: 19%) as an off-white solid. $^1$H NMR [400 MHz, DMSO-d$_6$]: 8.37-8.32 (m, 1H), 7.91-7.86 (m, 1H), 7.13-7.06 (m, 1H), 4.76 (s, 2H), 4.44 (d, J=5.6 Hz, 2H), 1.11 (s, 9H).

Synthesis of tert-butyl 3-(5-(2-bromoacetyl)thiophen-2-yl)pyrrolidine-1-carboxylate (I-5), according to Method 3 (Scheme 3):

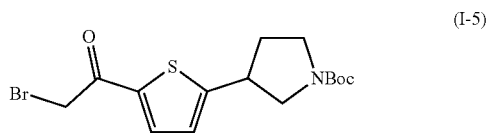 [SMILES: CC(C)(C)OC(=O)N1CCC(c2ccc(C(=O)CBr)s2)C1]

Synthesis of tert-butyl 3-(((trifluoromethyl)sulfonyl)oxy)-2,5-dihydro-1H-pyrrole-1-carboxylate (I-5a) To a solution of tert-butyl 3-oxopyrrolidine-1-carboxylate (1 g, 5.398 mmol) in dry THF (10 mL) cooled to −78° C. was added dropwise LiHMDS (1.0 M soln. in THF) (6.0 mL, 5.934 mmol), and the resulting mixture was stirred for 60 min. N-(5-chloropyridin-2-yl)-1,1,1-trifluoro-N-(trifluoromethylsulfonyl)methanesulfonamide in THF (2.33 g, 5.934 mmol) was added to the solution and stirred for 30 min at the same temperature. Next, the reaction mixture was warmed to rt, quenched with sat. aq. NaHCO$_3$ (10 mL) and extracted with EtOAc (2×50 mL). The organic layer was separated, dried over Na$_2$SO$_4$, and concentrated under reduced pressure. The residue was purified by column chromatography over silica gel (60-120 mesh) eluting with 10% EtOAc in hexane to afford compound I-5a (0.63 g, 37% yield) as gummy liquid. Synthesis of tert-butyl 3-(5-acetylthiophen-2-yl)-2,5-dihydro-1H-pyrrole-1-carboxylate (I-5b) To a stirred solution of (5-acetylthiophen-2-yl) boronic acid (1.6 g, 9.463 mmol) and tert-butyl 3-(((trifluoromethyl)sulfonyl)oxy)-2,5-dihydro-1H-pyrrole-1-carboxylate 2 (3 g, 9.463 mmol) in dioxane:H$_2$O (30 mL, 3:1), K$_2$CO$_3$ (3.9 g, 28.389 mmol) and Pd(dppf)Cl$_2$ (1.0 g, 0.9463 mmol) was added. The reaction was purged with N$_2$ for 15 min, then heated to 100° C. for 16 h. Next, the mixture was quenched with sat. aq. NaHCO$_3$ (20 mL), and then extracted with EtOAc (2×50 mL). The organic layer was separated, dried over Na$_2$SO$_4$, and the solvent evaporated under reduced pressure. The residue was purified by column chromatography using a silica gel (60-120 mesh, eluent: 50% EtOAc in hexane) to afford the title compound I-5b (2.7 g, 75% yield) as a gummy liquid. Synthesis of tert-butyl 3-(5-acetylthiophen-2-yl)pyrrolidine-1-carboxylate (I-5c) To a stirred solution of tert-butyl 3-(5-acetylthiophen-2-yl)-2,5-dihydro-1H-pyrrole-1-carboxylate I-5b (2 g, 6.825 mmol) in MeOH (20 mL) was added 10% Pd—C (2.0 g), then H$_2$ gas was inserted for 5 h at 60 psi. The reaction mixture was filtered through a celite bed under vacuo. The solvent was evaporated under reduced pressure and the residue purified by column chromatography over silica gel (60-120 mesh, eluent: 50% EtOAc in hexane) to afford the title compound I-5c (1.5 g, 74% yield) as yellow liquid. Synthesis of tert-butyl 3-(5-(2-bromoacetyl)thiophen-2-yl)pyrrolidine-1-carboxylate (I-5) To a solution of compound I-5c (0.2 g, 0.680 mmol) in dry THF (5 mL) tetrabutylammonium tribromide (0.8 g, 1.360 mmol) added then stirred at room temperature for 16 h. The reaction mixture was concentrated to get crude compound, which was purified by Combi-flash reversed phase chromatography to afford I-5 (0.07 g, 27% yield) as a white solid. $^1$H NMR [400 MHz, DMSO-d$_6$]: 7.95 (d, J=3.6 Hz, 1H), 7.15 (d, J=4 Hz, 1H), 4.78 (s, 2H), 3.73-3.69 (m, 2H), 3.40-3.23 (m, 4H), 2.33-2.29 (m, 1H), 1.40 (s, 9H).

Synthesis of 1-((5-(2-bromoacetyl)thiophen-2-yl)methyl)-3-methylpyrrolidin-2-one (I-6), according to Method 4 (Scheme 4)

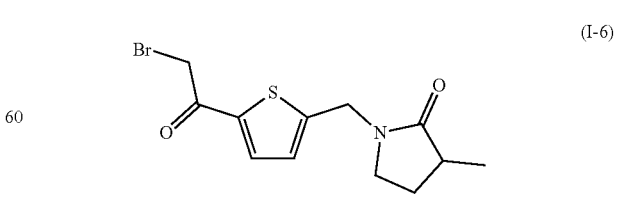

Synthesis of 2-(chloromethyl)thiophene (I-6a) according to Method 4, Step 1: To a solution of thiophen-2-ylmethanol (2.0 g, 17.518 mmol) in THF (20 mL) was added SOCl$_2$ (2.5 g, 21.021 mmol) at 0° C. The reaction mixture was stirred at 50° C. for 3 h. The progress of the reaction was monitored by TLC. After complete consumption of starting material, the reaction mixture was concentrated. The crude residue was taken to the next step without further purification. Synthesis of 3-methyl-1-(thiophen-2-ylmethyl)pyrrolidin-2-one (I-6b) To a solution of compound I-6a (0.5 g, 5.043 mmol) in dry THF (5.0 mL) was added NaH (60% in oil) (0.3 g, 7.575 mmol) at 0° C. 3-Methylpyrrolidin-2-one (0.66 g, 5.043 mmol) was added at same temperature and the mixture stirred for 30 min. The reaction mixture before it was brought to rt and stirred for another 16 h. After completion of reaction, the reaction mixture was concentrated and purified by column chromatography over silica gel (60-120 mesh, eluent: 10% EtOAc in hexane) to afford compound I-6b (0.45 g, 50% yield) as a yellow gummy liquid. Synthesis of 1-((5-bromothiophen-2-yl)methyl)-3-methylpyrrolidin-2-one (I-6c) To a solution of compound I-6b (0.45 g, 2.304 mmol) in acetonitrile (5.0 mL) was added NBS (0.4 g, 2.304 mmol) at 0° C. and the reaction mixture was stirred for 2 h at rt. After completion of reaction, the reaction mixture was concentrated, diluted with water (20 mL) and extracted with EtOAc (2×50 mL). The organic layer was separated, dried over Na$_2$SO$_4$, and the solvent concentrated under reduced pressure. The crude was purified by combi-flash reversed phase chromatography to afford compound I-6c (0.5 g, 79% yield) as a yellow gummy liquid. Synthesis of 1-((5-acetylthiophen-2-yl)methyl)-3-methylpyrrolidin-2-one (I-6d) A stirred solution of compound I-6c (0.5 g, 1.824 mmol) in toluene was purged with N$_2$ followed by addition of tributyl(1-ethoxyvinyl)stannane (0.78 g, 2.160 mmol) and Pd (PPh$_3$)$_4$ (0.2 g, 0.182 mmol). The reaction mixture was stirred at 110° C. for 16 h. Saturated KF solution was added to the reaction mixture and stirring continued for 30 min at rt. The organic layer was separated and concentrated under reduced pressure to get the crude compound. THF (20 mL) and conc. HCl were added to the crude reaction mixture. After stirring for 30 min, solid Na$_2$CO$_3$ was added until pH ~7. The mixture was diluted with water (20 mL) and extracted with DCM (2×50 mL). The combined organic layers were dried over Na$_2$SO$_4$ and concentrated under reduced pressure. The crude was purified by column chromatography column chromatography over silica gel (60-120 mesh, eluent 20% EtOAc in hexane) to afford compound I-6d (0.3 g, 70% yield) as a white solid. Synthesis of 1-((5-(2-bromoacetyl)thiophen-2-yl)methyl)-3-methylpyrrolidin-2-one (I-6) To a solution of compound I-6d (0.3 g, 1.265 mmol) in dry THF (5 mL) was added tetrabutylammonium tribromide (0.6 g, 1.265 mmol) and the reaction mixture was stirred at room temperature for 16 h. Next, the reaction mixture was concentrated and the residue was purified by Combi-flash reversed phase chromatography to afford I-6 (0.07 g, 16% yield) as a white solid.

Synthesis of N-((5-(2-bromoacetyl)-3-fluorothiophen-2-yl)methyl)pivalamide (I-7), according to Method 2 (Scheme 2)

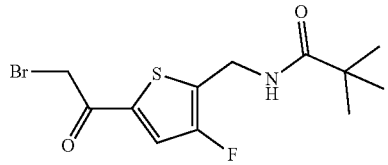

(I-7)

Synthesis of (3-fluorothiophen-2-yl)methanol (I-7a) To a stirred solution of methyl 3-fluorothiophene-2-carboxylate (5.0 g, 31.25 mmol) in dry THF (50 mL) was added lithium aluminium hydride (1 M solution in THF, 30 mL) dropwise at 0° C. and reaction mixture was stirred for 1 h at 0° C. under nitrogen. After completion of reaction, mixture was quenched with 10 mL water, 15% NaOH solution (10 mL) and stirred for 1 h. The reaction mixture was filtered over celite and the celite pad washed with EtOAc and THF. The aqueous layer was extracted, and combined organic layers were dried over Na$_2$SO$_4$ and concentrated under reduced pressure. The residue was purified by column chromatography over silica gel eluting with 8% EtOAc/hexane to get pure yellowish liquid compound I-7a (3.0 g, Yield: 73%). $^1$H NMR [400 MHz, DMSO-d$_6$]: 7.464-7.440 (m, 1H), 6.936-6.920 (m, 1H), 5.46 (t, J=5.6 Hz, 1H), 4.54 (dd, J=6.0, 1.6 Hz, 2H). Synthesis of 2-(azidomethyl)-3-fluorothiophene (I-7b) To a stirred solution of compound I-7a (3 g, 22.7 mmol) in toluene (30 mL) was added DPPA (5.8 mL, 27.2 mmol) followed by DBU (4 mL, 27.2 mmol) at 0° C. and resulting mixture was stirred at rt for 1 h under N$_2$. After completion of reaction (TLC monitoring), the mixture was quenched with water and extracted with EtOAc. The organic layer was dried over Na$_2$SO$_4$ and concentrated under reduced pressure. The crude was purified by column chromatography eluting with 2% EtOAc/hexane to afford compound I-7b (2.5 g, Yield: 71%) colourless oil. $^1$H NMR [400 MHz, CDCl$_3$]: 7.22-7.19 (m, 1H), 6.83-6.61 (m, 1H), 4.44 (s, 2H). Synthesis of (3-fluorothiophen-2-yl)methanamine (I-7c) To a stirred solution of compound I-7b (2.6 g, 16.5 mmol) in dry THF (40 mL) was added solution of LAH in THF (1.2 g, 33.1 mmol) at 0° C. Then reaction mixture was stirred at 0° C. for 30 min. The reaction was monitored by TLC. After completion of reaction, mixture was quenched with water and 10% NaOH solution. The reaction mixture was washed with EtOAc (2×50 mL). The combined organic layers were dried over Na$_2$SO$_4$ and concentrated under reduced pressure. The crude was purified by column chromatography over silica gel eluting with 2% MeOH/DCM to get yellowish oily compound I-7c (2 g, Yield: 95%). $^1$H NMR [400 MHz, DMSO-d$_6$]: 7.37-7.35 (m, 1H), 6.92-6.89 (m, 1H), 3.83 (s, 2H). Synthesis of N-((3-fluorothiophen-2-yl)methyl)pivalamide (I-7d) According to Method 2 (Step 1): to a stirred solution of compound I-7c (2.5 g, 19.08 mmol) in DCM (25 mL) was added TEA (6.7 mL, 47.7 mmol) followed by pivaloyl chloride (3.5 mL, 28.6 mmol) and the resulting mixture was stirred at rt for 2 h. The reaction was monitored by TLC and after completion, the mixture was quenched in water and extracted with EtOAc (2×50 mL). The combined organic layers were dried over Na$_2$SO$_4$ and concentrated under reduced pressure. The crude was purified using column chromatography using 10% to 30% ethyl acetate:petroleum ether as an eluent providing compound I-7d (2.5 g, Yield: 61%). Synthesis of N-((5-bromo-3-fluorothiophen-2-yl)methyl)pivalamide (I-7e) According to Method 2 (Step 2): to a stirred solution of compound I-7d (1.2 g, 5.6 mmol) in ACN (12 mL) was added NBS (1 g, 5.6 mmol) and the resulting mixture was stirred at rt for 1 h. After completion of reaction, the crude compound was purified using RP combi-flash column chromatography using 10% acetonitrile:H$_2$O (0.01% FA) as an eluent to afford compound I-7e (400 mg, Yield: 25%). Synthesis of N-((5-acetyl-3-fluorothiophen-2-yl)methyl)pivalamide (I-7f) According to Method 2 (Step 3): To a stirred solution of compound I-7e (770 mg, 2.6 mmol) in dioxane (10 mL) was added tributyl(1-ethoxyvinyl)tin (1.2 g, 3.4 mmol) followed by Pd (PPh$_3$)$_4$ (0.3 g, 2.6 mmol) and resulting mixture was stirred at 110° C. for 16 h under N₂. After completion of reaction, mixture was cooled to rt. Saturated KF solution was added and the mixture stirred for 30 minutes before EtOAc (20 mL) was added. The aqueous layer was extracted, and the combined organic layers were dried over Na₂SO₄ and concentrated. The solid residue was dissolved in 2 N HCl and the mixture stirred for 30 minutes. Solid Na₂CO₃ was next added to the mixture until pH >7 and the aqueous layer was extracted with EtOAc (20 mL). The combined organic layers were dried over Na₂SO₄, and concentrated under reduced pressure. The crude was purified by column chromatography using 20% ethyl acetate: petroleum ether as an eluent to get pure compound I-7f (290 mg, Yield: 43%). Synthesis of N-((5-(2-bromoacetyl)-3-fluorothiophen-2-yl)methyl)pivalamide (I-7) According to Method 2 (Step 4): To a stirred solution of compound 7 (290 mg, 1.1 mmol) in dry THF (4 mL) was added tetrabutylammonium tribromide (1 g, 2.2 mmol) at 0° C. and resulting mixture was stirred at 50° C. for 16 h. After completion of reaction, solvent was concentrated under reduced pressure to get crude compound which was purified using combi-flash to afford compound I-7 (130 mg, Yield: 34%) as gummy solid.

Synthesis of N-((2-(2-bromoacetyl)thiazol-5-yl)methyl)pivalamide (I-8), According to Method 2 (Scheme 2)

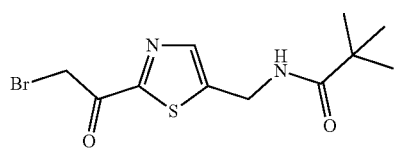

(I-8)

Synthesis of (2-bromothiazol-5-yl)methanol (I-8a) To a solution of methyl 2-bromothiazole-5-carboxylate (24.0 g, 101.69 mmol) in dry THF (200 mL) was added DIBAL-H (1.0 M in toluene) (203.0 mL, 203.38 mmol) at 0° C. The resulting mixture was stirred for 15 min, then slowly warmed to rt for 2 h. Next, the reaction mixture was quenched with sat. aq. NH₄Cl (200 mL) and extracted with EtOAc (2×200 mL). The organic layer was separated, dried over Na₂SO₄, and concentrated under reduced pressure. The residue was purified by column chromatography over silica gel (60-120 mesh, eluent: 10% EtOAc in hexane) to afford compound I-8a (11.1 g, 56% yield) as a gummy solid. Synthesis of 2-((2-bromothiazol-5-yl)methyl)isoindoline-1,3-dione (I-8b) To a stirred solution of triphenylphosphine (16.2 g, 61.8 mmol.) in dry THF (100 mL) was added DEAD (9.8 g, 56.6 mmol) dropwise at 0° C. and the reaction mixture was stirred for 15 min at this temperature. Compound I-8a (10.0 g, 51.5 mmol) in THF (20 mL) was added to the reaction mixture followed by isoindoline-1,3-dione (8.3 g, 56.6 mmol) at 0° C. The reaction mixture was then concentrated under reduced pressure. The crude residue was diluted with water (150 mL) extracted with DCM (2×100 mL), the organic layer separated, dried over Na₂SO₄, and concentrated under reduced pressure. The crude was purified by column chromatography over silica gel (60-120 mesh, eluent: 30% EtOAc in hexane) to afford compound-I-8b (8.0 g, 50% yield) as a white solid. Synthesis of (2-bromothiazol-5-yl)methanamine (I-8c) To a stirred solution of compound I-8b (8.0 g, 24.76 mmol) in EtOH (80 mL) was added hydrazine hydrate (3.9 g, 123.8 mmol) dropwise at 0° C. The mixture was stirred for 15 min at 0° C., and then stirred at 75° C. for 2 h. The reaction mixture was then concentrated under reduced pressure. The crude residue was diluted with water (100 mL) extracted with DCM (2×100 mL). The organic layer was separated, dried over Na₂SO₄, and concentrated under reduced pressure to get crude compound I-8c (4.0 g crude, 46% pure by LCMS). The crude was taken next step without further purification. Synthesis of N-((2-bromothiazol-5-yl)methyl)pivalamide (I-8d) According to Method 2 (Step 1): To a stirred solution of compound I-8c (1.0 g, 5.177 mmol) in DCM (10 mL) was added Et₃N (1.0 g, 10.354 mmol) followed by pivaloyl chloride (0.92 g, 7.765 mmol) at 0° C. and. The reaction mixture was stirred for 2 h at rt, and then concentrated under reduced pressure. The crude residue was diluted with water (50 mL) and extracted with DCM (2×50 mL). The combined organic layers were dried over Na₂SO₄ and concentrated under reduced pressure. The crude was purified by column chromatography over silica gel (60-120 mesh, eluent: 20% EtOAc in hexane) to afford the crude compound I-8d (0.7 g) as a white solid. Synthesis of N-((2-acetylthiazol-5-yl)methyl)pivalamide (I-8e) According to Method 1 (Step 2 and Step 3): To a stirred solution of compound I-8d (2.0 g, 7.220 mmol) and tributyl(1-ethoxyvinyl)stannane (3.3 g, 9.386 mmol) in toluene (20 mL) was added Pd(PPh₃)₄ (0.8 g, 0.72 mmol) under N₂ and the reaction mixture was stirred to 110° C. for 16 h. To the reaction mixture saturated potassium fluoride solution was added and stirring was continued for 30 min at rt. The organic layer was separated and concentrated under reduced pressure. THF followed by conc. HCl was added to the residue and the biphasic mixture was stirred for 30 min. The reaction mixture pH was adjusted to >7 by slow addition of solid Na₂CO₃. Next, the mixture was diluted with water (80 mL) and extracted with DCM (2×100 mL). The combined organic layers were dried over Na₂SO₄, and concentrated under reduced pressure. The crude was purified by column chromatography over silica gel (60-120 mesh) using 10% ethyl acetate:petroleum ether as an eluent to afford the crude compound I-8e (0.5 g, 36% product by LCMS) as a gummy solid, which was used as such. Synthesis of N-((2-(2-bromoacetyl)thiazol-5-yl)methyl)pivalamide (I-8) According to Method 2 (Step 3): To a solution of compound I-8e (0.450 g, 1.87 mmol) in dry THF (4.0 mL) was added tetrabutylammoniumtribromide (0.9 g, 1.8 mmol) and stirred at room temperature for 16 h. The reaction mixture was concentrated, and the crude residue was purified by Combi-flash reversed phase chromatography to afford I-8 (0.15 g, 68% yield) as a white solid.

Synthesis of N-(1-(5-(2-bromoacetyl)thiophen-2-yl)ethyl)-2-hydroxyacetamide (I-9), according to Method 2 (Scheme 2):

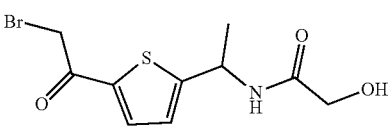

(I-9)

Synthesis of (S,E)-N-((5-bromothiophen-2-yl)methylene)-2-methylpropane-2-sulfinamide (I-9a) To a solution of 5-bromothiophene-2-carbaldehyde (12.0 g, 62.8 mmol, 7.45 mL) in THF (150 mL) was added Ti(OEt)₄ (28.7 g, 126 mmol, 26.1 mL) and (S)-2-methylpropane-2-sulfinamide (9.14 g, 75.4 mmol). The mixture was stirred at 25° C. for 12 h. The reaction mixture was quenched by addition H₂O (50.0 mL) at 25° C., and then extracted with EtOAc (30.0 mL×4). The combined organic layers were washed with brine (30.0 mL), dried over Na₂SO₄, filtered and concentrated under reduced pressure to give a residue. The residue was purified by column chromatography (SiO₂, petroleum ether/ethyl acetate=100/1 to 0/1) to give compound I-9a (17.0 g, 90% yield, 98.1% purity) as a light yellow solid. Synthesis of (S)—N—((S)-1-(5-bromothiophen-2-yl)ethyl)-2-methylpropane-2-sulfinamide (I-9b) To a solution of compound I-9a (17.0 g, 57.8 mmol) in THF (119 mL) was added dropwise MeMgBr (3 M, 57.8 mL) at 0° C. The resulting mixture was stirred at 25° C. for 1 h. The reaction mixture was then quenched by addition NH₄Cl (50.0 mL) at 25° C., and then extracted with DCM (50.0 mL×3). The combined organic layers were washed with brine (30.0 mL), dried over Na₂SO₄, filtered and concentrated under reduced pressure to give a residue. The residue was purified by column chromatography (SiO₂, petroleum ether/ethyl acetate=100/1 to 0/1) to give compound I-9b (13.4 g, 62% yield, 83.5% purity) as a light yellow solid. Synthesis of (S)-1-(5-bromothiophen-2-yl)ethan-1-amine (I-9c) To a solution of compound I-9b (3.00 g, 9.67 mmol) in MeOH (21.0 mL) was added dropwise acetyl chloride (2.28 g, 29.0 mmol, 2.07 mL) at 25° C. After addition, the mixture was stirred at this temperature for 1 h. The solvent was removed in vacuo and then TEA (10.3 g, 102 mmol, 14.1 mL) and THF (30.0 mL) was added dropwise at 25° C. The resulting mixture was stirred at 25° C. for 1 h. The reaction mixture was filtered and concentrated under reduced pressure to give a residue. The residue was purified by column chromatography (SiO₂, petroleum ether/ethyl acetate=100/1 to 0/1) to give compound I-9c (7.40 g, 60.2% yield) as a light yellow oil. Synthesis of (S)—N-(1-(5-bromothiophen-2-yl)ethyl)-2-((tert-butyldiphenylsilyl)oxy)acetamide (I-9d) To a solution of 2-[tert-butyl(diphenyl)silyl]oxyacetic acid (12.4 g, 39.5 mmol) in DCM (66.6 mL) and DMF (7.40 mL) was added HOBt (7.28 g, 53.9 mmol), EDCI (10.3 g, 53.9 mmol) and DIPEA (13.9 g, 108 mmol, 18.8 mL) at 25° C. And then compound I-9c (7.40 g, 35.9 mmol) was added at 25° C. The resulting mixture was stirred at 25° C. for 2 h. The reaction mixture was quenched by addition H₂O (30.0 mL) at 25° C., and then extracted with EtOAc (13.0 mL×3). The combined organic layers were washed with brine (20.0 mL), dried over Na₂SO₄, filtered and concentrated under reduced pressure to give a residue. The residue was purified by column chromatography (SiO₂, petroleum ether/ethyl acetate=I/O to 0/1) to give compound I-9d (9.60 g, 52% yield, 96.7% purity) as a light yellow oil. Synthesis of N-(1-(5-acetylthiophen-2-yl)ethyl)-2-((tert-butyldiphenylsilyl)oxy)acetamide (I-9e) To a solution of compound I-9d (9.50 g, 18.9 mmol) in toluene (66.5 mL) was added dropwise tributyl(1-ethoxyvinyl)stannane (13.7 g, 37.8 mmol, 12.8 mL) at 25° C., and then Pd(PPh₃)₄ (1.09 g, 945 umol) was added at 25° C. The resulting mixture was stirred at 120° C. for 2 h. Saturated potassium fluoride solution (50.0 ml) was added to the reaction mixture and stirred for 30 min at rt. The organic layer was separated and concentrated under reduced pressure to get the crude compound. THF (50.0 mL) and 1 M HCl (20.0 mL) was added to the crude reaction mixture and stirred for 30 min and solid Na₂CO₃ was added until pH-7. The reaction mixture diluted with water (50.0 mL) extracted with DCM (50.0 mL×3). Organic layer is separated, dried over Na₂SO₄, concentrate under reduced pressure to get crude compound. The residue was purified by column chromatography (SiO₂, petroleum ether/ethyl acetate=3/1) to give compound I-9e (6.40 g, 71% yield, 98.0% purity) as a yellow oil. Synthesis of N-(1-(5-(2-bromoacetyl)thiophen-2-yl)ethyl)-2-hydroxyacetamide (I-9) To a solution of compound I-9e (6.30 g, 13.5 mmol) in DCM (37.8 mL) and MeOH (94.5 mL) was added TBATB (6.85 g, 14.2 mmol). The mixture was stirred at 20° C. for 2 h. The reaction mixture was quenched by addition H₂O (20.0 mL) at 25° C., and then extracted with EtOAc (40.0 mL×3). The combined organic layers were washed with brine (30.0 mL), dried over Na₂SO₄, filtered and concentrated under reduced pressure. The residue was purified by column chromatography (SiO₂, petroleum ether/ethyl acetate=I/O to 0/1) to give compound I-9 (3.00 g, 61% yield, 83.8% purity) as a light yellow oil.

Synthesis of 1-((5-(2-bromoacetyl)thiophen-2-yl)methyl)pyrrolidin-2-one (I-10), According to Method 4a (Scheme 4)

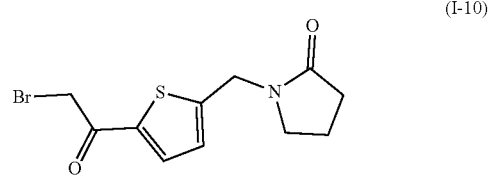 [SMILES: O=C(CBr)c1ccc(CN2CCCC2=O)s1]

(I-10)

Synthesis of 4-chloro-N-(thiophen-2-ylmethyl)butanamide (I-10a) According to Method 4a (Step 1): To a solution mixture of thiophen-2-ylmethanamine (5.0 g, 44.1 mmol) and Et₃N (19.8 mL, 141.0 mmol) in DCM (130.0 mL) was added drop wise a solution of 4-chlorobutanoyl chloride (6.57 mL, 58.3 mmol) in DCM (20.0 mL) at 0° C. The reaction mixture was stirred for 1 h at 0° C. before it was quenched with cold water (100 mL) and extracted with EtOAc (2×300 mL). The combined organic layers were dried over Na₂SO₄ and concentrated in vacuo. The crude compound was taken to next step without further purification, to afford compound I-10a (7.0 g, Yield: 73%) as gummy liquid. Synthesis of 1-(thiophen-2-ylmethyl)pyrrolidin-2-one (I-10b) According to Method 4a (Step 2): To a solution mixture of compound I-10a (3.0 g, 13.7 mmol) in DMF (30.0 mL) was added NaH (826 mg, 20.6 mmol (60% in mineral oil)) at rt, and the mixture was stirred for 3 h. Next, the reaction mixture was quenched with cold water (100 mL) and extracted with EtOAc (2×100 mL). The combined organic layers were dried over Na₂SO₄ and concentrated in vacuo. The residue was purified by column chromatography over silica gel (100-200 mesh) eluting with 12% EtOAc in hexane to afford compound I-10b (1.8 g, Yield: 72%) as a gummy liquid. Synthesis of 1-((5-acetylthiophen-2-yl)methyl)pyrrolidin-2-one (I-10c) According to Method 2 (Step 3): To a solution of AlCl₃ (1.95 g, 14.91 mmol) in DCM (50.0 mL) was added acetyl chloride (0.80 mL, 11.93 mmol) drop wise at 0° C. After 5 min, compound I-10b (1.8 g, 9.94 mmol) was added stirring was continued for 1 h at 0° C. The reaction mixture was then quenched with cold water (50 mL) and extracted with DCM (2×50 mL). The combined organic layers were dried over Na₂SO₄ and concentrated in vacuo. The crude compound was purified by column chromatography over silica gel (100-200 mesh) eluting with 30% EtOAc in hexane to afford compound I-10c (0.99 g, Yield: 45%) as a gummy liquid. Synthesis of 1-((5-(2-bromoacetyl)thiophen-2-yl)methyl)pyrrolidin-2-one (I-10) According to Method 2 (Step 4): To a solution mixture of compound I-10c (500 mg, 2.242 mmol) in THF (10 mL) and added phenyltrimethyl ammonium tribromide (576.0 mg, 1.569 mmol) at 0° C. The reaction mixture was stirred for 16 h at rt after which it was filtered through a celite bed and concentrated in vacuo. The crude compound was purified using Combi-flash reversed phase purification (using ACN and 0.001% TFA in water as eluent) to afford compound I-10 (0.25 g, Yield: 36%) as an off-white solid.

Synthesis of 1-(2-(5-(2-bromoacetyl)thiophen-2-yl) ethyl)pyrrolidin-2-one (I-11), According to Method 4a (Scheme 4)

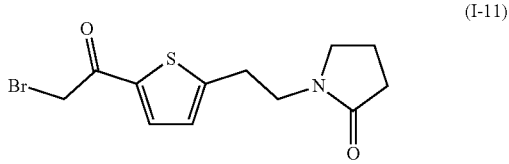 [SMILES: O=C(CBr)c1ccc(CCN2CCCC2=O)s1]

(I-11)

Synthesis of N-((5-(2-bromoacetyl)-1,3,4-thiadiazol-2-yl) methyl)pivalamide (I-12): The synthesis of 1-(2-(5-(2-bromoacetyl)thiophen-2-yl)ethyl)pyrrolidin-2-one (I-11) was performed in similar experimental conditions than intermediate I-10, starting from 2-(thiophen-2-yl)ethan-1-amine and reacting with chlorobutanoyl chloride to afford compound I-11 (0.45 g, Yield: 26%) as an off-white solid.

Synthesis of N-((5-(2-bromoacetyl)-1,3,4-thiadiazol-2-yl)methyl)pivalamide (I-12), According to Method 2 (Scheme 2)

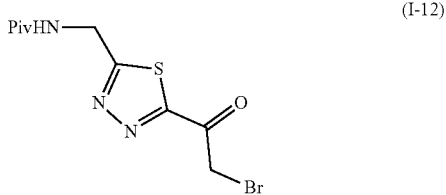

(I-12)

Synthesis of 2-bromo-5-(bromomethyl)-1,3,4-thiadiazole (I-12a) To a stirred solution of 2-bromo-5-methyl-1,3,4-thiadiazole (4.5 g, 25.1 mmol) in CCl₄ (100 mL) cooled to 0° C. was added N-bromosuccinimide (4.4 g, 25.1 mmol) followed by AIBN (0.4 g, 2.51 mmol). Then, the reaction mixture was stirred at 80° C. for 16 h after which it was diluted with water (100 mL) and extracted with DCM (2×200 mL). The combined organic layers were dried over Na₂SO₄, and the solvent evaporated under reduced pressure. The residue was purified by column chromatography over silica gel (60-120 mesh) eluting with 50% EtOAc in hexane to afford compound I-12a (2.0 g, 31% yield) as a white solid. Synthesis of (5-bromo-1,3,4-thiadiazol-2-yl)methanamine (I-12b): To a stirred solution of 2-bromo-5-(bromomethyl)-1,3,4-thiadiazole I-12a (2.0 g, 7.81 mmol) in MeOH (20 mL) cooled to 0° C. was added 7 N methanolic ammonia (40 mL). The reaction mixture was then stirred at rt for 16 h after which it was concentrated in vacuo. The residue was purified by column chromatography using silica gel (60-120 mesh) eluting with 30% EtOAc in hexane to afford compound I-12b (1.5 g) as a gummy solid. Synthesis of N-((5-bromo-1,3,4-thiadiazol-2-yl)methyl)pivalamide (I-12c) To a stirred solution of (5-bromothiazol-2-yl)methanamine I-12b (1.6 g, 8.24 mmol) was dissolved in DCM (20 mL) cooled to 0° C. added Et₃N (1.6 g, 16.2 mmol) followed by pivaloyl chloride (1.4 g, 12.3 mmol) was added then slowly warmed to rt and stirred for 2 h at rt. The reaction mixture was concentrated under reduced pressure and the residue was diluted with water (50 mL) and extracted with DCM (2×80 mL). The combined organic layers were dried over Na₂SO₄, and the solvent evaporated under reduced pressure. The crude was purified by column chromatography over silica gel (60-120 mesh) eluting with 30% EtOAc in hexane to afford compound I-12c (1.0 g, 45% yield) as a gummy solid. Synthesis of N-((5-acetyl-1,3,4-thiadiazol-2-yl)methyl) pivalamide (I-12d): To a stirred solution of N-((5-bromo-1, 3,4-thiadiazol-2-yl)methyl)pivalamide I-12c (1.0 g, 3.597 mmol) and tributyl(1-ethoxyvinyl)stannane (1.6 g, 4.676 mmol) in toluene (10 mL) was added Pd(PPh₃)₄ (0.4 g, 0.346 mmol). Next, the mixture was slowly heated to 110° C. for 16 h. After cooling to rt, saturated KF solution was added stirring was continued for 30 min at rt. The organic layer was separated, dried over Na₂SO₄, and concentrated under reduced pressure. To the residue was added THF and then conc. HCl, and the resulting biphasic mixture was stirred for 30 min. Next, the pH of the mixture was adjusted to >7 by slow addition of solid Na₂CO₃. The mixture was then diluted with water (50 mL), extracted with DCM (2×100 mL). The combined organic layers were dried over Na₂SO₄, and the solvent evaporated under reduced pressure. The residue was purified by column chromatography over silica gel (60-120 mesh) eluting with 30% EtOAc in hexane to afford compound I-12d (0.7 g, 81% yield) as a pale-yellow solid. Synthesis of N-((5-(2-bromoacetyl)-1,3,4-thiadiazol-2-yl)methyl)pivalamide (I-12) To a solution of N-((5-acetyl-1,3,4-thiadiazol-2-yl)methyl)pivalamide I-12d (0.4 g, 1.659 mmol) in dry THF (5 mL) tetrabutylammonium tribromide (0.8 g, 1.659 mmol) was added, and the resulting mixture was stirred at rt for 16 h. The reaction mixture was concentrated to get crude compound. The crude was purified by Combi-flash reversed phase chromatography to afford compound I-12 (0.2 g, Yield: 38%, 70% pure by LCMS) as a white solid.

Synthesis of N-((5-(2-bromoacetyl)thiophen-2-yl) methyl)-2-hydroxyacetamide (I-13), according to Method 2 (Scheme 2):

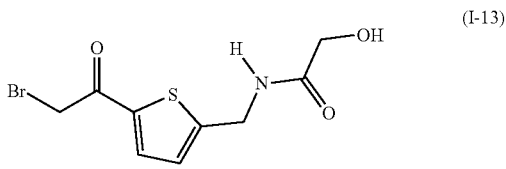 [SMILES: O=C(CO)NCc1ccc(C(=O)CBr)s1]

(I-13)

Synthesis of 2-((tert-butyldiphenylsilyl)oxy)acetic acid (I-13a) To a solution of glycolic acid (110 g, 1.45 mol) in THF (770 mL) was added TEA (293 g, 2.89 mol, 403 mL), DMAP (17.7 g, 145 mmol) and TBDPSCl (477 g, 1.74 mol, 446 mL) at 0° C., and the resulting mixture was stirred at 25° C. for 2 h. The reaction mixture was acidified with aqueous HCl (1 M) until pH=1 was reached and extracted with EtOAc (300 mL×3). The organic layers were dried over anhydrous Na₂SO₄, filtered and concentrated in vacuum. The residue was purified by SiO₂ column chromatography (petroleum ether/ethyl acetate=10/1 to 3/1) to give compound I-13a (283 g, 57% yield, 91.0% purity) as light red oil. ¹H NMR: (400 MHz, CDCl₃) δ 7.70-7.68 (m, 4H), 7.45-7.43 (m, 6H), 4.28 (s, 2H), 1.13 (s, 9H). Synthesis of 2-((tert-butyldiphenylsilyl)oxy)-N-(thiophen-2-ylmethyl) acetamide (I-13b) To a solution of I-13a (281 g, 894 mmol) in DMF (644 mL) was added DIEA (420 g, 3.25 mol, 566 mL), EDCI (233 g, 1.22 mol) and HOBt (165 g, 1.22 mol) at 15° C. and this mixture was stirred at 15° C. for 30 min. To this mixture was added thiophen-2-ylmethanamine (92.0 g, 813 mmol, 83.6 mL). This mixture was stirred at 15° C. for 2 h. The reaction mixture was then diluted with H$_2$O (1.50 L) and extracted with EtOAc (500 mL×3). The combined organic layers were dried over anhydrous Na$_2$SO$_4$, filtered and concentrated in vacuum. The residue was purified by column chromatography (SiO$_2$, ethyl acetate/petroleum ether=100/1 to 0/1; TLC: ethyl acetate/petroleum ether=5/1, compound I-13b R$_f$=0.60) to give compound I-13b (246 g, 70% yield, 94.2% purity) as light yellow oil. $^1$H NMR: ET45071-646-P1B (400 MHz, CDCl$_3$) δ 7.53-7.50 (m, 4H), 7.38-7.27 (m, 6H), 7.17-7.16 (m, 1H), 7.69 (s, 1H), 6.92-6.88 (m, 2H), 4.62 (d, J=5.6 Hz, 2H), 4.09 (s, 2H), 0.98 (s, 9H). Synthesis of N-((5-bromothiophen-2-yl)methyl)-2-((tert-butyldiphenylsilyl)oxy)acetamide (I-13c) Two reactions were carried out in parallel on the same scale. To the solution of compound I-13b (82.0 g, 200 mmol) in DMF (574 mL) was added NBS (39.2 g, 220 mmol). The mixture was stirred at 20° C. for 1 hr. The two reactions were combined for work up. The reaction mixture was diluted with H$_2$O (3.40 L) and extracted with EtOAc (1.50 L×3). The combined organic layers were washed with H$_2$O (500 mL×8) and dried over anhydrous Na$_2$SO$_4$, filtered and concentrated in vacuum to give compound I-13c (199 g, 85% yield, 83.1% purity) as a light yellow solid. $^1$H NMR: (400 MHz, CDCl$_3$) δ 7.61-7.59 (m, 4H), 7.48-7.37 (m, 6H), 7.20 (s, 1H), 6.92 (d, J=3.6 Hz, 1H), 6.74 (d, J=3.6 Hz, 1H), 4.60 (d, J=6.0 Hz, 2H), 4.18 (s, 2H), 1.08 (s, 9H). Synthesis of N-((5-acetylthiophen-2-yl)methyl)-2-((tert-butyldiphenylsilyl)oxy)acetamide (I-13d) To a solution of compound I-13c (94.0 g, 192 mmol) in toluene (658 mL) was added tributyl(1-ethoxyvinyl)tin (90.4 g, 250 mmol, 84.5 mL) and Pd(PPh$_3$)$_4$ (22.2 g, 19.2 mmol). The mixture was degassed and purged with N$_2$ for 3 times and then it was stirred at 110° C. for 16 h under N$_2$ atmosphere. The same reaction was performed in parallel with 105 g of I-13c, and both mixtures were combined for work-up. Saturated KF solution (2.00 L) was added to the reaction mixture and the mixture was stirred for 30 min at 20° C. The organic layer was separated and HCl (0.5 M, 2.0 L) was added to the crude reaction mixture and the mixture was stirred for 30 min. The organic layer was separated and extracted with EtOAc (500 mL×2). The combined organic layers were dried over Na$_2$SO$_4$, concentrated in vacuum. The residue was purified by column chromatography (SiO$_2$, petroleum ether/ethyl acetate=3/1 to 1/1) to give compound I-13d (124 g, 63% yield, 93.6% purity) as a yellow solid. $^1$H NMR: (400 MHz, CDCl$_3$) δ 7.62-7.58 (m, 5H), 7.48-7.38 (m, 6H), 7.30 (s, 1H), 7.01 (d, J=3.6 Hz, 1H), 4.72 (d, J=3.6 Hz, 1H), 4.20 (s, 2H), 2.55 (s, 3H), 1.09 (s, 9H). Synthesis of N-((5-(2-bromoacetyl)thiophen-2-yl)methyl)-2-hydroxyacetamide (I-13) To the solution of compound I-13d (119 g, 263 mmol) in DCM (714 mL) and MeOH (1.78 L) was added TBATB (133 g, 276 mmol) and the mixture was stirred at 15° C. for 12 h. The reaction mixture was concentrated in vacuum and the residue was diluted with DCM (100 mL) and washed with H$_2$O (40.0 mL×3). The organic layer was concentrated in vacuum. The residue was purified by column chromatography (SiO$_2$, petroleum ether/ethyl acetate=0/1 to 1/0) to give compound I-13 (46.0 g, 55% yield, 91.3% purity) as colorless oil. $^1$H NMR: (400 MHz, DMSO-d$_6$) δ 8.55 (t, J=6.0 Hz, 1H), 7.91 (d, J=4.0 Hz, 1H), 7.09 (d, J=4.0 Hz, 1H), 4.75 (s, 2H), 4.49 (d, J=6.0 Hz, 2H), 3.86 (s, 2H).

4-((5-(2-bromoacetyl)thiophen-2-yl)methyl)morpholin-3-one (I-14), according to Method 4 (Scheme 4):

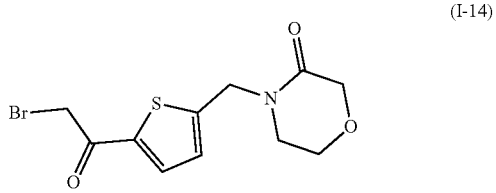 [SMILES: O=C(CBr)c1ccc(CN2CCOCC2=O)s1]

(I-14)

Synthesis of 2-(chloromethyl)thiophene (I-14a) To the solution of 2-thienylmethanol (2.00 g, 17.5 mmol, 1.65 mL) in DCM (14.0 mL) was added SOCl$_2$ (4.17 g, 35.0 mmol, 2.54 mL) dropwise at 0° C. under N$_2$ atmosphere. The mixture was stirred at 0° C. for 30 min, after which the mixture was stirred at 25° C. for 30 min. The reaction mixture was quenched by NaHCO$_3$ (110 mL) and extracted with EtOAc (80.0 mL×3). The combined organic layers were dried over anhydrous Na$_2$SO$_4$, filtered and concentrated in vacuum to give compound I-14a (1.50 g, 65% yield) as a brown oil. Synthesis of 4-(thiophen-2-ylmethyl)morpholin-3-one (I-14b) To a solution of morpholin-3-one (2.29 g, 22.6 mmol) in THF (10.0 mL) was added dropwise LiHMDS (1 M, 17.0 mL) at 0° C. After addition, the mixture was stirred at this temperature for 30 min, and then compound I-14a (1.50 g, 11.3 mmol) in THF (8.00 mL) was added dropwise at 0° C. The resulting mixture was stirred at 60° C. for 7 h. The reaction was quenched by addition of 10.0 mL of NH$_4$Cl at 0° C. and then diluted with H$_2$O (10.0 mL) and extracted with EtOAc (5.00 mL×3). The combined organic layers were washed with brine (5.00 mL), dried over Na$_2$SO$_4$, filtered and concentrated under reduced pressure. The residue was purified by column chromatography (SiO$_2$, petroleum ether/ethyl acetate=100/1 to 0/1) to give compound I-14b (1.10 g, 42% yield, 85.4% purity) as a brown oil. $^1$H NMR [400 MHz, CDCl$_3$]: 7.26 (t, J=1.2 Hz, 1H), 7.00 (d, J=2.4 Hz, 1H), 4.76 (s, 2H), 4.20 (s, 2H) 3.86-3.83 (m, 2H) 3.36 (t, J=5.2 Hz, 2H). Synthesis of 4-((5-bromothiophen-2-yl)methyl)morpholin-3-one (I-14c) To a solution of compound I-14b (1.10 g, 5.58 mmol) in DMF (7.70 mL) was added NBS (993 mg, 5.58 mmol). The mixture was stirred at 25° C. for 12 h. The reaction mixture was diluted with H$_2$O (10.0 mL) and washed with EtOAc (10.0 mL×3). The combined organic layers were washed with brine (10.0 mL), dried over Na$_2$SO$_4$, filtered and concentrated under reduced pressure. The residue was purified by prep-TLC (SiO$_2$, petroleum ether/ethyl acetate=1/1) to give compound I-14c (crude) (2.00 g, 88.8% purity) as a light yellow solid. $^1$H NMR [400 MHz, CDCl$_3$]: 6.89 (d, J=3.6 Hz, 1H), 6.75 (d, J=3.6 Hz, 1H), 4.64 (s, 2H), 4.19 (s, 2H), 3.85 (t, J=4.8 Hz, 2H), 3.36 (t, J=5.2 Hz, 2H), 2.73 (s, 3H). Synthesis of 4-((5-acetylthiophen-2-yl)methyl)morpholin-3-one (I-14d) To a solution of compound I-14c (2.00 g, 7.24 mmol) in toluene (14.0 mL) was added tributyl(1-ethoxyvinyl)stannane (3.22 g, 8.91 mmol, 3.01 mL) and Pd(PPh$_3$)$_4$ (837 mg, 724 umol). The mixture was stirred at 110° C. for 16 h. Saturated KF solution (20.0 mL) was added to the reaction mixture and the mixture was stirred for 30 min at 20° C. The organic layer was separated and HCl (0.5 M, 20.0 mL) was added to the crude reaction mixture and the mixture was stirred for 30 mins. The organic layer was separated and extracted with EtOAc (20.0 mL×2). The combined organic layers were dried over Na₂SO₄, concentrated in vacuum. The residue was purified by column chromatography (SiO₂, DCM/Ethyl acetate=50/1 to 0/1) to give compound I-14d (1.00 g, 58% yield) as a black solid. Synthesis of 4-((5-(2-bromoacetyl)thiophen-2-yl)methyl)morpholin-3-one (I-14) To a solution of compound I-14d (1.00 g, 4.18 mmol) in DCM (2.00 mL) and IPA (5.00 mL) was added TBATB (2.32 g, 4.81 mmol). And the mixture was stirred at 60° C. for 2 h. The reaction mixture was diluted with H₂O (25.0 mL) and washed with EtOAc (25.0 mL×3). The combined organic layers were washed with brine (25.0 mL), dried over Na₂SO₄, filtered and concentrated under reduced pressure to give compound I-14 (1.00 g, 3.14 mmol, 75% yield) as a brown oil.

Synthesis of 1-((5-(2-bromoacetyl)thiophen-2-yl)methyl)-3-hydroxypyrrolidin-2-one (I-15), According to Method 4 (Scheme 4)

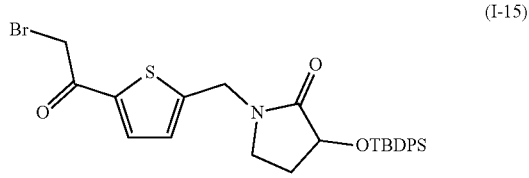

(I-15)

Synthesis of 3-((tert-butyldiphenylsilyl)oxy)-1-(thiophen-2-ylmethyl) pyrrolidin-2-one (I-15a) To a solution of 3-((tert-butyldiphenylsilyl)oxy)pyrrolidin-2-one (25.0 g, 73.6 mmol) in THF (170 mL) was added dropwise LiHMDS (1 M, 110 mL) at 0° C. After addition, the mixture was stirred at this temperature for 30 min, and then 2-(chloromethyl)thiophene (19.5 g, 147 mmol) was added dropwise at 0° C. The resulting mixture was stirred at 60° C. for 7 h. LCMS showed the 3-((tert-butyldiphenylsilyl)oxy)pyrrolidin-2-one was consumed completely and 27% desired compound detected. The reaction mixture was quenched by addition H₂O (100 mL) at 25° C., and then extracted with EtOAc 300 mL (100 mL×3). The combined organic layers were washed with brine (100 mL), dried over Na₂SO₄, filtered and concentrated under reduced pressure to give a residue. The residue was purified by prep-TLC (SiO₂, petroleum ether/ethyl acetate=3/1) to give compound I-15a (9.00 g, 28.0% yield) as a yellow oil. Synthesis of 1-((5-bromothiophen-2-yl)methyl)-3-((tert-butyldiphenylsilyl) oxy)pyrrolidin-2-one (I-15b) To a solution of compound I-15a (9.00 g, 20.7 mmol) in DMF (50.0 mL) was added NBS (4.04 g, 22.7 mmol). The mixture was stirred at 20° C. for 2 h after which it was quenched by addition H₂O (100 mL) at 25° C., and then extracted with EtOAc 150 mL (50.0 mL×3). The combined organic layers were washed with brine (100 mL), dried over Na₂SO₄, filtered, and concentrated under reduced pressure. The residue was purified by column chromatography (SiO₂, petroleum ether/ethyl acetate=50/1 to 5/1) to give compound I-15b (6.70 g, 63% yield) as a brown oil. Synthesis of 1-((5-acetylthiophen-2-yl)methyl)-3-((tert-butyldiphenylsilyl) oxy)pyrrolidin-2-one (I-15c) To the solution of compound I-15b (6.70 g, 13.0 mmol) in Tol (42.0 mL) was added tributyl(1-ethoxyvinyl)stannane (6.58 g, 18.2 mmol, 6.15 mL) and Pd(PPh₃)₄ (1.50 g, 1.30 mmol). The mixture was degassed and purged with N₂ for three times, and then the mixture was stirred at 110° C. for 16 h under N₂ atmosphere. Saturated potassium fluoride solution was added to the reaction mixture and stirred for 30 min at 15° C. The organic layer was separated and concentrated under reduced pressure to get the crude compound. HCl (0.5 M, 90.0 mL) was added to the crude and the mixture was stirred for 30 min and solid Na₂CO₃ (~5 g) was added until pH=~7. The reaction mixture was diluted with water (50.0 mL) extracted with ethyl acetate (50.0 mL×2). The combined organic layers were dried over Na₂SO₄ and concentrated under reduced pressure. The residue was purified by column chromatography (SiO₂, petroleum ether/ethyl acetate=50/1 to 5/1) to give compound I-15c (5.50 g, 88% yield) as a yellow solid. Synthesis of 1-((5-(2-bromoacetyl)thiophen-2-yl)methyl)-3-((tert-butyldiphenylsilyl)oxy)pyrrolidin-2-one (I-15) To a solution of compound I-15c (0.50 g, 1.05 mmol) in DCM (3.00 mL) and IPA (7.50 mL) was added trimethylphenylammonium tribromide (413 mg, 1.10 mmol). The mixture was stirred at 50° C. for 2 h. The reaction mixture was quenched by H₂O 10.0 mL at 25° C., and then extracted with EtOAc 15.0 mL (5.00 mL×3). The combined organic layers were washed with brine (10.0 mL), dried over Na₂SO₄, filtered, and concentrated under reduced pressure to give compound I-15 (0.90 g, 46% yield, 30% purity) as a white solid.

Synthesis of 1-(2-(5-(2-bromoacetyl)thiophen-2-yl)ethyl)-3-hydroxypyrrolidin-2-one (I-16), According to Method 4 (Scheme 4)

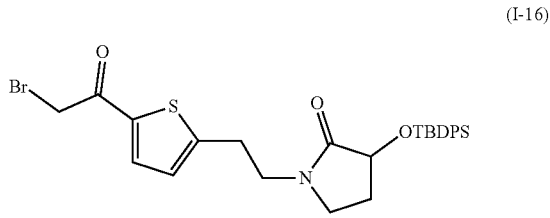

(I-16)

Synthesis of 3-((tert-butyldiphenylsilyl)oxy)-1-(2-(thiophen-2-yl)ethyl)pyrrolidin-2-one (I-16a) To a solution of 3-((tert-butyldiphenylsilyl)oxy)pyrrolidin-2-one (10.8 g, 31.8 mmol) in THF (70.0 mL) was added dropwise LiHMDS (1 M, 47.7 mL) at 0° C. After addition, the mixture was stirred at this temperature for 30 min, and then 2-(2-thienyl)ethyl 4-methylbenzenesulfonate (10.8 g, 38.2 mmol) in THF (30.0 mL) was added dropwise at 0° C. The resulting mixture was stirred at 60° C. for 7 h. The reaction mixture was quenched by addition H₂O (100 mL) at 25° C., and then extracted with EtOAc 150 mL (50.0 mL×3). The combined organic layers were washed with brine (50.0 mL), dried over Na₂SO₄, filtered, and concentrated under reduced pressure to give a residue. The residue was purified by column chromatography (SiO₂, petroleum ether/ethyl acetate=50/1 to 5/1) to give compound I-16a (7.00 g, 49% yield) as a white solid. Synthesis of (S)-1-(2-(5-bromothiophen-2-yl)ethyl)-3-((tert-butyldiphenylsilyl)oxy)pyrrolidin-2-one (I-16b) To a solution of compound I-16a (7.00 g, 15.6 mmol) in DMF (56.0 mL) was added NBS (3.05 g, 17.1 mmol). The mixture was stirred at 20° C. for 2 h. The reaction mixture was quenched by addition H₂O (50.0 mL) at 25° C., and then extracted with EtOAc (20.0 mL×3). The combined organic layers were washed with brine (50.0 mL), dried over Na₂SO₄, filtered, and concentrated under reduced pressure to give a residue. The residue was purified by column chromatography (SiO₂, petroleum ether/ethyl acetate=50/1 to 5/1) to give compound I-16b (4.60 g, 56% yield) as a colorless oil. Synthesis of 1-(2-(5-acetylthiophen-2-yl)ethyl)-3-((tert-butyldiphenylsilyl)oxy)pyrrolidin-2-one (I-16c) To the solution of compound I-16b (4.60 g, 8.70 mmol) in Tol. (32.0 mL) was added tributyl(1-ethoxyvinyl)stannane (4.40 g, 12.1 mmol, 4.11 mL) and Pd(PPh$_3$)$_4$ (1.01 g, 870 umol). The mixture was degassed and purged with N$_2$ for three times, and then the mixture was stirred at 110° C. for 16 h under N$_2$ atmosphere. Saturated potassium fluoride solution was added to the reaction mixture and stirred for 30 min at 15° C. The organic layer was separated and concentrated under reduced pressure to get the crude compound. HCl (0.5 M, 90.0 mL) was added to the crude reaction mixture and stirred for 30 min and solid Na$_2$CO$_3$ (~15.0 g) was added until pH=~7. The reaction mixture diluted with water (50.0 mL) extracted with Ethyl acetate (10.0 mL×2). The combined organic layers were dried over Na$_2$SO$_4$, concentrated under reduced pressure to get crude compound. The residue was purified by column chromatography (SiO$_2$, petroleum ether/ethyl acetate=50/1 to 5/1) to give compound I-16c (3.49 g, 82% yield) as a yellow oil. Synthesis of 1-(2-(5-(2-bromoacetyl)thiophen-2-yl)ethyl)-3-((tert-butyldiphenylsilyl)oxy)pyrrolidin-2-one (I-16) To a solution of compound I-16c (1.00 g, 2.03 mmol) in MeOH (5.00 mL) and DCM (1.50 mL) was added TBATB (1.03 g, 2.14 mmol). The mixture was stirred at 20° C. for 2 h. The reaction mixture was quenched by addition H$_2$O (10.0 mL) at 25° C., and then extracted with EtOAc (5.00 mL×3). The combined organic layers were washed with brine (5.00 mL), dried over Na$_2$SO$_4$, filtered and concentrated under reduced pressure to give a residue. The residue was purified by column chromatography (SiO$_2$, petroleum ether/ethyl acetate=50/1 to 5/1) to give compound I-16 (0.80 g, 69% yield) as a yellow oil.

Preparation of Intermediate Compounds of Formula Y$^1$—SH, Wherein R$^2$=H

Synthesis of 1-methyl-1H-pyrazolo[3,4-d]pyrimidine-4-thiol (J-1)

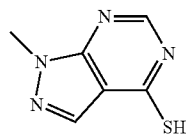

(J-1)

Synthesis of 1-methyl-1H-pyrazolo[3,4-d]pyrimidin-4-ol (J-1-1) A solution mixture of ethyl 5-amino-1-methyl-1H-pyrazole-4-carboxylate (10 g, 59.1 mmol) in formamide (40 mL) was stirred at 180° C. for 4 h. The reaction mixture was cooled to rt, after which a precipitate formed. The resulting precipitate was filtered in vacuo, washed with hexane and dried in vacuo to afford J-1-1 (7.2 g, Yield: 79%) as an off-white solid. Synthesis of 1-methyl-1H-pyrazolo[3,4-d]pyrimidine-4-thiol (J-1) To a solution of compound J-1-1 (3.4 g, 22.6 mmol) in toluene (50.0 mL) was added Lawesson's reagent (5.4 g, 13.5 mmol) at 0° C. The reaction mixture was stirred for 2 h at 120° C. Next, the mixture was concentrated in vacuo, and the residue was purified by column chromatography over silica gel (60-120 mesh) eluting with 10% EtOAc in hexane to afford J-1 (3.0 g, Yield: 81%) as a pale-yellow solid.

Synthesis of 1,7-naphthyridine-8-thiol (J-5)

(J-5)

Synthesis of 1,7-naphthyridine-8-thiol (J-5) To a solution of 8-chloro-1,7-naphthyridine (500 mg, 3.04 mmol) in DMF (3.00 mL) was added NaSH (681 mg, 12.2 mmol). The mixture was stirred at 80° C. for 2 h. The reaction mixture was used into the next step directly without work-up.

The following compounds have been prepared using the experimental conditions described above from commercially available or art known hydroxy-substituted heteroaryls of formula Y$^1$—OH by thionation using P$_2$S$_5$ reagent or Lawesson's reagent or, alternatively, from chloro-substituted heteroaryls of formula Y—C$_1$ by thiol substitution using NaSH or Na$_2$S. Alternatively, some of the following compounds could be obtained commercially:

| Cpd number | Structure | Name |
|---|---|---|
| J-2 | ![](quinazoline-4-thiol structure) | quinazoline-4-thiol |
| J-3 | ![](1,6-naphthyridine-5-thiol structure) | 1,6-naphthyridine-5-thiol |
| J-4 | ![](2,7-naphthyridine-1-thiol structure) | 2,7-naphthyridine-1-thiol |
| J-6 | ![](imidazo[1,2-a]pyrazine-8-thiol structure) | imidazo[1,2-a]pyrazine-8-thiol |
| J-7 | ![](imidazo[1,5-a]pyrazine-8-thiol structure) | imidazo[1,5-a]pyrazine-8-thiol |
| J-8 | ![](pyrazolo[1,5-a]pyrazine-4-thiol structure) | pyrazolo[1,5-a]pyrazine-4-thiol |

Preparation of Intermediate Compounds of Formula Y¹—SH, Wherein R²=Haloalkyl, CF₃ or CHF₂

Synthesis of 2-(trifluoromethyl)quinazoline-4-thiol (K-1)

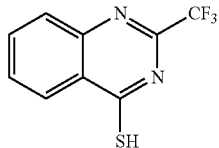
(K-1)

Synthesis of 2-(trifluoromethyl)quinazolin-4-ol (K-1-1) To a stirred solution of 2-aminobenzamide (1.0 g, 7.344 mmol) in dry DCM was added trifluoroacetic anhydride (1.7 g, 8.022 mmol), pyridine (1.0 mL) and DMAP (0.018 mg, 0.147 mmol) at room temperature. The reaction mixture was stirred at rt for 16 h. The progress of the reaction was monitored by TLC consumption of starting material. After consumption of starting material, the reaction mixture was diluted with water and extracted with DCM. The combined organic layers were dried over Na₂SO₄, and the solvent concentrated under reduced pressure. The residue was purified by column chromatography using a silica gel (100:200 mesh, solvents: 10% EtOAc in hexane) to obtain K-1-1 (1.0 g, 63% yield). Synthesis of 2-(trifluoromethyl)quinazoline-4-thiol (K-1) To a stirred solution of 2-(trifluoromethyl) quinazolin-4 (1H)-one (K-1-1) (0.5 g, 7.344 mmol) in dry toluene was added Lawesson's reagent (1.01 g, 7.344 mmol) under an atmosphere of dry argon, the reaction was then heated under reflux for 16 h until no more starting material could be detected by TLC. Next, a solution of 3 N NaOH was added to the mixture. After neutralizing with 1 N HCl, the formed solid was filtered and dried under vacuum to afford K-1 (0.28 g, 52% yield) as an off-white solid.

Synthesis of 3-(trifluoromethyl)isoquinoline-1-thiol (K-22)

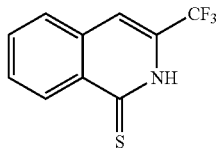 [SMILES: FC(F)(F)c1cc2ccccc2c(=S)[nH]1]

Synthesis of 3-(trifluoromethyl)-1H-isochromen-1-one (K-22-1) To a stirred solution of 2-(carboxymethyl)benzoic acid (2.0 g, 11.10 mmol) was added trifluroacetic anhydride (2.1 mL) at room temperature and the reaction mixture was stirred at 100° C. for 48 h. The reaction mixture was concentrated under reduced pressure to get K-22-1 (2.5 g, Crude) was taken to next step without any further purification. Synthesis of 3-(trifluoromethyl)isoquinolin-1 (2H)-one (K-22-2): 3-(trifluoromethyl)-1H-isochromen-1-one K-22-1 (2.5 g (crude), 11.62 mmol) was added to NH₄OH (37.0 mL) at rt. The resulting mixture was stirred at 100° C. for 3 h. The reaction mixture was concentrated under reduced pressure to give crude compound K-22-2 (160 mg, Yield: 7%) as a white solid. Synthesis of 3-(trifluoromethyl)isoquinoline-1-thiol (K-22): To a stirred solution of 3-(trifluoromethyl)isoquinolin-1 (2H)-one K-22-2 (160 mg, 0.751 mmol) in dry toluene (6.0 mL) was added Lawesson's reagent (303 g, 0.751 mmol) under nitrogen atmosphere. The reaction mixture was stirred at 120° C. for 4 h, then concentrated under vacuum. The residue was purified using combi-flash reversed phase purification (eluent: ACN and 0.001% TFA in water) to afford compound K-22 (50 mg, Yield 29%) as an off-white solid.

The following intermediate compounds (K-2) to (K-21) have been prepared using the experimental conditions described above from the reaction of substituted amino carboxamide aryl and heteroaryl, and trifluoroacetic anhydride or CHF₂-based reagents. Alternatively, they were prepared from art known or commercial hydroxy-substituted heteroaryls of formula Y¹—OH by thionation using P₂S₅ reagent or Lawesson's reagent. Alternatively, some of the following compounds could be obtained commercially:

| Cpd number | Structure | Name |
|---|---|---|
| K-2 | 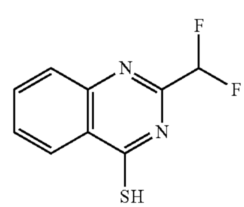 [SMILES: FC(F)c1nc(S)c2ccccc2n1] | 2-(difluoromethyl)quinazoline-4-thiol |
| K-3 | 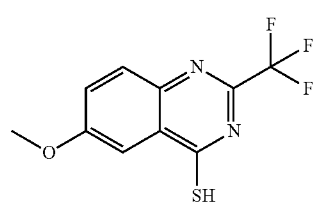 [SMILES: COc1ccc2nc(C(F)(F)F)nc(S)c2c1] | 6-methoxy-2-(trifluoromethyl)quinazoline-4-thiol |

-continued

| Cpd number | Structure | Name |
|---|---|---|
| K-4 | 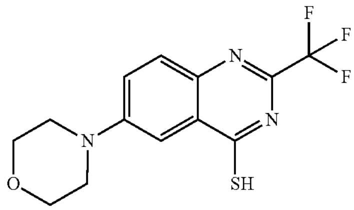 [SMILES: FC(F)(F)c1nc(S)c2cc(N3CCOCC3)ccc2n1] | 6-morpholino-2-(trifluoromethyl)quinazoline-4-thiol |
| K-5 | 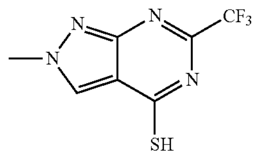 | 2-methyl-6-(trifluoromethyl)-2H-pyrazolo[3,4-d]pyrimidine-4-thiol |
| K-6 | 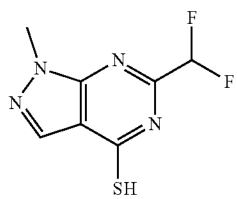 | 6-(difluoromethyl)-1-methyl-1H-pyrazolo[3,4-d]pyrimidine-4-thiol |
| K-7 | 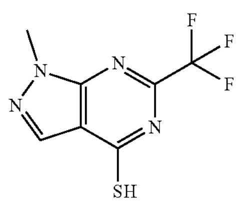 | 1-methyl-6-(trifluoromethyl)-1H-pyrazolo[3,4-d]pyrimidine-4-thiol |
| K-8 | 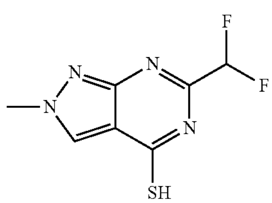 | 6-(difluoromethyl)-2-methyl-2H-pyrazolo[3,4-d]pyrimidine-4-thiol |
| K-9 | 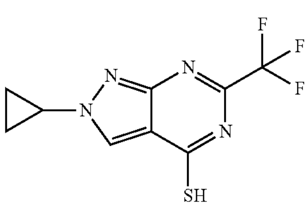 [SMILES: FC(F)(F)c1nc(S)c2cn(C3CC3)nc2n1] | 2-cyclopropyl-6-(trifluoromethyl)-2H-pyrazolo[3,4-d]pyrimidine-4-thiol |
| K-10 | 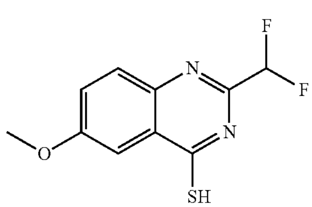 [SMILES: COc1ccc2nc(C(F)F)nc(S)c2c1] | 2-(difluoromethyl)-6-methoxyquinazoline-4-thiol |

-continued

| Cpd number | Structure | Name |
|---|---|---|
| K-11 | 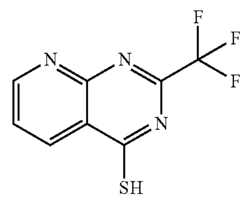 [SMILES: FC(F)(F)c1nc(S)c2cccnc2n1] | 2-(trifluoromethyl)pyrido[2,3-d]pyrimidine-4-thiol |
| K-12 | 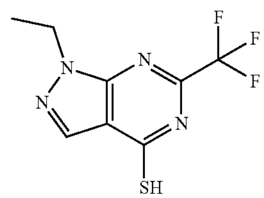 [SMILES: CCn1ncc2c(S)nc(C(F)(F)F)nc21] | 1-ethyl-6-(trifluoromethyl)-1H-pyrazolo[3,4-d]pyrimidine-4-thiol |
| K-13 | 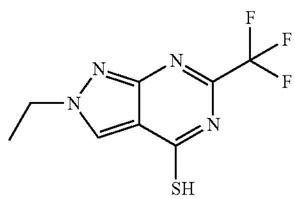 [SMILES: CCn1cc2c(S)nc(C(F)(F)F)nc2n1] | 2-ethyl-6-(trifluoromethyl)-2H-pyrazolo[3,4-d]pyrimidine-4-thiol |
| K-14 | 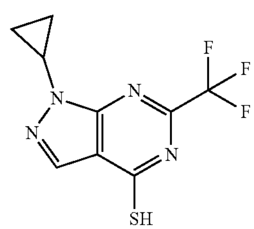 [SMILES: FC(F)(F)c1nc(S)c2cnn(C3CC3)c2n1] | 1-cyclopropyl-6-(trifluoromethyl)-1H-pyrazolo[3,4-d]pyrimidine-4-thiol |
| K-15 | 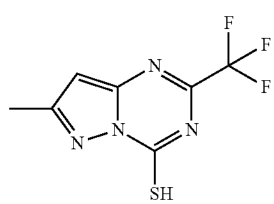 | 7-methyl-2-(trifluoromethyl)pyrazolo[1,5-a][1,3,5]triazine-4-thiol |
| K-16 | 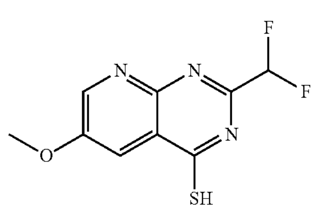 | 2-(difluoromethyl)-6-methoxypyrido[2,3-d]pyrimidine-4-thiol |
| K-17 | 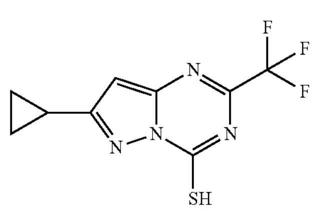 [SMILES: FC(F)(F)c1nc(S)n2nc(C3CC3)cc2n1] | 7-cyclopropyl-2-(trifluoromethyl)pyrazolo[1,5-a][1,3,5]triazine-4-thiol |

| Cpd number | Structure | Name |
|---|---|---|
| K-18 | 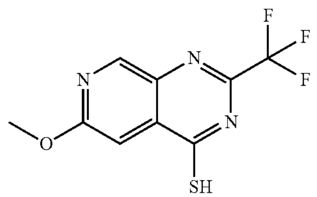 [SMILES: COc1cc2c(S)nc(C(F)(F)F)nc2cn1] | 6-methoxy-2-(trifluoromethyl)pyrido[3,4-d]pyrimidine-4-thiol |
| K-19 | 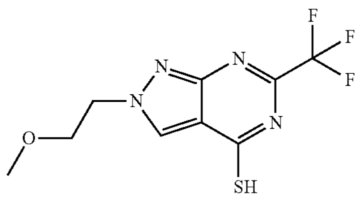 [SMILES: COCCn1cc2c(S)nc(C(F)(F)F)nc2n1] | 2-(2-methoxyethyl)-6-(trifluoromethyl)-2H-pyrazolo[3,4-d]pyrimidine-4-thiol |
| K-20 | 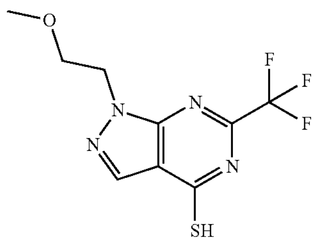 [SMILES: COCCn1ncc2c(S)nc(C(F)(F)F)nc21] | 1-(2-methoxyethyl)-6-(trifluoromethyl)-1H-pyrazolo[3,4-d]pyrimidine-4-thiol |
| K-21 | 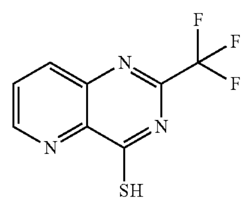 [SMILES: FC(F)(F)c1nc(S)c2ncccc2n1] | 2-(trifluoromethyl)pyrido[3,2-d]pyrimidine-4-thiol |

Preparation of Intermediate Compounds of Formula Y¹—SH, Wherein R²=Alkyl and the Like Synthesis of 7-chloro-2-methylquinazoline-4-thiol (M-1)

(M-1)

Synthesis of 7-chloro-2-methylquinazolin-4-ol (M-1-1) To a solution of 2-amino-4-chlorobenzamide (1.5 g, 8.823 mmol) in dioxane (10 mL) was added DIPEA (1.61 mL, 9.264 mmol) followed by acetyl chloride (0.63 mL, 8.823 mmol) at 0° C. and the reaction mixture was stirred for 15 min at 0° C. The reaction mixture was heated to reflux for 16 h after which it was concentrated in vacuo. The residue was diluted with EtOAc (100 mL) and washed with water (2×50 mL). The organic layer was dried over $Na_2SO_4$ and concentrated in vacuo. The crude 7-chloro-2-methylquinazolin-4-ol (M-1-1) was taken to next step without further purification. Synthesis of 7-chloro-2-methylquinazoline-4-thiol (M-1) To a solution of compound M-1-1 (400 mg, 2.061 mmol) in toluene (6.0 mL) was added $P_2S_5$ (457.7 mg, 2.061 mmol) at 0° C. The reaction mixture was stirred for 2 h at 120° C. after which it was concentrated in vacuo. The residue was diluted with DCM (100 mL) and washed with water (2×50 mL). The organic layer was dried over $Na_2SO_4$ and concentrated in vacuo. The residue compound was washed with hexane and dried in vacuo to afford 7-chloro-2-methylquinazoline-4-thiol (M-1) (190 mg, crude).

Synthesis of 6-methoxy-2-methylquinazoline-4-thiol (M-11)

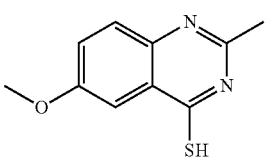

(M-11)

Synthesis of 6-methoxy-2-methylquinazolin-4-ol (M-11-1) To EtOH (500 mL) was added NaH (42.1 g, 1.05 mol, 60% purity) in portions at 0° C. and then 2-amino-5-methoxybenzamide (25.0 g, 150 mmol) was added followed by EtOAc (53.0 g, 601 mmol, 58.91 mL). The resulting mixture was stirred at 90° C. for 12 h. The reaction mixture was quenched by 1 M HCl (500 mL) and filtered. The filter cake was collected. The collected filter cake was dissolved in EtOAc/MeOH (V/V=1/1, 200 mL) and filtered. The filtrate was concentrated in vacuum to give compound M-11-1 (34.0 g, crude) as an off-white solid. $^1$H NMR: (400 MHz, DMSO-$d_6$) δ 12.2 (s, 1H), 7.51 (d, J=9.2 Hz, 1H), 7.45 (d, J=2.8 Hz), 7.36 (dd, J=8.8 Hz, 1H), 3.84 (s, 1H), 2.32 (s, 3H). Synthesis of 6-methoxy-2-methylquinazoline-4-thiol (M-11) To a solution of compound M-11-1 (20.0 g, 105 mmol) in toluene (140 mL) was added Lawesson's reagent (46.8 g, 115 mmol) and the mixture was stirred at 120° C. for 12 h under $N_2$ atmosphere. Two additional runs were done of this reaction on 18.0 g scale and 7.20 g scale of M-11-1, and the crude mixtures of all three runs were combined for work-up. The reaction mixture was concentrated in vacuum to remove solvent. The residue was triturated with EtOAc/MeOH (V/V=10/1, 10 V, 3 times) at 25° C. for 6 h to give compound M-11 (25.5 g, 72% yield, 85.3% purity) as a yellow solid. $^1$H NMR: (400 MHz, DMSO-$d_6$) δ 13.9 (s, 1H), 7.91 (d, J=2.4 Hz, 1H), 7.65 (d, J=8.8 Hz, 1H), 7.51 (dd, J=8.8 Hz, 1H), 3.87 (s, 3H), 2.48 (s, 3H).

The following intermediate compounds M-2 to M-48 have been prepared using the experimental conditions described above from the reaction of substituted amino carboxamide aryl and heteroaryl, and trifluoroacetic anhydride or $CHF_2$-based reagents. Alternatively, they were prepared from art known or commercial hydroxy-substituted heteroaryls of formula $Y^1$—OH by thionation using $P_2S_5$ reagent or Lawesson's reagent. Alternatively, some of the following compounds could be obtained commercially:

| Cpd number M | Structure | Name |
|---|---|---|
| M-2 | | 2,7-dimethyl-quinazoline-4-thiol |
| M-3 | | 2-isopropyl-quinazoline-4-thiol |
| M-4 | | 2-methyl-quinazoline-4-thiol |
| M-5 | | 2-cyclobutyl-quinazoline-4-thiol |
| M-6 | 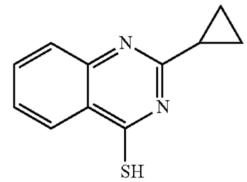 [SMILES: Sc1nc(C2CC2)nc2ccccc12] | 2-cyclopropyl-quinazoline-4-thiol |
| M-7 | 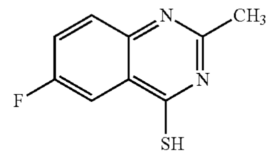 | 6-fluoro-2-methyl-quinazoline-4-thiol |
| M-8 | 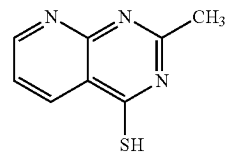 | 2-methylpyrido[2,3-d]pyrimidine-4-thiol |
| M-9 | 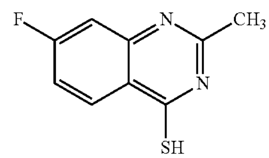 | 7-fluoro-2-methyl-quinazoline-4-thiol |
| M-10 | 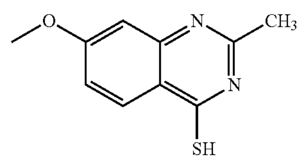 | 7-methoxy-2-methyl-quinazoline-4-thiol |
| M-12 | 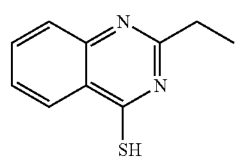 | 2-ethyl-quinazoline-4-thiol |
| M-13 | 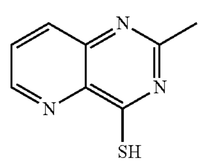 | 2-methylpyrido[3,2-d]pyrimidine-4-thiol |
| M-14 | 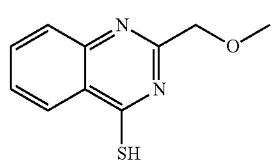 | 2-(methoxymethyl)quinazoline-4-thiol |
| M-15 | 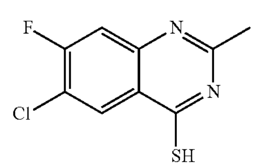 | 6-chloro-7-fluoro-2-methyl-quinazoline-4-thiol |

| Cpd number M | Name |
|---|---|
| M-16 | 7-fluoro-6-methoxy-2-methyl-quinazoline-4-thiol |
| M-17 | 2-methyl-6-(trifluoromethyl)quinazoline-4-thiol |
| M-18 | 6-cyclopropoxy-2-methyl-quinazoline-4-thiol |
| M-19 | 6-((cyclopropylmethyl)amino)-2-methyl-quinazoline-4-thiol |
| M-20 | 2-methyl-6-morpholino-quinazoline-4-thiol |
| M-21 | 2-methyl-6-(piperidin-1-yl)quinazoline-4-thiol |
| M-22 | 2-methyl-6-(1,4-oxazepan-4-yl)quinazoline-4-thiol |
| M-23 | 6-(3,3-difluoropyrrolidin-1-yl)-2-methyl-quinazoline-4-thiol |
| M-24 | 2-methyl-6-(4-methylpiperazin-1-yl)quinazoline-4-thiol |
| M-25 | 2,6-dimethyl-2H-pyrazolo[3,4-d]pyrimidine-4-thiol |
| M-26 | 6-cyclopropyl-1-methyl-1H-pyrazolo[3,4-d]pyrimidine-4-thiol |
| M-27 | 1,6-dimethyl-1H-pyrazolo[3,4-d]pyrimidine-4-thiol |
| M-28 | 2-methyl-quinazoline-4-thiol |
| M-29 | 6-chloro-8-fluoro-2-methyl-quinazoline-4-thiol |
| M-30 | 8-fluoro-2-methyl-quinazoline-4-thiol |
| M-31 | 2-methyl-8-(methylamino)-6-(trifluoromethyl)quinazoline-4-thiol |
| M-32 | 8-(dimethylamino)-2-methyl-6-(trifluoromethyl)quinazoline-4-thiol |

-continued

| Cpd number M | Structure | Name |
|---|---|---|
| M-33 | 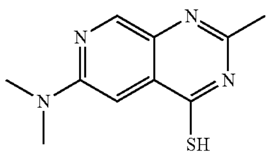 | 6-(dimethylamino)-2-methylpyrido[3,4-d]pyrimidine-4-thiol |
| M-34 | 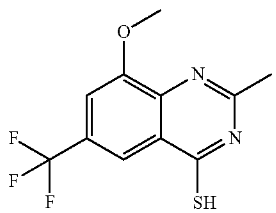 [SMILES: COc1cc(C(F)(F)F)cc2c(S)nc(C)nc12] | 8-methoxy-2-methyl-6-(trifluoromethyl)quinazoline-4-thiol |
| M-35 | 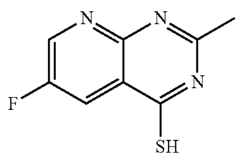 | 6-fluoro-2-methylpyrido[2,3-d]pyrimidine-4-thiol |
| M-36 | 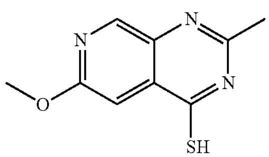 | 6-methoxy-2-methylpyrido[3,4-d]pyrimidine-4-thiol |
| M-37 | 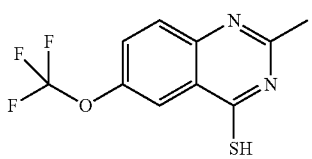 [SMILES: Cc1nc(S)c2cc(OC(F)(F)F)ccc2n1] | 2-methyl-6-(trifluoromethoxy)quinazoline-4-thiol |
| M-38 | 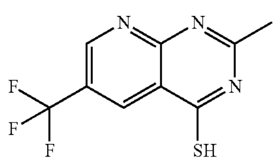 [SMILES: Cc1nc(S)c2cc(C(F)(F)F)cnc2n1] | 2-methyl-6-(trifluoromethyl)pyrido[2,3-d]pyrimidine-4-thiol |
| M-39 | 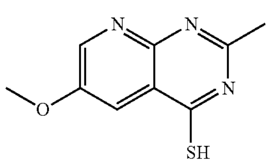 | 6-methoxy-2-methylpyrido[2,3-d]pyrimidine-4-thiol |
| M-40 | 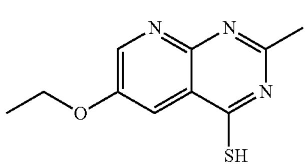 | 6-ethoxy-2-methylpyrido[2,3-d]pyrimidine-4-thiol |
| M-41 | 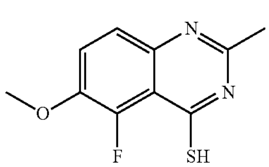 | 5-fluoro-6-methoxy-2-methylquinazoline-4-thiol |

-continued

| Cpd number M | Structure | Name |
|---|---|---|
| M-42 | 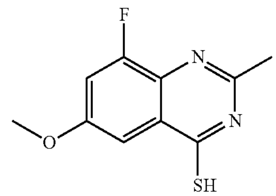 | 8-fluoro-6-methoxy-2-methylquinazoline-4-thiol |
| M-43 | 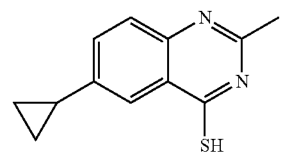 | 6-cyclopropyl-2-methylquinazoline-4-thiol |
| M-44 | 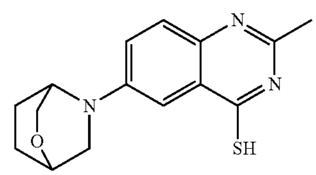 [SMILES: Cc1nc(S)c2cc(N3CC4CCC3CO4)ccc2n1] | 6-(2-oxa-5-azabicyclo[2.2.2]octan-5-yl)-2-methylquinazoline-4-thiol |
| M-45 | 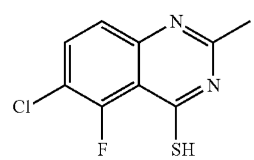 | 6-chloro-5-fluoro-2-methylquinazoline-4-thiol |
| M-46 | 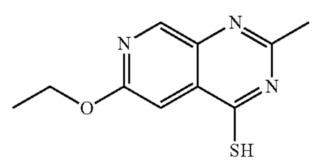 | 6-ethoxy-2-methylpyrido[3,4-d]pyrimidine-4-thiol |
| M-47 | 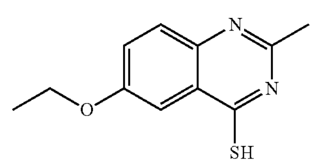 | 6-ethoxy-2-methylquinazoline-4-thiol |
| M-48 | 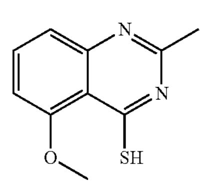 | 5-methoxy-2-methylquinazoline-4-thiol |

Preparation of Intermediate Compounds of Formula Y¹—SH, Wherein R²—=NR²

Synthesis of 2-(dimethylamino)quinazoline-4-thiol (N-1)

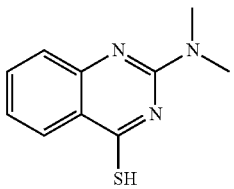

(N-1)

Synthesis of 2-(dimethylamino)quinazolin-4-ol (N-1-1) To a solution mixture of 2-iodobenzoic acid (1.0 g, 4.00 mmol) and compound-2 (743 mg, 6.0 mmol) in ACN (10 mL) was added K₂CO₃ (2.2 g, 16.1 mmol) and copper chloride hydrate (13 mg, 0.08 mmol) at rt. The reaction mixture was heated at 90° C. for 16 h. After cooling to rt, water (100 mL) was added, and the mixture was extracted with EtOAc (2×100 mL). The combined organic layers were dried over Na₂SO₄ and concentrated in vacuo affording compound N-1-1 (700 mg, Yield: 91%) as an off-white solid, which was taken to the next step without further purification. Synthesis of 2-(dimethylamino)quinazoline-4-thiol (N-1) To a stirred solution of compound N-1-1 (300 mg, 1.67 mmol) in dry toluene (4.0 mL) was added Lawesson's reagent (677 g, 1.675 mmol) under nitrogen atmosphere. The reaction mixture was stirred at 80° C. for 4 h, then concentrated under vacuum. The crude compound was purified by column chromatography over silica gel (100-200 mesh) to afford compound N-1 (150 mg, Yield: 46%) as a yellow solid.

Preparation of Intermediate Compounds of Formula Y¹—SH, Wherein G¹=N

Synthesis of 4-methylphthalazine-1-thiol (0-1)

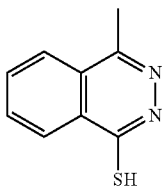

To a solution mixture of 4-methylphthalazin-1 (2H)-one (300 mg, 1.875 mmol) in toluene (5.0 mL) was added Lawesson's reagent (757.5 mg, 1.875 mmol) at 0° C. The reaction mixture was stirred for 2 h at 110° C. after which it was concentrated in vacuo. The residue (0-1) was taken to next step without further purification.

Synthesis of 4-(trifluoromethyl)phthalazine-1-thiol (0-2)

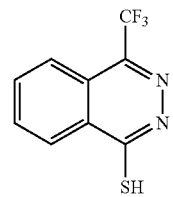 [SMILES: FC(F)(F)c1nnc(S)c2ccccc12]

Synthesis of 3-hydroxy-3-(trifluoromethyl)isobenzofuran-1 (3H)-one (0-2-1): To a stirred solution of isobenzofuran-1,3-dione (0.5 g, 3.378 mmol) in THF were added cuprous iodide (0.062 g, 0.337 mmol), PPh₃ (0.086 g, 0.338 mmol) and anhydrous KF (0.38 g, 6.551 mmol) under argon atmosphere. TMSCF₃ (0.5 g, 3.378 mmol) was added to the reaction mixture and stirring was continued for 6 h at 50° C. The progress of the reaction was monitored by TLC. After consumption of the starting material, the reaction mixture was diluted with water and extracted with EtOAc. The combined organic layers were dried over Na₂SO₄, concentrated under reduced pressure. The residue was purified by column chromatography by using silica gel affording O-2-1 (0.25 g, 35% yield) as an off-white solid. Synthesis of ethyl 2-(2,2,2-trifluoroacetyl)benzoate (O-2-2): To a stirred solution of 3-hydroxy-3-(trifluoromethyl)isobenzofuran-1 (3H)-one (O-2-1) (0.2 g, 0.917 mmol) in NMP was added bromoethane (0.1 g, 0.929 mmol) and K₂CO₃ (0.15 g, 1.086 mmol) at 0° C., and the resulting mixture was stirred at 70° C. for 6 h. The progress of the reaction was monitored by TLC. After consumption of the starting material, the reaction mixture was diluted with water and extracted with EtOAc. The combined organic layers were dried over Na₂SO₄ and concentrated under reduced pressure. The crude was purified by column chromatography by using silica gel affording O-2-2 (0.18 g, 48% pure by LCMS) as a white solid. Synthesis 4-(trifluoromethyl)phthalazine-1 (2H)-one (O-2-3): To a stirred solution of ethyl 2-(2,2,2-trifluoroacetyl) benzoate (O-2-2) (0.2 g, 0.81 mmol) in EtOH (2.0 mL) was added hydrazine hydrate (0.052 g, 1.60 mmol) at 0° C. slowly warmed to 90° C. for 16 h. The reaction was monitored by TLC. After consumption of the starting material, the mixture was diluted with water and extracted with EtOAc. The combined organic layers were dried over Na₂SO₄ and the solvent concentrated under reduced pressure. The residue was purified by column chromatography by using silica gel afford O-2-3 (0.18 g, 78% yield) as a white solid. Synthesis of 4-(trifluoromethyl)phthalazine-1-thiol (0-2) To a stirred solution of 4-(trifluoromethyl)phthalazin-1 (2H)-one (O-2-3) (0.2 g, 0.934 mmol, 1.0 eq.) in dry toluene was added Lawesson's reagent (0.37 g, 0.936 mmol, 1.0 eq) under an atmosphere of dry argon. The reaction mixture was then heated under pw conditions for 1 h at 110° C. The crude was purified by column chromatography on silica gel to afford compound (0-2) (0.07 g, 10% pure by LCMS) as a yellow solid.

The following intermediate compound 0-3 has been prepared using the experimental conditions described above from a commercial hydroxy-substituted heteroaryl of formula Y¹—OH by thionation using P₂S₅ reagent or Lawesson's reagent:

| Cpd number | Structure | Name |
|---|---|---|
| O-3 | ![phthalazine structure] | phthalazine-1(2H)-thione |

Preparation of Intermediate Compounds of Formula Y¹—SH with [5,6] Bicyclic Heteroaryl, Wherein G²=O or N—R⁴

Synthesis of 5-(trifluoromethyl)oxazolo[5,4-b]pyridine-2-thiol (P-1)

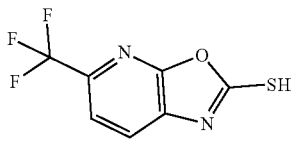

Synthesis of 3-amino-6-(trifluoromethyl)pyridin-2-ol (P-1-1) To a stirred solution of 3-nitro-6-(trifluoromethyl)pyridin-2-ol (200 mg, 0.961 mmol) in MeOH (1 mL) was added 15% Pd—C(30 mg). Then H₂ gas was inserted for 3 h at 60 psi., after which the mixture was heated to 50° C. for 3 h. The reaction mixture was filtered through a celite bed under vacuum. The solvent was evaporated under reduced pressure to get title compound P-1-1 (142 mg, 75% yield). Synthesis of 5-(trifluoromethyl)oxazole[5,4-b]pyridine-2-thiol (P-1) To a solution of 3-amino-6-(trifluoromethyl)pyridin-2-ol P-1-1 (1.8 g, 0.010 mol) in EtOH (18 mL) was added KOH (1.13 g, 0.0202 mol) followed by CS₂ (1.13 mL, 0.0202 mol) at 0° C. The resultant reaction mixture was stirred at 80° C. for 16 h. After completion of the reaction, the solvent was evaporated under reduced pressure and purified by C18-reversed phase combi-flash chromatography (eluent: 0.1% formic acid in ACN) to get title compound P-1 (1.8 g, 81% yield) as an off-white solid.

Synthesis of 6-(trifluoromethyl)oxazolo[4,5-c]pyridine-2-thiol (P-6)

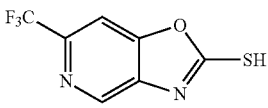

Synthesis of 5-nitro-2-(trifluoromethyl)pyridin-4-ol (P-6-1) To a solution of 2-(trifluoromethyl)pyridin-4-ol (7.50 g, 45.9 mmol) in H₂SO₄ (40.0 mL) was added fuming nitric acid (68.6 g, 980 mmol) and H₂SO₄ (82.8 g, 844 mmol) at 0° C. The mixture was stirred at 120° C. for 8 h. The reaction mixture was quenched by addition ice-cold water (300 mL) at 0° C. and extracted with EtOAc (100 mL×3). The combined organic layers were washed with brine (100 mL×2), dried over Na₂SO₄, filtered, and concentrated under reduced pressure. The residue was purified by column chromatography (SiO₂, petroleum ether/ethyl acetate=100/1 to 0/1) to give 5-nitro-2-(trifluoromethyl)pyridin-4-ol (P-6-1) (3.62 g, 38% yield) as a yellow solid. Synthesis of 5-amino-2-(trifluoromethyl)pyridin-4-ol (P-6-2) To a solution of Pd/C (2.00 g, 64.8 mmol, 10% purity) in MeOH (100 mL) was added compound P-6-1 (13.5 g, 64.8 mmol) under Ar. The suspension was degassed under vacuum and purged with H₂ several times after which the mixture was stirred under H₂ (15 psi) at 25° C. for 5 h. The suspension was filtered, and the filter cake was washed with MeOH (100 mL×3). The combined filtrates were concentrated to dryness. The residue was purified by column chromatography (SiO₂, petroleum ether/ethyl acetate=100/1 to 0/1) to give 5-amino-2-(trifluoromethyl) pyridin-4-ol (P-6-2) (9.10 g, 67% yield) as a brown solid. Synthesis of 6-(trifluoromethyl)oxazolo[4,5-c]pyridine-2-thiol (P-6) To a solution of compound P-6-2 (1.00 g, 5.61 mmol) in Py (10.0 mL) was added dropwise potassium ethylxanthate (1.08 g, 6.74 mmol) at 25° C. The resulting mixture was stirred at 110° C. for 12 h. The reaction mixture was poured into 1 N HCl to pH=4-5, and then extracted with EtOAc (30.0 mL×3), The combined organic layers were washed with brine (30.0 mL×2), dried over Na₂SO₄, filtered, and concentrated under reduced pressure. The residue was purified by column chromatography (SiO₂, petroleum ether/ethyl acetate=100/1 to 0/1, petroleum ether/ethyl acetate=2/1, R_f=0.2) to give 6-(trifluoromethyl)oxazolo[4,5-c]pyridine-2-thiol (P-6) (400 mg, 32% yield) as a brown solid.

Synthesis of 6-(trifluoromethyl)oxazolo[4,5-b]pyridine-2-thiol (P-7)

Synthesis of 3-(4,4,5,5-tetramethyl-1,3,2-dioxaborolan-2-yl)-5-(trifluoromethyl)pyridin-2-amine (P-7-1) To a solution of 3-bromo-5-(trifluoromethyl)pyridin-2-amine (8.00 g, 33.2 mmol) in dioxane (40.0 mL) was added 4,4,4',4',5,5,5',5'-octamethyl-2,2'-bi(1,3,2-dioxaborolane) (9.27 g, 36.5 mmol), KOAc (9.77 g, 99.6 mmol) and Pd(dppf)Cl₂ (729 mg, 996 umol). The mixture was stirred at 90° C. for 6 h. The reaction mixture was quenched by addition H₂O (20.0 mL) at 25° C., and then extracted with EtOAc (20.0 mL×3). The combined organic layers were washed with brine (10.0 mL), dried over Na₂SO₄, filtered, and concentrated under reduced pressure to give a residue. The residue was purified by column chromatography (SiO₂, petroleum ether/ethyl acetate=100/1 to 0/1) to give 3-(4,4,5,5-tetramethyl-1,3,2-dioxaborolan-2-yl)-5-(trifluoromethyl)pyridin-2-amine P-7-1 (9.00 g, 94% yield) as a white solid. Synthesis of 2-amino-5-(trifluoromethyl)pyridin-3-ol (P-7-2) To a solution of compound P-7-1 (9.00 g, 31.2 mmol) in THF (90.0 mL) was added H₂O₂ (43.4 g, 383 mmol, 36.8 mL, 30% purity). The mixture was stirred at 25° C. for 2 h. The reaction mixture was quenched by addition aq. sat. NH₄Cl (80.0 mL) at 5° C., and then extracted with EtOAc (40.0 mL×3). The combined organic layers were washed with brine (30.0 mL), dried over Na₂SO₄, filtered, and concentrated under reduced pressure. The residue was dissolved in DCM (40.0 mL), and then extracted with 1 M HCl (40 mL).

The aqueous phase was adjusted to pH=8 with NaHCO₃, and then extracted with EtOAc (40.0 mL×3) to give 2-amino-5-(trifluoromethyl)pyridin-3-ol (P-7-2) (5.00 g, 79% yield, 87.5% purity) as a light yellow solid. Synthesis of 6-(trifluoromethyl)oxazolo[4,5-b]pyridine-2-thiol (P-7) To a solution of compound P-7-2 (3.00 g, 16.8 mmol) in EtOH (30.0 mL) was added CS₂ (3.85 g, 50.5 mmol, 3.05 mL) and KOH (2.84 g, 50.5 mmol). The mixture was stirred at 80° C. for 16 h. The reaction mixture was quenched by addition 2 M HCl (30.0 mL) at 25° C., and then extracted with EtOAc (30.0 mL×3). The combined organic layers were washed with 2 M HCl (30.0 mL), dried over Na₂SO₄, filtered and concentrated under reduced pressure to give 6-(trifluoromethyl)oxazolo[4,5-b]pyridine-2-thiol (P-7) (2.47 g, 67% yield) as a yellow solid.

The following intermediate thiols (P-2) to (P-15) have been prepared using the experimental conditions described above for K-1, from the reaction of substituted bicyclic oxazole 2-hydroxyl and Lawesson's reagent. Alternatively, some of the following compounds could be obtained commercially:

| Cpd number | Structure | Name |
|---|---|---|
| P-2 | 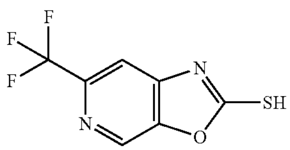 [SMILES: FC(F)(F)c1cc2nc(S)oc2cn1] | 6-(trifluoromethyl)oxazolo[5,4-c]pyridine-2-thiol |
| P-3 | 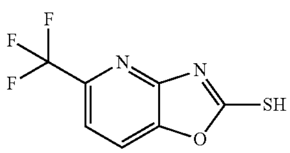 [SMILES: FC(F)(F)c1ccc2oc(S)nc2n1] | 5-(trifluoromethyl)oxazolo[4,5-b]pyridine-2-thiol |
| P-4 | 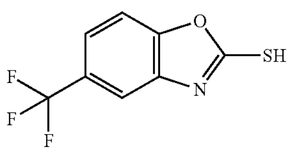 [SMILES: FC(F)(F)c1ccc2oc(S)nc2c1] | 5-(trifluoromethyl)benzo[d]oxazole-2-thiol |
| P-5 | 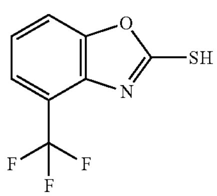 [SMILES: FC(F)(F)c1cccc2oc(S)nc12] | 4-(trifluoromethyl)benzo[d]oxazole-2-thiol |
| P-8 | 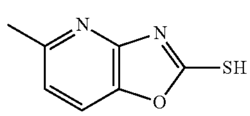 | 5-methyloxazolo[4,5-b]pyridine-2-thiol |
| P-9 | 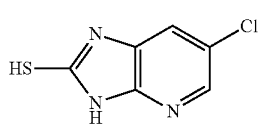 [SMILES: Sc1nc2cc(Cl)cnc2[nH]1] | 6-chloro-3H-imidazo[4,5-b]pyridine-2-thiol |
| P-10 | 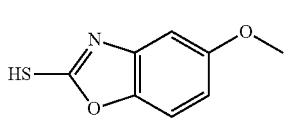 | 5-methoxybenzo[d]oxazole-2-thiol |
| P-11 | | 4-methoxybenzo[d]oxazole-2-thiol |
| P-12 | | 1-methyl-1H-benzo[d]imidazole-2-thiol |
| P-13 | | 5-methylbenzo[d]oxazole-2-thiol |
| P-14 | | 5-methoxy-3H-imidazo[4,5-b]pyridine-2-thiol |
| P-15 | | 5-chlorobenzo[d]oxazole-2-thiol |

Preparation of Example Compounds

Example 1: N-((5-(2-((2-isopropylquinazolin-4-yl)thio)acetyl)thiophen-2-yl)methyl)pivalamide

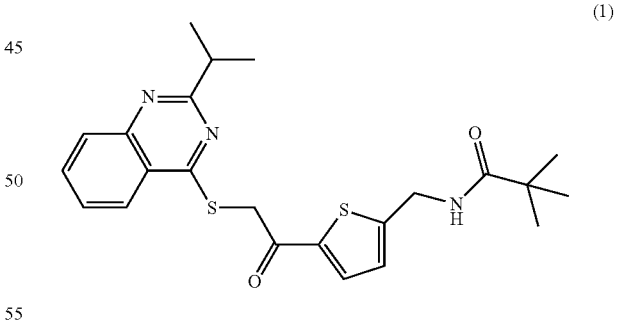

(1)

According to Method 2 (Scheme 2), Step 4: To a solution mixture of intermediate M-3 (100 mg, 0.49 mmol, 1 eq.) in DMF (3.0 mL) and added NaOMe (29.12 mg, 0.539 mmol) at 0° C. The resultant reaction mixture was stirred for 30 min at 0° C. and was added compound I-4 (171 mg, 0.539 mmol). The reaction mixture was stirred for 16 h at rt. After completion of reaction, cold water was added to reaction mixture was extracted using EtOAc (2×50 mL), total organic layer was dried over Na₂SO₄ and concentrated in vacuo. The crude compound was purified by Combi-Flash chromatography to afford example 1 (70 mg, 30% yield).

Example 60: 2-Hydroxy-N-((5-(2-((6-methoxy-2-methylquinazolin-4-yl)thio)acetyl)thiophen-2-yl)methyl)acetamide

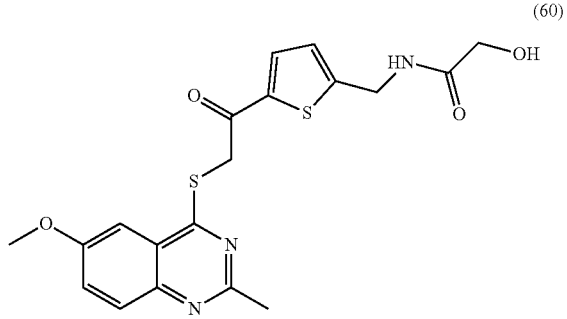 [SMILES: COc1ccc2nc(C)nc(SCC(=O)c3ccc(CNC(=O)CO)s3)c2c1]

(60)

To a solution of M-11 (10.0 g, 48.5 mmol) in DMF (108 mL) was added NaOMe (2.62 g, 48.5 mmol) at 0° C. and the mixture was stirred at 0° C. for 30 min. Then compound I-13 was added to the mixture (15.6 g, 53.3 mmol) and the mixture was stirred at 25° C. for 2 h. Three additional runs were done of this reaction on 5.0 g scale, 10 g scale and 10 g scale of M-11, and the crude mixtures of all four runs were combined for work-up. The combined reaction mixture was poured into $H_2O$ (651 mL) and filtered to collect the solid. The solid was triturated with MTBE (10 V×2) at 25° C. for 2 h to give example 60 (16.25 g, 31.7% yield, 98.9% purity) as a light-yellow solid. 1H NMR: (400 MHz, DMSO-$d_6$) δ 8.55 (t, J=12.0 Hz, 1H), 8.09 (d, J=4.00 Hz, 1H), 7.80 (d, J=9.20 Hz, 1H), 7.57-7.60 (m, 1H), 7.28 (d, J=4.00 Hz, 1H), 5.55-5.58 (m, 1H), 4.84 (s, 2H), 4.52 (d, J=6.40 Hz, 2H), 3.94 (s, 3H), 3.87 (d, J=6.00 Hz, 2H), 2.41 (s, 4H). LCMS: $[M+H]^+$ 418.1. M.P. (DSC): 185.65° C.

The following Examples have been prepared using similar experimental conditions described above for the synthesis of Example 1 (General Method 2, Scheme 2, Step 4), obtained from the reaction of intermediate of Formula $Y^1$—SH M, N, O or P with compound I-4:

| Ex | Cpd $Y^1$-SH | Name |
|---|---|---|
| 2 | M-6 | N-((5-(2-((2-cyclopropylquinazolin-4-yl)thio)acetyl)thiophen-2-yl)methyl)pivalamide |
| 3 | M-4 | N-((5-(2-((2-methylquinazolin-4-yl)thio)acetyl)thiophen-2-yl)methyl)pivalamide |
| 4 | M-14 | N-((5-(2-((2-(methoxymethyl)quinazolin-4-yl)thio)acetyl)thiophen-2-yl)methyl)pivalamide |
| 5 | M-27 | N-((5-(2-((1,6-dimethyl-1H-pyrazolo[3,4-d]pyrimidin-4-yl)thio)acetyl)thiophen-2-yl)methyl)pivalamide |
| 6 | M-26 | N-((5-(2-((6-cyclopropyl-1-methyl-1H-pyrazolo[3,4-d]pyrimidin-4-yl)thio)acetyl)thiophen-2-yl)methyl)pivalamide |
| 7 | M-8 | N-((5-(2-((2-methylpyrido[2,3-d]pyrimidin-4-yl)thio)acetyl)thiophen-2-yl)methyl)pivalamide |
| 8 | M-1 | N-((5-(2-((7-chloro-2-methylquinazolin-4-yl)thio)acetyl)thiophen-2-yl)methyl)pivalamide |
| 9 | M-7 | N-((5-(2-((6-fluoro-2-methylquinazolin-4-yl)thio)acetyl)thiophen-2-yl)methyl)pivalamide |
| 10 | M-9 | N-((5-(2-((7-fluoro-2-methylquinazolin-4-yl)thio)acetyl)thiophen-2-yl)methyl)pivalamide |
| 11 | M-2 | N-((5-(2-((2,7-dimethylquinazolin-4-yl)thio)acetyl)thiophen-2-yl)methyl)pivalamide |
| 12 | M-10 | N-((5-(2-((7-methoxy-2-methylquinazolin-4-yl)thio)acetyl)thiophen-2-yl)methyl)pivalamide |
| 13 | M-12 | N-((5-(2-((2-ethylquinazolin-4-yl)thio)acetyl)thiophen-2-yl)methyl)pivalamide |
| 14 | M-5 | N-((5-(2-((2-cyclobutylquinazolin-4-yl)thio)acetyl)thiophen-2-yl)methyl)pivalamide |
| 15 | M-30 | N-((5-(2-((8-fluoro-2-methylquinazolin-4-yl)thio)acetyl)thiophen-2-yl)methyl)pivalamide |
| 16 | N-1 | N-((5-(2-((2-(dimethylamino)quinazolin-4-yl)thio)acetyl)thiophen-2-yl)methyl)pivalamide |
| 17 | M-11 | N-((5-(2-((6-methoxy-2-methylquinazolin-4-yl)thio)acetyl)thiophen-2-yl)methyl)pivalamide |
| 18 | M-13 | N-((5-(2-((2-methylpyrido[3,2-d]pyrimidin-4-yl)thio)acetyl)thiophen-2-yl)methyl)pivalamide |
| 23 | P-8 | N-((5-(2-((5-methyloxazolo[4,5-b]pyridine-2-yl)thio)acetyl)thiophen-2-yl)methyl)pivalamide |
| 194 | O-1 | N-((5-(2-((4-methylphthalazin-1-yl)thio)acetyl)thiophen-2-yl)methyl)pivalamide |
| 195 | O-2 | N-((5-(2-((4-(trifluoromethyl)phthalazin-1-yl)thio)acetyl)thiophen-2-yl)methyl)pivalamide) |

The following Examples have been prepared using similar experimental conditions described above for the synthesis of Example 1 (Method 2, Scheme 2, Step 4), obtained from the reaction of intermediate of Formula $Y^1$—SH K with compound I-4:

| Ex. | Cpd $Y^1$-SH | Name |
|---|---|---|
| 19 | K-2 | N-((5-(2-((2-(difluoromethyl)quinazolin-4-yl)thio)acetyl)thiophen-2-yl)methyl)pivalamide |
| 20 | K-7 | N-((5-(2-((1-methyl-6-(trifluoromethyl)-1H-pyrazolo[3,4-d]pyrimidin-4-yl)thio)acetyl)thiophen-2-yl)methyl)pivalamide |
| 21 | K-6 | N-((5-(2-((6-(difluoromethyl)-1-methyl-1H-pyrazolo[3,4-d]pyrimidin-4-yl)thio)acetyl)thiophen-2-yl)methyl)pivalamide |
| 22 | K-5 | N-((5-(2-((2-methyl-6-(trifluoromethyl)-2H-pyrazolo[3,4-d]pyrimidin-4-yl)thio)acetyl)thiophen-2-yl)methyl)pivalamide |
| 38 | K-1 | N-((5-(2-((2-(trifluoromethyl)quinazolin-4-yl)thio)acetyl)thiophen-2-yl)methyl)pivalamide |
| 191 | K-22 | N-((5-(2-((3-(trifluoromethyl)isoquinolin-1-yl)thio)acetyl)thiophen-2-yl)methyl)pivalamide |

The following Examples have been prepared using the experimental conditions described above for the synthesis of compound (1) (according to Method 4, Scheme 4, Step 4), obtained from the reaction of intermediate compound of Formula $Y^1$—SH J, M or K with intermediate compound I-n, where applicable:

| Ex. | Cpd $Y^1$-SH | Cpd I | NAME |
|---|---|---|---|
| 24 | J-1 | I-6 | 3-methyl-1-((5-(2-((1-methyl-1H-pyrazolo[3,4-d]pyrimidin-4-yl)thio)acetyl)thiophen-2-yl)methyl)pyrrolidin-2-one |
| 25 | J-1 | I-10 | 1-((5-(2-((1-methyl-1H-pyrazolo[3,4-d]pyrimidin-4-yl)thio)acetyl)thiophen-2-yl)methyl)pyrrolidin-2-one |
| 26 | K-1 | I-11 | 1-(2-(5-(2-((2-(trifluoromethyl)quinazolin-4-yl)thio)acetyl)thiophen-2-yl)ethyl)pyrrolidin-2-one |
| 115 | M-11 | I-16 | 3-hydroxy-1-(2-(5-(2-((6-methoxy-2-methylquinazolin-4-yl)thio)acetyl)thiophen-2-yl)ethyl)pyrrolidin-2-one |
| 137 | M-11 | I-14 | 4-((5-(2-((6-methoxy-2-methylquinazolin-4-yl)thio)acetyl)thiophen-2-yl)methyl)morpholin-3-one |

-continued

| Ex. | Cpd Y¹-SH | Cpd I | NAME |
|---|---|---|---|
| 138 | K-11 | I-14 | 4-((5-(2-((2-(trifluoromethyl)pyrido[2,3-d]pyrimidin-4-yl)thio)acetyl)thiophen-2-yl)methyl)morpholin-3-one |
| 157 | K-11 | I-10 | 1-((5-(2-((2-(trifluoromethyl)pyrido[2,3-d]pyrimidin-4-yl)thio)acetyl)thiophen-2-yl)methyl)pyrrolidin-2-one |
| 161 | M-39 | I-14 | 4-((5-(2-((6-methoxy-2-methylpyrido[2,3-d]pyrimidin-4-yl)thio)acetyl)thiophen-2-yl)methyl)morpholin-3-one |

The following Examples have been prepared using the experimental conditions described above for the synthesis of compound (1) (according to Method 2, Scheme 2, Step 4), obtained from the reaction of intermediate compound of Formula Y¹—SH J, M or K with intermediate compound I-n, where applicable:

| Ex. | Cpd Y¹-SH | Cpd I | NAME |
|---|---|---|---|
| 27 | J-1 | I-8 | N-((2-(2-((1-methyl-1H-pyrazolo[3,4-d]pyrimidin-4-yl)thio)acetyl)thiazol-5-yl)methyl)pivalamide |
| 28 | J-1 | I-7 | N-((3-fluoro-5-(2-((1-methyl-1H-pyrazolo[3,4-d]pyrimidin-4-yl)thio)acetyl)thiophen-2-yl)methyl)pivalamide |
| 128 | M-11 | I-9 | (S)-2-hydroxy-N-(1-(5-(2-((6-methoxy-2-methylquinazolin-4-yl)thio)acetyl)thiophen-2-yl)ethyl)acetamide |
| 129 | P-6 | I-9 | (S)-2-hydroxy-N-(1-(5-(2-((6-(trifluoromethyl)oxazolo[4,5-c]pyridin-2-yl)thio)acetyl)thiophen-2-yl)ethyl)acetamide |
| 130 | K-7 | I-9 | (S)-2-hydroxy-N-(1-(5-(2-((1-methyl-6-(trifluoromethyl)-1H-pyrazolo[3,4-d]pyrimidin-4-yl)thio)acetyl)thiophen-2-yl)ethyl)acetamide |
| 115 | M-11 | I-16 | 3-hydroxy-1-(2-(5-(2-((6-methoxy-2-methylquinazolin-4-yl)thio)acetyl)thiophen-2-yl)ethyl)pyrrolidin-2-one |
| 141 | M-11 | I-15 | 3-hydroxy-1-((5-(2-((6-methoxy-2-methylquinazolin-4-yl)thio)acetyl)thiophen-2-yl)methyl)pyrrolidin-2-one |
| 165 | J-5 | I-13 | N-((5-(2-((1,7-naphthyridin-8-yl)thio)acetyl)thiophen-2-yl)methyl)-2-hydroxyacetamide |
| 166 | P-9 | I-13 | N-((5-(2-((6-chloro-3H-imidazo[4,5-b]pyridin-2-yl)thio)acetyl)thiophen-2-yl)methyl)-2-hydroxyacetamide |
| 167 | P-10 | I-13 | 2-hydroxy-N-((5-(2-((5-methoxybenzo[d]oxazol-2-yl)thio)acetyl)thiophen-2-yl)methyl)acetamide |
| 168 | P-11 | I-13 | 2-hydroxy-N-((5-(2-((4-methoxybenzo[d]oxazol-2-yl)thio)acetyl)thiophen-2-yl)methyl)acetamide |
| 169 | P-12 | I-13 | 2-hydroxy-N-((5-(2-((1-methyl-1H-benzo[d]imidazol-2-yl)thio)acetyl)thiophen-2-yl)methyl)acetamide |
| 170 | P-13 | I-13 | 2-hydroxy-N-((5-(2-((5-methylbenzo[d]oxazol-2-yl)thio)acetyl)thiophen-2-yl)methyl)acetamide |
| 173 | P-14 | I-13 | 2-hydroxy-N-((5-(2-((5-methoxy-3H-imidazo[4,5-b]pyridin-2-yl)thio)acetyl)thiophen-2-yl)methyl)acetamide |
| 174 | P-15 | I-13 | N-((5-(2-((5-chlorobenzo[d]oxazol-2-yl)thio)acetyl)thiophen-2-yl)methyl)-2-hydroxyacetamide |
| 176 | J-6 | I-13 | 2-hydroxy-N-((5-(2-(imidazo[1,2-a]pyrazin-8-ylthio)acetyl)thiophen-2-yl)methyl)acetamide |
| 179 | J-3 | I-13 | N-((5-(2-((1,6-naphthyridin-5-yl)thio)acetyl)thiophen-2-yl)methyl)-2-hydroxyacetamide |
| 180 | J-4 | I-13 | N-((5-(2-((2,7-naphthyridin-1-yl)thio)acetyl)thiophen-2-yl)methyl)-2-hydroxyacetamide |
| 181 | J-7 | I-13 | 2-hydroxy-N-((5-(2-(imidazo[1,5-a]pyrazin-8-ylthio)acetyl)thiophen-2-yl)methyl)acetamide |
| 182 | J-8 | I-13 | 2-hydroxy-N-((5-(2-(pyrazolo[1,5-a]pyrazin-4-ylthio)acetyl)thiophen-2-yl)methyl)acetamide |

| Ex. | Cpd Y¹-SH | Cpd I | NAME |
|---|---|---|---|
| 192 | J-1 | I-12 | N-((5-(2-(1-methyl-1H-pyrazolo[3,4-d]pyrimidin-4-ylthio)acetyl)-1,3,4-thiadiazol-2-yl)methyl)pivalamide |
| 193 | O-3 | I-4 | N-((5-(2-(phthalazin-1-ylthio)acetyl)thiophen-2-yl)methyl)pivalamide |

The following Examples have been prepared using the experimental conditions described above for the synthesis of compound (1) (according to Method 2, Scheme 2, Step 4), obtained from the reaction of intermediate compound of Formula Y¹—SH K-11 with intermediate compound I-15, followed by a separation of enantiomers using chiral SFC (Waters SFC80 preparative SFC; Column: DAICEL CHIRALPAK JH (250 mm*30 mm, 10 um); Mobile phase: A for $CO_2$ and B for MeOH; Gradient: B %=40% isocratic elution mode; Flow rate: 70 g/min; Wavelength: 220 nm; Column temperature: 40° C. System back pressure: 100 bar):

| Ex. | NAME |
|---|---|
| 155 | (S)-3-hydroxy-1-((5-(2-((2-(trifluoromethyl)pyrido[2,3-d]pyrimidin-4-yl)thio)acetyl)thiophen-2-yl)methyl)pyrrolidin-2-one |
| 156 | (R)-3-hydroxy-1-((5-(2-((2-(trifluoromethyl)pyrido[2,3-d]pyrimidin-4-yl)thio)acetyl)thiophen-2-yl)methyl)pyrrolidin-2-one |

Synthesis of 1-(5-(2-aminoethyl)thiophen-2-yl)-2-((2-(trifluoromethyl)quinazolin-4-yl)thio)ethan-1-one (Q-1)

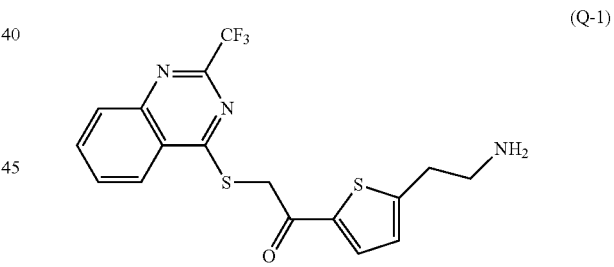

(Q-1)

To a solution mixture of compound K-1 (390 mg, 130 mmol) in DMF (5 mL) is added NaOMe (77 mg, 1.43 mmol) at 0° C. The resultant reaction mixture was stirred for 30 min at 0° C. and was added compound I-2 (549 mg, 156 mmol). The reaction mixture was stirred for 2 h at rt. The reaction mixture was quenched with cold water and extracted with EtOAc (2×50 mL). Organic layer was dried over $Na_2SO_4$ and concentrated in vacuo. The crude compound was purified by column chromatography over silica gel (60-120 mesh). The compound was eluted using 30% EtOAc in hexane to afford compound (Q-1-1). To a solution mixture of compound (Q-1-1) in dioxane (3.0 mL) was added 4 M HCl in dioxane (6.0 mL) at 0° C. The reaction mixture was stirred for 2 h at rt. The reaction mixture was concentrated in vacuo. The crude compound was washed with n-pentane and dried in vacuo to afford the hydrochloride salt of compound (Q-1) as a white solid.

The following intermediate compounds Q have been prepared using the experimental conditions described above (General Method 1) from the reaction of compounds J, K and M of Formula Y¹—SH with bromo-ketone I-1, I-2, I-3 or I-5, followed by deprotection of the Boc protecting group to provide a terminal amino group.

| Cpd Q | Structure | Cpd Y¹-SH | Cpd I | IUPAC name |
|---|---|---|---|---|
| Q-2 | 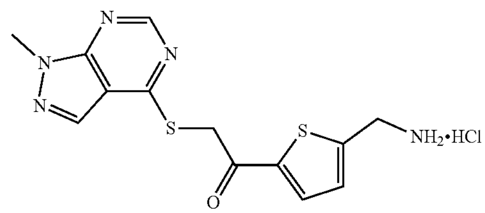 | J-1 | I-1 | 1-(5-(aminomethyl)thiophen-2-yl)-2-((1-methyl-1H-pyrazolo[3,4-d]pyrimidin-4-yl)thio)ethanone hydrochloride |
| Q-3 | 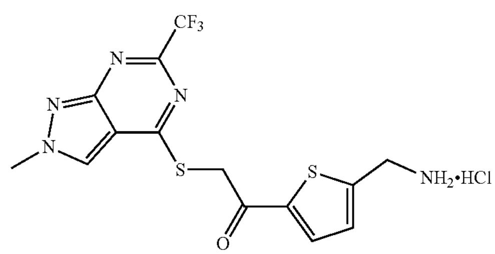 | K-5 | I-1 | 1-(5-(aminomethyl)thiophen-2-yl)-2-((2-methyl-6-(trifluoromethyl)-2H-pyrazolo[3,4-d]pyrimidin-4-yl)thio)ethanone hydrochloride |
| Q-4 | 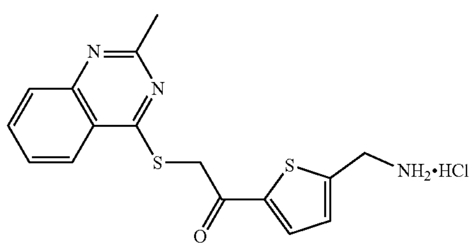 | M-4 | I-1 | 1-(5-(aminomethyl)thiophen-2-yl)-2-((2-methylquinazolin-4-yl)thio)ethanone hydrochloride |
| Q-5 | 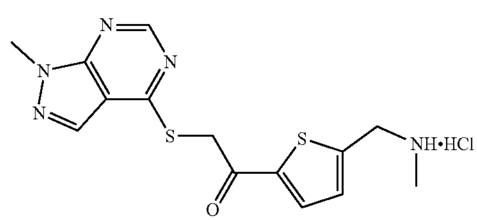 | J-1 | I-3 | 2-((1-methyl-1H-pyrazolo[3,4-d]pyrimidin-4-yl)thio)-1-(5-((methylamino)methyl)thiophen-2-yl)ethanone hydrochloride |
| Q-6 | 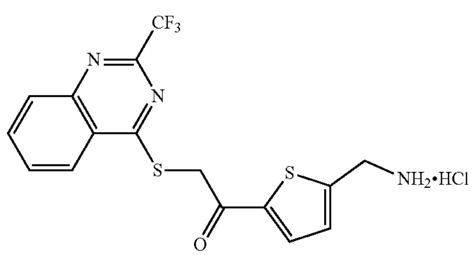 | K-1 | I-1 | 1-(5-(aminomethyl)thiophen-2-yl)-2-((2-(trifluoromethyl)quinazolin-4-yl)thio)ethanone hydrochloride |
| Q-7 | 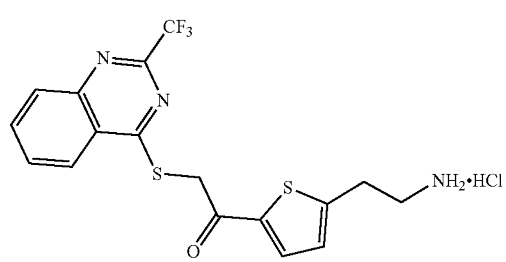 | K-1 | I-2 | 1-(5-(2-aminoethyl)thiophen-2-yl)-2-((2-(trifluoromethyl)quinazolin-4-yl)thio)ethanone hydrochloride |

-continued

| Cpd Q | Structure | Cpd Y¹-SH | Cpd I | IUPAC name |
|---|---|---|---|---|
| Q-8 | 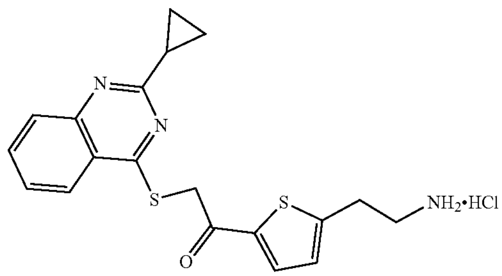 | M-6 | I-2 | 1-(5-(2-aminoethyl)thiophen-2-yl)-2-((2-cyclopropylquinazolin-4-yl)thio)ethanone hydrochloride |
| Q-9 | 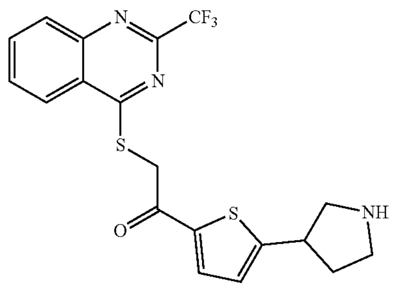 [SMILES: O=C(CSc1nc(C(F)(F)F)nc2ccccc12)c1ccc(C2CCNC2)s1] | K-1 | I-5 | 1-(5-(pyrrolidin-3-yl)thiophen-2-yl)-2-((2-(trifluoromethyl)quinazolin-4-yl)thio)ethanone |
| Q-10 | 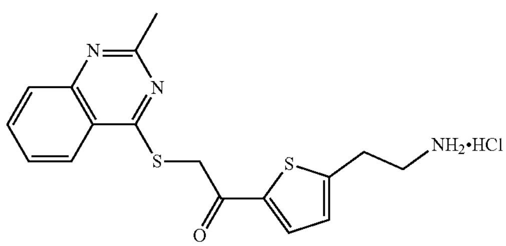 | M-28 | I-2 | 1-(5-(2-aminoethyl)thiophen-2-yl)-2-((2-methylquinazolin-4-yl)thio)ethanone hydrochloride |
| Q-11 | 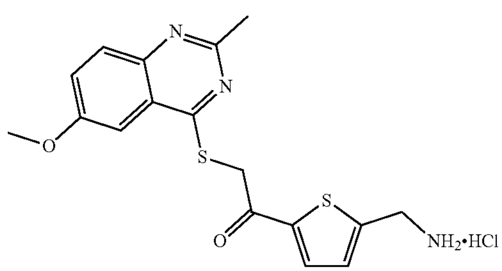 | M-11 | I-1 | 1-(5-(aminomethyl)thiophen-2-yl)-2-((6-methoxy-2-methylquinazolin-4-yl)thio)ethanone hydrochloride |
| Q-12 | 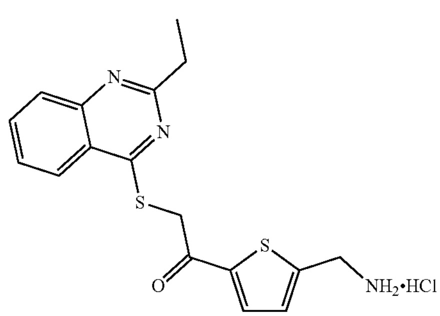 | M-12 | I-1 | 1-(5-(aminomethyl)thiophen-2-yl)-2-((2-ethylquinazolin-4-yl)thio)ethanone hydrochloride |

-continued

| Cpd Q | Structure | Cpd Y¹-SH | Cpd I | IUPAC name |
|---|---|---|---|---|
| Q-13 | 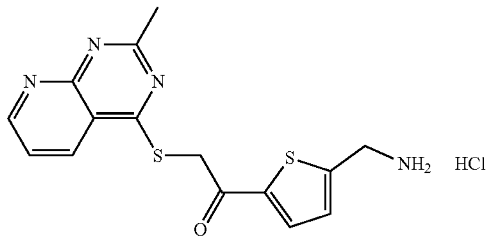 [SMILES: Cc1nc(SCC(=O)c2ccc(CN)s2)c2cccnc2n1 ; Cl] | M-8 | I-1 | 1-(5-(aminomethyl)thiophen-2-yl)-2-((2-methylpyrido[2,3-d]pyrimidin-4-yl)thio)ethan-1-one hydrochloride |
| Q-14 | 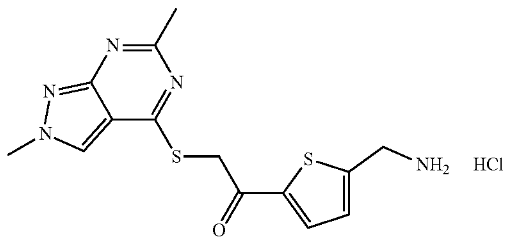 [SMILES: Cc1nc(SCC(=O)c2ccc(CN)s2)c2cn(C)nc2n1 ; Cl] | M-25 | I-1 | 1-(5-(aminomethyl)thiophen-2-yl)-2-((2,6-dimethyl-2H-pyrazolo[3,4-d]pyrimidin-4-yl)thio)ethan-1-one hydrochloride |
| Q-15 | 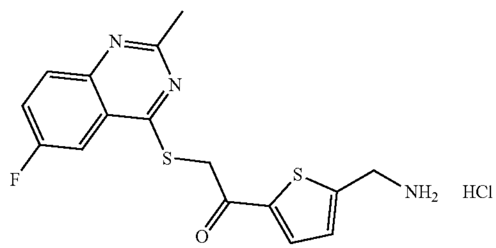 [SMILES: Cc1nc(SCC(=O)c2ccc(CN)s2)c2cc(F)ccc2n1 ; Cl] | M-7 | I-1 | 1-(5-(aminomethyl)thiophen-2-yl)-2-((6-fluoro-2-methylquinazolin-4-yl)thio)ethan-1-one hydrochloride |
| Q-16 | 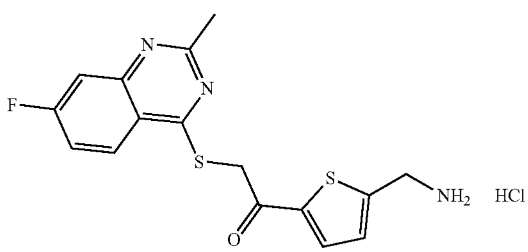 [SMILES: Cc1nc(SCC(=O)c2ccc(CN)s2)c2ccc(F)cc2n1 ; Cl] | M-9 | I-1 | 1-(5-(aminomethyl)thiophen-2-yl)-2-((7-fluoro-2-methylquinazolin-4-yl)thio)ethan-1-one hydrochloride |
| Q-17 | 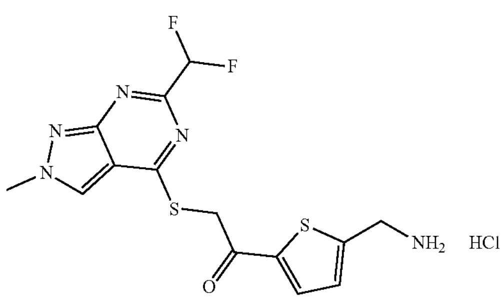 [SMILES: Cn1cc2c(SCC(=O)c3ccc(CN)s3)nc(C(F)F)nc2n1 ; Cl] | K-8 | I-1 | 1-(5-(aminomethyl)thiophen-2-yl)-2-((6-(difluoromethyl)-2-methyl-2H-pyrazolo[3,4-d]pyrimidin-4-yl)thio)ethan-1-one hydrochloride |
| Q-18 | 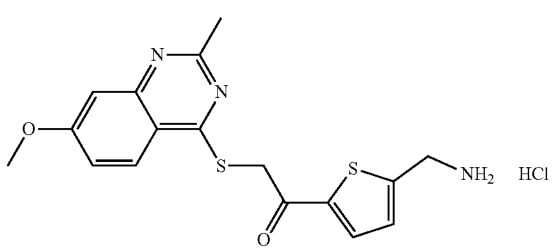 [SMILES: COc1ccc2c(SCC(=O)c3ccc(CN)s3)nc(C)nc2c1 ; Cl] | M-10 | I-1 | 1-(5-(aminomethyl)thiophen-2-yl)-2-((7-methoxy-2-methylquinazolin-4-yl)thio)ethan-1-one hydrochloride |

| Cpd Q | Structure | Cpd Y¹-SH | Cpd I | IUPAC name |
|---|---|---|---|---|
| Q-19 | 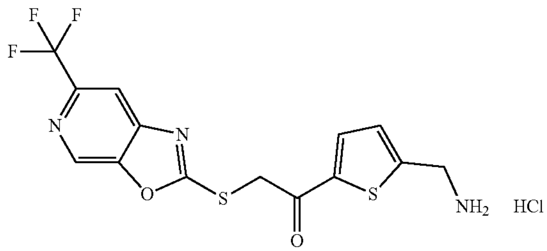 [SMILES: NCc1ccc(C(=O)CSc2nc3cc(C(F)(F)F)ncc3o2)s1 ; Cl] | P-2 | I-1 | 1-(5-(aminomethyl)thiophen-2-yl)-2-((6-(trifluoromethyl)oxazolo[5,4-c]pyridin-2-yl)thio)ethan-1-one hydrochloride |
| Q-20 | 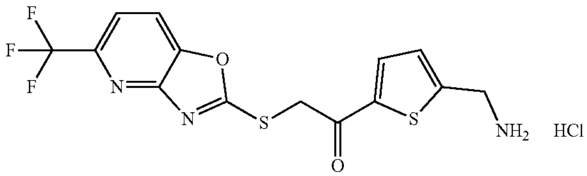 [SMILES: NCc1ccc(C(=O)CSc2nc3nc(C(F)(F)F)ccc3o2)s1 ; Cl] | P-3 | I-1 | 1-(5-(aminomethyl)thiophen-2-yl)-2-((5-(trifluoromethyl)oxazolo[4,5-b]pyridin-2-yl)thio)ethan-1-one hydrochloride |
| Q-21 | 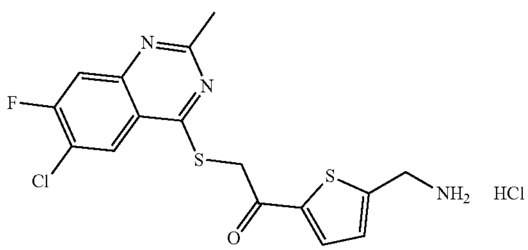 [SMILES: Cc1nc(SCC(=O)c2ccc(CN)s2)c2cc(Cl)c(F)cc2n1 ; Cl] | M-15 | I-1 | 1-(5-(aminomethyl)thiophen-2-yl)-2-((6-chloro-7-fluoro-2-methylquinazolin-4-yl)thio)ethan-1-one hydrochloride |
| Q-22 | 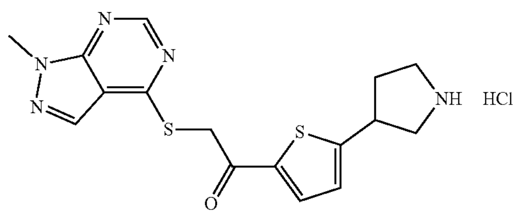 [SMILES: Cn1ncc2c(SCC(=O)c3ccc(C4CCNC4)s3)ncnc21 ; Cl] | J-1 | I-5 | 2-((1-methyl-1H-pyrazolo[3,4-d]pyrimidin-4-yl)thio)-1-(5-(pyrrolidin-3-yl)thiophen-2-yl)ethan-1-one hydrochloride |
| Q-23 | 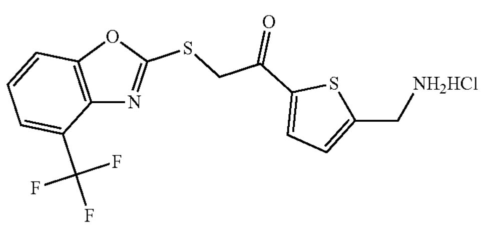 | P-5 | I-1 | 1-(5-(aminomethyl)thiophen-2-yl)-2-((4-(trifluoromethyl)benzo[d]oxazol-2-yl)thio)ethan-1-one hydrochloride |
| Q-24 | 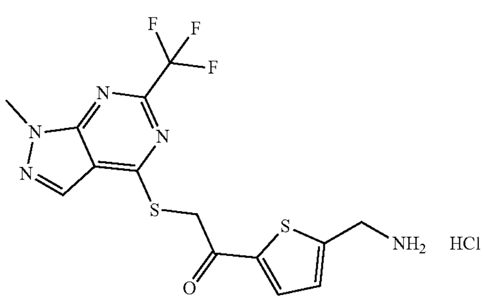 [SMILES: Cn1ncc2c(SCC(=O)c3ccc(CN)s3)nc(C(F)(F)F)nc21 ; Cl] | K-7 | I-1 | 1-(5-(aminomethyl)thiophen-2-yl)-2-((1-methyl-6-(trifluoromethyl)-1H-pyrazolo[3,4-d]pyrimidin-4-yl)thio)ethan-1-one hydrochloride |

-continued

| Cpd Q | Structure | Cpd Y¹-SH | Cpd I | IUPAC name |
|---|---|---|---|---|
| Q-25 | 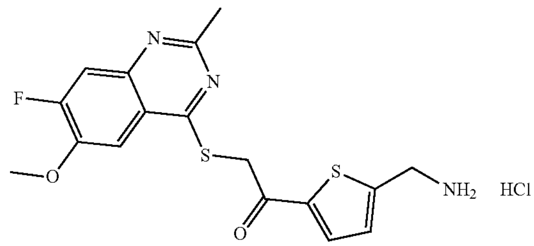 [SMILES: COc1cc2c(SCC(=O)c3ccc(CN)s3)nc(C)nc2cc1F ; Cl] | M-16 | I-1 | 1-(5-(aminomethyl)thiophen-2-yl)-2-((7-fluoro-6-methoxy-2-methylquinazolin-4-yl)thio)ethan-1-one hydrochloride |
| Q-26 | 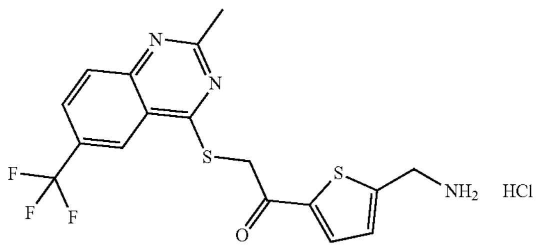 [SMILES: Cc1nc(SCC(=O)c2ccc(CN)s2)c2cc(C(F)(F)F)ccc2n1 ; Cl] | M-17 | I-1 | 1-(5-(aminomethyl)thiophen-2-yl)-2-((2-methyl-6-(trifluoromethyl)quinazolin-4-yl)thio)ethan-1-one hydrochloride |
| Q-27 | 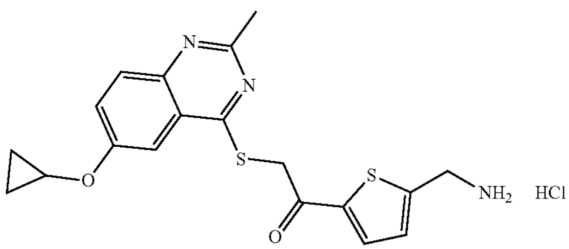 [SMILES: Cc1nc(SCC(=O)c2ccc(CN)s2)c2cc(OC3CC3)ccc2n1 ; Cl] | M-18 | I-1 | 1-(5-(aminomethyl)thiophen-2-yl)-2-((6-cyclopropoxy-2-methylquinazolin-4-yl)thio)ethan-1-one hydrochloride |
| Q-28 | 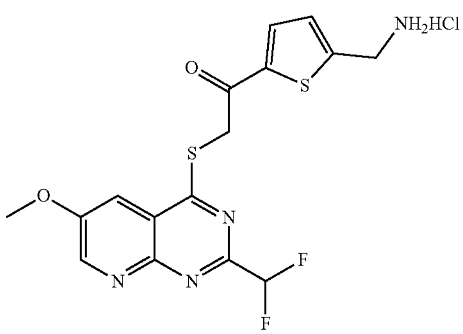 | K-16 | I-1 | 1-(5-(aminomethyl)thiophen-2-yl)-2-((2-(difluoromethyl)-6-methoxypyrido[2,3-d]pyrimidin-4-yl)thio)ethan-1-one hydrochloride |
| Q-29 | 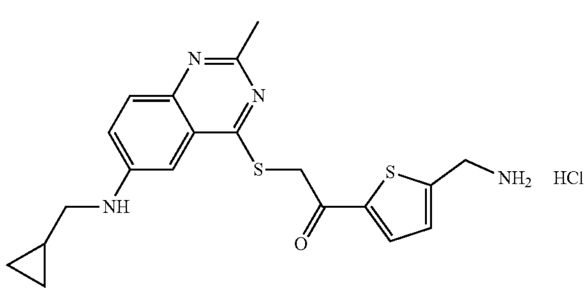 [SMILES: Cc1nc(SCC(=O)c2ccc(CN)s2)c2cc(NCC3CC3)ccc2n1 ; Cl] | M-19 | I-1 | 1-(5-(aminomethyl)thiophen-2-yl)-2-((6-((cyclopropylmethyl)amino)-2-methylquinazolin-4-yl)thio)ethan-1-one hydrochloride |

-continued

| Cpd Q | Structure | Cpd Y¹-SH | Cpd I | IUPAC name |
|---|---|---|---|---|
| Q-30 | 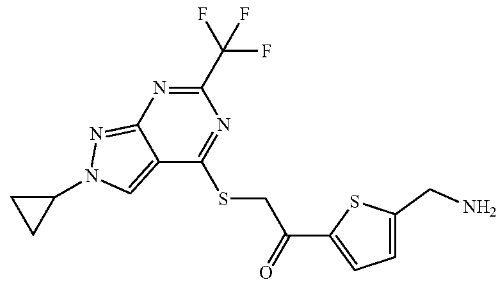 | K-9 | I-1 | 1-(5-(aminomethyl)thiophen-2-yl)-2-((2-cyclopropyl-6-(trifluoromethyl)-2H-pyrazolo[3,4-d]pyrimidin-4-yl)thio)ethan-1-one hydrochloride |
| Q-31 | 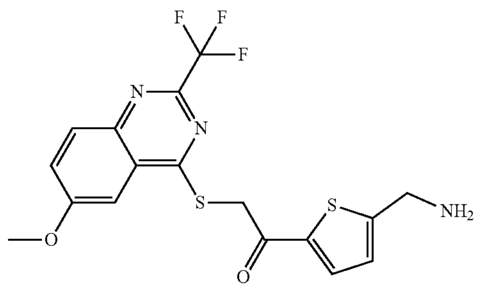 | K-3 | I-1 | 1-(5-(aminomethyl)thiophen-2-yl)-2-((6-methoxy-2-(trifluoromethyl)quinazolin-4-yl)thio)ethan-1-one hydrochloride |
| Q-32 | 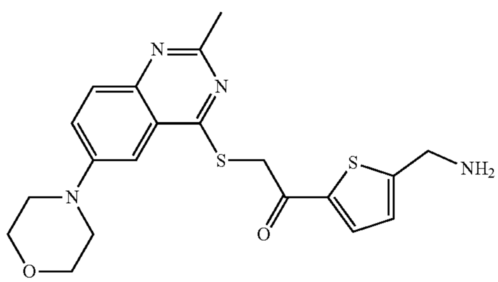 | M-20 | I-1 | 1-(5-(aminomethyl)thiophen-2-yl)-2-((2-methyl-6-morpholinoquinazolin-4-yl)thio)ethan-1-one hydrochloride |
| Q-33 | 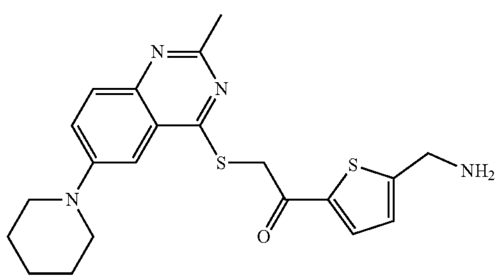 | M-21 | I-1 | 1-(5-(aminomethyl)thiophen-2-yl)-2-((2-methyl-6-(piperidin-1-yl)quinazolin-4-yl)thio)ethan-1-one hydrochloride |
| Q-34 | 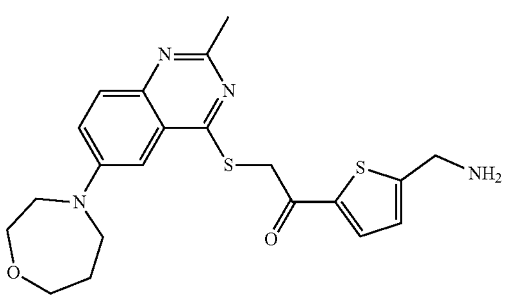 | M-22 | I-1 | 1-(5-(aminomethyl)thiophen-2-yl)-2-((2-methyl-6-(1,4-oxazepan-4-yl)quinazolin-4-yl)thio)ethan-1-one hydrochloride |

-continued

| Cpd Q | Structure | Cpd Y¹-SH | Cpd I | IUPAC name |
|---|---|---|---|---|
| Q-35 | 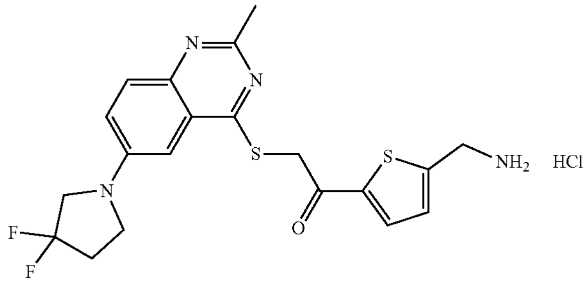 [SMILES: Cc1nc(SCC(=O)c2ccc(CN)s2)c2cc(N3CCC(F)(F)C3)ccc2n1 ; Cl] | M-23 | I-1 | 1-(5-(aminomethyl)thiophen-2-yl)-2-((6-(3,3-difluoropyrrolidin-1-yl)-2-methylquinazolin-4-yl)thio)ethan-1-one hydrochloride |
| Q-36 | 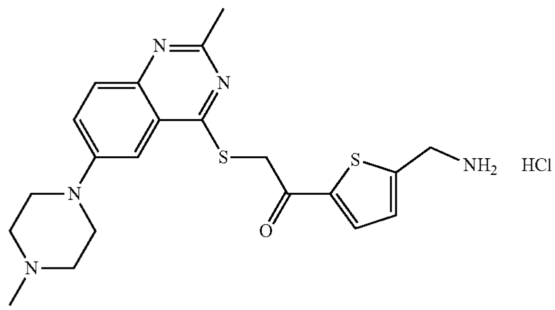 [SMILES: Cc1nc(SCC(=O)c2ccc(CN)s2)c2cc(N3CCN(C)CC3)ccc2n1 ; Cl] | M-24 | I-1 | 1-(5-(aminomethyl)thiophen-2-yl)-2-((2-methyl-6-(4-methylpiperazin-1-yl)quinazolin-4-yl)thio)ethan-1-one hydrochloride |
| Q-37 | 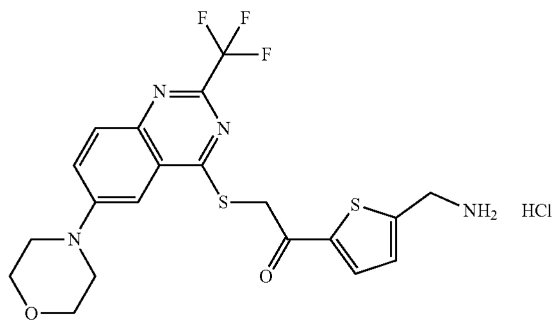 [SMILES: NCc1ccc(C(=O)CSc2nc(C(F)(F)F)nc3ccc(N4CCOCC4)cc23)s1 ; Cl] | K-4 | I-1 | 1-(5-(aminomethyl)thiophen-2-yl)-2-((6-morpholino-2-(trifluoromethyl)quinazolin-4-yl)thio)ethan-1-one hydrochloride |
| Q-38 | 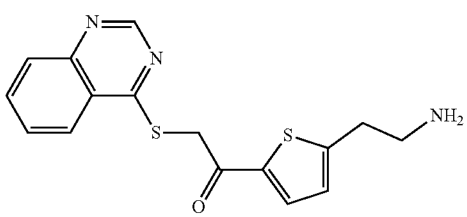 [SMILES: NCCc1ccc(C(=O)CSc2ncnc3ccccc23)s1] | J-2 | I-2 | 1-(5-(2-aminoethyl)thiophen-2-yl)-2-(quinazolin-4-ylthio)ethan-1-one |
| Q-39 | 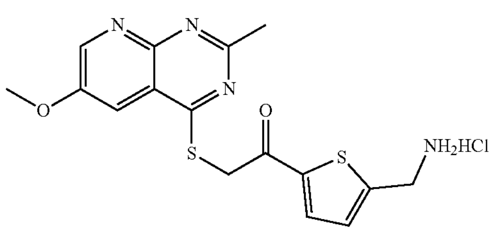 | M-39 | I-1 | 1-(5-(aminomethyl)thiophen-2-yl)-2-((6-methoxy-2-methylpyrido[2,3-d]pyrimidin-4-yl)thio)ethan-1-one hydrochloride |
| Q-40 | 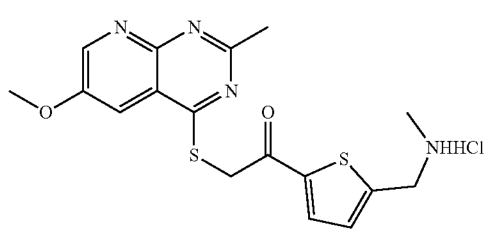 | M-39 | I-3 | 2-((6-methoxy-2-methylpyrido[2,3-d]pyrimidin-4-yl)thio)-1-(5-((methylamino)methyl)thiophen-2-yl)ethan-1-one hydrochloride |

-continued

| Cpd Q | Structure | Cpd Y¹-SH | Cpd I | IUPAC name |
|---|---|---|---|---|
| Q-41 | 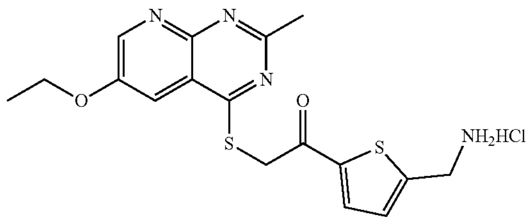 | M-40 | I-1 | 1-(5-(aminomethyl)thiophen-2-yl)-2-((6-ethoxy-2-methylpyrido[2,3-d]pyrimidin-4-yl)thio)ethan-1-one hydrochloride |
| Q-42 | 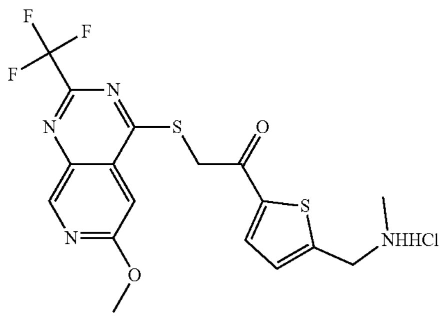 | K-18 | I-3 | 2-((6-methoxy-2-(trifluoromethyl)pyrido[3,4-d]pyrimidin-4-yl)thio)-1-(5-((methylamino)methyl)thiophen-2-yl)ethan-1-one hydrochloride |
| Q-43 | 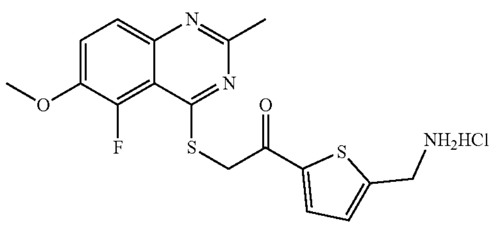 | M-41 | I-1 | 1-(5-(aminomethyl)thiophen-2-yl)-2-((5-fluoro-6-methoxy-2-methylquinazolin-4-yl)thio)ethan-1-one hydrochloride |
| Q-44 | 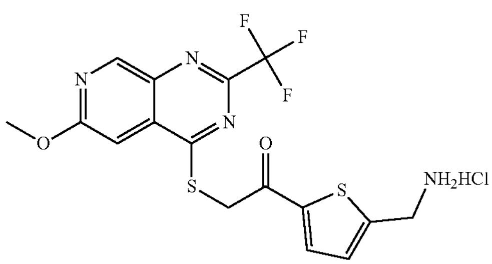 | K-18 | I-1 | 1-(5-(aminomethyl)thiophen-2-yl)-2-((6-methoxy-2-(trifluoromethyl)pyrido[3,4-d]pyrimidin-4-yl)thio)ethan-1-one hydrochloride |
| Q-45 | 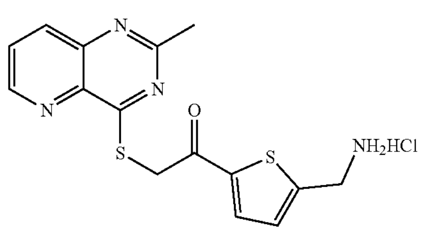 | M-13 | I-1 | 1-(5-(aminomethyl)thiophen-2-yl)-2-((2-methylpyrido[3,2-d]pyrimidin-4-yl)thio)ethan-1-one hydrochloride |
| Q-46 | 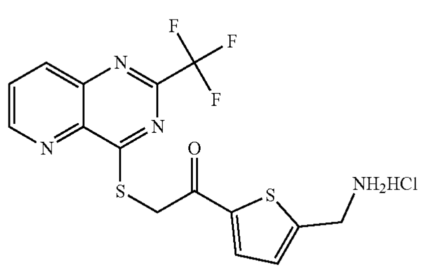 | K-21 | I-1 | 1-(5-(aminomethyl)thiophen-2-yl)-2-((2-(trifluoromethyl)pyrido[3,2-d]pyrimidin-4-yl)thio)ethan-1-one hydrochloride |

-continued

| Cpd Q | Structure | Cpd Y¹-SH | Cpd I | IUPAC name |
|---|---|---|---|---|
| Q-47 | 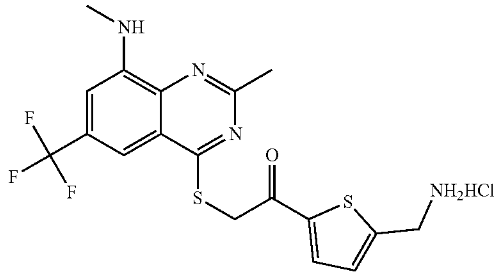 | M-31 | I-1 | 1-(5-(aminomethyl)thiophen-2-yl)-2-((2-methyl-8-(methylamino)-6-(trifluoromethyl)quinazolin-4-yl)thio)ethan-1-one hydrochloride |
| Q-48 | 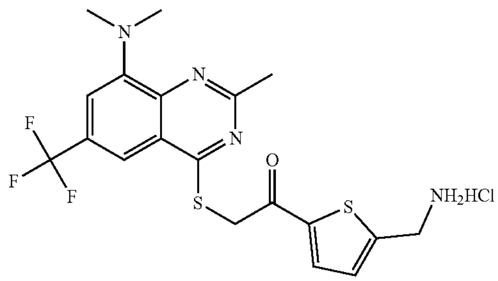 | M-32 | I-1 | 1-(5-(aminomethyl)thiophen-2-yl)-2-((8-(dimethylamino)-2-methyl-6-(trifluoromethyl)quinazolin-4-yl)thio)ethan-1-one hydrochloride |
| Q-49 | 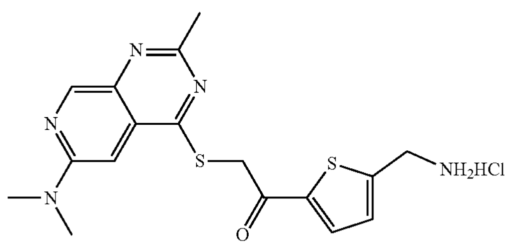 | M-33 | I-1 | 1-(5-(aminomethyl)thiophen-2-yl)-2-((6-(dimethylamino)-2-methylpyrido[3,4-d]pyrimidin-4-yl)thio)ethan-1-one hydrochloride |
| Q-50 | 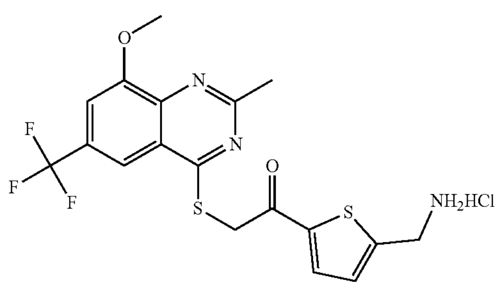 | M-34 | I-1 | 1-(5-(aminomethyl)thiophen-2-yl)-2-((8-methoxy-2-methyl-6-(trifluoromethyl)quinazolin-4-yl)thio)ethan-1-one hydrochloride |
| Q-51 | 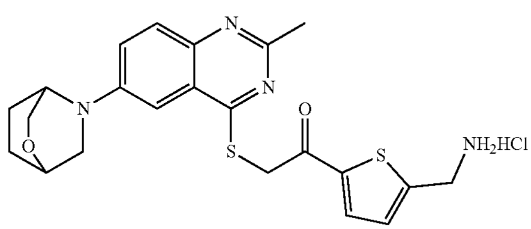 | M-44 | I-1 | 2-((6-(2-oxa-5-azabicyclo[2.2.2]octan-5-yl)-2-methylquinazolin-4-yl)thio)-1-(5-(aminomethyl)thiophen-2-yl)ethan-1-one hydrochloride |
| Q-52 | 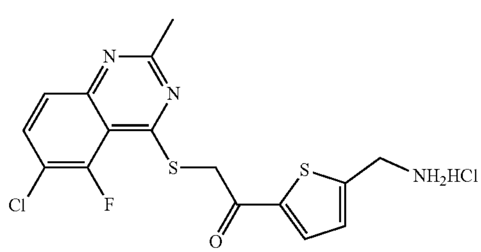 | M-45 | I-1 | 1-(5-(aminomethyl)thiophen-2-yl)-2-((6-chloro-5-fluoro-2-methylquinazolin-4-yl)thio)ethan-1-one hydrochloride |

-continued

| Cpd Q | Structure | Cpd Y¹-SH | Cpd I | IUPAC name |
|---|---|---|---|---|
| Q-53 | 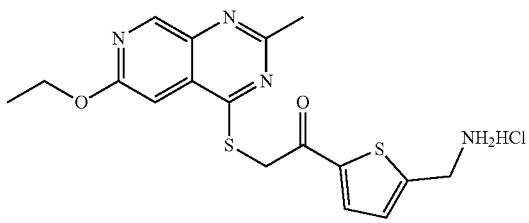 | M-46 | I-1 | 1-(5-(aminomethyl)thiophen-2-yl)-2-((6-ethoxy-2-methylpyrido[3,4-d]pyrimidin-4-yl)thio)ethan-1-one hydrochloride |
| Q-54 | 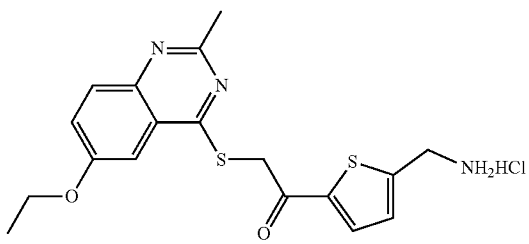 | M-47 | I-1 | 1-(5-(aminomethyl)thiophen-2-yl)-2-((6-ethoxy-2-methylquinazolin-4-yl)thio)ethan-1-one hydrochloride |
| Q-55 | 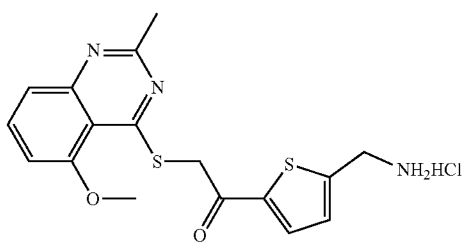 | M-48 | I-1 | 1-(5-(aminomethyl)thiophen-2-yl)-2-((5-methoxy-2-methylquinazolin-4-yl)thio)ethan-1-one hydrochloride |
| Q-56 | 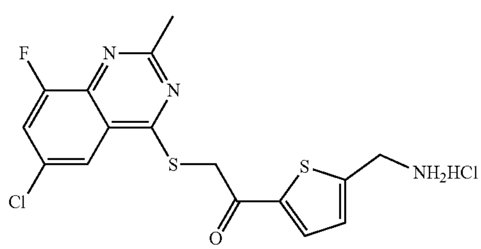 | M-29 | I-1 | 1-(5-(aminomethyl)thiophen-2-yl)-2-((6-chloro-8-fluoro-2-methylquinazolin-4-yl)thio)ethan-1-one hydrochloride |
| Q-57 | 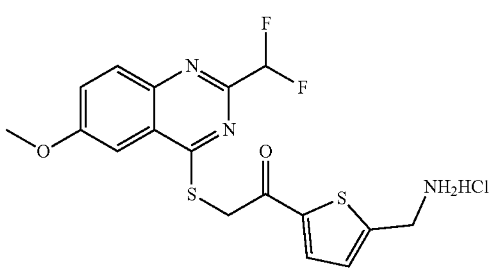 | K-10 | I-1 | 1-(5-(aminomethyl)thiophen-2-yl)-2-((2-(difluoromethyl)-6-methoxyquinazolin-4-yl)thio)ethan-1-one hydrochloride |
| Q-58 | 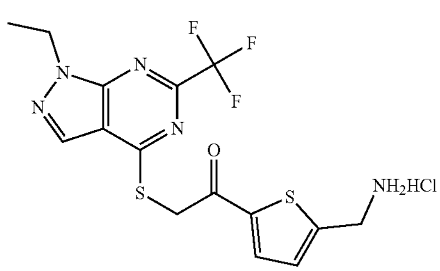 | K-12 | I-1 | 1-(5-(aminomethyl)thiophen-2-yl)-2-((1-ethyl-6-(trifluoromethyl)-1H-pyrazolo[3,4-d]pyrimidin-4-yl)thio)ethan-1-one hydrochloride |

| Cpd Q | Structure | Cpd Y¹-SH | Cpd I | IUPAC name |
|---|---|---|---|---|
| Q-59 | 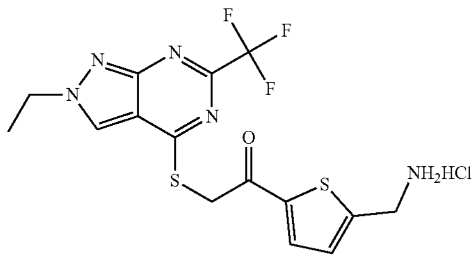 | K-13 | I-1 | 1-(5-(aminomethyl)thiophen-2-yl)-2-((2-ethyl-6-(trifluoromethyl)-2H-pyrazolo[3,4-d]pyrimidin-4-yl)thio)ethan-1-one hydrochloride |
| Q-60 | 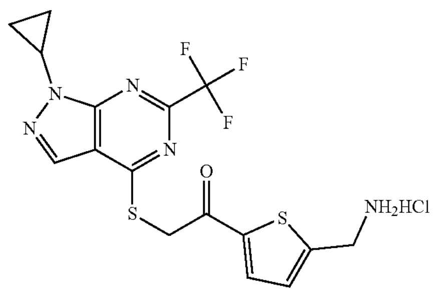 | K-14 | I-1 | 1-(5-(aminomethyl)thiophen-2-yl)-2-((1-cyclopropyl-6-(trifluoromethyl)-1H-pyrazolo[3,4-d]pyrimidin-4-yl)thio)ethan-1-one hydrochloride |
| Q-61 | 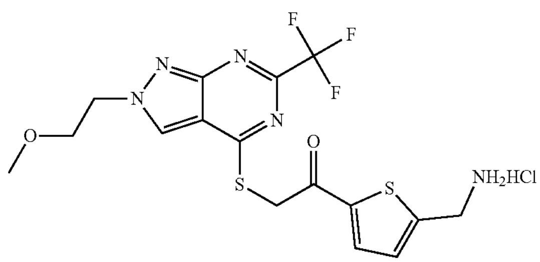 | K-19 | I-1 | 1-(5-(aminomethyl)thiophen-2-yl)-2-((2-(2-methoxyethyl)-6-(trifluoromethyl)-2H-pyrazolo[3,4-d]pyrimidin-4-yl)thio)ethan-1-one hydrochloride |
| Q-62 | 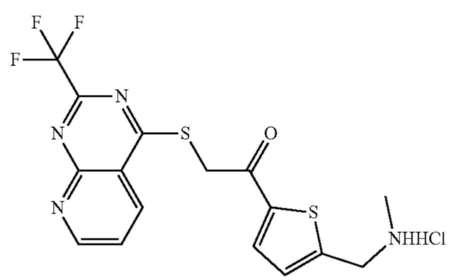 | K-11 | I-3 | 1-(5-((methylamino)methyl)thiophen-2-yl)-2-((2-(trifluoromethyl)pyrido[2,3-d]pyrimidin-4-yl)thio)ethan-1-one hydrochloride |
| Q-63 | 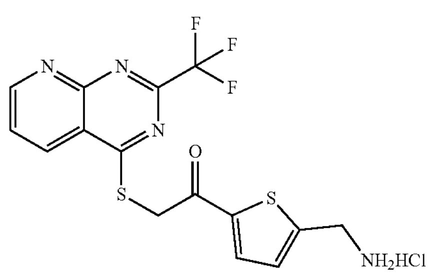 | K-11 | I-1 | 1-(5-(aminomethyl)thiophen-2-yl)-2-((2-(trifluoromethyl)pyrido[2,3-d]pyrimidin-4-yl)thio)ethan-1-one hydrochloride |
| Q-64 | 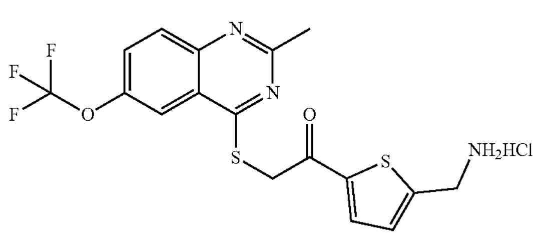 | M-37 | I-1 | 1-(5-(aminomethyl)thiophen-2-yl)-2-((2-methyl-6-(trifluoromethoxy)quinazolin-4-yl)thio)ethan-1-one hydrochloride |

-continued

| Cpd Q | Structure | Cpd Y¹-SH | Cpd I | IUPAC name |
|---|---|---|---|---|
| Q-65 | 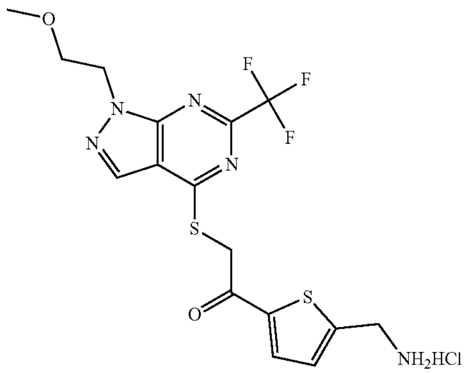 | K-20 | I-1 | 1-(5-(aminomethyl)thiophen-2-yl)-2-((1-(2-methoxyethyl)-6-(trifluoromethyl)-1H-pyrazolo[3,4-d]pyrimidin-4-yl)thio)ethan-1-one hydrochloride |
| Q-66 | 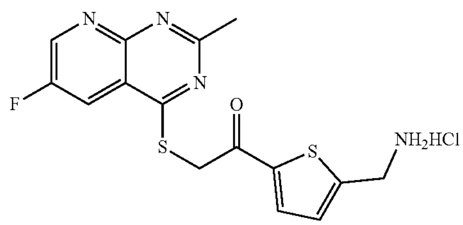 | M-35 | I-1 | 1-(5-(aminomethyl)thiophen-2-yl)-2-((6-fluoro-2-methylpyrido[2,3-d]pyrimidin-4-yl)thio)ethan-1-one hydrochloride |
| Q-67 | 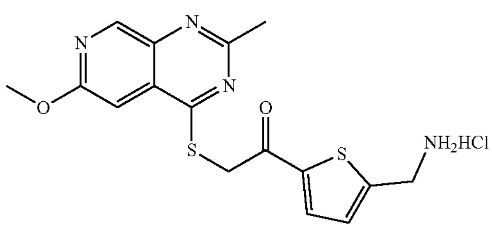 | M-36 | I-1 | 1-(5-(aminomethyl)thiophen-2-yl)-2-((6-methoxy-2-methylpyrido[3,4-d]pyrimidin-4-yl)thio)ethan-1-one hydrochloride |
| Q-68 | 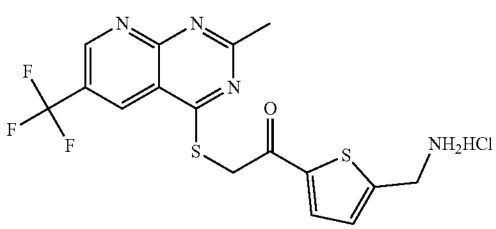 | M-38 | I-1 | 1-(5-(aminomethyl)thiophen-2-yl)-2-((2-methyl-6-(trifluoromethyl)pyrido[2,3-d]pyrimidin-4-yl)thio)ethan-1-one hydrochloride |
| Q-69 | 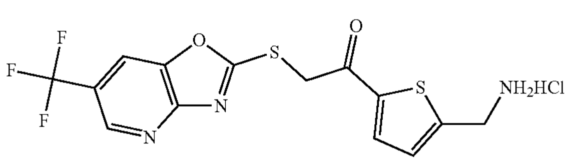 | P-7 | I-1 | 1-(5-(aminomethyl)thiophen-2-yl)-2-((6-(trifluoromethyl)oxazolo[4,5-b]pyridin-2-yl)thio)ethan-1-one hydrochloride |
| Q-70 | 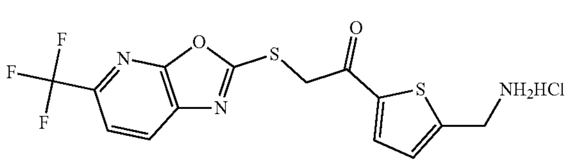 | P-1 | I-1 | 1-(5-(aminomethyl)thiophen-2-yl)-2-((5-(trifluoromethyl)oxazolo[5,4-b]pyridin-2-yl)thio)ethan-1-one hydrochloride |

-continued

| Cpd Q | Structure | Cpd Y¹-SH | Cpd I | IUPAC name |
|---|---|---|---|---|
| Q-71 | 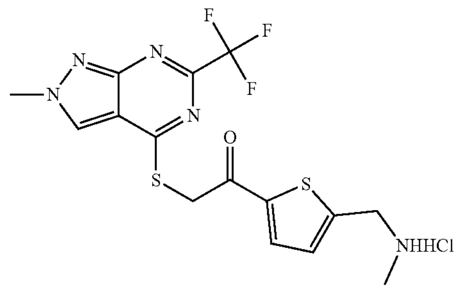 | K-5 | I-3 | 2-((2-methyl-6-(trifluoromethyl)-2H-pyrazolo[3,4-d]pyrimidin-4-yl)thio)-1-(5-((methylamino)methyl)thiophen-2-yl)ethan-1-one hydrochloride |
| Q-72 | 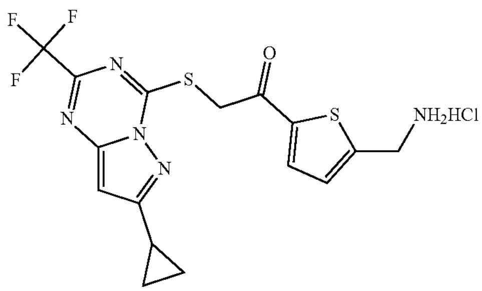 | K-17 | I-1 | 1-(5-(aminomethyl)thiophen-2-yl)-2-((7-cyclopropyl-2-(trifluoromethyl)pyrazolo[1,5-a][1,3,5]triazin-4-yl)thio)ethan-1-one hydrochloride |
| Q-73 | 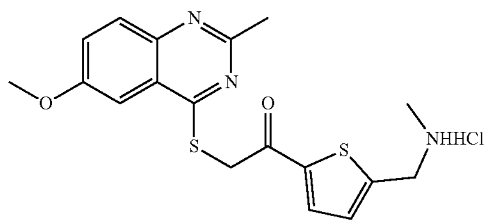 | M-11 | I-3 | 2-((6-methoxy-2-methylquinazolin-4-yl)thio)-1-(5-((methylamino)methyl)thiophen-2-yl)ethan-1-one hydrochloride |
| Q-74 | 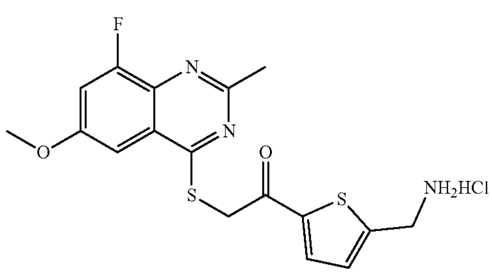 | M-42 | I-1 | 1-(5-(aminomethyl)thiophen-2-yl)-2-((8-fluoro-6-methoxy-2-methylquinazolin-4-yl)thio)ethan-1-one hydrochloride |
| Q-75 | 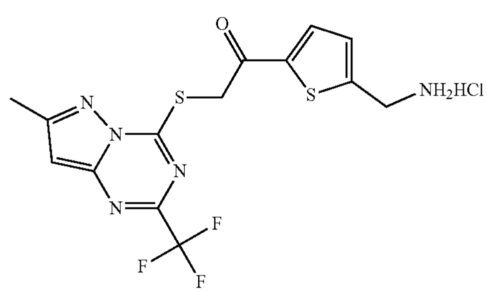 | K-15 | I-1 | 1-(5-(aminomethyl)thiophen-2-yl)-2-((7-methyl-2-(trifluoromethyl)pyrazolo[1,5-a][1,3,5]triazin-4-yl)thio)ethan-1-one hydrochloride |
| Q-76 | 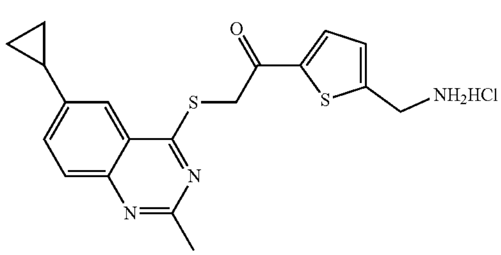 | M-43 | I-1 | 1-(5-(aminomethyl)thiophen-2-yl)-2-((6-cyclopropyl-2-methylquinazolin-4-yl)thio)ethan-1-one hydrochloride |

-continued

| Cpd Q | Structure | Cpd Y¹-SH | Cpd I | IUPAC name |
|---|---|---|---|---|
| Q-77 | ![structure] | P-4 | I-1 | 1-(5-(aminomethyl)thiophen-2-yl)-2-((5-(trifluoromethyl)benzo[d]oxazol-2-yl)thio)ethan-1-one hydrochloride |

Example 190: tert-butyl ((5-(2-((6-methoxy-2-methylpyrido[2,3-d]pyrimidin-4-yl)thio)acetyl)thiophen-2-yl)methyl)carbamate (190)

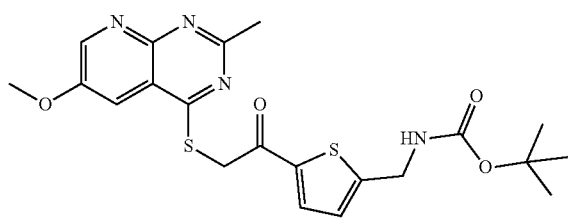

Example 190 has been prepared using the experimental conditions described above for intermediate Q-1-1 from the reaction of intermediate M-39 with intermediate I-1.

Example 189: Synthesis of 3-((5-(2-((6-methoxy-2-methylquinazolin-4-yl)thio)acetyl)thiophen-2-yl)methyl)-1,1-dimethylurea (189)

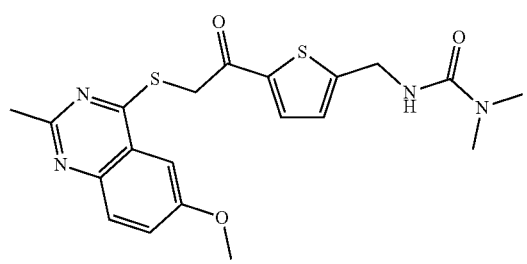

To a solution of compound Q-11 (100 mg, 278 mol) in THF (2.00 mL) was added DIEA (108 mg, 835 mol, 145 μL) and dimethylcarbamic chloride (32.9 mg, 306 mol, 28.1 μL). The mixture was stirred at 50° C. for 2 h. The reaction mixture was concentrated to dryness. The residue was purified by prep-HPLC (column: waters Xbridge BEH C18 100×30 mm×10 um; mobile phase: [water (NH₄HCO₃)-ACN]; gradient:30%-60% B over 8 min) to give example 189 (32 mg, 27% yield, 100% purity) as a light yellow solid.

Example 29: N-(2-(5-(2-((2-(trifluoromethyl)quinazolin-4-yl)thio)acetyl)thiophen-2-yl)ethyl)pivalamide (29)

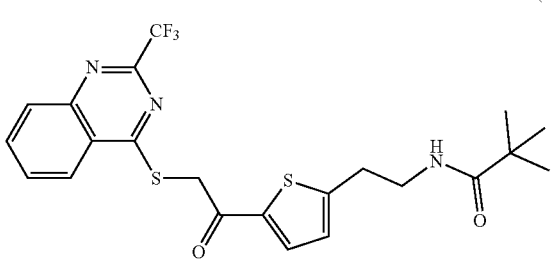

To a solution mixture of compound Q-1 (190 mg, 25 mmol) in DCM (2.0 mL) was added Et₃N (2 eq) and (CH₃)₃CCOCl (29 mg, 1.5 equiv.) at 0° C. The resultant reaction mixture was stirred for 1 h at rt. The reaction mixture was quenched with water (20 mL), extracted with EtOAc (2×20 mL) and the combined organic layers dried over Na₂SO₄, and concentrated in vacuo. The residue compound was purified using column chromatography to afford example compound (29) as a white solid (60 mg, 50% yield).

The following Examples have been prepared using the experimental conditions described above in Example 29 from the reaction of compounds Q with an acyl chloride of formula R⁹—COCl:

| Ex. | Cpd Q | R⁹-COCl | IUPAC name |
|---|---|---|---|
| 30 | Q-2 | PhCOCl | N-((5-(2-((1-methyl-1H-pyrazolo[3,4-d]pyrimidin-4-yl)thio)acetyl)thiophen-2-yl)methyl)benzamide |
| 31 | Q-2 | cyclopropyl-C(O)Cl | N-((5-(2-((1-methyl-1H-pyrazolo[3,4-d]pyrimidin-4-yl)thio)acetyl)thiophen-2-yl)methyl)cyclopropanecarboxamide |
| 32 | Q-2 | PhCH₂C(O)Cl | N-((5-(2-((1-methyl-1H-pyrazolo[3,4-d]pyrimidin-4-yl)thio)acetyl)thiophen-2-yl)methyl)-2-phenylacetamide |

| Ex. | Cpd Q | R⁹-COCl | IUPAC name |
|---|---|---|---|
| 33 | Q-5 | tBuCOCl | N-methyl-N-((5-(2-((1-methyl-1H-pyrazolo[3,4-d]pyrimidin-4-yl)thio)acetyl)thiophen-2-yl)methyl)pivalamide |
| 34 | Q-5 | cyclopropanecarbonyl chloride | N-methyl-N-((5-(2-((1-methyl-1H-pyrazolo[3,4-d]pyrimidin-4-yl)thio)acetyl)thiophen-2-yl)methyl)cyclopropanecarboxamide |
| 35 | Q-4 | cyclopropanecarbonyl chloride | N-((5-(2-((2-methylquinazolin-4-yl)thio)acetyl)thiophen-2-yl)methyl)cyclopropanecarboxamide |
| 36 | Q-1 | cyclopropanecarbonyl chloride | N-(2-(5-(2-((2-(trifluoromethyl)quinazolin-4-yl)thio)acetyl)thiophen-2-yl)ethyl)cyclopropanecarboxamide |
| 37 | Q-1 | PhCOCl | N-(2-(5-(2-((2-(trifluoromethyl)quinazolin-4-yl)thio)acetyl)thiophen-2-yl)ethyl)benzamide |
| 39 | Q-11 | 2,2-difluorocyclopropanecarbonyl chloride | 2,2-difluoro-N-((5-(2-((6-methoxy-2-methylquinazolin-4-yl)thio)acetyl)thiophen-2-yl)methyl)cyclopropane-1-carboxamide |
| 40 | Q-11 | 2,2,3,3,3-pentafluoropropanoyl chloride | 2,2,3,3,3-pentafluoro-N-((5-(2-((6-methoxy-2-methylquinazolin-4-yl)thio)acetyl)thiophen-2-yl)methyl)propanamide |
| 41 | Q-3 | cyclopropanecarbonyl chloride | N-((5-(2-((2-methyl-6-(trifluoromethyl)-2H-pyrazolo[3,4-d]pyrimidin-4-yl)thio)acetyl)thiophen-2-yl)methyl)cyclopropanecarboxamide |
| 43 | Q-30 | 2,2-difluorocyclopropanecarbonyl chloride | N-((5-(2-((2-cyclopropyl-6-(trifluoromethyl)-2H-pyrazolo[3,4-d]pyrimidin-4-yl)thio)acetyl)thiophen-2-yl)methyl)-2,2-difluorocyclopropane-1-carboxamide |
| 44 | Q-30 | 2,2,3,3,3-pentafluoropropanoyl chloride | N-((5-(2-((2-cyclopropyl-6-(trifluoromethyl)-2H-pyrazolo[3,4-d]pyrimidin-4-yl)thio)acetyl)thiophen-2-yl)methyl)-2,2,3,3,3-pentafluoropropanamide |
| 51 | Q-11 | cyclopropanecarbonyl chloride | N-((5-(2-((6-methoxy-2-methylquinazolin-4-yl)thio)acetyl)thiophen-2-yl)methyl)cyclopropanecarboxamide |
| 101 | Q-8 | CH₃COCl | N-(2-(5-(2-((2-cyclopropylquinazolin-4-yl)thio)acetyl)thiophen-2-yl)ethyl)acetamide |
| 103 | Q-2 | CH₃COCl | N-((5-(2-((1-methyl-1H-pyrazolo[3,4-d]pyrimidin-4-yl)thio)acetyl)thiophen-2-yl)methyl)acetamide |

Example 63: 2-hydroxy-N-((5-(2-((2-methyl-6-morpholinoquinazolin-4-yl)thio)acetyl)thiophen-2-yl)methyl)acetamide (63)

Synthesis of 2-((tert-butyldiphenylsilyl)oxy)-N-((5-(2-((2-methyl-6-morpholino-quinazolin-4-yl)thio)acetyl)thiophen-2-yl)methyl)acetamide (R-1-1) To a solution of 2-((tert-butyldiphenylsilyl)oxy)acetic acid I-13a (699 mg, 2.22 mmol) in DMF (4.00 mL) was added HATU (699 mg, 2.02 mmol) at 0° C. After addition, the mixture was stirred at 0° C., and a mixture of compound Q-37 (837 mg, 2.02 mmol) and DIEA (1.41 mL, 8.08 mmol) in DMF (4.00 mL) was added dropwise to the above mixture at 0° C. The resulting mixture was stirred at 25° C. for 2 h. The reaction mixture was diluted with water (10.0 mL) and extracted with EtOAc (20.0 mL×3). The combined organic layers were dried over Na₂SO₄, filtered and concentrated under reduced pressure to yield 2-((tert-butyldiphenylsilyl)oxy)-N-((5-(2-((2-methyl-6-morpholino-quinazolin-4-yl)thio)acetyl)thiophen-2-yl)methyl)acetamide (R-1-1) which was used without further purification. Synthesis of 2-hydroxy-N-((5-(2-((2-methyl-6-morpholinoquinazolin-4-yl)thio)acetyl)thiophen-2-yl)methyl)acetamide (63) To a solution of compound R-1-1 (0.60 g, 862 umol) in THF (6.00 mL) was added TBAF (1 M, 905 uL). The mixture was stirred at 20° C. for 1 h. The reaction mixture was quenched by addition H₂O (10.0 mL) at 25° C., and then extracted with EtOAc (5.00 mL×3). The combined organic layers were washed with brine (5.00 mL), dried over Na₂SO₄, filtered and concentrated under reduced pressure to give a residue. The residue was purified by column chromatography (SiO₂, petroleum ether/ethyl acetate=50/1 to 5/1) TLC (petroleum ether/ethyl acetate 1/1, product RT=0.2) to give compound 63 (200 mg, 57.4% yield).

The following Examples have been prepared using the experimental conditions described above in Example 63 from the reaction of compounds Q with protected hydroxy-acid derivatives of formula HO₂C—CH₂—OTBDPS and HO₂C—CH₂—OTBS:

| Ex. | Cpd Q | IUPAC name |
|---|---|---|
| 60 | Q-11 | 2-hydroxy-N-((5-(2-((6-methoxy-2-methylquinazolin-4-yl)thio)acetyl)thiophen-2-yl)methyl)acetamide |
| 64 | Q-13 | 2-hydroxy-N-((5-(2-((2-methylpyrido[2,3-d]pyrimidin-4-yl)thio)acetyl)thiophen-2-yl)methyl)acetamide |
| 65 | Q-14 | N-((5-(2-((2,6-dimethyl-2H-pyrazolo[3,4-d]pyrimidin-4-yl)thio)acetyl)thiophen-2-yl)methyl)-2-hydroxyacetamide |
| 66 | Q-4 | 2-hydroxy-N-((5-(2-((2-methylquinazolin-4-yl)thio)acetyl)thiophen-2-yl)methyl)acetamide |
| 67 | Q-15 | N-((5-(2-((6-fluoro-2-methylquinazolin-4-yl)thio)acetyl)thiophen-2-yl)methyl)-2-hydroxyacetamide |
| 68 | Q-16 | N-((5-(2-((7-fluoro-2-methylquinazolin-4-yl)thio)acetyl)thiophen-2-yl)methyl)-2-hydroxyacetamide |
| 69 | Q-17 | N-((5-(2-((6-(difluoromethyl)-2-methyl-2H-pyrazolo[3,4-d]pyrimidin-4-yl)thio)acetyl)thiophen-2-yl)methyl)-2-hydroxyacetamide |
| 70 | Q-18 | 2-hydroxy-N-((5-(2-((7-methoxy-2-methylquinazolin-4-yl)thio)acetyl)thiophen-2-yl)methyl)acetamide |
| 71 | Q-19 | 2-hydroxy-N-((5-(2-((6-(trifluoromethyl)oxazolo[5,4-c]156yrrolid-2-yl)thio)acetyl)thiophen-2-yl)methyl)acetamide |
| 72 | Q-20 | 2-hydroxy-N-((5-(2-((5-(trifluoromethyl)oxazolo[4,5-b]156yrrolid-2-yl)thio)acetyl)thiophen-2-yl)methyl)acetamide |
| 73 | Q-21 | N-((5-(2-((6-chloro-7-fluoro-2-methylquinazolin-4-yl)thio)acetyl)thiophen-2-yl)methyl)-2-hydroxyacetamide |
| 74 | Q-24 | 2-hydroxy-N-((5-(2-((1-methyl-6-(trifluoromethyl)-1H-pyrazolo[3,4-d]pyrimidin-4-yl)thio)acetyl)thiophen-2-yl)methyl)acetamide |
| 75 | Q-25 | N-((5-(2-((7-fluoro-6-methoxy-2-methylquinazolin-4-yl)thio)acetyl)thiophen-2-yl)methyl)-2-hydroxyacetamide |
| 76 | Q-26 | 2-hydroxy-N-((5-(2-((2-methyl-6-(trifluoromethyl)quinazolin-4-yl)thio)acetyl)thiophen-2-yl)methyl)acetamide |
| 77 | Q-27 | N-((5-(2-((6-cyclopropoxy-2-methylquinazolin-4-yl)thio)acetyl)thiophen-2-yl)methyl)-2-hydroxyacetamide |
| 78 | Q-29 | N-((5-(2-((6-((cyclopropylmethyl)amino)-2-methylquinazolin-4-yl)thio)acetyl)thiophen-2-yl)methyl)-2-hydroxyacetamide |
| 79 | Q-30 | N-((5-(2-((2-cyclopropyl-6-(trifluoromethyl)-2H-pyrazolo[3,4-d]pyrimidin-4-yl)thio)acetyl)thiophen-2-yl)methyl)-2-hydroxyacetamide |
| 80 | Q-31 | 2-hydroxy-N-((5-(2-((6-methoxy-2-(trifluoromethyl)quinazolin-4-yl)thio)acetyl)thiophen-2-yl)methyl)acetamide |
| 81 | Q-32 | 2-hydroxy-N-((5-(2-((2-methyl-6-morpholinoquinazolin-4-yl)thio)acetyl)thiophen-2-yl)methyl)acetamide |
| 82 | Q-33 | 2-hydroxy-N-((5-(2-((2-methyl-6-(piperidin-1-yl)quinazolin-4-yl)thio)acetyl)thiophen-2-yl)methyl)acetamide |
| 83 | Q-34 | 2-hydroxy-N-((5-(2-((2-methyl-6-(1,4-oxazepan-4-yl)quinazolin-4-yl)thio)acetyl)thiophen-2-yl)methyl)acetamide |
| 84 | Q-35 | N-((5-(2-((6-(3,3-difluoropyrrolidin-1-yl)-2-methylquinazolin-4-yl)thio)acetyl)thiophen-2-yl)methyl)-2-hydroxyacetamide |
| 85 | Q-36 | 2-hydroxy-N-((5-(2-((2-methyl-6-(4-methylpiperazin-1-yl)quinazolin-4-yl)thio)acetyl)thiophen-2-yl)methyl)acetamide |
| 86 | Q-2 | 2-hydroxy-1-(3-(5-(2-((1-methyl-1H-pyrazolo[3,4-d]pyrimidin-4-yl)thio)acetyl)thiophen-2-yl)157yrrolidine-1-yl)ethan-1-one |
| 105 | Q-77 | 2-hydroxy-N-((5-(2-((5-(trifluoromethyl)benzo[d]oxazol-2-yl)thio)acetyl)thiophen-2-yl)methyl)acetamide |
| 106 | Q-76 | N-((5-(2-((6-cyclopropyl-2-methylquinazolin-4-yl)thio)acetyl)thiophen-2-yl)methyl)-2-hydroxyacetamide |
| 107 | Q-75 | 2-hydroxy-N-((5-(2-((7-methyl-2-(trifluoromethyl)pyrazolo[1,5-a][1,3,5]triazin-4-yl)thio)acetyl)thiophen-2-yl)methyl)acetamide |
| 108 | Q-74 | N-((5-(2-((8-fluoro-6-methoxy-2-methylquinazolin-4-yl)thio)acetyl)thiophen-2-yl)methyl)-2-hydroxyacetamide |
| 109 | Q-73 | 2-hydroxy-N-((5-(2-((6-methoxy-2-methylquinazolin-4-yl)thio)acetyl)thiophen-2-yl)methyl)-N-methylacetamide |
| 112 | Q-72 | N-((5-(2-((7-cyclopropyl-2-(trifluoromethyl)pyrazolo[1,5-a][1,3,5]triazin-4-yl)thio)acetyl)thiophen-2-yl)methyl)-2-hydroxyacetamide |
| 113 | Q-63 | 2-hydroxy-N-((5-(2-((2-(trifluoromethyl)pyrido[2,3-d]pyrimidin-4-yl)thio)acetyl)thiophen-2-yl)methyl)acetamide |
| 116 | Q-71 | 2-hydroxy-N-methyl-N-((5-(2-((2-methyl-6-(trifluoromethyl)-2H-pyrazolo[3,4-d]pyrimidin-4-yl)thio)acetyl)thiophen-2-yl)methyl)acetamide |
| 117 | Q-70 | 2-hydroxy-N-((5-(2-((5-(trifluoromethyl)oxazolo[5,4-b]157yrrolid-2-yl)thio)acetyl)thiophen-2-yl)methyl)acetamide |
| 118 | Q-69 | 2-hydroxy-N-((5-(2-((6-(trifluoromethyl)oxazolo[4,5-b]157yrrolid-2-yl)thio)acetyl)thiophen-2-yl)methyl)acetamide |
| 119 | Q-68 | 2-hydroxy-N-((5-(2-((2-methyl-6-(trifluoromethyl)pyrido[2,3-d]pyrimidin-4-yl)thio)acetyl)thiophen-2-yl)methyl)acetamide |
| 121 | Q-67 | 2-hydroxy-N-((5-(2-((6-methoxy-2-methylpyrido[3,4-d]pyrimidin-4-yl)thio)acetyl)thiophen-2-yl)methyl)acetamide |
| 124 | Q-66 | N-((5-(2-((6-fluoro-2-methylpyrido[2,3-d]pyrimidin-4-yl)thio)acetyl)thiophen-2-yl)methyl)-2-hydroxyacetamide |
| 125 | Q-65 | 2-hydroxy-N-((5-(2-((1-(2-methoxyethyl)-6-(trifluoromethyl)-1H-pyrazolo[3,4-d]pyrimidin-4-yl)thio)acetyl)thiophen-2-yl)methyl)acetamide |
| 126 | Q-64 | 2-hydroxy-N-((5-(2-((2-methyl-6-(trifluoromethoxy)quinazolin-4-yl)thio)acetyl)thiophen-2-yl)methyl)acetamide |
| 131 | Q-63 | 2-hydroxy-N-methyl-N-((5-(2-((2-(trifluoromethyl)pyrido[2,3-d]pyrimidin-4-yl)thio)acetyl)thiophen-2-yl)methyl)acetamide |
| 132 | Q-61 | 2-hydroxy-N-((5-(2-((2-(2-methoxyethyl)-6-(trifluoromethyl)-2H-pyrazolo[3,4-d]pyrimidin-4-yl)thio)acetyl)thiophen-2-yl)methyl)acetamide |
| 133 | Q-60 | N-((5-(2-((1-cyclopropyl-6-(trifluoromethyl)-1H-pyrazolo[3,4-d]pyrimidin-4-yl)thio)acetyl)thiophen-2-yl)methyl)-2-hydroxyacetamide |
| 135 | Q-59 | N-((5-(2-((2-ethyl-6-(trifluoromethyl)-2H-pyrazolo[3,4-d]pyrimidin-4-yl)thio)acetyl)thiophen-2-yl)methyl)-2-hydroxyacetamide |
| 136 | Q-58 | N-((5-(2-((1-ethyl-6-(trifluoromethyl)-1H-pyrazolo[3,4-d]pyrimidin-4-yl)thio)acetyl)thiophen-2-yl)methyl)-2-hydroxyacetamide |
| 139 | Q-57 | N-((5-(2-((2-(difluoromethyl)-6-methoxyquinazolin-4-yl)thio)acetyl)thiophen-2-yl)methyl)-2-hydroxyacetamide |
| 140 | Q-39 | 2-hydroxy-N-((5-(2-((6-methoxy-2-methylpyrido[2,3-d]pyrimidin-4-yl)thio)acetyl)thiophen-2-yl)methyl)acetamide |
| 142 | Q-56 | N-((5-(2-((6-chloro-8-fluoro-2-methylquinazolin-4-yl)thio)acetyl)thiophen-2-yl)methyl)-2-hydroxyacetamide |
| 143 | Q-55 | 2-hydroxy-N-((5-(2-((5-methoxy-2-methylquinazolin-4-yl)thio)acetyl)thiophen-2-yl)methyl)acetamide |
| 144 | Q-54 | N-((5-(2-((6-ethoxy-2-methylquinazolin-4-yl)thio)acetyl)thiophen-2-yl)methyl)-2-hydroxyacetamide |
| 145 | Q-53 | N-((5-(2-((6-ethoxy-2-methylpyrido[3,4-d]pyrimidin-4-yl)thio)acetyl)thiophen-2-yl)methyl)-2-hydroxyacetamide |
| 146 | Q-52 | N-((5-(2-((6-chloro-5-fluoro-2-methylquinazolin-4-yl)thio)acetyl)thiophen-2-yl)methyl)-2-hydroxyacetamide |
| 147 | Q-51 | N-((5-(2-((6-(2-oxa-5-azabicyclo[2.2.2]octan-5-yl)-2-methylquinazolin-4-yl)thio)acetyl)thiophen-2-yl)methyl)-2-hydroxyacetamide |
| 148 | Q-50 | 2-hydroxy-N-((5-(2-((8-methoxy-2-methyl-6-(trifluoromethyl)quinazolin-4-yl)thio)acetyl)thiophen-2-yl)methyl)acetamide |
| 149 | Q-49 | N-((5-(2-((6-(dimethylamino)-2-methylpyrido[3,4-d]pyrimidin-4-yl)thio)acetyl)thiophen-2-yl)methyl)-2-hydroxyacetamide |
| 150 | Q-48 | N-((5-(2-((8-(dimethylamino)-2-methyl-6-(trifluoromethyl)quinazolin-4-yl)thio)acetyl)thiophen-2-yl)methyl)-2-hydroxyacetamide |
| 151 | Q-47 | 2-hydroxy-N-((5-(2-((2-methyl-8-(methylamino)-6-(trifluoromethyl)quinazolin-4-yl)thio)acetyl)thiophen-2-yl)methyl)acetamide |
| 152 | Q-46 | 2-hydroxy-N-((5-(2-((2-(trifluoromethyl)pyrido[3,2-d]pyrimidin-4-yl)thio)acetyl)thiophen-2-yl)methyl)acetamide |
| 153 | Q-45 | 2-hydroxy-N-((5-(2-((2-methylpyrido[3,2-d]pyrimidin-4-yl)thio)acetyl)thiophen-2-yl)methyl)acetamide |

-continued

| Ex. | Cpd Q | IUPAC name |
|---|---|---|
| 154 | Q-44 | 2-hydroxy-N-((5-(2-((6-methoxy-2-(trifluoromethyl)pyrido[3,4-d]pyrimidin-4-yl)thio)acetyl)thiophen-2-yl)methyl)acetamide |
| 158 | Q-43 | N-((5-(2-((5-fluoro-6-methoxy-2-methylquinazolin-4-yl)thio)acetyl)thiophen-2-yl)methyl)-2-hydroxyacetamide |
| 159 | Q-42 | 2-hydroxy-N-((5-(2-((6-methoxy-2-(trifluoromethyl)pyrido[3,4-d]pyrimidin-4-yl)thio)acetyl)thiophen-2-yl)methyl)-N-methylacetamide |
| 160 | Q-41 | N-((5-(2-((6-ethoxy-2-methylpyrido[2,3-d]pyrimidin-4-yl)thio)acetyl)thiophen-2-yl)methyl)-2-hydroxyacetamide |
| 162 | Q-40 | 2-hydroxy-N-((5-(2-((6-methoxy-2-methylpyrido[2,3-d]pyrimidin-4-yl)thio)acetyl)thiophen-2-yl)methyl)-N-methylacetamide |
| 164 | Q-28 | N-((5-(2-((2-(difluoromethyl)-6-methoxypyrido[2,3-d]pyrimidin-4-yl)thio)acetyl)thiophen-2-yl)methyl)-2-hydroxyacetamide |
| 196 | Q-23 | 2-hydroxy-N-((5-(2-((4-(trifluoromethyl)benzo[d]oxazol-2-yl)thio)acetyl)thiophen-2-yl)methyl)acetamide |

The following Examples have been prepared using the experimental conditions described above from the reaction of compounds Q with carboxylic acids $R^9$—$CO_2H$. In some cases, the $R^9$ group contained an alcohol group, which was protected with a suitable protective group such as TBS or TBDPS, and later removed similarly as described herein for the conversion of R-1-1 to example compound 63. In other cases, the $R^9$ group contained an amino group, which was protected with a suitable protective group known in the art such as Boc, and later removed using conditions known in the art, such as TFA/DCM.

| Ex. | Cpd Q | $R^9$-$CO_2H$ | IUPAC name |
|---|---|---|---|
| 42 | Q-2 | | 3,3,3-trifluoro-2-hydroxy-N-((5-(2-((1-methyl-1H-pyrazolo[3,4-d]pyrimidin-4-yl)thio)acetyl)thiophen-2-yl)methyl)propanamide |
| 45 | Q-20 | | 1-hydroxy-N-((5-(2-((5-(trifluoromethyl)oxazolo[4,5-b]157yrrolid-2-yl)thio)acetyl)thiophen-2-yl)methyl)cyclopropane-1-carboxamide |
| 46 | Q-3 | | 3,3,3-trifluoro-2-hydroxy-N-((5-(2-((2-methyl-6-(trifluoromethyl)-2H-pyrazolo[3,4-d]pyrimidin-4-yl)thio)acetyl)thiophen-2-yl)methyl)propanamide |
| 47 | Q-37 | | 1-hydroxy-N-((5-(2-((6-morpholino-2-(trifluoromethyl)quinazolin-4-yl)thio)acetyl)thiophen-2-yl)methyl)cyclopropane-1-carboxamide |
| 48 | Q-3 | | 2-hydroxy-2-methyl-N-((5-(2-((2-methyl-6-(trifluoromethyl)-2H-pyrazolo[3,4-d]pyrimidin-4-yl)thio)acetyl)thiophen-2-yl)methyl)propanamide |
| 49 | Q-3 | | 1-hydroxy-N-((5-(2-((2-methyl-6-(trifluoromethyl)-2H-pyrazolo[3,4-d]pyrimidin-4-yl)thio)acetyl)thiophen-2-yl)methyl)cyclopropane-1-carboxamide |
| 50 | Q-11 | | 1-hydroxy-N-((5-(2-((6-methoxy-2-methylquinazolin-4-yl)thio)acetyl)thiophen-2-yl)methyl)cyclopropane-1-carboxamide |
| 52 | Q-2 | | 2-hydroxy-2-methyl-N-((5-(2-((1-methyl-1H-pyrazolo[3,4-d]pyrimidin-4-yl)thio)acetyl)thiophen-2-yl)methyl)propanamide |
| 55 | Q-2 | | N-((5-(2-((1-methyl-1H-pyrazolo[3,4-d]pyrimidin-4-yl)thio)acetyl)thiophen-2-yl)methyl)-2-(158yrrolid-2-yl)acetamide |
| 56 | Q-2 | | N-((5-(2-((1-methyl-1H-pyrazolo[3,4-d]pyrimidin-4-yl)thio)acetyl)thiophen-2-yl)methyl)-2-(158yrrolid-3-yl)acetamide |
| 57 | Q-2 | | N-((5-(2-((1-methyl-1H-pyrazolo[3,4-d]pyrimidin-4-yl)thio)acetyl)thiophen-2-yl)methyl)-2-(158yrrolid-4-yl)acetamide |
| 58 | Q-2 | | 2-methoxy-N-((5-(2-((1-methyl-1H-pyrazolo[3,4-d]pyrimidin-4-yl)thio)acetyl)thiophen-2-yl)methyl)acetamide |
| 59 | Q-2 | | 2-hydroxy-N-((5-(2-((1-methyl-1H-pyrazolo[3,4-d]pyrimidin-4-yl)thio)acetyl)thiophen-2-yl)methyl)acetamide |
| 60 | Q-11 | | 2-hydroxy-N-((5-(2-((6-methoxy-2-methylquinazolin-4-yl)thio)acetyl)thiophen-2-yl)methyl)acetamide |
| 61 | Q-3 | | 2-hydroxy-N-((5-(2-((2-methyl-6-(trifluoromethyl)-2H-pyrazolo[3,4-d]pyrimidin-4-yl)thio)acetyl)thiophen-2-yl)methyl)acetamide |
| 62 | Q-12 | | N-((5-(2-((2-ethylquinazolin-4-yl)thio)acetyl)thiophen-2-yl)methyl)-2-hydroxyacetamide |
| 110 | Q-13 | | 2,2-difluoro-N-((5-(2-((2-methylpyrido[2,3-d]pyrimidin-4-yl)thio)acetyl)thiophen-2-yl)methyl)cyclopropane-1-carboxamide |

| Ex. | Cpd Q | $R^9$-CO$_2$H | IUPAC name |
|---|---|---|---|
| 111 | Q-3 | (2,2-difluorocyclopropane-1-carboxylic acid) | 2,2-difluoro-N-((5-(2-((2-methyl-6-(trifluoromethyl)-2H-pyrazolo[3,4-d]pyrimidin-4-yl)thio)acetyl)thiophen-2-yl)methyl)cyclopropane-1-carboxamide |
| 114 | Q-63 | (2,2-difluorocyclopropane-1-carboxylic acid) | 2,2-difluoro-N-((5-(2-((2-(trifluoromethyl)pyrido[2,3-d]pyrimidin-4-yl)thio)acetyl)thiophen-2-yl)methyl)cyclopropane-1-carboxamide |
| 120 | Q-64 | (2,2-difluorocyclopropane-1-carboxylic acid) | 2,2-difluoro-N-((5-(2-((2-methyl-6-(trifluoromethoxy)quinazolin-4-yl)thio)acetyl)thiophen-2-yl)methyl)cyclopropane-1-carboxamide |
| 134 | Q-31 | (2-hydroxy-2-methylpropanoic acid) | 2-hydroxy-N-((5-(2-((6-methoxy-2-(trifluoromethyl)quinazolin-4-yl)thio)acetyl)thiophen-2-yl)methyl)-2-methylpropanamide |
| 163 | Q-39 | (methoxyacetic acid) | 2-methoxy-N-((5-(2-((6-methoxy-2-methylpyrido[2,3-d]pyrimidin-4-yl)thio)acetyl)thiophen-2-yl)methyl)acetamide |
| 171 | Q-11 | (tetrahydrofuran-2-carboxylic acid) | N-((5-(2-((6-methoxy-2-methylquinazolin-4-yl)thio)acetyl)thiophen-2-yl)methyl)tetrahydrofuran-2-carboxamide |
| 172 | Q-11 | (difluoroacetic acid) | 2,2-difluoro-N-((5-(2-((6-methoxy-2-methylquinazolin-4-yl)thio)acetyl)thiophen-2-yl)methyl)acetamide |
| 177 | Q-11 | (glycine) | 2-amino-N-((5-(2-((6-methoxy-2-methylquinazolin-4-yl)thio)acetyl)thiophen-2-yl)methyl)acetamide |
| 178 | Q-11 | (1-methylazetidine-3-carboxylic acid) | N-((5-(2-((6-methoxy-2-methylquinazolin-4-yl)thio)acetyl)thiophen-2-yl)methyl)-1-methylazetidine-3-carboxamide |
| 183 | Q-11 | (N-methylglycine) | N-((5-(2-((6-methoxy-2-methylquinazolin-4-yl)thio)acetyl)thiophen-2-yl)methyl)-2-(methylamino)acetamide |
| 184 | Q-11 | (proline) | N-((5-(2-((6-methoxy-2-methylquinazolin-4-yl)thio)acetyl)thiophen-2-yl)methyl)pyrrolidine-2-carboxamide |
| 185 | Q-11 | ((S)-lactic acid) | (S)-2-hydroxy-N-((5-(2-((6-methoxy-2-methylquinazolin-4-yl)thio)acetyl)thiophen-2-yl)methyl)propanamide |
| 186 | Q-11 | ((R)-alanine) | (R)-2-hydroxy-N-((5-(2-((6-methoxy-2-methylquinazolin-4-yl)thio)acetyl)thiophen-2-yl)methyl)propanamide |

Example 87: N-(5-(2-((1-methyl-1H-pyrazolo[3,4-d]pyrimidin-4-yl)thio)acetyl)thiophen-2-yl)methyl)methanesulfonamide

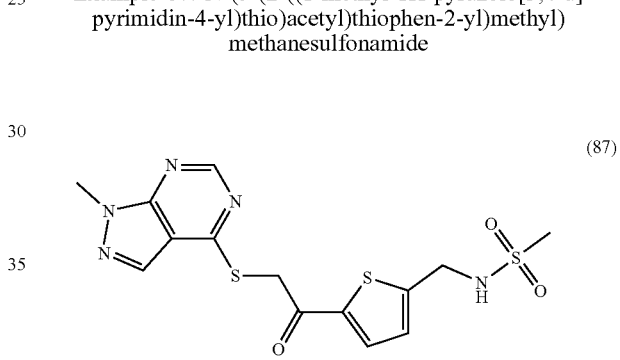

(87)

To a solution mixture of compound Q-2 (100 mg, 0.281 mmol, 1 eq.) in DCM (3.0 mL) was added E$_{t3}$N (0.075 mL, 2 eq.) at 0° C. The resultant reaction mixture was stirred for 10 min at 0° C. and methane sulfonyl chloride (0.032 mL, 0.422 mmol) was added. The reaction mixture was stirred for 3 h at rt. The reaction mixture was concentrated in vacuo. Cold water (10 mL) was added to crude compound and extracted with EtOAc to afford crude compounds which after final purification gave compound (87) as a white solid (40 mg, 31% yield) solid.

The following Examples have been prepared using the experimental conditions described above in Example 87 from the reaction of compounds Q with sulfonyl chloride derivatives of Formula $R^9$—SO$_2$Cl:

| Ex. | Cpd Q | $R^9$-SO$_2$Cl | IUPAC name |
|---|---|---|---|
| 88 | Q-2 | PhSO$_2$Cl | N-((5-(2-((1-methyl-1H-pyrazolo[3,4-d]pyrimidin-4-yl)thio)acetyl)thiophen-2-yl)methyl)benzenesulfonamide |
| 89 | Q-2 | (cyclopropanesulfonyl chloride) | N-((5-(2-((1-methyl-1H-pyrazolo[3,4-d]pyrimidin-4-yl)thio)acetyl)thiophen-2-yl)methyl)cyclopropanesulfonamide |

-continued

| Ex. | Cpd Q | R⁹-SO₂Cl | IUPAC name |
|---|---|---|---|
| 90 | Q-2 | benzyl sulfonyl chloride | N-((5-(2-((1-methyl-1H-pyrazolo[3,4-d]pyrimidin-4-yl)thio)acetyl)thiophen-2-yl)methyl)-1-phenylmethanesulfonamide |
| 91 | Q-5 | cyclopropanesulfonyl chloride | N-methyl-N-((5-(2-((1-methyl-1H-pyrazolo[3,4-d]pyrimidin-4-yl)thio)acetyl)thiophen-2-yl)methyl)cyclopropanesulfonamide |
| 92 | Q-5 | (pyridin-4-yl)methanesulfonyl chloride | N-methyl-N-((5-(2-((1-methyl-1H-pyrazolo[3,4-d]pyrimidin-4-yl)thio)acetyl)thiophen-2-yl)methyl)-1-(160yrrolid-4-yl)methanesulfonamide |
| 93 | Q-4 | cyclopropylmethanesulfonyl chloride | 1-cyclopropyl-N-((5-(2-((2-methylquinazolin-4-yl)thio)acetyl)thiophen-2-yl)methyl)methanesulfonamide |
| 94 | Q-10 | $CH_3SO_2Cl$ | N-(2-(5-(2-((2-methylquinazolin-4-yl)thio)acetyl)thiophen-2-yl)ethyl)methanesulfonamide |
| 95 | Q-9 | $CH_3SO_2Cl$ | 1-(5-(1-(methylsulfonyl)161yrrolidine-3-yl)thiophen-2-yl)-2-((2-(trifluoromethyl)quinazolin-4-yl)thio)ethanone |
| 96 | Q-9 | $Cl-SO_2-NH_2$ | 3-(5-(2-((1-methyl-1H-pyrazolo[3,4-d]pyrimidin-4-yl)thio)acetyl)thiophen-2-yl)pyrrolidine-1-sulfonamide |
| 97 | Q-4 | $CH_3SO_2Cl$ | N-((5-(2-((2-methylquinazolin-4-yl)thio)acetyl)thiophen-2-yl)methyl)methanesulfonamide |
| 98 | Q-1 | $CH_3SO_2Cl$ | N-(2-(5-(2-((2-(trifluoromethyl)quinazolin-4-yl)thio)acetyl)thiophen-2-yl)ethyl)methanesulfonamide |
| 122 | Q-63 | cyclopropanesulfonyl chloride | N-((5-(2-((2-(trifluoromethyl)pyrido[2,3-d]pyrimidin-4-yl)thio)acetyl)thiophen-2-yl)methyl)cyclopropanesulfonamide |
| 123 | Q-63 | 2,2,2-trifluoroethanesulfonyl chloride | 2,2,2-trifluoro-N-((5-(2-((2-(trifluoromethyl)pyrido[2,3-d]pyrimidin-4-yl)thio)acetyl)thiophen-2-yl)methyl)ethane-1-sulfonamide |
| 127 | Q-63 | ethanesulfonyl chloride | N-((5-(2-((2-(trifluoromethyl)pyrido[2,3-d]pyrimidin-4-yl)thio)acetyl)thiophen-2-yl)methyl)ethanesulfonamide |

Properties of Examples Compounds

The properties of synthetized example compounds are shown on Table 4 below.

TABLE 4

| Ex. | Form | LCMS m/z (Rt) | Method | ¹H-NMR [400 MHz] |
|---|---|---|---|---|
| 1 | Yellow solid | 442.32 [M + H]⁺, (16.27 min) | 1 | δ (DMSO-$d_6$): 8.33 (t, J = 6.0 Hz, 1H), 8.13-8.10 (m, 2H), 7.97-7.92 (m, 1H), 7.88-7.86 (m, 1H), 7.69-7.65 (m, 1H), 7.11 (d, J = 4.0 Hz, 1H), 4.87 (s, 2H), 4.46 (d, J = 6.0 Hz, 2H), 2.96-2.89 (m, 1H), 1.11 (s, 9H), 1.01 (m, 6H). |
| 2 | White solid | 440.29 [M + H]⁺, (16.19 min) | 4 | δ (DMSO-$d_6$): 8.36-8.32 (m, 1H), 8.10-8.07 (m, 2H), 7.92 (t, J = 8.4 Hz, 1H), 7.83-7.79 (m, 1H), 7.61 (t, J = 8.0 Hz, 1H) 7.11 (d, J = 3.6 Hz, 1H), 4.84 (s, 2H), 4.48-4.42 (m, 2H), 2.07-1.99 (m, 1H), 1.11 (s, 9H), 0.81 (t, J = 3.2 Hz, 4H). |
| 3 | Yellow solid | 414.28 [M + H]⁺, (13.87 min) | 4 | δ (DMSO-$d_6$): 8.33 (br s, 1H), 8.12-8.08 (m, 2H), 7.95-7.92 (m, 1H), 7.85 (d, J = 8.0 Hz, 1H), 7.69-7.66 (m, 1H), 7.11 (d, J = 4.0 Hz, 1H), 4.84 (s, 2H), 4.46 (d, J = 5.6 Hz, 2H), 2.42 (s, 3H), 1.11 (s, 9H). |
| 4 | Light yellow solid | 444.28 [M + H]⁺, (15.16 min) | 4 | δ (DMSO-$d_6$): 8.35 (t, J = 6.0 Hz, 1H), 8.18-8.16(m, 1H), 8.09 (d, J = 4.0 Hz, 1H), 8.02-7.83 (m, 2H), 7.76-7.71 (m, 1H), 7.11 (d, J = 4.0 Hz, 1H), 4.89 (s, 2H), 4.46 (d, J = 6.0 Hz, 2H), 4.38 (s, 2H), 3.23 (s, 3H), 1.11 (s, 9H). |
| 5 | White solid | 418.31 [M + H]⁺, (14.73 min) | 4 | δ (DMSO-$d_6$): 8.34 (t, J = 5.6 Hz, 1H), 8.29 (s, 1H), 8.06 (d, J = 3.6 Hz, 1H), 7.10 (d, J = 3.6 Hz, 1H), 4.85 (s, 2H), 4.46 (d, J = 6.0 Hz, 2H), 3.95 (s, 3H), 2.42 (s, 3H), 1.11 (s, 9H). |

TABLE 4-continued

| Ex. | Form | LCMS m/z (Rt) | Method | ¹H-NMR [400 MHz] |
|---|---|---|---|---|
| 6 | Yellow solid | 444.28 [M + H]⁺, (15.77 min) | 4 | δ (DMSO-d₆): 8.34 (t, J = 6.0 Hz, 1H), 8.24 (s, 1H), 8.07 (d, J = 3.6 Hz, 1H), 7.10 (d, J = 4.0 Hz, 1H), 4.84 (s, 2H), 4.46 (d, J = 5.6 Hz, 2H), 3.94 (s, 3H), 2.00-1.98 (m, 1H), 1.11 (s, 9H), 0.82 (q, J = 7.6 Hz, 4H). |
| 7 | Pale Yellow solid | 415.28 [M + H]⁺, (11.32 min) | 4 | δ (DMSO-d₆): 9.19 (q, J = 6.0 Hz, 1H), 8.61 (q, J = 8.4 Hz, 1H), 8.35 (t, J = 6.0 Hz, 1H), 8.10 (d, J = 4.0 Hz, 1H), 7.67 (q, J = 8.4 Hz, 1H), 7.12 (d, J = 3.6 Hz, 1H), 4.89 (s, 2H), 4.47 (d, J = 6.0 Hz, 2H), 2.47 (s, 3H) 1.11 (s, 9H). |
| 8 | Yellow solid | 448.24 [M + H]⁺, (16.45 min) | 4 | δ (DMSO-d₆): 8.34 (t, J = 6.0 Hz, 1H), 8.15 (d, J = 8.8 Hz, 1H), 8.09 (d, J = 3.6 Hz, 1H), 7.94 (s, 1H), 7.69 (dd, J = 8.8 Hz, J = 8.8 Hz, 1H), 7.11 (d, J = 4.0 Hz, 1H), 4.85 (s, 2H), 4.46 (d, J = 6.0 Hz, 2H), 2.41 (s, 3H), 1.11 (s, 9H). |
| 9 | Yellow solid | 432.24 [M + H]⁺, (15.02 min) | 1 | δ (DMSO-d₆): 8.34 (t, J = 6.0 Hz, 1H), 8.09 (d, J = 4.0 Hz, 1H), 7.97-7.85 (m, 3H), 7.11 (d, J = 4.0 Hz, 1H), 4.85 (s, 2H), 4.46 (d, J = 6.0 Hz, 2H), 2.41 (s, 3H), 1.11 (s, 9H). |
| 10 | Light yellow solid | 432.31 [M + H]⁺, (15.19 min) | 1 | δ (DMSO-d₆): 8.34 (t, J = 6.0 Hz, 1H), 8.24-8.21 (m, 1H), 8.09 (d, J = 4.0 Hz, 1H), 7.65-7.55 (m, 2H), 7.11 (d, J = 4.0 Hz, 1H), 4.85 (s, 2H), 4.46 (d, J = 6.0 Hz, 2H), 2.41 (s, 3H), 1.11 (s, 9H). |
| 11 | Light yellow solid | 428.17 [M + H]⁺, (15.04 min) | 1 | δ (DMSO-d₆): 8.33 (t, J = 6.0 Hz, 1H), 8.08 (d, J = 3.6 Hz, 1H), 7.99 (d, J = 8.4 Hz, 1H), 7.64 (s, 1H), 7.50 (dd, J = 8.4 Hz, J = 8.4 Hz, 1H), 7.10 (d, J = 3.6 Hz, 1H), 4.82 (s, 2H), 4.46 (d, J = 6.0 Hz, 2H), 2.51-2.49 (m, 3H), 2.39 (s, 3H), 1.11 (s, 9H). |
| 12 | Off white solid | 444.14 [M + H]⁺, (14.59 min) | 1 | δ (DMSO-d₆): 8.34 (t, J = 6.0 Hz, 1H), 8.08 (d, J = 4.0 Hz, 1H), 7.99 (d, J = 8.8 Hz, 1H), 7.26-7.23 (m, 2H), 7.10 (d, J = 4.0 Hz, 1H), 4.80 (s, 2H), 4.46 (d, J = 6.0 Hz, 2H), 3.92 (s, 3H), 2.37 (s, 3H), 1.11 (s, 9H). |
| 13 | Off white solid | 428.15 [M + H]⁺, (13.02 min) | 3 | δ (DMSO-d₆): 8.31 (t, J = 6.0 Hz, 1H), 8.10-8.06 (m, 2H), 7.95-7.83 (m, 2H), 7.67-7.63 (m, 1H), 7.08 (d, J = 3.6 Hz, 1H), 4.83 (s, 2H), 4.44 (d, J = 5.6 Hz, 2H), 2.66 (q, J = 8.0 Hz, 2H), 1.12-1.03 (m, 12H). |
| 14 | Off white solid | 454.16 [M + H]⁺, (14.08 min) | 3 | δ (DMSO-d₆): 8.32 (t, J = 6.0 Hz, 1H), 8.14-8.11 (m, 2H), 7.96-7.85 (m, 2H), 7.69-7.65 (m, 1H), 7.12 (d, J = 3.6 Hz, 1H), 4.90 (s, 2H), 4.45 (d, J = 6.0 Hz, 2H), 3.56-3.52 (m, 1H), 2.20-2.15 (m, 2H), 2.07-2.01 (m, 2H), 1.82-1.80 (m, 1H), 1.44-1.40 (m, 1H), 1.11 (s, 9H). |
| 15 | Off white solid | 432.07 [M + H]⁺, (14.63 min) | 1 | δ (DMSO-d₆): 8.34 (t, J = 6.0 Hz, 1H), 8.10 (d, J = 4.0 Hz, 1H), 7.95 (d, J = 8.4 Hz, 1H), 7.83-7.78 (m, 1H), 7.68-7.62 (m, 1H), 7.11 (d, J = 3.6 Hz, 1H), 4.86 (s, 2H), 4.47 (d, J = 6.0 Hz, 2H), 2.44 (s, 3H), 1.11 (s, 9H). |
| 16 | Off white solid | 443.28 [M + H]⁺, (12.13 min) | 4 | δ (DMSO-d₆): 8.33 (t, J = 6.0 Hz, 1H), 8.07 (d, J = 4.0 Hz, 1H), 7.87 (dd, J₁ = 8.4 Hz, , J₂ = 8.0 Hz, 1H), 7.69-7.65 (m, 1H), 7.44 (d, J = 8.4 Hz, 1H), 7.23-7.19 (m, 1H), 7.08 (d, J = 3.6 Hz, 1H), 4.86 (s, 2H), 4.45 (d, J = 6.0 Hz, 2H), 2.95 (br s, 6H), 1.12 (s, 9H). |
| 17 | Pale white solid | 444.11 [M + H]⁺, (14.07 min) | 4 | δ (DMSO-d₆): 8.32 (t, J = 6.0 Hz, 1H), 8.08 (d, J = 4.0 Hz, 1H), 7.79 (d, J = 9.2 Hz, 1H), 7.60-7.57 (m, 1H), 7.27 (d, J = 3.0 Hz, 1H), 7.10 (d, J = 4.0 Hz, 1H), 4.83 (s, 2H), 4.46 (d, J = 6.0 Hz, 2H), 3.94 (s, 3H), 2.39 (s, 3H), 1.11 (s, 9H). |
| 18 | Off white solid | 415.11 [M + H]⁺, (10.48 min) | 3 | δ (DMSO-d₆): 8.95 (q, J = 4.4 Hz, 1H), 8.34-8.26 (m, 2H), 8.08 (d, J = 4.0 Hz, 1H), 7.98-7.95 (m, 1H), 7.11 (d, J = 4.0 Hz, 1H), 4.76 (s, 2H), 4.45 (d, J = 4.4 Hz, 2H), 2.47 (s, 3H), 1.10 (m, 9H). |
| 19 | Off white solid | 450.27 [M + H]⁺, (15.45 min) | 1 | δ (DMSO-d₆): 8.35-8.28 (m, 2H), 8.14-8.07 (m, 3H), 7.90-7.86 (m, 1H), 7.10 (d, J = 4.0 Hz, 1H), 6.90-6.63 (m, 1H), 4.97 (s, 2H), 4.46 (d, J = 6.0 Hz, 2H), 1.11 (s, 9H). |
| 20 | Off white solid | 472.25 [M + H]⁺, (16.67 min) | 4 | δ (DMSO-d₆): 8.62 (s, 1H), 8.33 (t, J = 5.6 Hz, 1H), 8.04 (d, J = 4.0 Hz, 1H), 7.09 (d, J = 3.6 Hz, 1H), 4.97 (s, 2H), 4.46 (d, J = 6.0 Hz, 2H), 4.06(s, 3H), 1.11 (s, 9H). |
| 21 | Light yellow solid | 454.26 [M + H]⁺, (15.72 min) | 4 | δ (DMSO-d₆): 8.53 (s, 1H), 8.34 (t, J = 6.0 Hz, 1H), 8.05 (d, J = 4.0 Hz, 1H), 7.09 (d, J = 4.0 Hz, 1H), 6.90-6.63 (m, 1H), 4.98 (s, 2H), 4.45 (d, J = 6.0 Hz, 2H), 4.05 (s, 3H), 1.11 (s, 9H). |

TABLE 4-continued

| Ex. | Form | LCMS m/z (Rt) | Method | ¹H-NMR [400 MHz] |
|---|---|---|---|---|
| 22 | White solid | 472.12 [M + H]⁺, (13.19 min) | 4 | δ (DMSO-d₆): 9.05 (s, 1H), 8.32 (t, J = 6.0 Hz, 1H), 8.03 (d, J = 4.0 Hz, 1H), 7.09 (d, J = 4.0 Hz, 1H), 4.93 (s, 2H), 4.46 (d, J = 6.0 Hz, 2H), 4.25 (s, 3H), 1.11 (s, 9H). |
| 23 | Off white solid | 404.27 [M + H]⁺, (14.91 min) | 4 | δ (DMSO-d₆): 8.35 (t, J = 6.0 Hz, 1H), 8.05 (d, J = 4.0 Hz, 1H), 7.95 (d, J = 8.4 Hz, 1H), 7.19 (d, J = 8.4 Hz, 1H), 7.12 (d, J = 4.0 Hz, 1H), 5.03 (s, 2H), 4.46 (d, J = 5.6 Hz, 2H), 2.50 (s, 3H), 1.12 (s, 9H). |
| 24 | White solid | 402.27 [M + H]⁺, (12.35 min) | 1 | δ (DMSO-d₆): 8.67 (s, 1H), 8.40 (s, 1H), 8.09 (d, J = 4.0 Hz, 1H), 7.17 (d, J = 4.0 Hz, 1H), 4.99 (s, 2H), 4.61 (s, 2H), 4.02 (s, 3H), 3.29-3.26 (m, 2H), 2.45-2.38 (m, 1H), 2.25-2.15 (m, 1H), 1.60-1.51 (m, 1H), 1.07 (d, J = 7.2 Hz, 3H). |
| 25 | White solid | 388.26 [M + H]⁺, (11.45 min) | 1 | δ (DMSO-d₆): 8.67 (s, 1H), 8.40 (s, 1H), 8.08 (d, J = 3.6 Hz, 1H), 7.19 (d, J = 3.6 Hz, 1H), 4.90 (d, J = 8.8 Hz, 2H), 4.60 (s, 2H), 4.09 (s, 3H), 3.42 (d, J = 8.8 Hz, 1H), 3.33 (t, J = 8.2 Hz, 2H), 2.28 (t, J = 7.6 Hz, 2H), 1.95 (t, J = 7.6 Hz, 2H) |
| 26 | White solid | 466.23 [M + H]⁺, (15.42 min) | 1 | δ (DMSO-d₆): 8.40 (d, J = 8.0 Hz, 1H), 8.19-8.13 (m, 2H), 8.09 (d, J = 4.0 Hz, 1H), 7.96-7.92 (m, 1H), 7.12 (d, J = 3.6 Hz, 1H), 4.97 (s, 2H), 3.48 (t, J = 7.2 Hz, 2H), 3.30 (t, J = 6.8 Hz, 2H), 3.09 (t, J = 6.8 Hz, 2H), 2.19 (t, J = 8.0 Hz, 2H), 1.92-1.85 (m, 2H) |
| 27 | Off white solid | 405.27 [M + H]⁺, (12.85 min) | 1 | δ (DMSO-d₆): 8.62 (s, 1H), 8.40 (s, 1H), 8.37 (br t, J = 5.6 Hz, 1H), 8.02 (s, 1H), 5.08 (s, 2H), 4.52 (d, J = 6.0 Hz, 2H), 4.01 (s, 3H), 1.10 (s, 9H). |
| 28 | Off white solid | 422.26 [M + H]⁺, (13.74 min) | 1 | δ (DMSO-d₆): 8.66 (s, 1H), 8.41 (s, 1H), 8.34 (t, J = 6.0 Hz, 1H), 8.12 (s, 1H), 4.95 (s, 2H), 4.39 (d, J = 6.0 Hz, 2H), 4.01 (s, 3H), 1.09 (s, 9H). |
| 29 | White solid | 482.26 [M + H]⁺, (16.88 min) | 1 | δ (DMSO-d₆): 8.34 (d, J = 8.0 Hz, 1H), 8.19-8.13 (m, 2H), 8.08 (d, J = 4.0 Hz, 1H), 7.96-7.92 (m, 1H), 7.62 (t, J = 6.0 Hz, 1H), 7.07 (d, J = 3.6 Hz, 1H), 4.92 (s, 2H), 3.36-3.32 (m, 2H), 3.03 (t, J = 6.8 Hz, 2H), 1.06 (s, 9H). |
| 30 | White solid | 424.23 [M + H]⁺, (13.27 min) | 1 | δ (DMSO-d₆): 9.32 (t, d, J = 5.6 Hz, 1H), 8.67 (s, 1H), 8.40 (s, 1H), 8.06 (d, J = 4.0 Hz, 1H), 7.88 (d, J = 7.2 Hz, 2H), 7.56 (t, J = 7.6 Hz, 1H), 7.49 (t, J = 7.6 Hz, 2H), 7.20 (d, J = 4.0 Hz, 1H), 4.98 (s, 2H), 4.48 (d, J = 6.0 Hz, 2H), 4.01 (s, 3H) |
| 31 | White solid | 388.22 [M + H]⁺, (11.49 min) | 1 | δ (DMSO-d₆): 8.81 (brs, 1H), 8.67 (s, 1H), 8.39 (s, 1H), 8.05 (d, J = 3.2 Hz, 1H), 7.12 (d, J = 3.6 Hz, 1H), 4.99 (s, 2H), 4.49 (d, J = 5.6 Hz, 2H), 4.01 (s, 3H), 1.58 (br s, 1H), 0.70-0.68 (s, 4H) |
| 32 | White solid | 438.23 [M + H]⁺, (13.20 min) | 1 | δ (DMSO-d₆): 8.80 (t, J = 5.6 Hz, 1H), 8.66 (s, 1H), 8.39 (s, 1H), 8.04 (d, J = 4.0 Hz, 1H), 7.31-7.20 (m, 5H), 7.10 (d, J = 4.0 Hz, 1H), 4.97 (s, 2H), 4.48 (d, J = 5.6 Hz, 2H), 4.01 (s, 3H), 3.47 (s, 2H). |
| 33 | Light yellow solid | 418.27 [M + H]⁺, (14.59 min) | 1 | δ (DMSO-d₆): 8.67 (s, 1H), 8.39 (s, 1H), 8.06 (d, J = 4.0 Hz, 1H), 7.17 (d, J = 3.6 Hz, 1H), 4.99 (s, 2H), 4.69 (s, 2H), 4.02 (s, 3H), 3.07 (s, 3H), 1.22 (s, 9H). |
| 34 | Off white solid | 402.24 [M + H]⁺, (12.70 min) | 1 | δ (DMSO-d₆): 8.67 (s, 1H), 8.39 (s, 1H), 8.06 (d, J = 4.0 Hz, 1H), 7.17 (d, J = 3.6 Hz, 1H), 4.99 (s, 2H), 4.69 (s, 2H), 4.02 (s, 3H), 3.07 (s, 3H), 1.22 (s, 9H). |
| 35 | Pale Yellow solid | 398.25 [M + H]⁺, (12.23 min) | 4 | δ (DMSO-d₆): 8.83 (t, J = 5.6 Hz, 1H), 8.13-8.10 (m, 2H), 7.97-7.93 (m, 1H), 7.85 (d, J = 8.0 Hz, 1H), 7.69-7.65 (m, 1H), 7.14 (d, J = 4.0 Hz, 1H), 4.85 (s, 2H), 4.50 (d, J = 6.0 Hz, 2H), 2.43 (s, 3H), 1.60-1.57 (m, 1H), 0.71-0.67 (m, 4H). |
| 36 | Off white solid | 466.20 [M + H]⁺, (18.68 min) | 1 | δ (DMSO-d₆): 8.31 (d, J = 8.4 Hz, 1H), 8.23 (t, J = 5.6 Hz, 1H), 8.19 (d, J = 3.6 Hz, 1H), 7.97-7.92 (m, 1H), 7.45 (s, 1H), 7.12 (d, J = 3.6 Hz, 1H), 6.90 (d, J = 3.6 Hz, 1H), 3.34-3.29 (m, 2H), 2.95 (t, J = 6.8 Hz, 2H), 2.07-1.98 (m, 1H), 1.56-1.51 (m, 1H), 1.23-1.09 (m, 2H), 0.70-0.61 (m, 4H). |
| 37 | White solid | 502.20 [M + H]⁺, (16.84 min) | 1 | δ (DMSO-d₆): 8.66 (t, J = 5.2 Hz, 1H), 8.34 (d, J = 8.0 Hz, 1H), 8.16-8.09 (m, 3H), 7.96-7.92 (m, 1H), 7.83-7.81 (m, 2H), 7.54-7.44 (m, 3H), 7.14 (d, J = 4.0 Hz, 1H), 4.97 (s, 2H), 3.57 (q, J = 4.0 Hz, 2H), 3.17 (t, J = 6.8 Hz, 2H). |

TABLE 4-continued

| Ex. | Form | LCMS m/z (Rt) | Method | ¹H-NMR [400 MHz] |
|---|---|---|---|---|
| 38 | White solid | 468.23 [M + H]⁺, (16.57 min) | 1 | δ (DMSO-$d_6$): 8.35-8.33 (m, 2H), 8.16-8.13 (m, 2H), 8.06 (d, J = 4.0 Hz, 1H), 7.96-7.92 (m, 1H), 7.11 (d, J = 3.6 Hz, 1H), 4.99 (s, 2H), 4.47 (d, J = 6.0 Hz, 2H), 1.11 (s, 9H). |
| 39 | Yellow solid | 464.1 [M + H]⁺, (2.837 min) | 2 | δ (CDCl₃): 7.79 (d, J = 4.0 Hz, 1H), 7.73 (d, J = 8.4 Hz, 1H), 7.39 (dd, J = 9.2, 2.8 Hz, 1H), 7.17 (d, J = 2.4 Hz, 1H), 7.00 (d, J = 3.6 Hz, 1H), 6.15 (s, 1H), 4.54-4.71 (m, 4H), 3.87 (s, 3H), 2.52 (s, 3H), 2.27-2.21 (m, 1H), 2.00-2.15 (m, 1H), 1.58-1.72 (m, 1H) |
| 40 | Yellow solid | 506.1 [M + H]⁺, (3.166 min) | 2 | δ (DMSO-$d_6$): 8.13 (d, J = 3.6 Hz, 1H), 7.79 (d, J = 9.2 Hz, 1H), 7.59 (dd, J = 9.2, 2.8 Hz, 1H), 7.20 (d, J = 3.6 Hz, 1H), 7.27 (d, J = 2.4 Hz, 1H), 4.84 (s, 2H), 4.66 (d, J = 6.0 Hz, 2H), 3.95 (s, 3H), 2.36 (s, 3H) |
| 41 | White solid | 456.0 [M + H]⁺, (2.663 min) | 2 | δ (CDCl₃): 8.18 (s, 1H), 7.86 (d, J = 4.0 Hz, 1H), 7.06 (d, J = 4.0, 1H), 6.07 (s, 1H), 4.18 (s, 2H), 4.68 (d, J = 6.0 Hz, 2H), 4.15 (s, 3H), 1.42-1.36 (m, 1H), 1.06-1.02 (m, 2H), 0.83-0.78 (2H) |
| 42 | White solid | 446.1 [M + H]⁺, (2.481 min) | 2 | δ (DMSO-$d_6$): 8.06 (m, 1H), 8.67 (s, 1H), 8.40 (s, 1H), 7.31 (d, J = 6.8 Hz, 1H), 7.12 (d, J = 4.0 Hz, 1H), 4.98 (s, 2H), 4.62 (m, 3H), , 4.02 (s, 1H), , 2.67 (m, 1H), 2.33 (m, 1H) |
| 43 | Light yellow solid | 518.1 [M + H]⁺, (2.894 min) | 2 | δ (DMSO-$d_6$): 9.20 (s, 1H), 9.06 (t, J = 6.0 Hz, 1H), 8.05 (d, J = 3.6 Hz, 1H), 7.14 (d, J = 3.6 Hz, 1H), 4.94 (s, 2H), 4.55 (d, J = 6.0 Hz, 2H), 4.29-4.24 (m, 1H), 1.98-1.88 (m, 3H), 1.40-1.37 (m, 2H), 1.23-1.20 (m, 2H). |
| 44 | Light yellow solid | 560.1 [M + H]⁺, (3.145 min) | 2 | δ (DMSO-$d_6$): 10.3 (t, J = 6.0 Hz, 1H), 9.19 (s, 1H), 8.07 (d, J = 4.0 Hz, 1H), 7.18 (d, J = 3.6 Hz, 1H), 4.94 (s, 2H), 4.65 (d, J = 6.0 Hz, 2H), 4.29-4.24 (m, 1H), 1.41-1.37 (m, 2H), 1.23-1.20 (m, 2H). |
| 45 | Light yellow solid | 458.1 [M + H]⁺, (2.703 min) | 2 | δ (DMSO-$d_6$): 8.72 (t, J = 6.0 Hz, 1H), 8.33 (d, J = 8.4 Hz, 1H), 8.06 (d, J = 4.0 Hz, 1H), 7.88 (d, J = 8.4 Hz, 1H), 7.15 (d, J = 3.6 Hz, 1H), 5.10 (s, 2H), 4.51 (d, J = 6.0 Hz, 2H), 0.98-1.08 (m, 2H), 0.79-0.90 (m, 2H) |
| 46 | White solid | 514.1 [M + H]⁺, (2.852 min) | 2 | δ (CDCl₃): 8.19 (s, 1H), 7.87 (d, J = 4.0 Hz, 1H), 7.09 (d, J = 4.0 Hz, 1H), 6.70 (s, 1H), 4.79-4.76 (m, 4H), 4.53-4.41 (m, 1H), 4.15 (s, 3H), 3.92 (d, J = 5.6 Hz, 1H) |
| 47 | Yellow solid | 553.2 [M + H]⁺, (2.812 min) | 2 | δ (DMSO-$d_6$): 8.71 (m, 1H), 8.05 (d, J = 4.0 Hz, 1H), 7.98 (s, 2H), 7.17 (s, 1H), 7.12 (d, J = 4.0 Hz, 1H), 6.29 (s, 1H), 4.93 (s, 2H), 4.52 (d, J = 6.0 Hz, 2H) |
| 48 | Yellow solid | 474.1 [M + H]⁺, (2.713 min) | 2 | δ (CDCl₃): 8.18 (s, 1H), 7.86 (d, J = 4.0 Hz, 1H), 7.25 (s, 1H), 7.06 (d, J = 4.0 Hz, 1H), 4.78 (s, 2H), 4.67 (d, J = 6.0 Hz, 2H), 4.15 (s, 3H), 2.07 (s, 1H), 1.50 (s, 6H) |
| 49 | Light yellow solid | 472.1 [M + H]⁺, (2.689 min) | 2 | δ (CDCl₃): 8.18 (s, 1H), 7.86 (d, J = 4.0 Hz, 1H), 7.39-7.31 (m, 1H), 7.08 (d, J = 4.0 Hz, 1H), 4.78 (s, 2H), 4.15 (s, 3H), 2.54 (s, 1H), 1.43 (q, J = 2.8 Hz, 2H), 1.10 (q, J = 2.8 Hz, 2H) |
| 50 | Light yellow solid | 444.2 [M + H]⁺, (2.568 min) | 2 | δ (DMSO-$d_6$): 8.73 (m, 1H), 8.09 (d, J = 4.0 Hz, 1H), 7.80 (d, J = 9.2 Hz, 1H), 7.60 (m, 1H), 7.27 (d, J = 2.4 Hz, 1H), 7.14 (d, J = 4.0 Hz, 1H), 6.30 (s, 1H), 4.84 (s, 2H), 4.52 (d, J = 6.4 Hz, 2H), 3.94 (s, 3H), 2.41 (s, 3H), 1.04 (m, 2H), 0.87 (m, 2H) |
| 51 | Yellow solid | 428.1 [M + H]⁺, (2.733 min) | 2 | δ (CDCl₃): 7.79 (d, J = 9.2 Hz, 1H), 7.75 (d, J = 2.8 Hz, 1H), 7.48 (m, 1H), 7.48 (m, 1H), 7.10 (m, 1H), 7.07 (m, 1H), 6.10 (s, 1H), 4.73 (m, 2H), 4.68 (m, 2H), 3.95 (s, 3H), 2.60 (s, 1H), 1.40 (m, 1H), 1.05 (m, 2H), 0.80 (m, 2H) |
| 52 | White solid | 406 [M + H]⁺, (2.016 min) | 2 | δ (CDCl3): 8.65 (s, 1H), 8.08 (s, 1H), 7.83 (s, 1H), 7.04 (t, J = 3.6 Hz, 1H), 4.79 (s, 2H), 4.66 (d, J = 6.4 Hz, 2H), 4.09 (s, 3H), 1.49 (s, 6H) |
| 55 | Off white solid | 439.29 [M + H]⁺, (10.44 min) | 1 | δ (DMSO-$d_6$): 8.87 (t, J = 6.0 Hz, 1H), 8.67 (s, 1H), 8.49-8.47 (m, 1H), 8.40 (s, 1H), 8.05 (d, J = 4.0 Hz, 1H), 7.75-7.71 (m, 1H), 7.34 (d, J = 7.6 Hz, 1H), 7.27-7.23 (m, 1H), 7.13 (d, J = 4.0 Hz, 1H), 4.97 (s, 2H), 4.50 (d, J = 6.0 Hz, 2H), 4.02 (s, 3H), 3.68 (s, 2H). |

TABLE 4-continued

| Ex. | Form | LCMS m/z (Rt) | Method | ¹H-NMR [400 MHz] |
|---|---|---|---|---|
| 56 | Off white solid | 439.23 [M + H]⁺, (9.11 min) | 1 | δ (DMSO-d₆): 8.95 (d, J = 6.0 Hz, 1H), 8.66-8.62 (m, 3H), 8.40 (s, 1H), 8.06 (d, J = 4.0 Hz, 2H), 7.66 (t, J = 8.0 Hz, 1H), 7.14(d, J = 3.6 Hz, 1H), 4.98 (s, 2H), 4.58 (d, J = 6.0 Hz, 2H), 4.02 (s, 3H), 3.68 (s, 2H). |
| 57 | Light yellow solid | 439.23 [M + H]⁺, (8.55 min) | 1 | δ (DMSO-d₆): 8.91 (t, J = 6.0 Hz, 1H), 8.66 (s, 1H), 8.48 (d, J = 5.6 Hz, 2H), 8.39 (s, 1H), 8.04 (d, J = 3.6 Hz, 1H), 7.28 (d, J = 6.0 Hz, 2H), 7.12 (d, J = 4.0 Hz, 1H), 4.97 (s, 2H), 4.50 (d, J = 5.6 Hz, 2H), 4.02 (s, 3H), 3.54 (s, 2H). |
| 58 | Off white solid | 392.26 [M + H]⁺, (10.83 min) | 1 | δ (DMSO-d₆): 8.67 (s, 1H), 8.56 (t, J = 6.0 Hz, 1H), 8.39 (s, 1H), 8.04 (d, J = 4.0 Hz, 1H), 7.12 (d, J = 4.0 Hz, 1H), 4.97 (s, 2H), 4.50 (d, J = 6.4 Hz, 2H), 4.01 (s, 3H), 3.86 (s, 2H), 3.33 (s, 3H). |
| 59 | Off white solid | 378.23 [M + H]⁺, (9.46 min) | 1 | δ (DMSO-d₆): 8.67 (s, 1H), 8.56 (t, J = 6.0 Hz, 1H), 8.39 (s, 1H), 8.04 (d, J = 4.0 Hz, 1H), 7.12 (d, J = 4.0 Hz, 1H), 5.57 (t, J = 5.6 Hz, 1H), 4.97 (s, 2H), 4.50 (d, J = 6.0 Hz, 2H), 4.01 (s, 3H), 3.86 (d, J = 5.6 Hz, 2H). |
| 60 | White solid | 418.1 [M + H]⁺, (2.466 min) | 2 | δ (DMSO-d₆): 8.56 (m, 1H), 8.09 (m, 1H), 7.80 (m, 1H), 7.27 (d, J = 2.8 Hz, 1H), 7.14 (d, J = 3.6 Hz, 1H), 5.57 (m, 1H), 4.84 (s, 2H), 4.52 (d, J = 6.0 Hz, 2H), 3.94 (s, 3H), 3.85 (d, J = 4 Hz, 2H), 2.41 (s, 3H) |
| 61 | White solid | 446.07 [M + H]⁺, (9.74 min) | 4 | δ (DMSO-d₆): 9.06 (s, 1H), 8.56 (t, J = 6.4 Hz, 1H), 8.04 (d, J = 4.0 Hz, 1H), 7.12 (d, J = 4.0 Hz, 1H), 5.57 (t, J = 6.0 Hz, 1H), 4.94 (s, 2H), 4.50 (d, J = 6.4 Hz, 2H), 4.25 (s, 3H), 3.86 (d, J = 6.0 Hz, 2H). |
| 62 | Off white solid | 402.07 [M + H]⁺, (11.38 min) | 1 | δ (DMSO-d₆): 8.53 (t, J = 6.4 Hz, 1H), 8.13-8.09 (m, 2H), 7.95-7.86 (m, 2H), 7.69-7.67 (m, 1H), 7.13 (d, J = 3.6 Hz, 1H), 5.57 (t, J = 5.6 Hz, 1H), 4.86 (s, 2H), 4.51 (d, J = 6.0 Hz, 2H), 3.86 (d, J = 6.0 Hz, 2H), 2.70 (q, J = 7.6 Hz, 2H), 1.09 (t, J = 7.6 Hz, 3H). |
| 63 | Yellow solid | 527.1 [M + H]⁺, (2.697 min) | 2 | δ (DMSO-d₆): 8.56 (m, 1H), 8.05 (d, J = 4.0 Hz, 1H), 7.95 (s, 2H), 7.17 (s, 1H), 7.13 (d, J = 4.0 Hz, 1H), 5.57 (m, 1H), 4.93 (s, 2H), 4.52 (d, J = 6.4 Hz, 2H), 3.87 (d, J = 5.6 Hz, 2H), 3.82 (m, 4H), 3.43 (m, 4H), 3.29 (s, 1H) |
| 64 | Yellow solid | 389.1 [M + H]⁺, (2.023 min) | 2 | δ (DMSO-d₆): 9.20-9.18 (m, 1H), 8.62-8.59 (m, 1H), 8.57 (t, J = 6.4 Hz, 1H), 8.10 (d, J = 4.0 Hz, 1H), 7.70-7.67 (m, 1H), 5.59 (t, J = 5.6 Hz, 1H), 4.91 (s, 2H), 4.52 (d, J = 6.0 Hz, 2H), 3.87 (d, J = 5.6 Hz, 2H), 3.32 (s, 3H). |
| 65 | White solid | 392.1 [M + H]⁺, (2.225 min) | 2 | δ (CDCl₃): 8.00 (s, 1H), 7.86 (d, J = 4.0 Hz, 1H), 7.08 (d, J = 3.9 Hz, 1H), 4.78-4.69 (m, 4H), 4.21 (s, 2H), 4.05 (s, 3H), 2.58 (s, 3H). |
| 66 | Yellow solid | 388.1 [M + H]⁺, (2.406 min) | 2 | δ (MeOD): 8.15 (d, J = 8.4 Hz, 1H), 8.03 (d, J = 4.0 Hz, 1H), 7.95-7.89 (m, 1H), 7.85-7.80 (m, 1H), 7.64 (t, J = 7.6 Hz, 1H), 7.16 (d, J = 4.0 Hz, 1H), 4.66 (s, 2H), 4.03 (s, 2H), 2.49 (s, 3H) |
| 67 | Yellow solid | 406.1 [M + H]⁺, (2.477 min) | 2 | δ (DMSO-d₆): 8.54 (t, J = 6.0 Hz, 1H), 8.08 (d, J = 4.0 Hz, 1H), 7.96-7.92 (m, 1H), 7.89-7.84 (m, 2H), 7.14 (d, J = 3.6 Hz, 1H), 5.56 (s, 1H), 4.86 (s, 2H), 4.51 (d, J = 6.0 Hz, 2H), 3.86 (s, 2H), 2.43 (s, 3H). |
| 68 | Yellow solid | 406.1 [M + H]⁺, (2.493 min) | 2 | δ (DMSO-d₆): 8.54 (t, J = 6.4 Hz, 1H), 8.25-8.23 (m, 1H), 8.08 (d, J = 4.0 Hz, 1H), 7.65-7.56 (m, 2H), 7.14 (d, J = 3.6 Hz, 1H), 5.56 (t, J = 5.6 Hz, 1H), 4.86 (s, 2H), 4.51 (d, J = 6.0 Hz, 2H), 3.86 (d, J = 6.0 Hz, 2H), 2.43 (s, 3H) |
| 69 | White solid | 428.1 [M + H]⁺, (2.428 min) | 2 | δ (DMSO-d₆): 8.56-8.52 (m, 2H), 8.05 (d, J = 4.0 Hz, 1H), 7.12 (d, J = 4.0 Hz, 1H), 6.79 (t, J = 54 Hz, 1H), 5.61 (t, J = 5.6 Hz, 1H), 4.99 (s, 2H), 4.50 (d, J = 6.0 Hz, 2H), 4.05 (s, 3H), 3.86 (d, J = 5.6 Hz, 2H). |
| 70 | Yellow solid | 418.1 [M + H]⁺, (2.495 min) | 2 | δ (DMSO-d₆): 8.55 (t, J = 6.0 Hz, 1H), 8.07 (d, J = 4.0 Hz, 1H), 8.00 (d, J = 8.8 Hz, 1H), 7.27-7.23 (m, 2H), 7.13 (d, J = 4.0 Hz, 1H), 5.58-5.55 (m, 1H), 4.81 (s, 2H), 4.51 (d, J = 6.0 Hz, 2H), 3.93 (s, 3H), 3.86 (d, J = 5.2 Hz, 2H), 2.40 (s, 3H). |
| 71 | White solid | 432.0 [M + H]⁺, (2.258 min) | 2 | δ (CDCl₃): 8.91 (s, 1H), 7.95 (s, 1H), 7.84 (d, J = 4.0 Hz, 1H), 7.15 (d, J = 4.0 Hz, 1H), 7.08 (s, 1H), 4.86 (s, 2H), 4.78 (d, J = 6.0 Hz, 2H), 4.26 (s, 2H) |
| 72 | Off-white | 431.9 [M + H]⁺, | 2 | δ (DMSO-d₆): 8.56 (t, J = 6.4 Hz, 1H), 8.33 (d, J = 8.4 Hz, 1H), 8.07 (t, J = 7.2 Hz, 1H), 7.88 (d, J = |

TABLE 4-continued

| Ex. | Form | LCMS m/z (Rt) | Method | ¹H-NMR [400 MHz] |
|---|---|---|---|---|
| | solid | (2.599 min) | | 8.4 Hz, 1H), 7.16 (d, J = 4.0 Hz, 1H), 5.56 (s, 1H), 5.10 (s, 2H), 4.51 (d, J = 6.0 Hz, 2H), 3.86 (s, 2H). |
| 73 | Yellow solid | 440.1 [M + H]⁺, (2.746 min) | 2 | δ (DMSO-d₆): 8.55 (t, J = 6.0 Hz, 1H), 8.36 (d, J = 7.6 Hz, 1H), 8.08 (d, J = 4.0 Hz, 1H), 7.89 (d, J = 10.4 Hz, 1H), 7.14 (d, J = 4.0 Hz, 1H), 5.56 (t, J = 6.0 Hz, 1H), 4.87 (s, 2H), 4.51 (d, J = 6.0 Hz, 2H), 3.86 (d, J = 5.6 Hz, 2H), 2.43 (s, 3H). |
| 74 | Off-white solid | 446.1 [M + H]⁺, (2.560 min) | 2 | δ (DMSO-d₆): 8.61 (s, 1H), 8.57 (t, J = 6.4 Hz, 1H), 8.05 (d, J = 4.0, 1H), 7.12 (d, J = 4.4 Hz, 1H), 4.98 (s, 2H), 4.50 (d, J = 6.4 Hz, 2H), 4.06 (s, 3H), 3.86 (s, 2H) |
| 75 | Yellow soild | 436.1 [M + H]⁺, (2.548 min) | 2 | δ (DMSO-d₆): 8.54 (t, J = 6.4 Hz, 1H), 8.08 (d, J = 3.6 Hz, 1H), 7.69 (d, J = 12 Hz, 1H), 7.44 (d, J = 9.2 Hz, 1H), 7.13 (d, J = 4.0 Hz, 1H), 5.57-5.54 (m, 1H), 4.85 (s, 1H), 4.51 ((d, J = 6.0 Hz, 2H), 4.04 (s, 3H), 3.86 (d, J = 6.0 Hz, 2H), 2.41 (s, 3H) |
| 76 | Yellow solid | 456.1 [M + H]⁺, (2.753 min) | 2 | δ (DMSO-d₆): 8.59-8.56 (m, 1H), 8.39 (s, 1H), 8.24-8.22 (m, 1H), 8.11-8.05 (m, 2H), 7.14 (d, J = 3.6 Hz, 1H), 5.58 (t, J = 6.0 Hz, 1H), 4.91 (s, 2H), 4.51 (6.0 Hz, 2H), 3.86 (d, J = 6.0 Hz, 2H), 3.33 (s, 3H). |
| 77 | yellow solid | 444.1 [M + H]⁺, (2.672 min) | 2 | δ (DMSO-d₆): 8.55 (t, J = 6.0 Hz, 1H), 8.09 (d, J = 3.6 Hz, 1H), 7.79 (d, J = 8.8 Hz, 1H), 7.60-7.57 (m, 2H), 7.14 (d, J = 3.6 Hz, 1H), 5.57 (t, J = 6.0 Hz, 1H), 4.84 (s, 2H), 4.51 (d, J = 6.4 Hz, 2H), 4.10-4.07 (m, 1H), 3.86 (d, J = 5.6 Hz, 2H), 2.41 (s, 3H), 0.92-0.74 (m, 4H). |
| 78 | Yellow solid | 457.1 [M + H]⁺, (2.653 min) | 2 | δ (DMSO-d₆): 8.53 (t, J = 6.4 Hz, 1H), 8.06 (d, J = 4.0 Hz, 1H), 7.57 (d, J = 9.2 Hz, 1H), 7.38-7.41 (m, 1H), 7.13(d, J = 3.6 Hz, 1H), 6.64 (d, J = 2.4 Hz, 1H), 6.58 (t, J = 3.2 Hz, 1H), 5.55 (t, J = 6.0 Hz, 1H), 4.77 (s, 2H), 4.51(d, J = 6.4 Hz, 2H), 3.87 (d, J = 6.0 Hz, 2H), 3.00 (t, J = 6.0 Hz, 2H), 2.34 (s, 3H), 1.09-1.15 (m, 1H), 0.51-0.55 (m, 2H), 0.27-0.31 (m, 2H). |
| 79 | Yellow solid | 472.1 [M + H]⁺, (2.503 min) | 2 | δ (DMSO-d6): 9.19 (s, 1H), 8.53 (t, J = 6.8 Hz, 1H), 8.03 (d, J = 4.0 Hz, 1H), 7.11 (d, J = 3.6 Hz, 1H), 5.55 (t, J = 6.0 Hz, 1H), 4.94 (s, 2H), 4.50 (d, J = 6.4 Hz, 2H), 4.29-4.24 (m, 1H), 3.86 (d, J = 6.0 Hz, 2H), 1.41-1.38 (m, 2H), 1.24-1.20 (m, 2H). |
| 80 | White solid | 471.9 [M + H]⁺, (2.502 min) | 2 | δ (CDCl3): 8.01-7.99 (m, 2H), 7.72-7.69 (m, 1H), 7.47 (d, J = 2.8 Hz, 1H), 7.15 (d, J = 4.0 Hz, 1H), 4.90 (s, 2H), 4.66 (s, 2H), 4.04 (s, 2H), 4.03 (s, 3H). |
| 81 | Yellow solid | 473.2 [M + H]⁺, (2.397 min) | 2 | δ (DMSO-d6): 8.53 (t, J = 6.0 Hz, 1H), 8.07 (d, J = 4.0 Hz, 1H), 7.81-7.78 (m, 1H), 7.72 (d, J = 9.6 Hz, 1H), 7.13 (d, J = 4.0 Hz, 1H), 7.07 (d, J = 2.4 Hz, 1H), 5.52 (t, J = 5.6 Hz, 1H), 4.81 (s, 2H), 4.51 (d, J = 6.0 Hz, 2H), 3.86 (d, J = 6.0 Hz, 2H), 3.79 (t, J = 4.4 Hz, 4H), 3.28 (t, J = 4.0 Hz, 4H), 2.39 (s, 3H) |
| 82 | Yellow solid | 471.2 [M + H]⁺, (2.828 min) | 2 | δ (DMSO-d6): 8.54 (t, J = 6.4 Hz, 1H), 8.07 (d, J = 4.0 Hz, 1H), 7.76-7.79 (m, 1H), 7.67 (d, J = 9.6 Hz, 1H), 7.13 (d, J = 4.0 Hz, 1H), 7.04 (d, J = 2.4 Hz, 1H), 5.55 (t, J = 5.6 Hz, 1H), 4.80 (s, 2H), 4.51 (d, J = 6.4 Hz, 2H), 3.86 (d, J = 5.6 Hz, 2H), 3.32 (s, 4H), 2.38 (s, 3H), 1.66-1.67 (m, 4H), 1.56-1.60 (m, 2H). |
| 83 | Yellow solid | 487.2 [M + H]⁺, (2.458 min) | 2 | δ (DMSO-d₆): 8.54 (t, J = 6.0 Hz, 1H), 8.07 (d, J = 4.0 Hz, 1H), 7.68-7.61 (m, 2H), 7.13 (d, J = 4.0 Hz, 2H), 6.85 (d, J = 2.8 Hz, 1H), 5.57-5.53 (m, 1H), 4.79 (s, 2H), 4.51 (d, J = 6.0 Hz, 2H), 3.86 (d, J = 5.6 Hz, 2H), 3.78-3.71 (m, 7H), 3.62-3.32 (m, 2H), 2.36 (s, 3H), 1.97-1.94 (m, 2H) |
| 84 | Yellow solid | 493.1 [M + H]⁺, (2.691 min) | 2 | δ (DMSO-d6): 8.56 (t, J = 6.4 Hz, 1H), 8.08 (d, J = 4.0 Hz, 1H), 7.73 (d, J = 9.2 Hz, 1H), 7.47-7.44 (d, 1H), 7.13 (d, J = 4.0 Hz, 1H), 6.72 (d, J = 2.4 Hz, 1H), 5.58 (t, J = 5.6 Hz, 1H), 4.80 (s, 2H), 4.50 (d, J = 6.0 Hz, 2H), 3.87 (t, J = 7.6 Hz, 4H), 3.64 (t, J = 7.2 Hz, 2H), 2.64-2.56 (m, 2H), 2.36 (s, 3H). |

TABLE 4-continued

| Ex. | Form | LCMS m/z (Rt) | Method | ¹H-NMR [400 MHz] |
|---|---|---|---|---|
| 85 | Yellow solid | 486.2 [M + H]⁺, (2.337 min) | 2 | δ (DMSO-$d_6$): 8.51-8.61 (m, 1H), 8.09 (d, J = 4.0 Hz, 1H), 7.81 (d, J = 2.8 Hz, 1H), 7.67-7.76 (m, 1H), 6.97-7.20 (m, 2H), 5.57 (t, J = 6.0 Hz, 1H), 4.82 (s, 2H), 4.53 (d, J = 6.4 Hz, 2H), 3.88 (d, J = 6.0 Hz, 2H), 3.32 (s, 4H), 2.49-2.51 (m, 4H), 2.40 (s, 3H), 2.26 (s, 3H) |
| 86 | Yellow solid | 418.0 [M + H]⁺, (2.088 min) | 2 | δ (CD$_3$CN): 8.60 (s, 1H), 8.17 (s, 1H), 7.93-7.92(d, J = 3.6 Hz, 1H), 7.19-7.09 (t, J = 2.8 Hz, 1H), 4.84 (s, 2H), 4.01-3.98 (m, 5H), 3.78-3.69 (m, 2H), 3.51-3.46 (m, 2H), 3.44-3.32 (m, 1H), 2.46-2.39 (m, 1H), 2.05-2.04 (m, 1H) |
| 87 | White solid | 398.18 [M + H]⁺, (11.05 min) | 1 | δ (DMSO-$d_6$): 8.67 (s, 1H), 8.40 (s, 1H), 8.08 (d, J = 3.6 Hz, 1H), 7.88 (t, J = 6.4 Hz, 1H), 7.20 (d, J = 3.6 Hz, 1H), 4.99 (s, 2H), 4.42 (d, J = 6.0 Hz, 2H), 4.01 (s, 3H), 2.94 (s, 3H). |
| 88 | White solid | 460.15 [M + H]⁺, (13.93 min) | 1 | δ (DMSO-$d_6$): 8.67 (s, 1H), 8.48 (t, J = 6.4 Hz, 1H), 8.40 (s, 1H), 7.99 (d, J = 4.0 Hz, 1H), 7.80 (d, J = 7.2 Hz, 2H), 7.66-7.57 (m, 3H), 7.08 (d, J = 4.0 Hz, 1H), 4.96 (s, 2H), 4.26 (d, J = 6.0 Hz, 2H), 4.02 (s, 3H). |
| 89 | Light yellow solid | 424.19 [M + H]⁺, (12.16 min) | 1 | δ (DMSO-$d_6$): 8.66 (s, 1H), 8.40 (s, 1H), 8.07 (d, J = 4.0 Hz, 1H), 7.95 (t, J = 6.4 Hz, 1H), 7.21 (d, J = 4.0 Hz, 1H), 4.99 (s, 2H), 4.44 (d, J = 6.0 Hz, 2H), 4.01 (s, 3H), 2.57-2.50 (m, 1H), 0.92 (d, J = 8.0 Hz, 4H). |
| 90 | White solid | 474.21 [M + H]⁺, (14.16 min) | 1 | δ (DMSO-$d_6$): 8.66 (s, 1H), 8.39 (s, 1H), 8.06 (d, J = 4.0 Hz, 1H), 7.97 (d, J = 6.0 Hz, 1H), 7.37 (s, 5H), 7.15 (d, J = 4.0 Hz, 1H), 4.99 (s, 2H), 4.39 (s, 2H), 4.33 (d, J = 6.0 Hz, 2H), 4.01 (s, 3H). |
| 91 | Off white solid | 438.23 [M + H]⁺, (13.74 min | 1 | δ (DMSO-$d_6$): 8.67 (s, 1H), 8.40 (s, 1H), 8.10 (d, J = 4.0 Hz, 1H), 7.26 (d, J = 3.6 Hz, 1H), 5.00 (s, 2H), 4.59 (s, 2H), 4.02 (s, 3H), 2.82 (s, 3H), 2.69 (t, J = 6.4 Hz, 1H), 1.00 (d, J = 6.0 Hz, 4H). |
| 92 | Off white solid | 489.21 [M + H]⁺, (12.25 min) | 1 | δ (DMSO-$d_6$): 8.66 (s, 1H), 8.61 (q, J = 6.0 Hz, 2H), 8.39 (s, 1H), 8.08 (d, J = 4.0 Hz, 1H), 7.44 (q, J = 6.0 Hz, 2H), 7.21 (d, J = 4.0 Hz, 1H), 4.99 (s, 2H), 4.63(s, 2H), 4.47(s, 2H), 4.01 (s, 3H), 2.76 (s, 3H). |
| 93 | White solid | 448.14 [M + H]⁺, (14.18 min | 1 | δ (DMSO-$d_6$): 8.13-8.11 (m, 2H), 7.98-7.91 (m, 2H), 7.85 (d, J = 8.0 Hz, 1H), 7.70-7.66 (m, 1H), 7.21 (d, J = 4.0 Hz, 1H), 4.86 (s, 2H), 4.43 (d, J = 6.0 Hz, 2H), 2.99 (d, J = 7.2 Hz, 2H), 2.43 (s, 3H), 1.03-0.98 (m, 1H), 0.60-0.55 (m, 2H), 0.34-0.30 (m, 2H). |
| 94 | Light brown solid | 422.23 [M + H]⁺, (13.26 min) | 1 | δ (DMSO-$d_6$): 8.14-8.11 (m, 2H), 7.97-7.93 (m, 1H), 7.85 (d, J = 8.4 Hz, 1H), 7.69-7.65 (m, 1H), 7.24 (t, J = 5.6 Hz, 1H), 7.15 (d, J = 3.6 Hz, 1H), 4.85 (s, 2H), 3.34-3.23 (m, 2H), 3.07 (t, J = 7.2 Hz, 2H), 2.90 (s, 3H), 2.43 (s, 3H). |
| 95 | Off white solid | 502.22 [M + H]⁺, (17.22 min) | 4 | δ (DMSO-$d_6$): 8.35 (d, J = 8.0 Hz, 1H), 8.17-8.13 (m, 3H), 7.97-7.93 (m, 1H), 7.24 (d, J = 3.6 Hz, 1H), 4.98 (s, 2H), 3.81-3.75 (m, 2H), 3.48-3.43 (m, 1H), 3.40-3.34 (m, 1H), 3.24-3.22 (m, 1H), 2.97 (s, 3H), 2.41-2.38 (m, 1H), 2.07-2.01 (m, 1H). |
| 96 | Yellow solid | 439.1 [M + H]⁺, (2.485 min) | 2 | δ (CD$_3$CN): 8.59 (s, 1H), 8.16 (s, 1H), 7.92 (d, J = 4.0 Hz, 1H), 7.10 (d, J = 4.0 Hz, 1H), 5.27 (br s, 2 H), 4.84 (s, 2H), 4.01 (s, 3H), 3.73-3.83 (m, 1H), 3.69 (dd, J = 9.6, 7.2 Hz, 1H), 3.40-3.48 (m, 1H), 3.35-3.32 (m, 1H), 3.24-3.20 (m, 1H), 247-2.39 (m, 1H), 2.07-2.04 (m, 1H) |
| 97 | Off white solid | 408.09 [M + H]⁺, (12.45 min) | 1 | δ (DMSO-$d_6$): 8.14-8.12 (m, 2H), 7.98-7.94 (m, 1H), 7.91-7.84 (m, 2H), 7.70-7.66 (m, 1H), 7.23-7.21 (m, 1H), 4.87 (s, 2H), 4.43 (d, J = 6.4 Hz, 2H), 2.92 (s, 3H), 2.42 (s, 3H). |
| 98 | White solid | 476.10 [M + H]⁺, (15.28 min) | 1 | δ (DMSO-$d_6$): 8.35 (d, J = 8.0 Hz, 1H), 8.19-8.13 (m, 2H), 8.08 (d, J = 4.0 Hz, 1H), 8.06-7.999 (m, 1H), 7.96-7.92 (m, 1H), 7.09 (d, J = 4.0 Hz, 1H), 4.98 (s, 2H), 3.35-3.30 (m, 2H), 3.01 (t, J = 6.8 Hz, 2H), 1.80 (s, 3H) |
| 101 | Off white solid | 412.28 [M + H]+ (12.67 min) | 1 | δ (DMSO-$d_6$): 8.12-8.07 (m, 2H), 8.02 (t, J = 5.2 Hz, 1H), 7.93-7.89 (m, 1H), 7.80 (d, J = 8.4 Hz, 1H), 7.63-7.59 (m, 1H), 7.11 (d, J = 3.6 Hz, 1H), 4.84 (s, 2H), 3.34 (d, J = 6.8 Hz, 2H), 3.01 (t, J = 6.8 Hz, 2H), 2.03-2.01 (m, 1H), 1.80 (s, 3H), 0.82 (t, J = 5.6 Hz, 4H). |
| 103 | White solid | 362.19 [M + H]+ | 1 | δ (DMSO-$d_6$): 8.67 (s, 1H), 8.62 (t, d, J = 6 Hz, 1H), 8.40 (s, 1H), 8.05 (d, J = 4.0 Hz, 1H), 7.12 |

TABLE 4-continued

| Ex. | Form | LCMS m/z (Rt) | Method | $^1$H-NMR [400 MHz] |
|---|---|---|---|---|
| | | (10.12 min) | | (d, J = 4.0 Hz, 1H), 4.98 (s, 2H), 4.46 (d, J = 6.0 Hz, 2H), 4.01 (s, 3H), 1.87 (s, 3H) |
| 105 | White solid | 431.1 [M + H]$^+$, (0.988 min) | 2 | δ (DMSO-d$_6$): 7.77-7.89 (m, 2H), 7.54 (d, J = 0.8 Hz, 2H), 7.10 (d, J = 4.0 Hz, 1H), 6.96-7.04 (m, 1H), 4.79 (s, 2H), 4.73 (d, J = 6.0 Hz, 2H), 4.22 (d, J = 4.8 Hz, 2H), 2.38 (t, J = 5.2 Hz, 1H) |
| 106 | Yellow solid | 428.1 [M + H]$^+$, (2.710) | 2 | δ (DMSO-d$_6$): 8.54 (t, J = 6.4 Hz, 1H), 8.08 (d, J = 4.0 Hz, 1H), 7.76-7.73 (m, 2H), 7.61-7.58 (m, 1H), 7.14 (d, J = 3.6 Hz, 1H), 5.56 (t, J = 6.0 Hz, 1H), 4.83 (s, 2H), 4.51 (d, J = 6.0 Hz, 2H), 3.86 (d, J = 6.0 Hz, 2H), 2.41 (s, 3H), 2.24-2.20 (m, 1H), 1.09-1.06 (m, 2H), 0.86-0.83 (m, 2H) |
| 107 | Yellow solid | 446.1 [M + H]$^+$, (2.594 min) | 2 | δ (DMSO-d$_6$): 7.98 (d, J = 3.6 Hz, 1H), 7.16 (d, J = 4.0 Hz, 1H), 6.71 (s, 1H), 4.66 (s, 2H), 4.03 (s, 2H), 2.57 (s, 3H) |
| 108 | Yellow solid | 436.1 [M + H]$^+$, (2.531 min) | 2 | δ (DMSO-d$_6$): 8.55 (t, J = 6.0 Hz, 1H), 8.09 (d, J = 4.0 Hz, 1H), 7.58-7.54 (m, 1H), 7.14 (d, J = 2.8 Hz, 2H), 5.56 (t, J = 5.6 Hz, 1H), 4.86 (s, 2H), 4.51 (d, J = 6.4 Hz, 2H), 3.96 (s, 3H), 3.87 (d, J = 6.0 Hz, 2H), 2.43 (s, 3H) |
| 109 | Yellow solid | 432.2 [M + H]$^+$, (2.586 min) | 2 | δ (DMSO-d$_6$): 8.27 (t, J = 3.6 Hz, 1H), 8.22 (s, 1H), 7.90 (d, J = 9.2 Hz, 1H), 7.72-7.69 (m, 1H), 7.38 (d, J = 2.8 Hz, 1H), 7.33 (d, J = 4.0 Hz, 1H), 4.97 (d, J = 11.2 Hz, 2H), 4.86 (d, J = 13.2 Hz, 2H), 4.77 (t, J = 6.0 Hz, 1H), 4.29 (d, J = 5.6 Hz, 1H), 4.24 (d, J = 5.6 Hz, 2H), 3.00 (d, J = 17.2 Hz, 3H), 2.49 (d, J = 4.4 Hz, 3H) |
| 110 | Yellow solid | 435.1 [M + H]$^+$, (2.412 min) | 2 | δ (DMSO-d$_6$): 9.20-9.18 (m, 1H), 9.07 (t, J = 6.0 Hz, 1H), 8.62-8.59 (m, 1H), 8.11 (d, J = 3.6 Hz, 1H), 7.69-7.66 (m, 1H), 7.17 (d, J = 3.6 Hz, 1H), 4.90 (s, 2H), 4.56 (d, J = 6.0 Hz, 2H), 2.68-2.61 (m, 1H), 1.95-1.86 (m, 2H) |
| 111 | Off white solid | 492.1 [M + H]$^+$, (2.946 min) | 2 | δ (DMSO-d$_6$): 9.08 (t, J = 6.0 Hz, 1H), 8.61 (s, 1H), 8.06 (d, J = 4.0 Hz, 1H), 7.15 (d, J = 4.0 Hz, 1H), 4.98 (s, 2H), 4.55 (d, J = 6.0 Hz, 2H), 4.07 (s, 3H), 2.67-2.59 (m, 1H), 1.95-1.86 (m, 2H) |
| 112 | Off white solid | 472.1 [M + H]$^+$, (2.772 min) | 2 | δ (DMSO-d$_6$): 7.97 (d, J = 4.0 Hz, 1H), 7.15 (d, J = 4.0 Hz, 1H), 6.60 (s, 1H), 4.86 (s, 2H), 4.66 (s, 2H), 4.03 (s, 2H), 2.26-2.19 (m, 1H), 1.18-1.16 (m, 2H), 1.04-1.02 (m, 2H) |
| 113 | White solid | 442.9 [M + H]$^+$, (2.025 min) | 2 | δ (DMSO-d$_6$): 9.38 (dd, J = 1.6, 2.0 Hz, 1H), 8.82 (d, J = 6.4 Hz, 1H), 8.82 (t, J = 6.4 Hz, 1H), 8.07 (d, J = 4.0 Hz, 1H), 7.93-7.90 (m, 1H), 7.13 (d, J = 4.0 Hz, 1H), 5.01 (m, 2H), 4.51 (d, J = 6.0 Hz, 2H), 3.86 (m, 2H) |
| 114 | Brown solid | 488.9 [M + H]$^+$, (2.375 min) | 2 | δ (DMSO-d$_6$): 9.38 (dd, J = 1.6, 2.0 Hz, 1H), 9.07 (t, J = 5.6 Hz, 1H), 8.82 (dd, J = 1.6, 2.0 Hz, 1H), 8.08 (d, J = 4.0 Hz, 1H), 7.93-7.91 (m, 1H), 7.15 (d, J = 4.0 Hz, 1H), 5.01 (m, 2H), 4.56 (d, J = 6.0 Hz, 2H), 2.67-2.61 (m, 1H), 1.95-1.86 (m, 2H) |
| 115 | Yellow solid | 458.2 [M + H]$^+$, (2.567 min) | 2 | δ (DMSO-d$_6$): 8.12 (d, J = 4.0 Hz, 1H), 7.80 (d, J = 9.2 Hz, 1H), 7.59 (dd, J = 9.2, 2.8 Hz, 1H), 7.28 (d, J = 2.8 Hz, 1H), 7.13 (d, J = 4.0 Hz, 1H), 5.52 (d, J = 5.6 Hz, 1H), 4.84 (s, 2H), 4.06 (d, J = 5.6 Hz, 1H), 3.95 (s, 3H), 3.40-3.58 (m, 2H), 3.09-3.30 (m, 4H), 2.40 (s, 3H), 2.19-2.30 (m, 1H), 1.60-1.73 (m, 1H) |
| 116 | Yellow solid | 460.1 [M + H]$^+$, (2.674 min) | 2 | δ (DMSO-d$_6$): 8.61 (s, 1H), 8.12-8.06 (m, 1H), 7.30-7.20 (m, 1H), 4.97 (s, 2H), 4.75-4.64 (m, 3H), 4.17-4.12 (m, 2H), 4.11 (s, 3H), 2.90-2.85 (m, 3H) |
| 117 | White solid | 432.0 [M + H]$^+$, (2.689 min) | 2 | δ (DMSO-d$_6$): 8.56 (t, J = 6.4 Hz, 1H), 8.29 (d, J = 8.0 Hz, 1H), 8.05 (d, J = 3.6 Hz, 1H), 7.94 (d, J = 8.0 Hz, 1H), 7.15 (d, J = 3.6 Hz, 1H), 5.10 (s, 2H), 4.51 (d, J = 6.4 Hz, 2H), 3.86 (s, 2H). |
| 118 | Light yellow solid | 432.1 [M + H]$^+$, (2.590 min) | 2 | δ (DMSO-d$_6$): 8.83 (d, J = 1.2 Hz, 1H), 8.65 (d, J = 2.0 Hz, 1H), 8.57 (t, J = 6.0 Hz, 1H), 8.06 (d, J = 4.0 Hz, 1H), 7.16 (d, J = 4.0 Hz, 1H), 5.74-5.36 (m, 1H), 5.13 (s, 2H), 4.51 (d, J = 6.0 Hz, 2H), 3.86 s, 2H) |
| 119 | Yellow solid | 457.1 [M + H]$^+$, (2.454 min) | 2 | δ (DMSO-d$_6$): 9.53 (d, J = 2.4 Hz, 1H), 8.93 (d, J = 1.6 Hz, 1H), 8.57 (t, J = 6.0 Hz, 1H), 8.12 (d, J = 4.0 Hz, 1H), 7.17 (d, J = 4.0 Hz, 1H), 5.58 (t, J = 5.8 Hz, 1H), 4.97 (s, 2H), 4.54 (d, J = 6.0 Hz, 2H), 3.88 (d, J = 6.0 Hz, 2H), 3.31 (s, 3H) |
| 120 | Light yellow | 518.1 [M + H]$^+$, | 2 | δ (DMSO-d$_6$): 9.06 (t, J = 6.0 Hz, 1H), 8.11 (d, J = 4.0 Hz, 1H), 8.07-7.92 (m, 3H), 7.17 (d, J = 4.0 |

TABLE 4-continued

| Ex. | Form | LCMS m/z (Rt) | Method | ¹H-NMR [400 MHz] |
|---|---|---|---|---|
| | solid | (3.133 min) | | Hz, 1H), 4.89 (s, 2H), 4.56 (d, J = 6.0 Hz, 2H), 2.65-2.59 (m, 1H), 2.45 (s, 3H), 2.01-1.80 (m, 2H) |
| 121 | Yellow solid | 419.1 [M + H]⁺, (2.322 min) | 2 | δ (MeOD): 8.93 (s, 1H), 8.01 (d, J = 3.6 Hz, 1H), 7.23 (s, 1H), 7.20 (s, 1H), 4.85 (s, 2H), 4.66 (s, 2H), 4.05 (s, 3H), 4.03 (s, 2H), 2.48 (s, 3H) δ (CDCl₃): 9.03 (s, 1H), 8.85 (d, J = 3.6 Hz, 1H), 7.16 (s, 1H), 7.10 (d, J = 3.6 Hz, 1H), 6.96 (s, 1H), 4.73 (d, J = 6.0 Hz, 2H), 4.67 (s, 2H), 4.22 (s, 2H), 4.06 (s, 3H), 2.60 (s, 3H) |
| 122 | Yellow solid | 489.0 [M + H]⁺, (2.621 min) | 2 | δ (DMSO-d₆): 9.53-9.36 (m, 1H), 9.36-9.30 (m, 1H), 8.84 (dd, J = 8.3, 1.5 Hz, 1H), 8.11 (d, J = 3.8 Hz, 1H), 7.83-8.02 (m, 2H), 7.23 (d, J = 3.8 Hz, 1H), 5.03 (s, 2H), 4.46 (d, J = 6.3 Hz, 2H), 1.01-0.81 (m, 4H) |
| 123 | Light yellow solid | 531.0 [M + H]⁺, (2.770 min) | 2 | δ (DMSO-d₆): 9.57-9.27 (m, 1H), 8.83 (br d, J = 8.4 Hz, 1H), 8.67 (br t, J = 6.0 Hz, 1H), 8.11 (d, J = 3.6 Hz, 1H), 7.93 (dd, J = 8.4, 4.4 Hz, 1H), 7.23 (d, J = 3.6 Hz, 1H), 5.03 (s, 2H), 4.67-4.35 (m, 4H) |
| 124 | Light yellow solid | 407.1 [M + H]⁺, (2.128 min) | 2 | δ (DMSO-d₆): 9.24 (d, J = 2.4 Hz, 1H), 8.55 (t, J = 6.4 Hz, 1H), 8.51-8.48 (m, 1H), 8.09 (d, J = 3.6 Hz, 1H), 7.15 (d, J = 3.6 Hz, 1H), 5.55 (t, J = 6.0 Hz, 1H), 4.90 (s, 2H), 4.51 (d, J = 6.0 Hz, 2H), 3.86 (d, J = 6.0 Hz, 2H), 2.50 (s, 3H). |
| 125 | Light yellow solid | 490.1 [M + H]⁺, (2.564 min) | 2 | δ (DMSO-d₆): 8.64 (s, 1H), 8.54 (t, J = 6.2 Hz, 1H), 8.04 (d, J = 4.0 Hz, 1H), 7.12 (d, J = 4.0 Hz, 1H), 5.55 (t, J = 5.8 Hz, 1H), 4.98 (s, 2H), 4.61 (t, J = 5.2 Hz, 2H), 4.51 (d, J = 6.2 Hz, 2H), 3.86 (d, J = 5.8 Hz, 2H), 3.81 (t, J = 5.3 Hz, 2H), 3.17 (s, 3H) |
| 126 | Light yellow solid | 472.1 [M + H]⁺, (2.774 min) | 2 | δ (DMSO-d₆): 8.55 (t, J = 6.0 Hz, 1H), 8.09 (d, J = 4.0 Hz, 1H), 8.05-7.95 (m, 3H), 7.14 (d, J = 4.0 Hz, 1H), 5.56 (t, J = 5.6 Hz, 1H), 4.89 (s, 2H), 4.52 (d, J = 6.0 Hz, 2H), 3.87 (d, J = 6.0 Hz, 2H), 2.48-2.44 (m, 3H) |
| 127 | Yellow solid | 477.1 [M + H]⁺, (2.552 min) | 2 | δ (DMSO-d₆): 9.38 (q, J = 2.4 Hz, 1H), 8.83 (q, J = 6.4 Hz, 1H), 8.10 (d, J = 4.0 Hz, 1H), 7.94-7.91 (m, 2H), 7.21 (d, J = 4.0 Hz, 1H), 5.02 (s, 1H), 4.41 (d, J = 6.4 Hz, 2H), 3.02-2.96 (m, 2H), 1.18 (d, J = 7.2 Hz, 2H). |
| 128 | Light yellow solid | 432.1 [M + H]⁺, (2.548 min) | 2 | δ (DMSO-d₆): 8.34 (d, J = 8.4 Hz, 1H), 8.10 (d, J = 3.9 Hz, 1H), 7.79 (d, J = 9.3 Hz, 1H), 7.59 (dd, J = 9.1, 2.8 Hz, 1H), 7.27 (d, J = 2.8 Hz, 1H), 7.17 (d, J = 3.9 Hz, 1H), 5.48 (t, J = 5.9 Hz, 1H), 5.28 (quin, J = 7.3 Hz, 1H), 4.85 (s, 2H), 3.94 (s, 3H), 3.86 (d, J = 5.9 Hz, 2H), 2.42 (s, 3H), 1.53 (d, J = 7.2 Hz, 3H) |
| 129 | White solid | 446.1 [M + H]⁺, (2.670 min) | 2 | δ (DMSO-d₆): 9.07 (s, 1H), 8.42 (d, J = 0.8 Hz, 1H), 8.37 (d, J = 8.4 Hz, 1H), 8.06 (d, J = 4.0 Hz, 1H), 7.18 (d, J = 4.0 Hz, 1H), 5.49 (t, J = 5.2 Hz, 1H), 5.27 (t, J = 7.6 Hz, 1H), 5.12 (s, 3H), 3.86 (d, J = 4.4 Hz, 3H), 1.53 (d, J = 7.2 Hz, 4H) |
| 130 | Light yellow solid | 460.1 [M + H]⁺, (2.640 min) | 2 | δ (DMSO-d₆): 8.61 (s, 1H), 8.34 (d, J = 8.4 Hz, 1H), 8.05 (d, J = 4.0 Hz, 1H), 7.16 (d, J = 4.0 Hz, 1H), 5.47 (t, J = 6.0 Hz, 1H), 5.27 (t, J = 7.2 Hz, 1H), 4.99 (s, 2H), 4.07 (s, 3H), 3.86 (d, J = 6.0 Hz, 2H), 1.52 (d, J = 7.2 Hz, 3H) |
| 131 | Yellow solid | 457.1 [M + H]⁺, (2.367 min) | 2 | δ (DMSO-d₆): 9.40 (dd, J = 4.4, 1.6 Hz, 1H), 8.84 (dd, J = 8.4, 1.6 Hz, 1H), 8.07-8.18 (m, 1H), 7.93 (dd, J = 8.4, 4.4 Hz, 1H), 7.17-7.30 (m, 1H), 5.02 (s, 2H), 4.72-4.80 (m, 2H), 4.68 (d, J = 7.6 Hz, 1H), 4.10-4.22 (m, 2H), 2.83-2.95 ppm (m, 3H) |
| 132 | Yellow solid | 490.1 [M + H]⁺, (2.326 min) | 2 | δ (DMSO-d₆): 9.09 (s, 1H), 8.56 (t, J = 6.4 Hz, 1H), 8.04 (d, J = 4.0 Hz, 1H), 7.12 (d, J = 4.0 Hz, 1H), 5.57 (t, J = 5.8 Hz, 1H), 4.96 (s, 2H), 4.68 (t, J = 5.2 Hz, 2H), 4.50 (d, J = 6.2 Hz, 2H), 3.82-3.91 (m, 4H), 3.23 (s, 3H) |
| 133 | Light yellow solid | 472.3 [M + H]⁺, (2.717 min) | 2 | δ (DMSO-d₆): 8.55-8.52 (m, 2H), 8.04 (d, J = 3.6 Hz, 1H), 7.12 (d, J = 3.6 Hz, 1H), 5.55 (br t, J = 5.6 Hz, 1H), 4.97 (s, 2H), 4.51 (br d, J = 6.0 Hz, 2H), 4.06-3.90 (m, 1H), 3.86 (br d, J = 5.6 Hz, 2H), 1.08-1.28 (m, 4H) |
| 134 | Light yellow solid | 500.1 [M + H]⁺, (2.906 min) | 2 | δ (DMSO-d₆): 8.49 (s, 1H), 8.11-8.02 (m, 2H), 7.83-7.76 (m, 1H), 7.45 (s, 1H), 7.13-7.08 (m, 1H), 5.43 (s, 1H), 4.96 (s, 2H), 4.47 (d, J = 6.0 Hz, 2H), 4.02 (s, 3H), 1.25 (s, 6H) |

TABLE 4-continued

| Ex. | Form | LCMS m/z (Rt) | Method | ¹H-NMR [400 MHz] |
|---|---|---|---|---|
| 135 | Yellow solid | 459.9 [M + H]⁺, (2.373 min) | 2 | δ (DMSO-d₆): 9.11 (s, 1H), 8.54 (t, J = 6.4 Hz, 1H), 8.04 (d, J = 4.0 Hz, 1H), 7.12 (d, J = 3.6 Hz, 1H), 5.55 (t, J = 5.6 Hz, 1H), 4.95 (s, 2H), 4.58-4.44 (m, 5H), 3.86 (d, J = 5.6 Hz, 2H), 1.54 (t, J = 7.2 Hz, 3H) |
| 136 | Light yellow solid | 459.9 [M + H]⁺, (2.700 min) | 2 | δ (DMSO-d₆): 8.62 (s, 1H), 8.55 (br t, J = 6.4 Hz, 1H), 8.05 (d, J = 4.0 Hz, 1H), 7.13 (d, J = 4.0 Hz, 1H), 5.56 (t, J = 5.6 Hz, 1H), 4.98 (s, 2H), 4.58-4.41 (m, 4H), 3.87 (d, J = 6.0 Hz, 2H), 1.44 (t, J = 7.2 Hz, 3H) |
| 137 | Light yellow solid | 444.1 [M + H]⁺, (2.631 min) | 2 | δ (DMSO-d₆): 7.90 (d, J = 4.0 Hz, 1H), 7.78 (d, J = 9.2 Hz, 1H), 7.48 (d, J = 2.8 Hz, 1H), 7.25 (d, J = 2.8 Hz, 1H), 7.11 (d, J = 4.0 Hz, 1H), 4.81 (s, 2H), 4.70 (s, 2H), 4.25 (s, 2H), 3.95 (s, 3H), 3.90 (t, J = 5.2 Hz, 2H), 3.44 (t, J = 4.8 Hz, 2H), 2.59 (s, 3H) |
| 138 | Yellow solid | 469.1 [M + H]⁺, (2.438 min) | 2 | δ (DMSO-d₆): 9.34 (d, J = 2.4 Hz, 1H), 8.60 (d, J = 8.4 Hz, 1H), 7.89 (t, J = 4.0 Hz, 1H), 7.73-7.69 (m, 1H), 7.13 (d, J = 3.6 Hz, 1H), 4.81 (d, J = 10.0 Hz, 4H), 4.25 (s, 2H), 3.91 (t, J = 5.6 Hz, 2H), 3.44 (t, J = 5.2 Hz, 2H) |
| 139 | Light yellow solid | 454.1 [M + H]⁺, (2.615 min) | 2 | δ (DMSO-d₆): 8.54 (t, J = 6.4 Hz, 1H), 8.07 (d, J = 3.6 Hz, 1H), 8.02 (t, J = 9.2 Hz, 1H), 7.76-7.73 (m, 1H), 7.40 (d, J = 2.8 Hz, 1H), 7.13 (d, J = 3.6 Hz, 1H), 6.77 (t, J = 54.8 Hz, 1H), 5.56 (t, J = 5.6 Hz, 1H), 4.98 (s, 2H), 4.51 (d, J = 6.0 Hz, 2H), 4.01 (s, 3H), 3.86 (d, J = 5.6 Hz, 2H) |
| 140 | Yellow solid | 418.9 [M + H]⁺, (2.137 min) | 2 | δ (DMSO-d₆): 8.94 (d, J = 3.2 Hz, 1H), 8.55 (t, J = 6.0 Hz, 1H), 8.09 (d, J = 4.0 Hz, 1H), 7.70 (d, J = 3.2 Hz, 1H), 7.14 (d, J = 3.6 Hz, 1H), 5.56 (t, J = 5.6 Hz, 1H), 4.89 (s, 2H), 4.52 (d, J = 6.0 Hz, 2H), 4.01 (s, 3H), 3.87 (d, J = 5.6 Hz, 2H), 2.46 (s, 4H) |
| 141 | Yellow solid | 458.2 [M + H]⁺, (2.567 min) | 2 | δ (DMSO-d₆): 8.12 (d, J = 4.0 Hz, 1H), 7.80 (d, J = 9.2 Hz, 1H), 7.60-7.57 (m, 1H), 7.28 (d, J = 2.4 Hz, 1H), 7.13 (d, J = 4.0 Hz, 1H), 5.52 (d, J = 5.6 Hz, 1H), 4.84 (s, 2H), 4.08-4.03 (m, 1H), 3.95 (s, 3H), 3.41-3.59 (m, 2H), 3.05-3.30 (m, 4H), 2.40 (s, 3H), 2.19-2.30 (m, 1H), 1.57-1.75 (m, 1H) |
| 142 | Yellow solid | 440.1 [M + H]⁺, (2.669 min) | 2 | δ (DMSO-d₆): 8.54 (t, J = 6.4 Hz, 1H), 8.09-8.06 (m, 2H), 8.03-7.98 (m, 1H), 7.14 (d, J = 4.0 Hz, 1H), 5.55 (t, J = 6.0 Hz, 1H), 4.88 (s, 2H), 4.51 (d, J = 6.0 Hz, 2H), 3.86 (d, J = 5.6 Hz, 2H), 2.45 (s, 3H). |
| 143 | Yellow solid | 418.1 [M + H]⁺, (2.391 min) | 2 | δ (DMSO-d₆): 8.53 (t, J = 6.4 Hz, 1H), 8.06 (d, J = 3.6 Hz, 1H), 7.79 (t, J = 8.4 Hz, 1H), 7.35 (d, J = 8.0 Hz, 1H), 7.12 (t, J = 3.6 Hz, 2H), 5.56-5.53 (m, 1H), 4.57 (s, 2H), 4.51 (t, J = 6.4 Hz, 2H), 4.03 (s, 3H), 3.86 (s, 2H), 2.07 (s, 3H) |
| 144 | Yellow solid | 432.1 [M + H]⁺, (2.621 min) | 2 | δ (DMSO-d₆): 8.56 (t, J = 6.0 Hz, 1H), 8.10 (d, J = 4.0 Hz, 1H), 7.80 (d, J = 9.2 Hz, 1H), 7.59 (dd, J = 9.2, 2.8 Hz, 1H), 7.27 (d, J = 2.8 Hz, 1H), 7.15 (d, J = 4.0 Hz, 1H), 5.57 (t, J = 6.0 Hz, 1H), 4.85 (s, 2H), 4.53 (d, J = 6.2 Hz, 2H), 4.23 (q, J = 6.8 Hz, 2H), 3.88 (d, J = 5.6 Hz, 2H), 2.42 (s, 3H), 1.43 (t, J = 6.8 Hz, 3H) |
| 145 | Light yellow solid | 433.1 [M + H]⁺, (2.524 min) | 2 | δ (DMSO-d₆): 9.03 (s, 1H), 8.55 (s, 1H), 8.08 (d, J = 3.6 Hz, 1H), 7.17 (s, 1H), 7.15 (t, J = 4.0 Hz, 1H), 5.56 (t, J = 6.0 Hz, 1H), 4.87 (s, 2H), 4.51 (t, J = 6.4 Hz, 2H), 4.45-4.40 (m, 2H), 3.86 (d, J = 6.5 Hz, 2H), 2.49 (s, 3H), 1.38 (t, J = 7.2 Hz, 3) |
| 146 | Light yellow solid | 440.0 [M + H]⁺, (2.672 min) | 2 | δ (DMSO-d₆): 8.55 (t, J = 6.4 Hz, 1H), 8.12-8.03 (m, 2H), 7.72 (dd, J = 8.8, 1.1 Hz, 1H), 7.14 (d, J = 3.6 Hz, 1H), 5.56 (t, J = 6.0 Hz, 1H), 4.78 (s, 2H), 4.52 (d, J = 6.0 Hz, 2H), 3.87 (d, J = 6.0 Hz, 2H), 3.31-3.29 (m, 2H), 2.34 (s, 3H) |
| 147 | Yellow solid | 499.2 [M + H]⁺, (2.468 min) | 2 | δ (DMSO-d₆): 8.54 (s, 1H), 8.07 (d, J = 4.0 Hz, 1H), 7.68 (d, J = 4.0 Hz, 1H), 7.69-7.55 (m, 1H), 7.13 (d, J = 3.6 Hz, 1H), 6.72 (d, J = 2.4 Hz, 1H), 5.55 (t, J = 6.0 Hz, 1H), 4.79 (s, 2H), 4.51 (d, J = 6.4 Hz, 2H), 4.21 (s, 1H), 4.07-4.00 (m, 3H), 3.86 (d, J = 6.0 Hz, 2H), 3.76 (d, J = 10.4 Hz, 1H), 3.45 (d, J = 10.8 Hz, 1H), 2.37 (s, 3H), 2.15-2.00 (m, 1H), 1.98-1.94 (m, 2H), 1.78-1.60 (m, 1H) |
| 148 | Light yellow solid | 486.1 [M + H]⁺, (2.692 min) | 2 | δ (DMSO-d₆): 8.55 (t, J = 6.0 Hz, 1H), 8.09 (d, J = 4.0 Hz, 1H), 7.87 (s, 1H), 7.56 (s, 1H), 7.14 (d, J = 3.6 Hz, 1H), 5.56 (t, J = 5.6 Hz, 1H), 4.89 (s, |

TABLE 4-continued

| Ex. | Form | LCMS m/z (Rt) | Method | $^1$H-NMR [400 MHz] |
|---|---|---|---|---|
| | | | | 2H), 4.52 (d, J = 6.4 Hz, 2H), 4.04 (s, 3H), 3.87 (d, J = 6.0 Hz, 2H), 2.47-2.48 (m, 3H) |
| 149 | Yellow solid | 431.9 [M + H]$^+$, (2.443 min) | 2 | δ (DMSO-d$_6$): 8.92 (s, 1H), 8.53 (d, J = 6.4 Hz, 1H), 8.07 (d, J = 4.0 Hz, 1H), 7.12 (d, J = 4.0 Hz, 1H), 5.55 (t, J = 6.0 Hz, 1H), 4.83 (s, 2H), 4.51 (d, J = 6.0 Hz, 2H), 3.86 (d, J = 5.6 Hz, 2H), 3.17 (s, 6H), 2.32 (s, 3H). |
| 150 | Light yellow solid | 499.1 [M + H]$^+$, (3.066 min) | 2 | δ (DMSO-d$_6$): 8.55 (t, J = 6.0 Hz, 1H), 8.09 (d, J = 3.6 Hz, 1H), 7.69 (s, 1H), 7.21 (s, 1H), 7.14 (d, J = 3.6 Hz, 1H), 5.56 (t, J = 5.6 Hz, 1H), 4.86 (s, 2H), 4.52 (d, J = 6.4 Hz, 2H), 3.87 (d, J = 5.6 Hz, 2H), 3.14 (s, 6H), 2.47 (s, 3H) |
| 151 | Light yellow solid | 485.1 [M + H]$^+$, (3.086 min) | 2 | δ (DMSO-d$_6$): 8.55 (t, J = 6.4 Hz, 1H), 8.08 (d, J = 4.0 Hz, 1H), 7.33 (s, 1H), 7.14 (d, J = 3.6 Hz, 1H), 6.99 (q, J = 4.8 Hz, 1H), 6.80 (d, J = 1.2 Hz, 1H), 5.57 (s, 1H), 4.86 (s, 2H), 4.51 (d, J = 6.4 Hz, 2H), 3.87 (s, 2H), 2.91 (d, J = 5.2 Hz, 3H), 2.60-2.41 (m, 16H) |
| 152 | White solid | 443.1 [M + H]$^+$, (2.451 min) | 2 | δ (DMSO-d$_6$): 9.19 (dd, J = 4.4, 1.6 Hz, 1H), 8.51-8.62 (m, 2H), 8.16 (dd, J = 8.4, 4.4 Hz, 1H), 8.06 (d, J = 4.0 Hz, 1H), 7.13 (d, J = 4.0 Hz, 1H), 5.55 (t, J = 5.6 Hz, 1H), 4.89 (s, 2H), 4.51 (d, J = 6.0 Hz, 2H), 3.86 (d, J = 5.6 Hz, 2H) |
| 153 | White solid | 389.0 [M + H]$^+$, (2.084 min) | 2 | δ (DMSO-d$_6$): 8.96 (dd, J = 4.0, 1.6 Hz, 1H), 8.54 (t, J = 6.4 Hz, 1H), 8.27 (dd, J = 8.4, 1.6 Hz, 1H), 8.08 (d, J = 3.6 Hz, 1H), 7.97 (dd, J = 8.4, 4.0 Hz, 1H), 7.14 (d, J = 3.6 Hz, 1H), 5.56 (t, J = 5.6 Hz, 1H), 4.77 (s, 2H), 4.51 (d, J = 6.4 Hz, 2H), 3.87 (d, J = 6.0 Hz, 2H), 2.49-2.48 (m, 4H) |
| 154 | Light yellow solid | 473.1 [M + H]]$^+$, (2.700 min) | 2 | δ (DMSO-d$_6$): 9.33 (s, 1H), 8.55 (t, J = 6.4 Hz, 1H), 8.06 (d, J = 4.0 Hz, 1H), 7.40 (s, 1H), 7.13 (d, J = 4.0 Hz, 1H), 5.56 (t, J = 5.6 Hz, 1H), 4.99 (s, 3H), 4.51 (d, J = 6.0 Hz, 3H), 4.07 (s, 4H), 3.87 (d, J = 6.0 Hz, 3H) |
| 155 | Yellow solid | 453.0 [M + H]$^+$, (1.500 min) | 2 | δ (DMSO-d$_6$): 9.39 (dd, J = 4.4, 1.6 Hz, 1H), 8.83 (dd, J = 8.4, 1.6 Hz, 1H), 8.11 (d, J = 3.6 Hz, 1H), 7.92 (dd, J = 8.4, 4.4 Hz, 1H), 7.21 (d, J = 3.6 Hz, 1H), 5.01 (s, 2H), 4.62 (s, 2H), 2.28 (t, J = 8.0 Hz, 2H), 2.05-1.81 (m, 2H) |
| 156 | Yellow solid | 469.1 [M + H]$^+$, (2.329 min) | 2 | δ (DMSO-d$_6$): 9.34-9.45 (m, 1H), 8.84 (dd, J = 8.4, 1.2 Hz, 1H), 8.13 (d, J = 4.0 Hz, 1H), 7.93 (dd, J = 8.4, 4.4 Hz, 1H), 7.21 (d, J = 3.6 Hz, 1H), 5.63 (d, J = 5.6 Hz, 1H), 5.02 (s, 2H), 4.64 (s, 2H), 4.08-4.24 (m, 1H), 3.15-3.27 (m, 2H), 2.23-2.33 (m, 1H), 1.77-1.69 (m, 1H) |
| 157 | Yellow solid | 453.0 [M + H]$^+$, (1.500 min) | 2 | δ (DMSO-d$_6$): 9.39 (dd, J = 4.4, 1.6 Hz, 1H), 8.83 (dd, J = 8.4, 1.6 Hz, 1H), 8.11 (d, J = 3.6 Hz, 1H), 7.92 (dd, J = 8.4, 4.4 Hz, 1H), 7.21 (d, J = 3.6 Hz, 1H), 5.01 (s, 2H), 4.62 (s, 2H), 2.28 (t, J = 8.0 Hz, 2H), 2.05-1.81 (m, 2H) |
| 158 | Yellow solid | 436.1 [M + H]$^+$, (2.450 min) | 2 | δ (CD$_3$CN): 7.97-7.87 (m, 1H), 7.79-7.72 (m, 1H), 7.68-7.63 (m, 1H), 7.61-7.50 (m, 1H), 7.11 (d, J = 4.0 Hz, 1H), 4.62 (s, 4H), 4.00 (s, 3H), 3.96 (d, J = 6.0 Hz, 2H), 3.56 (t, J = 6.0 Hz, 1H), 2.35 (s, 3H) |
| 159 | Yellow solid | 487.1 [M + H]$^+$, (2.814 min) | 2 | δ (DMSO-d$_6$): 9.34 (s, 1H), 8.10 (d, J = 3.8 Hz, 1H), 7.41 (s, 1H), 7.22 (d, J = 3.8 Hz, 1H), 4.99 (s, 2H), 4.71-4.80 (m, 3H), 4.67 (t, J = 5.6 Hz, 1H), 4.13 (d, J = 5.6 Hz, 2H), 4.08 (s, 3H), 2.91 (s, 3H) |
| 160 | Light yellow solid | 433.1 [M + H]$^+$, (2.305 min) | 2 | δ (DMSO-d$_6$): 8.93 (d, J = 3.2 Hz, 1H), 8.55 (t, J = 6.0 Hz, 1H), 8.09 (d, J = 4.0 Hz, 1H), 7.68 (d, J = 3.2 Hz, 1H), 7.14 (d, J = 4.0 Hz, 1H), 5.56 (t, J = 5.6 Hz, 1H), 4.88 (s, 2H), 4.51 (d, J = 6.4 Hz, 2H), 4.29 (q, J = 7.2 Hz, 2H), 3.87 (d, J = 5.6 Hz, 2H), 2.46 (s, 4H), 1.43 (t, J = 6.8 Hz, 3H) |
| 161 | Yellow solid | 445.1 [M + H]$^+$, (2.305 min) | 2 | δ (DMSO-d$_6$): 8.95 (d, J = 3.2 Hz, 1H), 8.14 (d, J = 3.6 Hz, 1H), 7.71 (d, J = 3.2 Hz, 1H), 7.26 (d, J = 4.0 Hz, 1H), 4.90 (s, 2H), 4.77 (s, 2H), 4.11 (s, 3H), 4.02 (s, 3H), 3.92-3.75 (m, 3H), 3.42-3.35 (m, 3H), 2.47-2.41 (m, 5H) |
| 162 | Yellow solid | 433.1 [M + H]$^+$, (2.264 min) | 2 | δ (DMSO-d$_6$): 8.94 (d, J = 3.2 Hz, 1H), 8.12 (d, J = 3.6 Hz, 1H), 7.70 (d, J = 3.2 Hz, 1H), 7.22 (d, J = 3.6 Hz, 1H), 4.89 (s, 2H), 4.60-4.79 (m, 3H), 4.07-4.19 (m, 2H), 4.01 (s, 3H), 2.86-2.95 (m, 3H), 2.44 (s, 3H) |

TABLE 4-continued

| Ex. | Form | LCMS m/z (Rt) | Method | ¹H-NMR [400 MHz] |
|---|---|---|---|---|
| 163 | White solid | 431.1 [M − H]⁻, (2.363 min) | 2 | δ (DMSO-d₆): 8.94 (d, J = 3.2 Hz, 1H), 8.62 (t, J = 6.0 Hz, 1H), 8.09 (d, J = 4.0 Hz, 1H), 7.70 (d, J = 3.2 Hz, 1H), 7.15 (d, J = 3.6 Hz, 1H), 4.89 (s, 2H), 4.52 (d, J = 6.0 Hz, 3H), 4.01 (s, 4H), 3.87 (s, 3H), 3.31-3.30 (m, 3H), 2.46 (s, 3H) |
| 164 | Yellow solid | 455.1 [M + H]⁺, (2.286 min) | 2 | δ (DMSO-d₆): 9.11 (d, J = 3.2 Hz, 1H), 8.57 (t, J = 6.4 Hz, 1H), 8.08 (d, J = 3.8 Hz, 1H), 7.83 (d, J = 3.2 Hz, 1H), 7.14 (d, J = 4.0 Hz, 1H), 6.66-7.00 (m, 1H), 5.58 (t, J = 5.8 Hz, 1H), 5.03 (s, 2H), 4.52 (d, J = 6.2 Hz, 2H), 4.08 (s, 3H), 3.87 (d, J = 6.0 Hz, 2H) |
| 165 | Light yellow solid | 374.1 [M + H]⁺, (2.267 min) | 2 | δ (DMSO-d₆): 9.00 (dd, J = 4.0, 1.6 Hz, 1H), 8.54 (t, J = 6.0 Hz, 1H), 8.41 (dd, J = 8.4, 1.6 Hz, 1H), 8.28 (d, J = 5.6 Hz, 1H), 8.03 (d, J = 3.8 Hz, 1H), 7.83 (dd, J = 8.4, 4.4 Hz, 1H), 7.58 (d, J = 5.6 Hz, 1H), 7.11 (d, J = 4.0 Hz, 1H), 5.56 (t, J = 5.6 Hz, 1H), 4.76 (s, 2H), 4.50 (d, J = 6.0 Hz, 2H), 3.86 (d, J = 5.6 Hz, 2H) |
| 166 | Yellow solid | 397.0 [M + H]⁺, (2.310 min) | 6 | ¹H NMR (DMSO-d₆, 400 MHz) δ 13.30 (br s, 1H), 8.56 (brt, 1H, J = 6.3 Hz), 8.20 (d, 1H, J = 1.8 Hz), 7.9-8.0 (m, 2H), 7.12 (d, 1H, J = 3.7 Hz), 5.57 (t, 1H, J = 5.7 Hz), 4.95 (s, 2H), 4.49 (d, 2H, J = 6.2 Hz), 3.85 (d, 2H, J = 5.7 Hz), 2.07 (s, 1H) |
| 167 | Brown solid | 393.0 [M + H]⁺, (2.692 min) | 6 | N/A |
| 168 | Yellow solid | 393.0 [M + H]⁺, (2.706 min) | 6 | N/A |
| 169 | White solid | 376.1 [M + H]⁺, (2.206 min) | 6 | N/A |
| 170 | Yellow solid | 377.0 [M + H]⁺, (2.815 min) | 6 | N/A |
| 171 | Yellow solid | 458.1 [M + H]⁺, (2.674 min) | 2 | δ (DMSO-d₆): 8.68-8.55 (m, 1H), 8.09 (d, J = 3.6 Hz, 1H), 7.79 (d, J = 9.2 Hz, 1H), 7.59 (d, J = 9.2 Hz, 1H), 7.27 (d, J = 2.8 Hz, 1H), 7.12 (d, J = 3.6 Hz, 1H), 4.84 (s, 2H), 4.35-4.59 (m, 2H), 4.26 (d, J = 8.4 Hz, 1H), 3.94 (s, 3H), 3.93-3.86 (m, 1H), 3.83-3.65 (m, 1H), 2.40 (s, 3H), 2.19-2.02 (m, 1H), 1.95-1.63 (m, 3H) |
| 172 | Yellow solid | 438.1 [M + H]⁺, (2.741 min) | 2 | δ (DMSO-d₆): 9.57 (t, J = 5.6 Hz, 1H), 8.12 (d, J = 4.0 Hz, 1H), 7.79 (d, J = 9.1 Hz, 1H), 7.59 (dd, J = 9.1, 2.8 Hz, 1H), 7.27 (d, J = 2.8 Hz, 1H), 7.19 (d, J = 3.9 Hz, 1H), 6.12-6.47 (m, 1H), 4.85 (s, 2H), 4.58 (d, J = 6.0 Hz, 2H), 3.94 (s, 3H), 2.39 ppm (s, 3H) |
| 173 | Brown solid | 393.1 [M + H]⁺, (2.153 min) | 6 | N/A |
| 174 | Yellow solid | 397.0 [M + H]+ (2.772 min) | 6 | N/A |
| 176 | Light yellow solid | 362.9 [M + H]⁺, (1.928 min) | 2 | δ (DMSO-d₆): 8.55 (t, J = 6.0 Hz, 1H), 8.34 (d, J = 4.8 Hz, 1H), 8.13 (d, J = 1.2 Hz, 1H), 8.02 (d, J = 4.0 Hz, 1H), 7.71 (d, J = 1.2 Hz, 1H), 7.63 (d, J = 4.8 Hz, 1H), 7.11 (d, J = 4.0 Hz, 1H), 5.56 (s, 1H), 4.82 (s, 2H), 4.55 (d, J = 3.2 Hz, 2H), 3.86 (s, 2H). |
| 177 | Yellow solid | 417.0 [M + H]⁺, (2.369 min) | 2 | δ (DMSO-d₆): 8.65-8.50 (m, 1H), 8.09 (d, J = 4.0 Hz, 1H), 7.79 (d, J = 9.2 Hz, 1H), 7.59 (d, J = 9.2 Hz, 1H), 7.27 (d, J = 2.6 Hz, 1H), 7.15 (d, J = 4.0 Hz, 1H), 4.84 (s, 2H), 4.52 (s, 2H), 3.94 (s, 3H), 3.14 (s, 2H), 2.41 (s, 3H) |
| 178 | Yellow solid | 457.0 [M + H]]⁺, (2.512 min) | 2 | δ (DMSO-d₆): 8.60 (d, J = 9.2 Hz, 1H), 8.09(d, J = 4.0 Hz, 1H), 7.79 (d, J = 9.2 Hz, 1H), 7.603-7.537 (m, 1H), 7.27 (d, J = 2.8 Hz, 1H), 7.126 (s, 1H), 4.84 (s, 2H), 4.48 (d, J = 6.4 Hz, 2H), 3.944 (s, 3H), 3.33(s, 3H), 3.09(d, J = 6.4 Hz, 3H), 2.399 (s, 3H), 2.216 (s, 3H). |
| 179 | Yellow solid | 373.9 [M + H]⁺, (2.209 min) | 2 | δ (DMSO-d₆): 9.16-9.14 (m, 1H), 8.63 (d, J = 8.0 Hz, 1H), 8.55 (t, J = 6.2 Hz, 1H), 8.43 (d, J = 6.0 Hz, 1H), 8.05 (d, J = 3.9 Hz, 1H), 7.73-7.70 (m, 1H), 7.61 (d, J = 6.0 Hz, 1H), 7.13 (d, J = 4.0 Hz, 1H), 5.57 (t, J = 5.6 Hz, 1H), 4.92 (s, 2H), 4.51 (d, J = 6.0 Hz, 2H), 3.87 (d, J = 6.0 Hz, 2H) |

TABLE 4-continued

| Ex. | Form | LCMS m/z (Rt) | Method | ¹H-NMR [400 MHz] |
|---|---|---|---|---|
| 180 | Yellow solid | 406.1 [M + H]⁺, (2.477 min) | 2 | δ (DMSO-d₆): 9.58 (s, 1H), 8.79 (d, J = 5.6 Hz, 1H), 8.548 (t, J = 6.4 Hz, 1H), 8.40 (d, J = 5.6 Hz, 1H), 8.05 (d, J = 3.6 Hz, 1H), 7.87 (d, J = 5.6 Hz, 1H), 7.57 (d, J = 5.6 Hz, 1H), 7.12 (d, J = 4.0 Hz, 1H), 5.563 (t, J = 5.6 Hz, 1H), 4.93 (s, 2H), 4.50 (d, J = 6.4 Hz, 2H), 3.87 (d, J = 6.0 Hz, 2H) |
| 181 | Yellow solid | 362.9 [M + H]⁺, (2.000 min) | 2 | δ (DMSO-d₆): 8.54 (s, 2H), 8.12 (d, J = 4.8 Hz, 1H), 8.00 (d, J = 4.0 Hz, 1H), 7.79 (s, 1H), 7.33 (d, J = 4.8, 1H), 7.11 (d, J = 4.0, 1H), 5.56 (s, 1H), 4.85 (s, 2H), 4.49 (d, J = 6.4 Hz, 2H), 3.86 (d, J = 5.2, 2H) |
| 182 | Yellow solid | 362.9 [M + H]⁺, (2.215 min) | 2 | δ (DMSO-d₆): 8.53 (t, J = 6.0 Hz, 2H), 8.14 (d, J = 2.4 Hz, 1H), 8.02 (d, J = 3.6 Hz, 1H), 7.66 (d, J = 4.4 Hz, 1H), 7.12 (d, J = 4.0 Hz, 1H), 6.99 (d, J = 1.6 Hz, 1H), 5.56 (s, 1H), 4.90 (s, 2H), 4.50 (d, J = 6.4 Hz, 2H), 3.86 (d, J = 5.6 Hz, 2H) |
| 183 | Yellow solid | 431.1 [M + H]⁺, (2.452 min) | 2 | δ (DMSO-d₆): 8.55 (d, J = 6.0 Hz, 1H), 8.09 (d, J = 4.0 Hz, 1H), 7.79 (d, J = 9.2 Hz, 1H), 7.59 (d, J = 9.2 Hz, 1H), 7.27 (d, J = 2.8 Hz, 1H), 7.14 (d, J = 4.0 Hz, 1H), 6.08 (s, 1H), 4.84 (s, 2H), 4.52 (d, J = 4.8 Hz, 2H), 3.94 (s, 3H), 3.09 (s, 2H), 2.40 (s, 3H), 2.25 (s, 3H) |
| 184 | Light yellow solid | 229.0 [M + H]⁺, (2.482 min) | 2 | δ (DMSO-d₆): 8.06 (d, J = 3.2 Hz, 1H), 7.70-7.80 (m, 1H), 7.51-7.60 (m, 1H), 7.18-7.27 (m, 1H), 7.10 (s, 1H), 4.81 (s, 2H), 4.45 (s, 2H), 3.91 (s, 3H), 3.48-3.56 (m, 1H), 2.67-2.88 (m, 2H), 2.36 (d, J = 1.6 Hz, 3H), 1.75-2.08 (m, 2H), 1.55-1.73 (m, 2H) |
| 185 | Light yellow solid | 432.0 [M + H]⁺, (2.513 min) | 2 | δ (DMSO-d₆): 8.543-8.511 (m, 1H), 8.09 (d, J = 4.0 Hz, 1H), 7.79 (d, J = 9.2 Hz, 1H), 7.60-7.57 (m, 1H), 7.27 (d, J = 2.4 Hz, 1H), 7.12 (d, J = 3.6 Hz, 1H), 5.59 (d, J = 5.2 Hz, 1H), 4.84 (s, 2H), 4.48 (d, J = 6.0 Hz, 2H), 4.03-4.0 (m, 1H), 3.94 (s, 3H), 2.45 (s, 3H), 1.22 (d, J = 6.4 Hz, 3H). |
| 186 | White solid | 432.0 [M + H]⁺, (2.514 min) | 2 | δ (DMSO-d₆): 8.546-8.512 (m, 1H), 8.09 (d, J = 4.0 Hz, 1H), 7.79 (d, J = 9.2 Hz, 1H), 7.60-7.57 (m, 1H), 7.27 (d, J = 2.4 Hz, 1H), 7.12 (d, J = 3.6 Hz, 1H), 5.59 (d, J = 5.2 Hz, 1H), 4.84 (s, 2H), 4.48 (d, J = 6.0 Hz, 2H), 4.03-4.0 (m, 1H), 3.94 (s, 3H), 2.45 (s, 3H), 1.22 (d, J = 6.8 Hz, 3H). |
| 189 | Light yellow solid | 431.1 [M + H]⁺, (2.598 min) | 2 | δ (DMSO-d₆): 8.08 (d, J = 4.0 Hz, 1H), 7.80 (d, J = 9.2 Hz, 1H), 7.60 (d, J = 9.2 Hz, 1H), 7.28 (d, J = 2.8 Hz, 1H), 7.08-7.16 (m, 2H), 4.85 (s, 2H), 4.43 (d, J = 6.0 Hz, 2H), 3.95 (s, 3H), 2.82 (s, 6H), 2.43 (s, 3H) |
| 190 | Yellow solid | 461.2 [M + H]⁺, (2.835 min) | 2 | δ (CDCl₃): δ = 8.91 (d, J = 3.2 Hz, 1H), 7.86 (d, J = 4.0 Hz, 1H), 7.55 (d, J = 3.2 Hz, 1H), 7.06 (d, J = 4.0 Hz, 1H), 5.05 (s, 1H), 4.75 (s, 2H), 4.54 (d, J = 5.6 Hz, 2H), 3.99 (s, 3H), 2.68 (s, 3H), 1.48 (s, 9H) |
| 191 | White solid | 467.19 [M + H]⁺, (4.23 min) | 5 | 1H NMR [400 MHz, DMSO-d6]: δ1.11 (s, 9H), 4.46 (d, J = 6.0 Hz, 2H), 4.85 (s, 2H), 7.07 (d, J = 4.0 Hz, 1H), 7.88-7.99 (m, 2H), 8.04 (d, J = 4.0 Hz, 1H), 8.16-8.34 (m, 4H). |
| 192 | Yellow solid | 420.23 [M + H]⁺, (14.76 min). | 1 | 1H NMR [400 MHz, DMSO-d6]: δ1.11 (s, 9H), 4.02 (s, 3H), 4.71 (d, J = 5.6 Hz, 2H), 5.15 (s, 2H), 8.43 (s, 1H), 8.60 (s, 1H), 8.66 (t, J = 6.0 Hz, 1H). |
| 193 | Off-white solid | 400.28 [M + H]⁺, (14.66 min) | 4 | 1H NMR [400 MHz, DMSO-d6]: δ1.13 (s, 9H), 4.46 (d, J = 5.6 Hz, 2H), 5.00 (s, 2H), 7.11 (d, J = 3.6 Hz, 1H), 8.04-8.20 (m, 5H), 8.34 (t, J = 6.0 Hz, 1H), 9.42 (s, 1H). |
| 194 | Off-white solid | 414.28 [M + H]⁺, (14.38 min) | 4 | 1H NMR [400 MHz, DMSO-d6]: δ1.12 (s, 9H), 2.81(s, 3H), 4.46 (d, J = 5.6 Hz, 2H), 4.94 (s, 2H), 7.10 (d, J = 3.6 Hz, 1H), 8.02-8.23 (m, 5H), 8.34 (t, J = 6.0 Hz, 1H). |
| 195 | Off-white solid | 468.29 [M + H]⁺, (17.36 min) | 4 | 1H NMR [400 MHz, DMSO-d6]: δ1.12 (s, 9H), 4.47 (d, J = 6.0 Hz, 2H), 5.09 (s, 2H), 7.13 (d, J = 4.0 Hz, 1H), 8.23 (bs, 3H), 8.34 (t, J = 6.0 Hz, 1H), 8.43 (t, J = 4.4 Hz, 1H). |
| 196 | Light yellow solid | 430.9 [M + H]⁺, (2.440 min) | 2 | δ (DMSO-d₆): 7.98 (d, J = 4.0 Hz, 1H), 7.77 (d, J = 8.4 Hz, 1H), 7.59 (d, J = 7.6 Hz, 1H), 7.43 (t, J = 8.0 Hz, 1H), 7.14 (d, J = 3.6 Hz, 1H), 4.94 (s, 2H), 4.65 (s, 2H), 4.03 (s, 2H) |

Example 2: Cellular Target Engagement Assay—NanoBRET

Materials and Methods

NanoBRET target engagement was performed against the catalytic domain 2 (CD2) of HDAC6, with minor modifications of kit manufacturer protocol (Promega). Expression of exogenous NanoLuc-HDAC6(CD2) fusion and in HEK293T was achieved following transient transfection with FuGENE HD Transfection Reagent (Promega). The intracellular target engagement assay on HDAC6(CD2) was performed in a 384-well plate format with 8,000 cells per well and a tracer concentration of 0.125 μM or 0.600 μM for HDAC6(CD2). Compounds (dissolved in 100% DMSO) or DMSO (vehicle) were added either manually by diluting them in culture medium at 8× final assay concentration and then adding 5 μL to assay plate or in an automated way by adding 160 nL compound to 5 μL OptiMEM without phenol red (Gibco) using the Echo650 (Labcyte). Tracer solution was added to the cells before seeding 35 μL cell/tracer mixture in the assay plate. The final reaction volume was 40 μL, final DMSO concentration was 1.4% (manual compound addition) or 1.25% (automated compound addition). Assay plates were incubated at 37° C. in a humidified atmosphere containing 5% $CO_2$ for 2 hours. The NanoBRET Nano-glo Substrate/Inhibitor was prepared by diluting NanoBRET Nano-Glo Substrate (1:332) and Extracellular Inhibitor (1:1000) in assay medium (Promega). The NanoBRET TE Nano-glo Substrate/Inhibitor was added to cells and measurement of NanoBRET donor and acceptor signal (460-80 and 647-75, respectively) was performed at room temperature with either the EnVision Xcite (PerkinElmer) or the CLARIOstar (BMG Labtech) plate reader 1-2 minutes after NanoLuc substrate addition. BRET ratios were calculated from acceptor/donor signal ratio (mBRET=acceptor/donor*1000) and normalized for each plate. Percentage inhibition was calculated by setting the mBRET obtained with cells without tracer to 100%, while the mBRET obtained with uninhibited cells with tracer was set to 0%. IC50-values were calculated from the percentage inhibition with the log(inhibitor) vs. response—Variable slope (four parameters) nonlinear regression in GraphPad Prism software.

Results

The results of this assays are presented on Table 5 below, wherein "+" means: 1000 nM<$IC_{50}$≤10000 nM, "++" means: 500 nM<$IC_{50}$≤1000 nM, "+++" means: 100 nM<$IC_{50}$≤500 nM and "++++" means: $IC_{50}$≤100 nM.

TABLE 5

| Cpd # | $IC_{50}$ (HDAC6(CD2) interaction) |
|---|---|
| 1 | +++ |
| 2 | +++ |
| 3 | ++++ |
| 4 | ++ |
| 5 | ++ |
| 6 | +++ |
| 7 | ++++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | ++ |
| 22 | ++++ |
| 23 | +++ |
| 24 | +++ |
| 25 | +++ |
| 26 | +++ |
| 27 | +++ |
| 28 | ++ |
| 29 | +++ |
| 30 | ++++ |
| 31 | + |
| 33 | +++ |
| 34 | +++ |
| 35 | +++ |
| 36 | ++++ |
| 37 | + |
| 38 | ++++ |
| 39 | ++ |
| 40 | + |
| 41 | ++++ |
| 42 | ++ |
| 43 | +++ |
| 44 | +++ |
| 45 | ++++ |
| 46 | ++++ |
| 47 | +++ |
| 48 | ++++ |
| 49 | ++++ |
| 50 | +++ |
| 51 | +++ |
| 52 | ++ |
| 55 | ++ |
| 56 | ++++ |
| 57 | +++ |
| 58 | + |
| 59 | +++ |
| 60 | ++++ |
| 61 | ++++ |
| 62 | ++++ |
| 63 | +++ |
| 64 | ++++ |
| 65 | ++ |
| 66 | ++++ |
| 67 | +++ |
| 68 | +++ |
| 69 | +++ |
| 70 | +++ |
| 71 | ++++ |
| 72 | ++++ |
| 73 | ++++ |
| 74 | ++++ |
| 75 | +++ |
| 76 | ++++ |
| 77 | ++++ |
| 78 | ++++ |
| 79 | ++++ |
| 80 | ++++ |
| 81 | ++++ |
| 82 | ++++ |
| 83 | ++++ |
| 84 | ++++ |
| 85 | ++++ |
| 86 | + |
| 87 | +++ |
| 88 | + |
| 89 | + |
| 90 | + |
| 91 | +++ |
| 92 | +++ |
| 93 | +++ |
| 94 | +++ |
| 95 | +++ |
| 96 | ++ |

TABLE 5-continued

| Cpd # | IC$_{50}$ (HDAC6(CD2) interaction) |
|---|---|
| 97 | +++ |
| 98 | ++++ |
| 99 | ++++ |
| 100 | +++ |
| 101 | +++ |
| 102 | +++ |
| 103 | ++ |
| 104 | +++ |
| 105 | + |
| 106 | ++++ |
| 107 | +++ |
| 108 | +++ |
| 109 | ++ |
| 110 | +++ |
| 111 | +++ |
| 112 | ++++ |
| 113 | ++++ |
| 114 | ++++ |
| 115 | ++ |
| 116 | +++ |
| 117 | ++++ |
| 118 | ++++ |
| 119 | ++++ |
| 120 | +++ |
| 121 | ++++ |
| 122 | ++++ |
| 123 | ++++ |
| 124 | ++++ |
| 125 | ++++ |
| 126 | ++++ |
| 127 | ++++ |
| 128 | +++ |
| 129 | ++++ |
| 130 | +++ |
| 131 | ++++ |
| 132 | ++++ |
| 133 | ++++ |
| 134 | +++ |
| 135 | ++++ |
| 136 | ++++ |
| 137 | +++ |
| 138 | ++++ |
| 139 | +++ |
| 140 | ++++ |
| 141 | +++ |
| 142 | ++++ |
| 143 | +++ |
| 144 | ++++ |
| 145 | ++++ |
| 146 | ++++ |
| 147 | ++++ |
| 148 | ++++ |
| 149 | ++++ |
| 150 | ++++ |
| 151 | +++ |
| 152 | ++++ |
| 153 | ++++ |
| 154 | ++++ |
| 155 | ++++ |
| 156 | ++++ |
| 157 | ++++ |
| 158 | ++++ |
| 159 | ++++ |
| 160 | ++++ |
| 161 | +++ |
| 162 | +++ |
| 163 | ++++ |
| 164 | ++++ |
| 165 | +++ |
| 166 | + |
| 167 | + |
| 168 | + |
| 169 | + |
| 170 | + |
| 171 | +++ |
| 172 | +++ |
| 173 | + |
| 174 | + |
| 176 | + |
| 177 | +++ |
| 178 | ++++ |
| 179 | +++ |
| 180 | +++ |
| 181 | +++ |
| 182 | + |
| 183 | +++ |
| 184 | +++ |
| 185 | ++++ |
| 186 | +++ |
| 189 | +++ |
| 190 | +++ |
| 193 | +++ |
| 194 | +++ |
| 196 | + |

The results clearly evidence that the compounds of formula (I), effectively inhibit the interaction between HDAC6 catalytic domain 2 and its substrate, thereby inhibiting its deacetylation activity. Thus, this assay shows that the compounds of formula (I) may be used in the treatment and/or prevention of HDAC6-associated diseases.

Example 3: Acetylated α-Tubulin Measurement In Vitro

Materials and Methods

HeLa cells were cultured in UltraCulture serum-free medium (Lonza) supplemented with 2 mM glutamine (Lonza). Assays were performed at 96-well or 384-well format, differences in assay protocols are detailed in Table 6. Cells per well were plated and incubated overnight at 37° C. overnight in a humidified atmosphere containing 5% $CO_2$. Cell density and seeding volumes are detailed in Table 6. Compounds (dissolved in 100% DMSO) or DMSO (vehicle) were added manually by diluting them in culture medium at 10× final assay concentration and adding 10 μL to cells (96-well protocol). Alternatively, 50 nL compound was added directly to the cell culture using the Echo650 (Labcyte) (384-well protocol). In this assay, the final assay concentration of DMSO is 0.1%-0.4%. Trichostatin A (TSA) was used as a positive control. Cells were incubated with compounds at 37° C. in a humidified atmosphere containing 5% $CO_2$ for 6 hours. Levels of acetylated tubulin (Lys40) were assessed by immunocytochemistry using target-specific antibodies. Cells were fixed with 4% PFA at RT as detailed in Table 6. After 2-3 wash steps with PBS, cells were permeabilized with 0.5% Triton in PBS at RT for 10 minutes followed by 1-2 washes with PBS. To avoid non-specific antibody staining, cells were blocked with 3% BSA in PBS at room temperature for 1 hour. Then, cells were incubated for 1 h at RT with 1:3000 anti-acetylated tubulin (mouse monoclonal antibody, acetylated tubulin Lys40, clone 6-11B, Sigma) and 1:1000 anti-α-tubulin (rabbit monoclonal, abcam) diluted in 1% BSA. Cells were washed 2-3 times with PBS and labelled for 1 h at RT with goat anti-mouse conjugated with Alexa 647 (Thermofisher) and goat anti-rabbit conjugated with Alexa 555 (Thermofisher) secondary antibodies, diluted in 1% BSA to a final concentration of 1:1000. Simultaneously, nuclei were stained with 1:10000-1:15000 Hoechst (Thermofisher). Incubation time and temperature of the primary antibodies are detailed in Table 6. Cells were washed 2-3 times with PBS and they were imaged with the Operetta CLS or Opera Phenix (PerkinElmer). Imaging is further detailed in Table 6. For imaging analysis, the Harmony analysis software (PerkinElmer) was used. Cytoplasmic (defined by total α-tubulin staining) intensities per well were used for α-tubulin (acetylated and total) quantification. Intensities were measured per cell and then averaged per well. Mean intensity levels of acetylated tubulin were normalized to the mean intensity levels of total tubulin. The changes in acetylated tubulin were normalized for each plate using GraphPad Prism software: tubulin acetylation in vehicle (DMSO)-treated cells were set to 0% while tubulin acetylation in TSA-treated cells were set to 100%. EC50 values were calculated using the log(inhibitor) vs. response—Variable slope (four parameters) nonlinear regression in GraphPad Prism software.

TABLE 6

|  | Protocol 1 | Protocol 2 |
| --- | --- | --- |
| Plate format | 96-well | 384-well |
| #cells/well | 5000 | 2000 |
| Cell seeding volume | 90 μL | 50 μL |
| Fixation | 1-step 10% PFA added directly to the medium, 15 min at RT | 2-step 4% PFA added directly to the medium in 1:1 ratio, 10 min at RT 4% PFA added directly to the cells, 10 min at RT |
| Antibody incubation | α-tubulin (acetylated & total): ON, 4° C. | α-tubulin (acetylated & total): 1 h, RT |
| Imaging | Operetta CLS 40x water NA1.1 objective 16 fields | Opera Phenix 10x objective and spinning disc confocality 1 field, 3 focal planes, maximal intensity projection |

Results

The results of this assay are presented on Table 7 below, wherein "+" means: 1000 nM<$IC_{50}$≤3333 nM, "C++" means: 500 nM<$IC_{50}$≤1000 nM, "+++" means: 100 nM<$IC_{50}$≤500 nM, "++++" means: $IC_{50}$≤100 nM, and "–" means: $IC_{50}$>3333 nM.

TABLE 7

| Cpd # | $IC_{50}$ (Tubulin deacetylation) |
| --- | --- |
| 5 | – |
| 7 | +++ |
| 8 | – |
| 9 | + |
| 10 | + |
| 12 | + |
| 16 | + |
| 17 | ++ |
| 18 | + |
| 19 | + |
| 20 | +++ |
| 21 | + |
| 22 | +++ |
| 23 | ++ |
| 25 | – |
| 27 | + |
| 28 | + |
| 30 | + |
| 31 | + |
| 34 | + |
| 36 | – |
| 38 | ++ |
| 39 | ++ |
| 40 | ++ |
| 41 | + |
| 43 | +++ |
| 44 | +++ |
| 45 | ++++ |
| 46 | +++ |
| 47 | +++ |
| 48 | +++ |
| 49 | +++ |
| 50 | +++ |
| 51 | + |
| 59 | +++ |
| 60 | +++ |
| 61 | ++++ |
| 62 | +++ |
| 63 | +++ |
| 64 | ++++ |
| 65 | + |
| 66 | +++ |
| 67 | +++ |
| 68 | +++ |
| 69 | +++ |
| 70 | +++ |
| 71 | ++++ |
| 72 | ++++ |
| 73 | +++ |
| 74 | +++ |
| 75 | +++ |
| 76 | ++++ |
| 77 | +++ |
| 78 | +++ |
| 79 | ++++ |
| 80 | +++ |
| 81 | +++ |
| 82 | ++++ |
| 83 | ++++ |
| 84 | ++++ |
| 85 | ++++ |
| 86 | + |
| 87 | + |
| 91 | – |
| 95 | ++ |
| 97 | + |
| 98 | + |
| 106 | +++ |
| 107 | +++ |
| 108 | +++ |
| 109 | +++ |
| 110 | ++++ |
| 111 | +++ |
| 112 | +++ |
| 113 | ++++ |
| 114 | ++++ |
| 115 | ++ |
| 116 | +++ |
| 117 | ++++ |
| 118 | +++ |
| 119 | ++++ |
| 120 | +++ |
| 121 | ++++ |
| 122 | +++ |
| 123 | +++ |
| 124 | ++++ |
| 125 | ++++ |
| 126 | ++++ |
| 127 | +++ |
| 128 | +++ |
| 129 | +++ |
| 130 | +++ |
| 131 | +++ |
| 132 | ++++ |
| 133 | +++ |
| 134 | +++ |
| 135 | ++++ |
| 136 | +++ |
| 137 | +++ |
| 138 | +++ |
| 139 | +++ |
| 140 | +++ |
| 141 | +++ |

TABLE 7-continued

| Cpd # | IC$_{50}$ (Tubulin deacetylation) |
|---|---|
| 142 | ++++ |
| 143 | +++ |
| 144 | ++++ |
| 145 | ++++ |
| 146 | +++ |
| 147 | ++++ |
| 148 | ++++ |
| 149 | ++++ |
| 150 | +++ |
| 151 | + |
| 152 | ++++ |
| 153 | ++++ |
| 154 | ++++ |
| 155 | ++++ |
| 156 | ++++ |
| 157 | ++++ |
| 158 | +++ |
| 159 | ++++ |
| 160 | ++++ |
| 161 | +++ |
| 162 | +++ |
| 163 | +++ |
| 164 | ++++ |
| 171 | +++ |
| 172 | +++ |
| 177 | ++++ |
| 178 | ++++ |
| 179 | ++++ |
| 180 | +++ |
| 181 | +++ |
| 182 | ++ |
| 183 | +++ |
| 184 | +++ |
| 185 | ++++ |
| 186 | ++++ |
| 189 | +++ |
| 190 | +++ |
| 194 | ++ |

The results clearly evidence that the compounds of formula (I), increase acetylated α-tubulin over total α-tubulin ratio in HeLa cells, indicating HDAC6 inhibition, HDAC6 being the only HDAC enzyme enabling α-tubulin deacetylation. Thus, this assay shows that the compounds of formula (I) may be used in the treatment and/or prevention of HDAC6-associated diseases.

Example 4: HDAC6 Enzymatic Activity Assay

Materials and Methods

Dose response testing of HDAC6 and HDAC 1 were run at Reaction Biology Corporation (RBC). Inhibition of HDAC enzymes was performed using N-terminal GST tagged human full-length recombinant HDAC6 (H88-30G, SignalChem) and C-terminal FLAG His tag human full-length recombinant HDAC1 produced in insect cells (KDA-21-365, RBC). Enzyme reactions were run in 50 mM Tris-HCl, pH8.0, 137 mM NaCl, 2.7 mM KCl, and 1 mM MgCl2 with 1 mg/ml BSA, 1% DMSO freshly added. 2× enzyme was delivered in the wells of the reaction plate except for the "no enzyme" control wells. In the latter, buffer was added. Compounds in 100% DMSO were delved into the enzyme mixture by acoustic technology (Echo550). Plates are spun down and compounds were incubation with the enzyme for 10 min at room temperature. 2× Fluorogenic peptide from p53 residues 379-382 (RHKKAc, 10 μM final concentration) was added in all wells to initiate the reaction, followed by 1 h incubation at 30° C. Developer containing Trichostatin A was added to stop the reaction and generate fluorescent color. A kinetic measurement was carried out for 20 min with 5 min interval on the Envision plate reader (Perkin Elmer, Ex/Em=360/460). End point reading i.e., plateau of the development reaction was used for analysis. Data was reported by RBC as percentage enzyme activity. Percentage inhibition was calculated by subtracting percentage enzyme activity from 100. IC50 values were calculated using GraphPad Prism 9 based on the log(inhibitor) vs. response—Variable slope (four parameters) equation.

Results

The results of this assay are presented on Table 8 below, wherein "+" means: 1000 nM<IC$_{50}$≤10000 nM, "++" means: 500 nM<IC$_{50}$≤1000 nM, "+++" means: 100 nM<IC$_{50}$≤500 nM, "++++" means: IC$_{50}$≤100 nM, "−" means IC$_{50}$>10000 nM, and "NT" means "not tested".

TABLE 8

| Cpd # | HDAC6 biochem | HDAC1 biochem |
|---|---|---|
| 31 | ++++ | − |
| 43 | ++++ | − |
| 44 | ++++ | − |
| 60 | ++++ | − |
| 61 | ++++ | − |
| 64 | ++++ | − |
| 69 | ++++ | NT |
| 71 | ++++ | + |
| 72 | ++++ | ++ |
| 73 | ++++ | − |
| 74 | ++++ | − |
| 75 | ++++ | − |
| 76 | ++++ | − |
| 79 | ++++ | − |
| 85 | ++++ | − |
| 108 | ++++ | NT |
| 109 | ++++ | NT |
| 113 | ++++ | − |
| 114 | ++++ | − |
| 116 | ++++ | NT |
| 117 | ++++ | − |
| 118 | ++++ | ++ |
| 119 | ++++ | − |
| 124 | ++++ | − |
| 125 | ++++ | − |
| 126 | ++++ | − |
| 132 | ++++ | − |
| 133 | ++++ | − |
| 135 | ++++ | − |
| 138 | ++++ | − |
| 140 | ++++ | − |
| 142 | ++++ | − |
| 147 | ++++ | NT |
| 148 | ++++ | − |
| 152 | ++++ | − |
| 153 | ++++ | NT |
| 154 | ++++ | NT |
| 158 | ++++ | NT |
| 159 | ++++ | NT |
| 160 | ++++ | NT |
| 163 | ++++ | NT |
| 164 | ++++ | NT |

The results clearly evidence that the compounds of formula (I) inhibit fluorogenic substrate conversion by HDAC6, but not by HDAC1. Thus, this assay provides direct evidence that the compounds of formula (I) specifically inhibit HDAC6 over HDAC1, and may therefore be used in the treatment and/or prevention of HDAC6-associated diseases, with no or reduced toxicity due to inhibition of other HDAC proteins.

Example 5: HDAC6 Enzymatic Activity Assay
(Alternative Protocol)

Materials and Methods

Inhibition of HDAC enzymes was performed in 384-well plate format using human full-length recombinant HDAC1 and HDAC6, isolated from a baculovirus expression system in Sf9 cells (BPS Bioscience). Reaction buffer for HDAC1 contained 50 mM Tris-HCl pH 8.0, 137 mM NaCl, 2.7 mM KCl, 1 mM MgCl$_2$, 0.1 mg/mL BSA, and reaction buffer for HDAC6 contained 50 mM Tris/HCl, pH 8.0, 137 mM NaCl, 2.7 mM KCl, 250 µM EDTA, 1 mM DTT, 0.1 mg/mL BSA. Compounds (dissolved in 100% DMSO) or DMSO (vehicle) were diluted in assay buffer at 3× final assay concentration and then added to assay plates. SAHA (10 µM) was used as a positive control. 3× final assay concentration of recombinant enzymes (final assay concentration is 4 nM and 5 nM for HDAC1 and HDAC6, respectively) were preincubated for 10 minutes with test compounds at room temperature. Afterwards, 3× final assay concentration of an acetylated fluorogenic peptide (Ac-Gly-Ala-Lys(Ac))-AMC, Bachem; final assay concentration is 12 µM and 40 M for HDAC1 and HDAC6, respectively) was added to assay plate, allowing deacetylase reactions to incubate for 60 minutes at room temperature. The developer reagent containing 5 M SAHA and 50 M trypsin was added to stop the deacetylase reaction and generate AMC-fluorescence. 15 minutes after addition of developer reagent, endpoint measurements were taken using CLARIOstar (BMG Labtech) plate reader (excitation/emission: 360/450). Fluorescence signals were normalized for each plate using GraphPad Prism software: reaction HDAC-substrate in presence of DMSO was set to 100% while reaction HDAC-substrate in presence of 10 µM SATHA was set to 0%. IC50-values were calculated from normalized measurements using GraphPad Prism software and nonlinear regression with 0% bottom and 100% top constraints.

Results

The results of this assay are presented on Table 9 below, wherein "+" means: 1000 nM<IC$_{50}$≤10000 nM, "++" means: 500 nM<IC$_{50}$≤1000 nM, "+++" means: 100 nM<IC$_{50}$≤500 nM, "++++" means: IC$_{50}$≤100 nM, and "−" means IC$_{50}$>10000 nM.

TABLE 9

| Cpd # | HDAC6 biochem | HDAC1 biochem |
| --- | --- | --- |
| 1 | ++++ | − |
| 2 | ++++ | − |
| 3 | ++++ | + |
| 4 | ++++ | − |
| 5 | ++++ | − |
| 6 | ++++ | − |
| 7 | ++++ | + |
| 8 | ++++ | − |
| 9 | ++++ | − |
| 10 | ++++ | − |
| 11 | ++++ | − |
| 12 | ++++ | − |
| 15 | ++++ | − |
| 16 | ++++ | − |
| 19 | ++++ | − |
| 20 | ++++ | − |
| 21 | ++++ | − |
| 23 | ++++ | + |
| 24 | ++++ | − |
| 25 | ++++ | − |
| 26 | ++++ | − |

TABLE 9-continued

| Cpd # | HDAC6 biochem | HDAC1 biochem |
| --- | --- | --- |
| 28 | ++++ | − |
| 29 | ++++ | − |
| 30 | ++++ | − |
| 31 | ++++ | − |
| 32 | ++++ | − |
| 33 | ++++ | − |
| 34 | ++++ | − |
| 35 | ++++ | − |
| 36 | ++++ | − |
| 37 | ++++ | − |
| 38 | ++++ | − |
| 55 | ++++ | − |
| 56 | ++++ | − |
| 57 | ++++ | − |
| 58 | ++++ | − |
| 59 | ++++ | − |
| 87 | ++++ | − |
| 90 | ++++ | − |
| 91 | ++++ | − |
| 92 | ++++ | + |
| 93 | ++++ | − |
| 94 | ++++ | − |
| 95 | ++++ | − |
| 97 | ++++ | + |
| 98 | ++++ | − |
| 191 | + | − |
| 192 | +++ | ++ |
| 193 | ++++ | − |
| 194 | ++++ | − |
| 195 | ++++ | − |

The results clearly evidence that the compounds of formula (I) inhibit fluorogenic substrate conversion by HDAC6, but not by HDAC1. Thus, this assay provides direct evidence that the compounds of formula (I) specifically inhibit HDAC6 over HDAC1, and may therefore be used in the treatment and/or prevention of HDAC6-associated diseases, with no or reduced toxicity due to inhibition of other HDAC proteins.

Taken together, the aforementioned results demonstrate that the compounds of formula (I) act as specific HDAC6 inhibitors.

The invention claimed is:

1. A compound selected from the group consisting of:

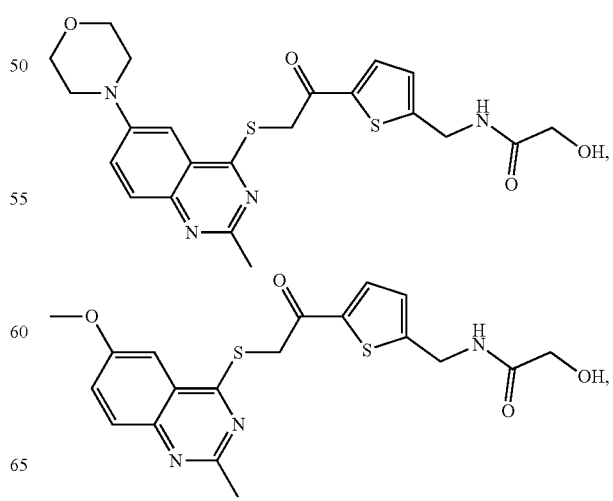

-continued

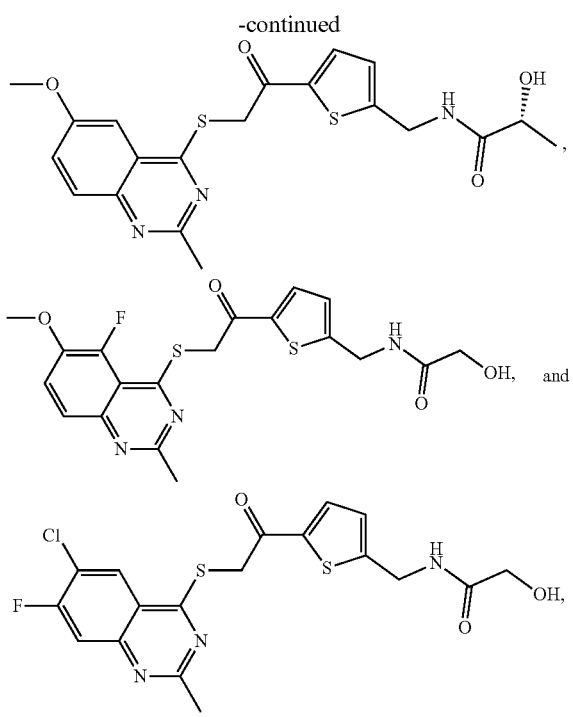

or a pharmaceutically salt.

2. The compound according to claim 1, wherein the compound is

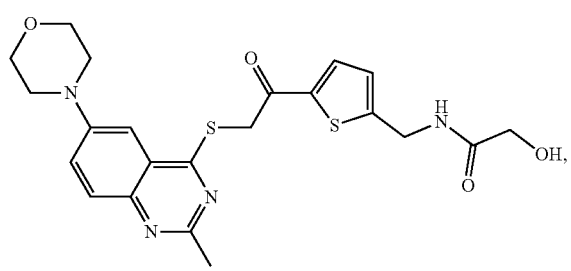 [SMILES: Cc1nc(SCC(=O)c2ccc(CNC(=O)CO)s2)c2cc(N3CCOCC3)ccc2n1]

or a pharmaceutically acceptable salt.

3. The compound according to claim 1, wherein the compound is

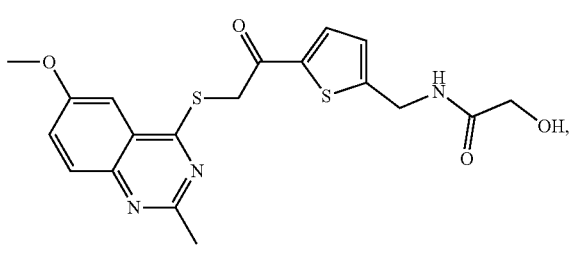 [SMILES: COc1ccc2nc(C)nc(SCC(=O)c3ccc(CNC(=O)CO)s3)c2c1]

or a pharmaceutically acceptable salt.

4. The compound according to claim 1, wherein the compound is

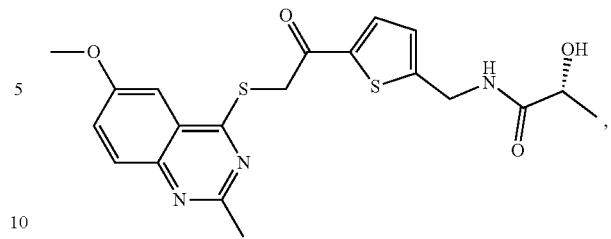

or a pharmaceutically acceptable salt thereof.

5. The compound according to claim 1, wherein the compound is

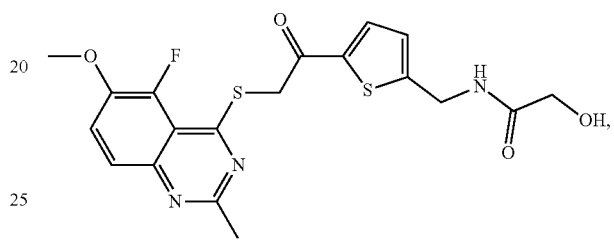

or a pharmaceutically acceptable salt thereof.

6. The compound according to claim 1, wherein the compound is

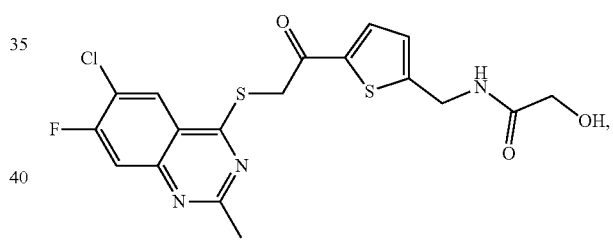

or a pharmaceutically acceptable salt.

7. The compound according to claim 1, wherein the compound is

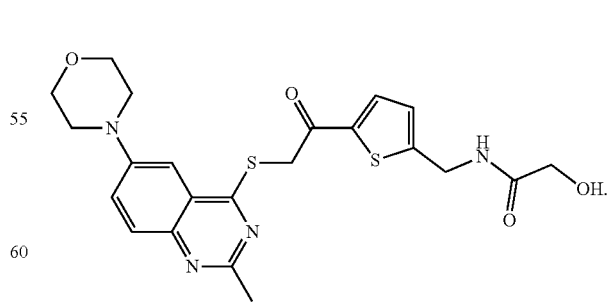

8. The compound according to claim 1, wherein the compound is

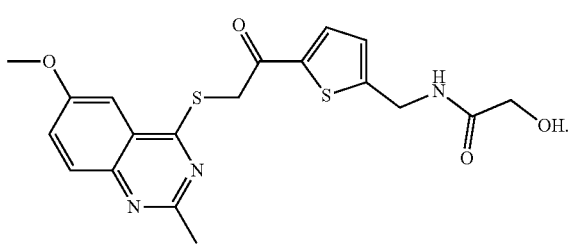 [SMILES: COc1ccc2nc(C)nc(SCC(=O)c3ccc(CNC(=O)CO)s3)c2c1]

9. The compound according to claim 1, wherein the compound is

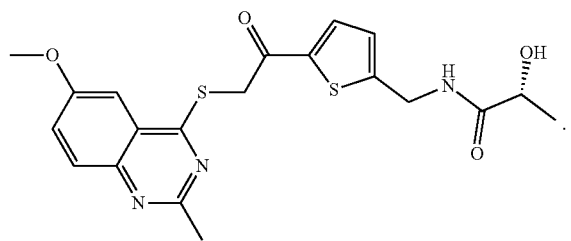 [SMILES: COc1ccc2nc(C)nc(SCC(=O)c3ccc(CNC(=O)[C@@H](C)O)s3)c2c1]

10. The compound according to claim 1, wherein the compound is

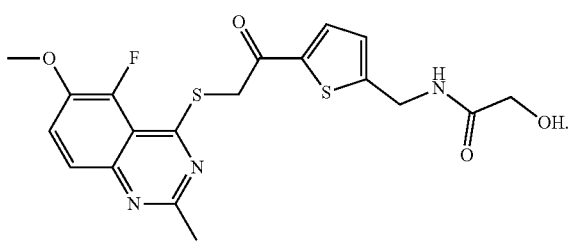 [SMILES: COc1ccc2nc(C)nc(SCC(=O)c3ccc(CNC(=O)CO)s3)c2c1F]

11. The compound according to claim 1, wherein the compound is

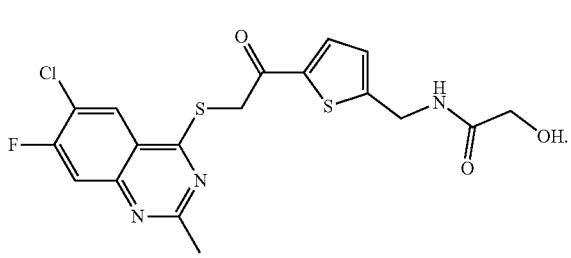 [SMILES: Cc1nc(SCC(=O)c2ccc(CNC(=O)CO)s2)c2cc(Cl)c(F)cc2n1]

12. A pharmaceutical composition comprising at least one pharmaceutically acceptable carrier and the compound according to claim 1, or a pharmaceutically acceptable salt thereof.

13. The pharmaceutical composition according to claim 12, wherein the compound is

or a pharmaceutically acceptable salt thereof.

14. The pharmaceutical composition according to claim 12, wherein the compound is or a pharmaceutically acceptable salt thereof.

15. The pharmaceutical composition according to claim 12, wherein the compound is or a pharmaceutically acceptable salt thereof.

16. The pharmaceutical composition according to claim 12, wherein the compound is or a pharmaceutically acceptable salt thereof.

17. The pharmaceutical composition according to claim 12, wherein the compound is

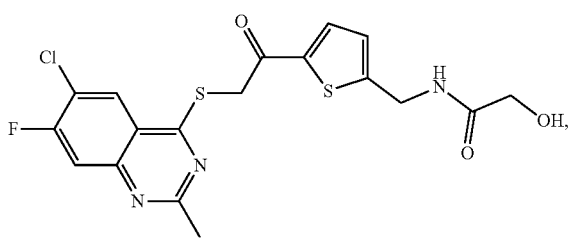 [SMILES: Cc1nc(SCC(=O)c2ccc(CNC(=O)CO)s2)c2cc(Cl)c(F)cc2n1]

or a pharmaceutically acceptable salt thereof.

18. The pharmaceutical composition according to claim 12, wherein the compound is

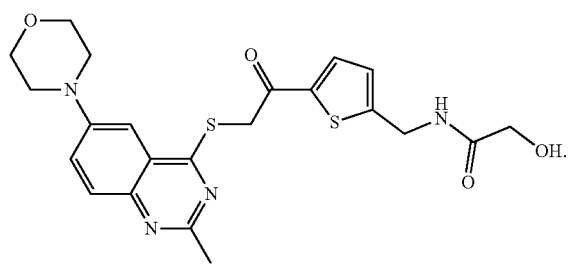 [SMILES: Cc1nc(SCC(=O)c2ccc(CNC(=O)CO)s2)c2cc(N3CCOCC3)ccc2n1]

19. The pharmaceutical composition according to claim 12, wherein the compound is

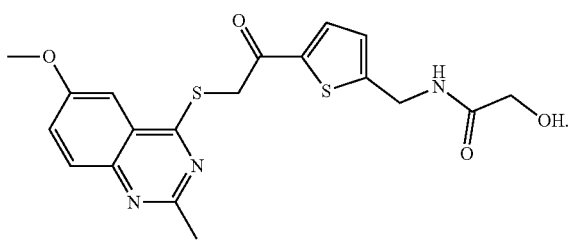

20. The pharmaceutical composition according to claim 12, wherein the compound is

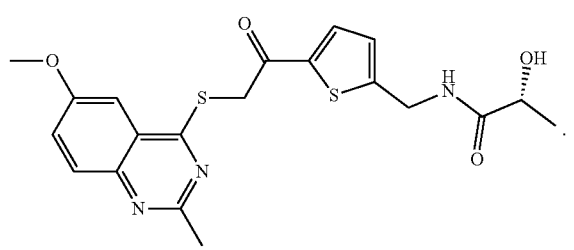 [SMILES: COc1ccc2nc(C)nc(SCC(=O)c3ccc(CNC(=O)[C@@H](C)O)s3)c2c1]

21. The pharmaceutical composition according to claim 12, wherein the compound is

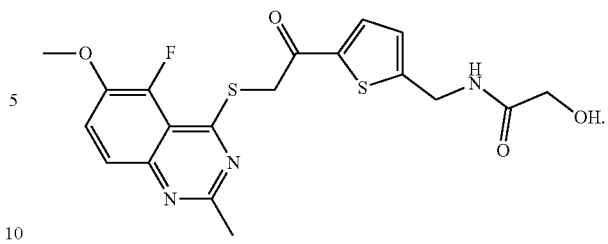

22. The pharmaceutical composition according to claim 12, wherein the compound is

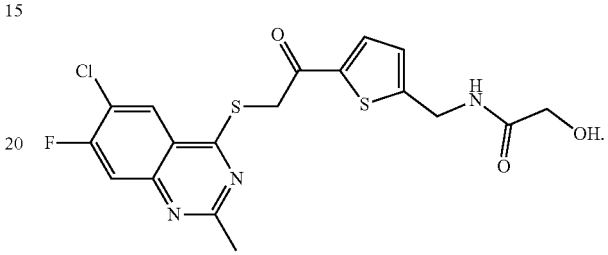

23. A method for inhibiting histone deacetylase subtype 6 (HDAC6) activity in a subject, wherein the method comprises administering to the subject in need thereof a therapeutically effective amount of the compound according to claim 1, or a pharmaceutically acceptable salt thereof.

24. The method according to claim 23, wherein the subject suffers from a histone deacetylase subtype 6 (HDAC6) associated disease or disorder selected from the group consisting of an autoimmune disease, a cardiovascular disease, a hormonal disorder, an inflammatory disease, a metabolic disorder, a neurodegenerative disease, a a neurodevelopmental disorder, a neuropathy, a pain, a proliferative disease, a psychiatric disease, and a sleep disorder.

25. The method according to claim 24, wherein the neuropathy is selected from the group consisting of autonomic neuropathy, Charcot-Marie-Tooth disease, chemotherapy-induced peripheral neuropathy (CIPN) using a chemotherapeutic anticancer agent, chronic inflammatory demyelinating polyneuropathy (CIDP), diabetic peripheral neuropathy (DPN), familial amyloidotic polyneuropathy, Guillain-Barre syndrome, hereditary sensory neuropathy, multifocal motor neuropathy (MMN), neuralgia, and pain.

26. The method according to claim 25, wherein the disease is pain and the pain is neuropathic pain.

27. The method according to claim 24, wherein the cardiovascular disease is selected from the group consisting of acute heart failure, cardiac disease, cardiomyopathy, chronic heart failure, congestive cardiac failure, hypertension, ischemic heart disease, cardiomyopathy, myocarditis, tachycardia, and valvular disease.

28. The method according to claim 25, wherein the disease is acute heart failure and the acute heart failure is acute decompensated heart failure.

29. The method according to claim 24, wherein the hormonal disorder or metabolic disorder is selected from the group consisting of acromegaly, diabetes, infertility, metabolic syndrome, and obesity.

\* \* \* \* \*